US008198508B2

(12) United States Patent
Kellermann et al.

(10) Patent No.: US 8,198,508 B2
(45) Date of Patent: Jun. 12, 2012

(54) REDUCING THE RISK OF HUMAN ANTI-HUMAN ANTIBODIES THROUGH V GENE MANIPULATION

(75) Inventors: Sirid-Aimee Kellermann, Menlo Park, CA (US); Larry L. Green, San Francisco, CA (US); Wouter Korver, Menlo Park, CA (US)

(73) Assignee: Amgen Fremont, Inc., Fremont, CA (US)

( * ) Notice: Subject to any disclaimer, the term of this patent is extended or adjusted under 35 U.S.C. 154(b) by 83 days.

(21) Appl. No.: 12/577,696

(22) Filed: Oct. 12, 2009

(65) Prior Publication Data

US 2010/0028906 A1 Feb. 4, 2010

Related U.S. Application Data

(60) Division of application No. 11/136,250, filed on May 23, 2005, now Pat. No. 7,625,549, which is a continuation-in-part of application No. 11/084,554, filed on Mar. 17, 2005, now abandoned, and a continuation-in-part of application No. PCT/US2005/009306, filed on Mar. 17, 2005.

(60) Provisional application No. 60/554,372, filed on Mar. 19, 2004, provisional application No. 60/574,661, filed on May 24, 2004.

(51) Int. Cl.
*A01K 67/00* (2006.01)
*A01K 67/027* (2006.01)
*A61K 49/00* (2006.01)

(52) U.S. Cl. .................. 800/18; 800/9; 424/9.1
(58) Field of Classification Search .............. 800/18, 800/9; 424/9.1
See application file for complete search history.

(56) References Cited

U.S. PATENT DOCUMENTS

| 4,998,931 | A | 3/1991 | Slichter et al. |
| 5,545,806 | A | 8/1996 | Lonberg et al. |
| 5,545,807 | A | 8/1996 | Surani et al. |
| 5,591,669 | A | 1/1997 | Krimpenfort et al. |
| 5,595,598 | A | 1/1997 | Yooda et al. |
| 5,612,205 | A | 3/1997 | Kay et al. |
| 5,625,126 | A | 4/1997 | Lonberg et al. |
| 5,625,825 | A | 4/1997 | Rostoker et al. |
| 5,633,425 | A | 5/1997 | Lonberg et al. |
| 5,643,763 | A | 7/1997 | Dunn et al. |
| 5,661,016 | A | 8/1997 | Lonberg et al. |
| 5,698,405 | A | 12/1997 | Goldenberg |
| 5,721,367 | A | 2/1998 | Kay et al. |
| 5,770,429 | A | 6/1998 | Lonberg et al. |
| 5,789,215 | A | 8/1998 | Berns et al. |
| 5,789,650 | A | 8/1998 | Lonberg et al. |
| 5,814,318 | A | 9/1998 | Lonberg et al. |
| 5,874,299 | A | 2/1999 | Lonberg et al. |
| 5,877,397 | A | 3/1999 | Lonberg et al. |
| 5,981,175 | A | 11/1999 | Loring et al. |
| 6,023,010 | A | 2/2000 | Krimpenfort |
| 6,075,181 | A | 6/2000 | Kucherlapati et al. |
| 6,114,598 | A | 9/2000 | Kucherlapati et al. |
| 6,150,584 | A | 11/2000 | Kucherlapati et al. |
| 6,162,963 | A | 12/2000 | Kucherlapati et al. |
| 6,235,883 | B1 | 5/2001 | Jakobovits et al. |
| 6,255,458 | B1 | 7/2001 | Lonberg et al. |
| 6,258,562 | B1 | 7/2001 | Salfeld et al. |
| 6,652,863 | B1 | 11/2003 | Jordan et al. |
| 7,625,549 | B2 | 12/2009 | Kellermann et al. |
| 2003/0229207 | A1 | 12/2003 | Studnicka |
| 2004/0005630 | A1 | 1/2004 | Studnicka |
| 2004/0018191 | A1 | 1/2004 | Wang et al. |
| 2005/0260679 | A1 | 11/2005 | Kellerman et al. |
| 2006/0021074 | A1 | 1/2006 | Kellerman et al. |

FOREIGN PATENT DOCUMENTS

| EP | 0 463 151 B1 | 1/1996 |
| EP | 546 073 B1 | 10/1997 |
| JP | 3 068 180 B2 | 3/1991 |
| JP | 3 068 506 B2 | 3/1991 |
| JP | 3 068 507 B2 | 3/1991 |
| WO | WO 90/07861 A | 7/1990 |
| WO | WO 92/03918 | 3/1992 |
| WO | WO 92/22645 | 12/1992 |
| WO | WO 92/22647 | 12/1992 |
| WO | WO 92/22670 | 12/1992 |
| WO | WO 93/12227 | 6/1993 |
| WO | WO 94/02602 | 2/1994 |
| WO | WO 94/25585 | 10/1994 |
| WO | WO 96/14436 | 5/1996 |
| WO | WO 96/34096 | 10/1996 |
| WO | WO 97/13852 | 4/1997 |
| WO | WO 98/24884 | 6/1998 |
| WO | WO 98/24893 | 6/1998 |
| WO | WO 00/76310 | 12/2000 |

(Continued)

OTHER PUBLICATIONS

U.S. Appl. No. 07/574,748, filed Aug. 29, 1990, GenPharm International.
U.S. Appl. No. 07/575,962, filed Aug. 31, 1990, GenPharm International.
U.S. Appl. No. 07/810,279, filed Dec. 17, 1991, GenPharm International.
U.S. Appl. No. 07/853,408, filed Mar. 18, 1992, GenPharm International.
U.S. Appl. No. 08/904,068, filed Jun. 23, 1992, GenPharm International.
U.S. Appl. No. 07/919,297, filed Jul. 24, 1992, Kucherlapati et al.
U.S. Appl. No. 07/922,649, filed Jul. 30, 1992, Kucherlapati et al.
U.S. Appl. No. 07/990,860, filed Dec. 16, 1992, GenPharm International.

(Continued)

*Primary Examiner* — Maria Leavitt
(74) *Attorney, Agent, or Firm* — Knobbe, Martens, Olson & Bear LLP

(57) ABSTRACT

The present embodiments relate to methods of identifying and creating human or humanized antibodies that possess a reduced risk of inducing a Human Anti-Human Antibody (HAHA) response when they are applied to a human host. Other methods are directed to predicting the likelihood of a HAHA response occurring. Methods for screening for anti-HAHA compounds are also included. Methods for determining if various conditions for administering an antibody to a subject enhance or suppress a HAHA response are also included. Some embodiments herein are directed to transgenic mouse embodiments relevant for HAHA responses.

15 Claims, 81 Drawing Sheets

FOREIGN PATENT DOCUMENTS

| | | |
|---|---|---|
| WO | WO 01/31065 A | 5/2001 |
| WO | WO 03/047336 | 12/2003 |

OTHER PUBLICATIONS

U.S. Appl. No. 08/031,801, filed Mar. 15, 1993, Kucherlapati et al.
U.S. Appl. No. 08/031,131, filed Apr. 26, 1993, GenPharm International.
U.S. Appl. No. 08/096,762, filed Jul. 22, 1993, GenPharm International.
U.S. Appl. No. 08/112,848, filed Aug. 27, 1993, Kucherlapati et al.
U.S. Appl. No. 08/155,301, filed Nov. 18, 1993, GenPharm International.
U.S. Appl. No. 08/161,739, filed Dec. 3, 1993, GenPharm International.
U.S. Appl. No. 08/165,699, filed Dec. 10, 1993, GenPharm International.
U.S. Appl. No. 08/309,741, filed Mar. 9, 1994, GenPharm International.
U.S. Appl. No. 08/234,145, filed Apr. 28, 1994, Kucherlapati et al.
U.S. Appl. No. 08/376,279, filed Jan. 20, 1995, Jakobovitz et al.
U.S. Appl. No. 08/430,938, filed Apr. 27, 1995, Kucherlapati et al.
U.S. Appl. No. 08/486,859, filed Jun. 5, 1995, Kucherlapati et al.
U.S. Appl. No. 08/486,853, filed Jun. 5, 1995, Kucherlapati et al.
U.S. Appl. No. 08/464,584, filed Jun. 5, 1995, Kucherlapati et al.
U.S. Appl. No. 08/464,582, Jun. 5, 1995, Kucherlapati et al.
U.S. Appl. No. 08/463,191, filed Jun. 5, 1995, Kucherlapati et al.
U.S. Appl. No. 08/462,837, filed Jun. 5, 1995, Kucherlapati et al.
U.S. Appl. No. 08/462,513, filed Jun. 5, 1995, Seong-Min K.
U.S. Appl. No. 08/724,752, filed Oct. 2, 1996, Kucherlapati et al.
U.S. Appl. No. 08/759,620, filed Dec. 3, 1996, Mendez et al.
U.S. Appl. No. 60/430,729, filed Dec. 2, 2002, Babcook et al.
U.S. Appl. No. 11/136,250, filed May 23, 2005, Kellermann et al.
Atkinson et al., *Immunogenetics*, 44(2), 115-120 (1996).
Babcook et al., Selected Lymphocyte Antibody Method, *Proc. Natl. Acad. Sci USA*, i93:7843-7848 (1996).
Brezinschek et al., *J. Immunol.*, 155:190-202 (1995).
Communication Pursuant to Article 94(3) EPC; received in European Patent Application No. 05727870.7; dated Oct. 1, 2008.
Communication pursuant to Article 96(2) EPC, received in EP Application No. 05 725 970.7-1222, dated Aug. 6, 2007, 2 pages.
Demaison et al., *Immunogenics*, 42:342-352 (1995).
Dijk-Hard et al., *Immunology*, 107:136-133 (2002).
Dijk-Hard et al., *J Autoimmune.* 12:57-63 (1999).
Ebeling et al., *Int Immunol.*, 4:313-320 (1992).
Feuchtenberger et al., *J Immunol Methods*, 276:121-127 (2003).
Glas et al., "Motif-specific probes identify individual genes and detect somatic mutations," *Molecular Immunology*, 1999, pp. 599-610, vol. 36, Elsevier Science Ltd.
Green et al., *J. Exp. Med*. 188:483-495 (1998).
Green et al., *Nature Genetics*, 7:13-21 (1994).
Hoogenboom, "Designing and optimizing library selection strategies for generating high-affinity antibodies", TIBTECH (1997), 62-70.
Hougs et al., *Tissue Antigens*, 61 (3), 231-239 (2003).
Huang et al., "$V_H$ usage and somatic hypermutation in peripheral blood B cells of patients with rheumatoid arthritis (RA)," *Clin Exp Immunol*, 1998, pp. 516-527, vol. 112, Blackwell Science.
Huang et al., *Mol Immuno.*, 33:553-560 (1996).
Hufnagle et al., *Ann Y Aced Sci.*, 764:293-295 (1995).
International Preliminary Report on Patentability, International Application No. PCT/US2005/009306, mailed Sep. 28, 2006, 7 pages.
International Preliminary Report on Patentability, International Application No. PCT/US2005/018143, mailed Dec. 7, 2006, 10 pages.
International Search Report and Written Opinion of the International Searching Authority, International Application No. PCT/US2005/009306, mailed Feb. 9, 2006, 11 pages.
International Search Report and Written Opinion of the International Searching Authority, International Application No. PCT/US2005/018143, mailed Feb. 14, 2006, 13 pages.
Johnson et al., *J Immunol.*, 158:235-246 (1997).
Juul et al., *Tissue Antigens*, 49(6), 595-604 (1997).
Kellermann et al. Developing the Xenomouse technology for evaluating immunogenicity. Retrieved from the Internet Mar. 23, 2004, from http://diagnosticscrc.org/publications/brochures/AntibOZ-2.pdf.
Krause et al. "Human monoclonal antibody 99mTc-88BV59: detection of colorectal cancer, recurrent of metastatic disease and immunogenicity assessment," European Journal of Nuclear Medicine, vol. 24, No. 1, Jan. 1997.
Lecerf et al., *J Immunology*, 161: 1274-1283 (1998).
Li et al., *Blood*, 103:4602-4609 (2004).
Logtenberg et al., *Int Immunol.*, 1:362-366 (1989).
Matsuda et al., *J Exp Med.*, 188:2151-2162 (1998).
Meffre et al., "Circulating human B cells that express surrogate light chains display a unique antibody repertoire," Abs of V-PREB$^+$L$^+$ B Cells Show Self-Reactivity Features, 2001, pp. 2150-2156, The American Association of Immunologists.
Mendez et al., *Nature Genetics* 15:146-156 (1997).
Messmer et al., *Blood*, 103:3490-3495 (2004).
Office Action dated Dec. 31, 2008, U.S. Appl. No. 11/084,554.
Office Action dated Nov. 14, 2006, U.S. Appl. No. 11/136,250.
Office Action dated Mar. 28, 2007, U.S. Appl. No. 11/136,250.
Office Action dated Mar. 18, 2008, U.S. Appl. No. 11/136,250.
Office Action dated Oct. 3, 2008, U.S. Appl. No. 11/136,250.
Office Action dated Oct. 26, 2009, European Patent Application No. 05 725 970.7, 7 pages.
Pandey, J.P., *Vaccine*, 19(6), 613-617 (2000).
Panina-Bordignon et al., *Eur. J. Immunel.* 19, 2237-2242 (1989).
Pramanik et al., *Am J Hum Genet.*, 71:1342-1352 (2002).
Rajewsky, *Nature*, 381 (6585): 751-758 (1996).
Rao et al., *Exp Clin Immunogenet.*, 13:131-138 (1996).
Rassenti et al., *Ann N Y Acad Sci.*, 764:463-473 (1995).
Roskos et al. Human Antiglobulin Responses. *Measuring Immunity*, 2005, 172-186, ed. Lotze and Thomas.
Sasso et al., *Ann N Y Acad Sci.*, 764:72-73 (1995).
Slide presentation, "Abgenix: Dedicated to developing novel antibody therapeutics," presented by Larry L. Green in Australia, not prior to Mar. 21, 2004.
Suleyman et al., "Molecular analysis of human immunoglobulin heavy chain variable region associated determinants recognized by anti-VH3 antibodies 7B4, B6 and D12," *Scand. J. Immunol.*, 2000, pp. 341-347, vol. 52, Blackwell Science, Ltd.
Tangri et al., *Curr. Med. Chem.* 9:2191-2199; 2002.
Wang et al., *Clin Immunol.*, 93:132-142 (1999).
Wiener, L.J. *Immunother.*, 29:1-9; 2006 (pp. 1-14).
Wilson et al. "Somatic Hypermutation Introduces Insertions and Deletions in to Immunoglobulin V Genes," *J Exp. Med.* 1998, 187:59-70.
Wilson et al., *J Exp Med.*, 188(11): 1973-1975 (1998).
File History of U.S. Appl. No. 11/136250, filed May 23, 2005.
File History of U.S. Appl. No. 11/084554, filed Mar. 17, 2005.
Office Action dated Apr. 11, 2011, received in European Patent Application No. 05725970.7.
AntibOZ 2: An International Forum: Predicting the Next Wave of Protein-based Therapies and Immunodiagnostics. Conference Brochure, AntibOZ 2 Conference, Mar. 18-23, 2004, Heron Island, Queensland, Australia, hosted by CRC Diagnostics.
Office Action received in Canadian Patent Application No. 2564989, dated Feb. 15, 2012.

A.  Host    1   $V_a, V_b, V_c, V_d$      B.  Protein or mRNA (only ACDE)
         2   $V_b, V_c, V_d, V_e$          1   A , C , D
         3   $V_c, V_d, V_e, V_a$          2   C , E
         4   $V_a, V_d, V_e, V_c$          3   A , C , D , E
         5   $V_e, V_b, V_c, V_a$          4   A , C , D , E
                                           5   A , C , E C.  Frequencies as DNA              D.  Frequencies as Protein or mRNA
    $V_a$ = 80%                         $V_a$ = 80%
    $V_b$ = 60%                         $V_b$ = 0
    $V_c$ = 100%                        $V_c$ = 100%
    $V_d$ = 80%                         $V_d$ = 60%
    $V_e$ = 80%                         $V_e$ = 80%

*Fig. 1*

*Fig. 4*   *Methods of Making Gene Optimized Abs*

FIG. 8

| Functional VH | Reports in humans | Functional VKappa | Reports in humans | Functional Vlambda | | Reports in humans |
|---|---|---|---|---|---|---|
| 3-74 | | VK3-L25 | | 4b | V5-6 | |
| 3-73 | D young | VK1-L24 | | 8a | V3-4 | |
| 3-72 | | VK1-L23 | | 4a | V5-4 | D |
| 2-70 | | VK3-L20 | | 6a | V1-22 | |
| 1-69 | | VK1-L19 | | 10a | V1-20 | |
| 1-f | 50% | VK1-L18 | | 1b | V1-19 | |
| 1-e | insertion | VK3-L16 | C | 5b | V4-4 | D |
| 3-66 | | VK1-L15 | | 9a | V5-2 | D |
| 3-64 | A, E young | VK1-L14 | | 1g | V1-17 | |
| 4-61 | A, E young (I/D allele) | VK6-A14 | | 7b | V3-3 | G |
| 4-59 | | VK3-A11 | | 5c | V4-2 | |
| 1-58 | | VK6-A10 | | 1c | V1-16 | |
| 3-53 | | VK2-A3 | | 7a | V3-2 | |
| 5-51 | missing in 2/6 (E) | VK2-A2 | B | 1e | V1-13 | |
| 3-49 | E elderly | VK2-A1 | B | 5e | V4-1 | D |
| 3-48 | | VK1-O8 | | 1a | V1-11 | |
| 1-46 | | VK1-O2 | | 2-19 | | D |
| 1-45 | | VK2-O1 | | 3m | V2-17 | |
| 3-d | 27% insertion | VK2-O11 | | 2b2 | V1-7 | |
| 3-43 | A | VK1-O12 | B, C | 3e | V2-15 | D, F |
| 4-b | insertion, ?% | VK1-O18 | | 3h | V2-14 | |
| 4-39 | A | VK2-A17 | | 3l | V2-13 | |
| 4-34 | | VK2-A18 | C | 2d | V1-5 | |
| 3-33 | E young | VK2-A19 | | 3a | V2-11 | D |
| 4-31 | | VK1-A20 | rare: defects in 7-RSS | 2a2 | V1-4 | |

| | | | | | | | |
|---|---|---|---|---|---|---|---|
| 3-30.5 | insertion allele 73% | VK2-A23 | | | 2e | V1-3 | |
| 4-30.4 | | VK6-A26 | | | 3p | V2-7 | |
| 3-30.3 | | VK3-A27 | | | 3j | V2-6 | |
| 4-30.2 | | VK1-A30 | | | 2c | V1-2 | |
| 4-30.1 | | VK1-L1 | B | | 4c | V5-1 | D |
| 3-30 | polymorphic | VK3-L2 | | | 3r | V2-1 | |
| 4-28 | | VK1-L4 | | | | | |
| 2-26 | E young | VK1-L5 | | | | | |
| 1-24 | E elderly | VK3-L6 | | | | | |
| 3-23 | | VK1-L8 | | | | | |
| 3-21 | | VK1-L9 | | | | | |
| 3-20 | A, E elderly | VK1-L11 | | | | | |
| 1-18 | | VK1-L12 | B | | | | |
| 3-15 | E young | VK5-B2 | | | | | |
| 5-a | 75% | VK4-B3 | | | | | |
| 3-13 | E young | VK1-La | H | | | | |
| 3-11 | E elderly | | | | | | |
| 3-9 | A, E elderly | | | | | | |
| 1-8 | | | | | | | |
| 3-7 | A, E young | | | | | | |
| 2-5 | | | | | | | |
| 7-4.1 | insertion 91% | | | | | | |
| 4-4 | | | | | | | |
| 1-3 | | | | | | | |
| 1-2 | | | | | | | |
| 6-1 | missing in 2/6 (E) | | | | | | |

A. not rearranged in some people (Huang et al., 1996) or rare (Gallo et al., 2000)
B. low frequency of rearranged sequence in single individual (Cox et al., 1994)
C. possible allele(s) with stop codon (Tomlinson et al., 1995)
D. low or undetectable in transcripts of pooled cDNAs (Ignatovitch et al., 1997)
E. missing in 5/5 elderly libraries or 4/4 young libraries (Wang & Stollar, 1999)
F. a nonfunctional allele (insertion or deletion) described by Frippiat & Lefranc, 1994
G. a nonfunctional allele (insertion or deletion) described by Williams & Winter, 1993
H. present in 21% of 57 Caucasians (Juul, 1998)

```
54  4-59  QVQLQESGPGLVKPSETLSLTCTVSGGSISS----YYNSWIRQPPGKGLEWIGYIY----YSGSTNYNPSLKSRVTISVDTSKNQFSLKLSSVTAADTAVYYCAR
55  4-61  QVQLQESGPGLVKPSETLSLTCTVSGGSVSSYYWSWIRQPPGKGLEWIGYIY----YSGSTNYNPSLKSRVTISVDTSKNQFSLKLSSVTAADTAVYYCAR
56  5-51  EVQLVQSGAEVKKPGESLKISCKGSGYSFTS--YWIGWVRQMPGKGLEWMGIIYP--GDSDTRYSPSFQGQVTISADKSISTAYLQWSSLKASDTAMYYCAR
267 5-a   EVQLVQSGAEVKKPGESLRISCKGSGYSFTS--YWISWVRQMPGKGLEWMGRIDP--SDSYTNYSPSFQGHVTISADKSISTAYLQWSSLKASDTAMYYCAR
57  6-01  QVQLQQSGPGLVKPSQTLSLTCAISGDSVSSNSAAWNWIRQSPSRGLEWLGRTYYR-SKWYNDYAVSVKSRITINPDTSKNQFSLQLNSVTPEDTAVYYCAR
268 7-4.1 QVQLVQSGSELKKPGASVKVSCKASGYTFTS--YAMNWVRQAPGQGLEWMGWINT-
          NTGNPTYAQGFTGRFVFSLDTSVSTAYLQICSLKAEDTAVYYCAR
```

FIG. 16B

V_H Gene Sequences

>VH1-18
QVQLVQSGAEVKKPGASVKVSCKASGYTFTSYGISWVRQAPGQGLEWMGWISAYNGNTNY
AQKLQGRVTMTTDTSTSTAYMELRSLRSDDTAVYYCAR (SEQ ID NO: 15)

>VH1-2
QVQLVQSGAEVKKPGASVKVSCKASGYTFTGYYMHWVRQAPGQGLEWMGWINPNSGGTNY
AQKFQGRVTMTRDTSISTAYMELSRLRSDDTAVYYCAR (SEQ ID NO: 16)

>VH1-24
QVQLVQSGAEVKKPGASVKVSCKVSGYTLTELSMHWVRQAPGKGLEWMGGFDPEDGETIY
AQKFQGRVTMTEDTSTDTAYMELSSLRSEDTAVYYCAT (SEQ ID NO: 17)

>VH1-3
QVQLVQSGAEVKKPGASVKVSCKASGYTFTSYAMHWVRQAPGQRLEWMGWSNAGNGNTKY
SQEFQGRVTITRDTSASTAYMELSSLRSEDMAVYYCAR (SEQ ID NO: 18)

>VH1-45
QMQLVQSGAEVKKTGSSVKVSCKASGYTFTYRYLHWVRQAPGQALEWMGWITPFNGNTNY
AQKFQDRVTITRDRSMSTAYMELSSLRSEDTAMYYCAR (SEQ ID NO: 19)

FIG. 17A

>VH1-46
QVQLVQSGAEVKKPGASVKVSCKASGYTFTSYYMHWVRQAPGQGLEWMGIINPSGGSTSY
AQKFQGRVTMTRDTSTSTVYMELSSLRSEDTAVYYCAR (SEQ ID NO: 20)

>VH1-58
QMQLVQSGPEVKKPGTSVKVSCKASGFTFTSSAMQWVRQARGQRLEWIGWIVVGSGNTNY
AQKFQERVTITRDMSTSTAYMELSSLRSEDTAVYYCAA (SEQ ID NO: 21)

>VH1-69
QVQLVQSGAEVKKPGSSVKVSCKASGGTFSSYAISWVRQAPGQGLEWMGGIIPIFGTANY
AQKFQGRVTITADKSTSTAYMELSSLRSEDTAVYYCAR (SEQ ID NO: 22)

>VH1-8
QVQLVQSGAEVKKPGASVKVSCKASGYTFTSYDINWVRQATGQGLEWMGWMNPNSGNTGY
AQKFQGRVTMTRNTSISTAYMELSSLRSEDTAVYYCARG (SEQ ID NO: 23)

>VH2-26
QVTLKESGPVLVKPTETLTLTCTVSGFSLSNARMGVSWIRQPPGKALEWLAHIFSNDEKS
YSTSLKSRLTISKDTSKSQVVLTMTNMDPVDTATYYCARI (SEQ ID NO: 24)

FIG. 17B

>VH2-5
QITLKESGPTLVKPTQTLTLTCTFSGFSLSTSGVGVGWIRQPPGKALEWLALIYWNDDKR
YSPSLKSRLTITKDTSKNQVVLTMTNMDPVDTATYYCAHR (SEQ ID NO: 25)

>VH2-70
QVTLRESGPALVKPTQTLTLTCTFSGFSLSTSGMCVSWIRQPPGKALEWLALIDWDDDKY
YSTSLKTRLTISKDTSKNQVVLTMTNMDPVDTATYYCARI (SEQ ID NO: 26)

>VH3-11
QVQLVESGGGLVKPGGSLRLSCAASGFTFSDYYMSWIRQAPGKGLEWVSYISSSGSTIYY
ADSVKGRFTISRDNAKNSLYLQMNSLRAEDTAVYYCAR (SEQ ID NO: 27)

>VH3-13
EVQLVESGGGLVQPGGSLRLSCAASGFTFSSYDMHWVRQATGKGLEWVSAIGTAGDTYYP
GSVKGRFTISRENAKNSLYLQMNSLRAGDTAVYYCAR (SEQ ID NO: 28)

>VH3-15
EVQLVESGGGLVKPGGSLRLSCAASGFTFSNAWMSWVRQAPGKGLEWVGRIKSKTDGGTT
DYAAPVKGRFTISRDDSKNTLYLQMNSLKTEDTAVYYCTT (SEQ ID NO: 29)

FIG. 17C

>VH3-16
EVQLVESGGGLVQPGGSLRLSCAASGFTFSNSDMNWARKAPGKGLEWVSGVSWNGSRTHY
VDSVKRRFIISRDNSRNSLYLQKNRRAEDMAVYYCVR (SEQ ID NO: 30)

>VH3-20
EVQLVESGGGVVRPGGSLRLSCAASGFTFDDYGMSWVRQAPGKGLEWVSGINWNGGSTGY
ADSVKGRFTISRDNAKNSLYLQMNSLRAEDTALYHCAR (SEQ ID NO: 31)

>VH3-21
EVQLVESGGGLVKPGGSLRLSCAASGFTFSSYSMNWVRQAPGKGLEWVSSISSSSYIYY
ADSVKGRFTISRDNAKNSLYLQMNSLRAEDTAVYYCAR (SEQ ID NO: 32)

>VH3-23
EVQLLESGGGLVQPGGSLRLSCAASGFTFSSYAMSWVRQAPGKGLEWVSAISGSGGSTYY
ADSVKGRFTISRDNSKNTLYLQMNSLRAEDTAVYYCAK (SEQ ID NO: 33)

>VH3-30
QVQLVESGGGVVQPGRSLRLSCAASGFTFSSYGMHWVRQAPGKGLEWVAVISYDGSNKYY
ADSVKGRFTISRDNSKNTLYLQMNSLRAEDTAVYYCAR (SEQ ID NO: 34)

FIG. 17D

>VH3-33
QVQLVESGGGVVQPGRSLRLSCAASGFTFSSYGMHWVRQAPGKGLEWVAVIWYDGSNKYY
ADSVKGRFTISRDNSKNTLYLQMNSLRAEDTAVYYCAR (SEQ ID NO: 35)

>VH3-35
EVQLVESGGGLVQPGGSLRLSCAASGFTFSNSDMNWVHQAPGKGLEWVSGVSWNGSRTHY
ADSVKGRFTISRDNSRNTLYLQTNSLRAEDTAVYYCVR (SEQ ID NO: 36)

>VH3-38
EVQLVESGGGLVQPRGSLRLSCAASGFTVSSNEMSWIRQAPGKGLEWVSSISGGSTYYAD
SRKGRFTISRDNSKNTLYLQMNNLRAEGTAVYYCAR (SEQ ID NO: 37)

>VH3-43
EVQLVESGGGVVVQPGGSLRLSCAASGFTFDDYTMHWVRQAPGKGLEWVSLISWDGGSTYY
ADSVKGRFTISRDNSKNSLYLQMNSLRTEDTALYYCAKD (SEQ ID NO: 38)

>VH3-48
EVQLVESGGGLVQPGGSLRLSCAASGFTFSSYSMNWVRQAPGKGLEWVSYISSSSTIYY
ADSVKGRFTISRDNAKNSLYLQMNSLRDEDTAVYYCAR (SEQ ID NO: 39)

FIG. 17E

>VH3-49
EVQLVESGGGLVQPGRSLRLSCTASGFTFGDYAMSWFRQAPGKGLEWVGFIRSKAYGGTT
EYAASVKGRFTISRDDSKSIAYLQMNSLKTEDTAVYYCTR (SEQ ID NO: 40)

>VH3-53
EVQLVESGGGLIQPGGSLRLSCAASGFTVSSNYMSWVRQAPGKGLEWVSVIYSGGSTYYA
DSVKGRFTISRDNSKNTLYLQMNSLRAEDTAVYYCAR (SEQ ID NO: 41)

>VH3-64
EVQLVESGEGLVQPGGSLRLSCAASGFTFSSYAMHWVRQAPGKGLEYVSAISSNGGSTYY
ADSVKGRFTISRDNSKNTLYLQMGSLRAEDMAVYYCAR (SEQ ID NO: 42)

>VH3-66
EVQLVESGGGLIQPGGSLRLSCAASGFTVSSNYMSWVRQAPGKGLEWVSVIYSCGSTYYA
DSVKGRFTISRDNSKNTLYLQMNSLRAEDTAVYYCAR (SEQ ID NO: 43)

>VH3-7
EVQLVESGGGLVQPGGSLRLSCAASGFTFSSYWMSWVRQAPGKGLEWVANIKQDGSEKYY
VDSVKGRFTISRDNAKNSLYLQMNSLRAEDTAVYYCAR (SEQ ID NO: 44)

FIG. 17F

>VH3-72
EVQLVESGGGLVQPGGSLRLSCAASGFTFSDHYMDWVRQAPGKGLEWVGRTRNKANSYTT
EYAASVKGRFTISRDDSKNSLYLQMNSLKTEDTAVYYCAR (SEQ ID NO: 45)

>VH3-73
EVQLVESGGGLVQPGGSLKLSCAASGFTFSSGSAMHWVRQASGKGLEWVGRIRSKANSYAT
AYAASVKGRFTISRDDSKNTAYLQMNSLKTEDTAVYYCTR (SEQ ID NO: 46)

>VH3-74
EVQLVESGGGLVQPGGSLRLSCAASGFTFSSYWMHWVRQAPGKGLVWVSRINSDGSSTSY
ADSVKGRFTISRDNAKNTLYLQMNSLRAEDTAVYYCAR (SEQ ID NO: 47)

>VH3-9
EVQLVESGGGLVQPGRSLRLSCAASGFTFDDYAMHWVRQAPGKGLEWVSGISWNSGSIGY
ADSVKGRFTISRDNAKNSLYLQMNSLRAEDTALYYCAKD (SEQ ID NO: 48)

>VH4-28
QVQLQESGPGLVKPSDTLSLTCAVSGYSISSSNWWGWIRQPPGKGLEWIGYIYYSGSTYY
NPSLKSRVTMSVDTSKNQFSLKLSSVTAVDTAVYYCAR (SEQ ID NO: 49)

FIG. 17G

>VH4-31
QVQLQESGPGLVKPSQTLSLTCTVSGGSISSGGYYWSWIRQHPGKGLEWIGYIYYSGSTY
YNPSLKSRVTISVDTSKNQFSLKLSSVTAADTAVYYCAR (SEQ ID NO: 50)

>VH4-34
QVQLQQWGAGLLKPSETLSLTCAVYGGSFSGYYWSWIRQPPGKGLEWIGEINHSGSTNYN
PSLKSRVTISVDTSKNQFSLKLSSVTAADTAVYYCARG (SEQ ID NO: 51)

>VH4-39
QLQLQESGPGLVKPSETLSLTCTVSGGSISSSSYYWSWIRQPPGKGLEWIGSIYYSGSTY
YNPSLKSRVTISVDTSKNQFSLKLSSVTAADTAVYYCAR (SEQ ID NO: 52)

>VH4-4
QVQLQESGPGLVKPSETLSLTCTVSGGSISSSYYWSWIRQPAGKGLEWIGRIYTSGSTNYN
PSLKSRVTMSVDTSKNQFSLKLSSVTAADTAVYYCAR (SEQ ID NO: 53)

>VH4-59
QVQLQESGPGLVKPSETLSLTCTVSGGSISSYYWSWIRQPPGKGLEWIGYIYYSGSTNYN
PSLKSRVTISVDTSKNQFSLKLSSVTAADTAVYYCAR (SEQ ID NO: 54)

FIG. 17H

>VH4-61
QVQLQESGPGLVKPSETLSLTCTVSGGSVSSGGYYWSWIRQPPGKGLEWIGYIYYSGSTN
YNPSLKSRVTISVDTSKNQFSLKLSSVTAADTAVYYCAR (SEQ ID NO: 55)

>VH5-51
EVQLVQSGAEVKKPGESLKISCKGSGYSFTSYWIGWVRQMPGKGLEWMGIIYPGDSDTRY
SPSFQGQVTISADKSISTAYLQWSSLKASDTAMYYCAR (SEQ ID NO: 56)

>VH6-1
QVQLQQSGPGLVKPSQTLSLTCAISGDSVSSNSAAWNWIRQSPSRGLEWLGRTYYRSKWY
NDYAVSVKSRITINPDTSKNQFSLQLNSVTPEDTAVYYCAR (SEQ ID NO: 57)

>VH7-81
QVQLVQSGHEVKQPGASVKVSCKASGYSFTTYGMNWVPQAPGQGLEWMGWFNTYTGNPTY
AQGFTGRFVFSMDTSASTAYLQISSLKAEDMAMYYCAR (SEQ ID NO: 58)

FIG. 17I

>VH1-18
CAGGTTCAGCTGGTGCAGTCTGGAGCTGAGGTGAAGAAGCCTGGGGCCTCAGTGAAGGTC
TCCTGCAAGGCTTCTGGTTACACCTTTACCAGCTATGGTATCAGCTGGGTGCGACAGGCC
CCTGGACAAGGGCTTGAGTGGATGGGATGGATCAGCGCTTACAATGGTAACACAAACTAT
GCACAGAAGCTCCAGGGCAGAGTCACCATGACCACAGACACATCCACGAGCACAGCCTAC
ATGGAGCTGAGGAGCCTGAGATCTGACGACACGGCCGTGTATTACTGTGCGAGAGA
(SEQ ID NO: 59)

>VH1-2
CAGGTGCAGCTGGTGCAGTCTGGGGCTGAGGTGAAGAAGCCTGGGGCCTCAGTGAAGGTC
TCCTGCAAGGCTTCTGGATACACCTTCACCGGCTACTATATGCACTGGGTGCGACAGGCC
CCTGGACAAGGGCTTGAGTGGATGGGATAATCAACCCTAACAGTGGTGGCACAAACTAT
GCACAGAAGTTTCAGGGCAGGGTCACCATGACCAGGGACACGTCCATCAGCACAGCCTAC
ATGGAGCTGAGCAGGCTGAGATCTGACGACACGGCCGTGTATTACTGTGCGAGAGA
(SEQ ID NO: 60)

FIG. 18A

>VH1-24
CAGGTCCAGCTGGTACAGTCTGGGGCTGAGGTGAAGAAGCCTGGGGCCTCAGTGAAGGTC
TCCTGCAAGGTTTCCGGATACACCCTCACTGAATTATCCATGCACTGGGTGCGACAGGCT
CCTGGAAAAGGGCTTGAGTGGATGGGAGGTTTTGATCCTGAAGATGTGAAACAATCTAC
GCACAGAAGTTCCAGGGCAGAGTCACCATGACCGAGGACACATCTACAGACACAGCCTAC
ATGGAGCTGAGCAGCCTGAGATCTGAGGACACGGCCGTGTATTACTGTGCAACAGA
(SEQ ID NO: 61)
>VH1-3
CAGGTTCAGCTGGTGCAGTCTGGGGCTGAGGTGAAGAAGCCTGGGGCCTCAGTGAAGGTT
TCCTGCAAGGCTTCTGGATACACCTTCACTAGCTATGCTATGCATTGGGTGCGCCAGGCC
CCCGGACAAAGGCTTGAGTGGATGGAGCAACGCTGGCAATGGTAACACAAAATAT
TCACAGGAGTTCCAGGGCAGAGTCACCATTACCAGGACATGGCTGTGTATTACTGTGCGAGAGA
ATGGAGCTGAGCAGCCTGAGATCTGAGGACACGGCCGTGTATTACTGTGCGAGAGA
(SEQ ID NO: 62)
>VH1-45
CAGATGCAGCTGGTGCAGTCTGGGGCTGAGGTGAAGAAGACTGGGTCCTCAGTGAAGGTT
TCCTGCAAGGCTTCCGGATACACCTTCACCTCACCCTGCACTGGGTGCGACAGGCC
CCCGGACAAGCGCTTGAGTGGATGGGATGGATCACACCTTTCAATGTAACACCAACTAC
GCACAGAAATTCCAGGACAGAGTCACCATTACCAGGGACACAGGTCTATGAGCACAGCCTAC
ATGGAGCTGAGCAGCCTGAGATCTGAGGACACAGCCATGTATTACTGTGCAAGATA
(SEQ ID NO: 63)

FIG. 18B

>VH1-46
CAGGTGCAGCTGGTGCAGTCTGGGGCTGAGGTGAAGAAGCCTGGGGCCTCAGTGAAGGTT
TCCTGCAAGGCATCTGGATACACCTTCACCAGCTACTATATGCACTGGGTGCGACAGGCC
CCTGGACAAGGGCTTGAGTGGATGGGAATAATCAACCCTAGTGGTGGTAGCACACAAGCTAC
GCACAGAAGTTCCAGGGCAGAGTCACCATGACCAGGGACACGTCCACGAGCACAGTCTAC
ATGGAGCTGAGCAGCCTGAGATCTGAGGACACGGCCGTGTATTACTGTGCGAGAGA
(SEQ ID NO: 64)

>VH1-58
CAAATGCAGCTGGTGCAGTCTGGGCCTGAGGTGAAGAAGCCTGGGACCTCAGTGAAGGTC
TCCTGCAAGGCTTCTGGATTCACCTTTACTAGCTCTGCTATGCAGTGGGTGCGACAGGCT
CGTGGACAACGCCTTGAGTGGATGGGATGGATCGTCGTTGGCAGTGGTAACACAAACTAC
GCACAGAAGTTCCAGGAAAGAGTCACCATTACCAGGGACATGTCCACAAGCACAGCCTAC
ATGGAGCTGAGCAGCCTGAGATCCGAGGACACGGCCGTGTATTACTGTGCGGGCAGA
(SEQ ID NO: 65)

>VH1-69
CAGGTGCAGCTGGTGCAGTCTGGGGCTGAGGTGAAGAAGCCTGGGTCCTCGGTGAAGGTC
TCCTGCAAGGCTTCTGGAGGCACCTTCAGCAGCTATGCTATCAGCTGGGTGCGACAGGCC
CCTGGACAAGGGCTTGAGTGGATGGGAGGGATCATCCCTATCTTTGGTACAGCAAACTAC
GCACAGAAGTTCCAGGGCAGAGTCACGATTACCGCGGACAAATCCACGAGCACAGCCTAC
ATGGAGCTGAGCAGCCTGAGATCTGAGGACACGGCCGTGTATTACTGTGCGAGAGA
(SEQ ID NO: 66)

FIG. 18C

>VH1-8
CAGGTGCAGCTGGTGCAGTCTGGGGCTGAGGTGAAGAAGCCTGGGGCCTCAGTGAAGGTC
TCCTGCAAGGCTTCTGGATACACCTTCACCAGTTATGATATCAACTGGGTGCGACAGGCC
ACTGGACAAGGGCTTGAGTGGATGGGATGGATGAACCCTAACAGTGGTAACACAGGCTAT
GCACAGAAGTTCCAGGGCAGAGTCACCATGACCAGGAACACCTCCATAAGCACAGCCTAC
ATGGAGCTGAGCAGCCTGAGATCTGAGGACACGGCCGTGTATTACTGTGCGAGAGG
(SEQ ID NO: 67)

>VH2-26
CAGGTCACCTTGAAGGAGTCTGGTCCTGTGCTGGTGAAACCCACAGAGACCCTCACGCTG
ACCTGCACCGTCTCTGGGTTCTCACTCAGCAATGCTAGAATGGGTGTGAGCTGGATCCGT
CAGCCCCCAGGAAAGGCCCTGGAGTGGCTTGCACACATTTTTTCGAATGACGAAAAATCC
TACAGCACATCTCTGAAGAGCAGGCTCACCATCTCCAAGGACACCTCCAAAAGCCAGGTG
GTCCTTACCATGACCAACATGGACCCTGTGGACACAGCCACATATTACTGTGCACGGATA
C (SEQ ID NO: 68)

FIG. 18D

>VH2-5
CAGATCACCTTGAAGGAGTCTGGTCCTACGCTGGTGAAACCCACACAGACCCTCACGCTG
ACCTGCACCTTCTCTGGGTTCTCACTCAGCACTAGTGGAGTGGGTGTGGGCTGGATCCGT
CAGCCCCCAGGAAAGGCCCCTGGAGTGGCTTGCACTCATTTATTGGAATGATGATAAGCGC
TACAGCCCATCTCTGAAGAGCAGGCTCACCATCACCAAGGACACCTCCAAAAACCAGGTG
GTCCTTACAATGACCAACATGGACCCCTGTGGACACAGCCACATATTACTGTGCACACAGA
C (SEQ ID NO: 69)
>VH2-70
CAGGTCACCTTGAGGGAGTCTGGTCCTGCGCTGGTGAAACCCACACAGACCCTCACACTG
ACCTGCACCTTCTCTGGGTTCTCACTCAGCACTAGTGGAATGTGTGTGAGCTGGATCCGT
CAGCCCCCAGGGAAGGCCCTGGAGTGGCTTGCACTCATTGATTGGGATGATGATAAATAC
TACAGCACATCTGAAGACCAGGCTCACCATCTCCAAGGACACCTCCAAAAACCAGGTG
GTCCTTACAATGACCAACAGCCACCGTATTATTGTGCACGGATA
C (SEQ ID NO: 70)
>VH3-11
CAGGTGCAGCTGGTGGAGTCTGGGGGAGGCTTGGTCAAGCCTGGAGGGTCCCTGAGACTC
TCCTGTGCAGCCTCTGGATTCACCTTCAGTGACTACTACATGAGCTGGATCCGCCAGGCT
CCAGGGAAGGGGCTGGAGTGGGTTTCATACATTAGTAGTAGTGGTAGTACCATATACTAC
GCAGACTCTGTGAAGGGCCGATTCACCATCTCCAGGGACAACGCCAAGAACTCACTGTAT
CTGCAAATGAACAGCCTGAGAGCCGAGGACACGGCCGTGTATTACTGTGCGAGAGA
(SEQ ID NO: 71)

FIG. 18E

>VH3-13
GAGGTGCAGCTGGTGGAGTCTGGGGGAGGCTTGGTACAGCCTGGGGGTCCCTGAGACTC
TCCTGTGCAGCCTCTGGATTCACCTTCAGTAGCTACGACATGCACTGGGTCCGCCAAGCT
ACAGGAAAAGGTCTGGAGTGGGTCTCAGCTATTGGTACTGCTGGTGTGACACATACTATCCA
GGCTCCGTGAAGGGCCGATTCACCATCTCCAGAGAAAATGCCAAGAACTCCTTGTATCTT
CAAATGAACAGCCTGAGAGCCGGGACACGGCTGTGTATTACTGTGCAAGAGA
(SEQ ID NO: 72)

>VH3-15
GAGGTGCAGCTGGTGGAGTCTGGGGGAGGCTTGGTAAAGCCTGGGGGGTCCCTTAGACTC
TCCTGTGCAGCCTCTGGATTCACTTTCAGTAACGCCTGGATGAGCTGGGTCCGCCAGGCT
CCAGGGAAGGGGCTGGAGTGGGTTGGCCGTATTAAAAGCAAAACTGATGGTGGGACAACA
GACTACGCTGCACCCGTGAAAGGCAGATTCACCATCTCAAGAGATGATTCAAAAACACG
CTGTATCTGCAAATGAACAGCCTGAAAACCGAGGACACAGCCGTGTATTACTGTACCACA
GA (SEQ ID NO: 73)

>VH3-16
GAGGTGCAGCTGGTGGAGTCTGGGGGAGGCTTGGTACAGCCTGGGGGGTCCCTGAGACTC
TCCTGTGCAGCCTCTGGATTCACCTTCAGTAACAGTGACATGAACTGGGTCCGCCAAGCT
CCAGGAAAGGGGCTGGAGTGGGTTGGGTATCGGGTGTTAGTTGGAATGGCAGTAGGACGCACTAT
GTGGACTCCGTGAAGCGCCGATTCATCATCTCCAGAGACAATTCCAGGAACTCCCTGTAT
CTGCAAAAGAACAGAGGACGGAGAGCCGAGGACATGGCTGTGTATTACTGTGTGAGAAA
(SEQ ID NO: 74)

FIG. 18F

>VH3-20
GAGGTGCAGCTGGTGGAGTCTGGGGGAGGTGTGGTACGGCCTGGGGGGTCCCTGAGACTC
TCCTGTGCAGCCTCTGGATTCACCTTTGATGATTATGCATGAGCTGGTCCGCCAAGCT
CCAGGGAAGGGCTGGAGTGGGTCTCTGGTATTAATTGGAATGGTGGTAGCACAGGTTAT
GCAGACTCTGTGAAGGGCCGATTCACCATCTCCAGAGACAACGCCAAGAACTCCCTGTAT
CTGCAAATGAACAGTCTGAGAGCCGAGGACACGGCCCTTGTATCACTGTGCGAGAGA (SEQ ID NO: 75)

>VH3-21
GAGGTGCAGCTGGTGGAGTCTGGGGGAGGCCTGGTCAAGCCTGGGGGGTCCCTGAGACTC
TCCTGTGCAGCCTCTGGATTCACCTTCAGTAGCTATAGCATGAACTGGGTCCGCCAGGCT
CCAGGGAAGGGGCTGGAGTGGGTCTCATCCATTAGTAGTAGTAGTAGTTACATATACTAC
GCAGACTCAGTGAAGGGCCGATTCACCATCTCCAGAGACAACGCCAAGAACTCACTGTAT
CTGCAAATGAACAGCCTGAGAGCCGAGGACACGGCTGTGTATTACTGTGCGAGAGA (SEQ ID NO: 76)

FIG. 18G

>VH3-23
GAGGTGCAGCTGTTGGAGTCTGGGGGAGGCTTGGTACAGCCTGGGGGGTCCCTGAGACTC
TCCTGTGCAGCCTCTGGATTCACCTTTAGCAGCTATGCCATGAGCTGGGTCCGCCAGGCT
CCAGGGAAGGGCCTGGAGTGGGTCTCAGCTATTAGTGGTAGTGGTAGCACATACTAC
GCAGACTCCGTGAAGGGCCGGTTCACCATCTCCAGAGACAATTCCAAGAACACGCTGTAT
CTGCAAATGAACAGCCTGAGAGCCGAGGACACGGCCGTATATTACTGTGCGAAAGA
(SEQ ID NO: 77)

>VH3-30
CAGGTGCAGCTGGTGGAGTCTGGGGGAGGCGTGGTCCAGCCTGGGAGGTCCCTGAGACTC
TCCTGTGCAGCCTCTGGATTCACCTTCAGTAGCTATGGCATGCACTGGGTCCGCCAGGCT
CCAGGCAAGGGGCTGGAGTGGGTGGCAGTTATATCATATGATGGAAGTAATAAATACTAT
GCAGACTCCGTGAAGGGCCGATTCACCATCTCCAGAGACAATTCCAAGAACACGCTGTAT
CTGCAAATGAACAGCCTGAGAGCTGAGGACACGGCTGTGTATTACTGTGCGAGAGA
(SEQ ID NO: 78)

>VH3-33
CAGGTGCAGCTGGTGGAGTCTGGGGGAGGCGTGGTCCAGCCTGGGAGGTCCCTGAGACTC
TCCTGTGCAGCCTCTGGATTCACCTTCAGTAGCTATGGCATGCACTGGGTCCGCCAGGCT
CCAGGCAAGGGGCTGGAGTGGGTGGCAGTTATATGGTATGATGGAAGTAATAAATACTAT
GCAGACTCCGTGAAGGGCCGATTCACCATCTCCAGAGACAATTCCAAGAACACGCTGTAT
CTGCAAATGAACAGCCTGAGAGCCGAGGACACGGCTGTGTATTACTGTGCGAGAGA
(SEQ ID NO: 79)

FIG. 18H

>VH3-35
GAGGTGCAGCTGGTGGAGTCTGGGGGAGGCTTGGTACAGCCTGGGGGATCCCTGAGACTC
TCCTGTGCAGCCTCTGGATTCACCTTCAGTAACAGTGACATGAACTGGGTCCATCAGGCT
CCAGGAAAGGGGCTGGAGTGGGTTAGTTGGGTGTGTTAGTTGGAATGGCAGTAGGACGCACTAT
GCAGACTCTGTGAAGGGCCGATTCATCATCTCCAGAGACACAATTCCAGGAACACCCTGTAT
CTGCAAACGAATAGCCTGAGGGCCGAGGACACGGCTGTGTATTACTGTGTGAGAAA
(SEQ ID NO: 80)

>VH3-38
GAGGTGCAGCTGGTGGAGTCTGGGGGAGGCTTGGTACAGCCTAGGGGTCCCTGAGACTC
TCCTGTGCAGCCTCTGGATTCACCGTCAGTAGCAATGAGATGAGCTGGATCCGCCAGGCT
CCAGGGAAGGGGCTGGAGTGGGTCTCATCCATTAGTGGTAGCACATACTACGCAGAC
TCCAGGAAGGGCAGATTCACCATCTCCAGAGACAATTCCAAGAACACGCTGTATCTTCAA
ATGAACAACCTGAGAGCTGAGGACACGGCCGTGTATTACTGTGCCAGATA
(SEQ ID NO: 81)

>VH3-43
GAAGTGCAGCTGGTGGAGTCTGGGGGAGTCGTGGTACAGCCTGGGGGTCCCTGAGACTC
TCCTGTGCAGCCTCTGGATTCACCTTTGATGATTATACCATGCACTGGGTCCGTCAAGCT
CCGGGGAAGGGTCTGGAGTGGGTCTCTCTTATTAGTTGGGATGGTGGTAGCACATACTAT
GCAGACTCTGTGAAGGGCCGATTCACCATCTCCAGAGACAACAGCAAAAACTCCCTGTAT
CTGCAAATGAACAGTCTGAGAACTGAGGACACCGCCTTGTATTACTGTGCAAAAGATA
(SEQ ID NO: 82)

FIG. 18I

>VH3-48
GAGGTGCAGCTGGTGGAGTCTGGGGGAGGCTTGGTACAGCCTGGGGGGTCCCTGAGACTC
TCCTGTGCAGCCTCTGGATTCACCTTCAGTAGCTATAGCATGAACTGGGTCCGCCAGGCT
CCAGGGAAGGGGCTGGAGTGGGTTTCATACATTAGTAGTAGTAGTACCATATACTAC
GCAGACTCTGTGAAGGGCCGATTCACCATCTCCAGAGACAATGCCAAGAACTCACTGTAT
CTGCAAATGAACAGCCTGAGAGACGAGGACACGGCTGTGTATTACTGTGCGAGAGA
(SEQ ID NO: 83)

>VH3-49
GAGGTGCAGCTGGTGGAGTCTGGGGGAGGCTTGGTACAGCCAGGGCGGTCCCTGAGACTC
TCCTGTACAGCTTCTGGATTCACCTTTGGTGATTATGCTATGAGCTGGTTCCGCCAGGCT
CCAGGGAAGGGGCTGGAGTGGGTAGGTTTCATTAGAAGCAAAGCTTATGTGGGACAACA
GAATACGCCGCGTCTGTGAAAGGCAGATTCACCATCTCAAGAGATGATTCCAAAAGCATC
GCCTATCTGCAAATGAACAGCCCTGAAAACCGAGGACACAGCCCGTGTATTACTGTACTAGA
GA (SEQ ID NO: 84)

>VH3-53
GAGGTGCAGCTGGTGGAGTCTGGAGGAGGCTTGATCCAGCCTGGGGGGTCCCTGAGACTC
TCCTGTGCAGCCTCTGGGTTCACCGTCAGTAGCAACTACATGAGCTGGGTCCGCCAGGCT
CCAGGGAAGGGGCTGGAGTGGGTCTCAGTTATTTATAGCGGTGGTAGCACATACTACGCA
GACTCCGTGAAGGGCCGATTCACCATCTCCAGAGACAATTCCAAGAACACGCTGTATCTT
CAAATGAACAGCCTGAGAGCCGAGGACACGGCCGTGTATTACTGTGCGAGAGA
(SEQ ID NO: 85)

FIG. 18J

>VH3-64
GAGGTGCAGCTGGTGGAGTCTGGGGAAGGCTTGGTCCAGCCTGGGGGGTCCCTGAGACTC
TCCTGTGCAGCCTCTGGATTCACCTTCAGTAGCTATGCACTGGTCCGCCAGGCT
CCAGGGAAGGGACTGGAATATGTTTCAGCTATTAGTAGTAATGGGGTAGCACATATTAT
GCAGACTCTGTGAAGGGCAGATTCACCATCTCCAGAGACAATTCCAAGAACACGCTGTAT
CTTCAAATGGGCAGCCTGAGAGCTGAGGACATGGCTGTGTATTACTGTGCGAGAGA
(SEQ ID NO: 86)

>VH3-66
GAGGTGCAGCTGGTGGAGTCTGGGGGAGGCTTGATCCAGCCTGGGGGGTCCCTGAGACTC
TCCTGTGCAGCCTCTGGGTTCACCGTCAGTAGCAACTACATGAGCTGGGTCCGCCAGGCT
CCAGGGAAGGGGCTGGAGTGGGTCTCAGTTATTTATAGCGGTGGTAGCACATACTACGCA
GACTCCGTGAAGGGCCGATTCACCATCTCCAGAGACAATTCCAAGAACACGCTGTATCTT
CAAATGAACAGCCTGAGAGCTGAGGACACGGCTGTGTATTACTGTGCGAGAGA
(SEQ ID NO: 87)

>VH3-7
GAGGTGCAGCTGGTGGAGTCTGGGGGAGGCTTGGTCCAGCCTGGGGGGTCCCTGAGACTC
TCCTGTGCAGCCTCTGGATTCACCTTTAGTAGCTATTGGATGAGCTGGGTCCGCCAGGCT
CCAGGGAAGGGGCTGGAGTGGGTGGCCAACATAAAGCAAGATGGAAGTGAGAAATACTAT
GTGGACTCTGTGAAGGGCCGATTCACCATCTCCAGAGACAACGCCAAGAACTCACTGTAT
CTGCAAATGAACAGCCTGAGAGCCGAGGACACGGCTGTGTATTACTGTGCGAGAGA
(SEQ ID NO: 88)

FIG. 18K

>VH3-72
GAGGTGCAGCTGGTGGAGTCTGGGGGAGGCTTGGTCCAGCCTGGAGGGTCCCTGAGACTC
TCCTGTGCAGCCTCTGGATTCACCTTCAGTGACCACTACATGAGCTGGGTCCGCCAGGCT
CCAGGGAAGGGGCTGGAGTGGGTTGGCCGTACTAGAAACAAAGCTAACAGTTACACCACA
GAATACGCCGCGTCTGTGAAAGGCAGATTCACCATCTCAAGAGATGATTCAAAGAACTCA
CTGTATCTGCAAATGAACAGCCTGAAAACCGAGGACACGGCCGTGTATTACTGTGCTAGA
GA (SEQ ID NO: 89)

>VH3-73
GAGGTGCAGCTGGTGGAGTCCGGGGGAGGCTTGGTCCAGCCTGGGGGGTCCCTGAAACTC
TCCTGTGCAGCCTCTGGGTTCACCTTCAGTGGCTCTGCTATGCACTGGGTCCGCCAGGCT
TCCGGGAAAGGGCTGGAGTGGGTTGGCCGTATTAGAAGCAAAGCTAACAGTTACGCGACA
GCATATGCTGCGTCGGTGAAATGAACAGCCTGAAAACCGAGGACACGGCCGTGTATTACTGTACTAGA
GCGTATCTGCAAATGAACAGCCTGAAAACCGAGGACACGGCCGTGTATTACTGTACTAGA
CA (SEQ ID NO: 90)

>VH3-74
GAGGTGCAGCTGGTGGAGTCCGGGGGAGGCTTAGTTCAGCCTGGGGGGTCCCTGAGACTC
TCCTGTGCAGCCTCTGGATTCACCTTCAGTAGCTACTGGATGCACTGGGTCCGCCAAGCT
CCAGGGAAGGGGCTGGTGTGGGTCTCACGTATTAATAGTGATGGGAGTAGCACAAGCTAC
GCGGACTCCGTGAAGGGCCGATTCACCATCTCCAGAGACAACGCCAAGAACACGCTGTAT
CTGCAAATGAACAGTCTGAGAGCCGAGGACACGGCTGTGTATTACTGTGCAAGAGA
(SEQ ID NO: 91)

FIG. 18L

>VH3-9
GAAGTGCAGCTGGTGGAGTCTGGGGGAGGCTTGGTGCAGCCTGGCAGGTCCCTGAGACTC
TCCTGTGCAGCCCTCTGGATTCACCTTTGATGATTATGCCATGCACTGGGTCCGGCAAGCT
CCAGGGAAGGGCCTGGAGTGGGTCTCAGGTATTAGTTGGAATAGTGGTAGCATAGGCTAT
GCGGACTCTGTGAAGGGCCGATTCACCATCTCCAGAGACAACGCCAAGAACTCCCTGTAT
CTGCAAATGAACAGTCTGAGAGCTGAGGACACGGCCTTGTATTACTGTGCAAAAGATA
(SEQ ID NO: 92)

>VH4-28
CAGGTGCAGCTGCAGGAGTCGGGCCCAGGACTGGTGAAGCCTTCGGACACCCTGTCCCTC
ACCTGCGCTGTCTCTGGTTACTCCATCAGCAGTAACTGGTGGGGCTGGATCCGGCAG
CCCCCAGGGAAGGACTGGAGTGGATTGGGGAGTCGACATCTATTATAGTGGAGCACTACTAC
AACCCGTCCCTCAAGAGTCGAGTCACCATGTCAGTAGACACGTCCAAGAACCAGTTCTCC
CTGAAGCTGAGCTCTGTGACCGCCGTGGACACGGCCGTGTATTACTGTGCGAGAAA
(SEQ ID NO: 93)

>VH4-31
CAGGTGCAGCTGCAGGAGTCGGGCCCAGGACTGGTGAAGCCTTCACAGACCCTGTCCCTC
ACCTGCACTGTCTCTGGTGGCTCCATCAGCAGTGGTGGTTACTACTGGAGCTGGATCCGC
CAGCACCCAGGGAAGGGCCTGGAGTGGATTGGGTACATCTATTACAGTGGGAGCACCTAC
TACAACCCGTCCCTCAAGAGTCGAGTTACCATATCAGTAGACACGTCTAAGAACCAGTTC
TCCCTGAAGCTGAGCTCTGTGACTGCCGCGGACACGGCCGTGTATTACTGTGCGAGAGA
(SEQ ID NO: 94)

FIG. 18M

>VH4-34
CAGGTGCAGCTACAGCAGTGGGGCGCAGGACTGTTGAAGCCTTCGGAGACCCTGTCCCTC
ACCTGCGCTGTCTATGGTGGGTCCTTCAGTGGTTACTACTGGAGCTGGATCCGCCAGCCC
CCAGGGAAGGGGCTGGAGTGGATTGGGGAAATCAATCATAGTGGAAGCACCAACTACAAC
CCGTCCCTCAAGAGTCGAGTCACCATATCAGTAGACACGTCCAAGAACCAGTTCTCCCTG
AAGCTGAGCTCTGTGACCGCCGCGGACACGGCTGTGTATTACTGTGCGAGAGG
(SEQ ID NO: 95)
>VH4-39
CAGCTGCAGCTGCAGGAGTCGGGCCCAGGACTGGTGAAGCCTTCGGAGACCCTGTCCCTC
ACCTGCACTGTCTCTGGTGGCTCCATCAGCAGTAGTAGTTACTACTGGGGCTGGATCCGC
CAGCCCCCAGGGAAGGGGCTGGAGTGGATTGGGAGTATCTATTATAGTGGGAGCACCTAC
TACAACCCGTCCCTCAAGAGTCGAGTCACCATATCCGTAGACACGTCCAAGAACCAGTTC
TCCCTGAAGCTGAGCTCTGTGACCGCCGCCGACACGGCTGTGTATTACTGTGCGAGAGACA
(SEQ ID NO: 96)
>VH4-4
CAGGTGCAGCTGCAGGAGTCGGGCCCAGGACTGGTGAAGCCTTCGGAGACCCTGTCCCTC
ACCTGCACTGTCTCTGGTGGCTCCATCAGCAGTAGTTACTACTGGAGCTGGATCCGGCAGCCC
GCCGGGAAGGACTGGAGTGGATTGGGCGTATCTATACCAGTGGGAGCACCAACTACAAC
CCCTCCCTCAAGAGTCGAGTCACCATGTCAGTAGACACGTCCAAGAACCAGTTCTCCCTG
AAGCTGAGCTCTGTGACCGCCGCGGACACGGCCGTGTATTACTGTGCGAGAGA
(SEQ ID NO: 97)

FIG. 18N

>VH4-59
CAGGTGCAGCTGCAGGAGTCGGGCCCAGGACTGGTGAAGCCTTCGGAGACCCTGTCCCTC
ACCTGCACTGTCTCTGGTGGCTCCATCAGTAGTTACTACTGGAGCTGGATCCGGCAGCCC
CCAGGGAAGGGACTGGAGTGGATTGGGTATATCTATTACAGTGGGAGCACCAACTACAAC
CCCTCCCTCAAGAGTCGAGTCACCATATCAGTAGACACGTCCAAGAACCAGTTCTCCCTG
AAGCTGAGCTCTGTGACCGCTGCGGACACGGCCGTGTATTACTGTGCGAGAGA
(SEQ ID NO: 98)

>VH4-61
CAGGTGCAGCTGCAGGAGTCGGGCCCAGGACTGGTGAAGCCTTCGGAGACCCTGTCCCTC
ACCTGCACTGTCTCTGGTGGCTCCGTCAGCAGTGGTTACTACTGGAGCTGGATCCGG
CAGCCCCCAGGGAAGGGACTGGAGTGGATTGGGTATATCTATTACAGTAGACACGTCCAAGAACCAGTTC
TACAACCCCCTCCCTCAAGAGTCGAGTCACCATATCAGTAGACACGGCCGTGTATTACTGTGCGAGAGA
TCCCTGAAGCTGAGCTCTGTGACCGCTGCGGACACGGCCGTGTATTACTGTGCGAGAGA
(SEQ ID NO: 99)

>VH5-51
GAGGTGCAGCTGGTGCAGTCTGGAGCAGAGGTGAAAAAGCCCGGGGAGTCTCTGAAGATC
TCCTGTAAGGGTTCTGGATACAGCTTTACCAGCTACTGGATCGGCTGGGTGCGCCAGATG
CCCGGGAAAGGCCTGGAGTGGATGGGGATCATCTATCCTGGTGACTCTGATACCAGATAC
AGCCCGTCCTTCCAAGGCCAGGTCACCATCTCAGCCGACAAGTCCATCAGCACCGCCTAC
CTGCAGTGGAGCAGCCTGAAGGCCTCGGACACCGCCATGTATTACTGTGCGAGACA
(SEQ ID NO: 100)

FIG. 180

>VH6-1
CAGGTACAGCTGCAGCAGTCAGGTCCAGGACTGGTGAAGCCCTCGCAGACCCTCTCACTC
ACCTGTGCCATCTCCGGGACAGTGTCTCTAGCAACAGTGCTGCTTGGAACTGGATCAGG
CAGTCCCCATCGAGAGGCCTTGAGTGGCTGGGAAGGACATACTACAGGTCCAAGTGGTAT
AATGATTATGCAGTATCTGTGAAAAGTCGAATAACCATCAACCCAGACACATCCAAGAAC
CAGTTCTCCCTGCAGCTGAACTCTGTGACTCCCGAGGACACGGCTGTGTATTACTGTGCA
AGAGA (SEQ ID NO: 101)

>VH7-81
CAGGTGCAGCTGGTGCAGTCTGGCCATGAGGTGAAGCAGCCTGGGGCCTCAGTGAAGGTC
TCCTGCAAGGCTTCTGGTTACAGTTTCACCACCTATGGTATGAATTGGGTGCCACAGGCC
CCTGGACAAGGGCTTGAGTGGATGGGTTCAACACCTACACTGGGAACCCAACATAT
GCCCAGGGGCTTCACAGACGGTTTGTCTTCTCCATGGACACCCTCTGCCAGCACAGCATAC
CTGCAGATCAGCAGCCTAAAGGCTGAGGACATGGCCATGTATTACTGTGCGAGATA
(SEQ ID NO: 102)

FIG. 18P

V_kappa Gene Sequences

>A1
DVVMTQSPLSLPVTLGQPASISCRSSQSLVYSDGNTYLNWFQQRPGQSPRRLIYKVSNWD
SGVPDRFSGSGSGTDFTLKISRVEAEDVGVYYCMQGTHWP (SEQ ID NO: 103)

>A10
EIVLTQSPDFQSVTPKEKVTITCRASQSIGSSLHWYQQKPDQSPKLLIKYASQSFSGVPS
RFSGSGSGTDFTLTINSLEAEDAATYYCHQSSSLP (SEQ ID NO: 104)

>A11
EIVLTQSPATLSLSPGERATLSCGASQSVSSSYLAWYQQKPGLAPRLLIYDASSRATGIP
DRFSGSGSGTDFTLTISRLEPEDFAVYYCQQYGSSP (SEQ ID NO: 105)

>A14
DVVMTQSPAFLSVTPGEKVTITCQASEGIGNYLYWYQQKPDQAPKLLIKYASQSISGVPS
RFSGSGSGTDFTFTISSLEAEDAATYYCQQGNKHP (SEQ ID NO: 106)

>A17
DVVMTQSPLSLPVTLGQPASISCRSSQSLVYSDGNTYLNWFQQRPGQSPRRLIYKVSNRD
SGVPDRFSGSGSGTDFTLKISRVEAEDVGVYYCMQGTHWP (SEQ ID NO: 107)

>A18
DIVMTQTPLSLSVTPGQPASICKSSQSLLHSDGKTYLYWYLQKPGQSPQLLIYEVSSRF
SGVPDRFSGSGSGTDFTLKISRVEAEDVGVYYCMQGIHLP (SEQ ID NO: 108)

>A19
DIVMTQSPLSLPVTPGEPASISCRSSQSLLHSNGYNYLDWYLQKPGQSPQLLIYLGSNRA
SGVPDRFSGSGSGTDFTLKISRVEAEDVGVYYCMQALQTP (SEQ ID NO: 109)

FIG. 19A

>A2
DIVMTQTPLSLSVTPGQPASISCKSSQSLLHSDGKTYLYWYLQKPGQPPQLLIYEVSNRF
SGVPDRFSGSGSGTDFTLKISRVEAEDVGVYYCMQSIQLP (SEQ ID NO: 110)

>A20
DIQMTQSPSSLSASVGDRVTITCRASQGISNYLAWYQQKPGKVPKLLIYAASTLQSGVPS
RFSGSGSGTDFTLTISSLQPEDVATYYCQKYNSAP (SEQ ID NO: 111)

>A23
DIVMTQTPLSSPVTLGQPASISCRSSQSLVHSDGNTYLSWLQQRPGQPPRLLIYKISNRF
SGVPDRFSGSGSGAGTDFTLKISRVEAEDVGVYYCMQATQFP (SEQ ID NO: 112)

>A26
EIVLTQSPDFQSVTPKEKVTITCRASQSIGSSLHWYQQKPDQSPKLLIKYASQSFSGVPS
RFSGSGSGTDFTLTINSLEAEDAATYCHQSSSLP (SEQ ID NO: 113)

>A27
EIVLTQSPGTLSLSPGERATLSCRASQSVSSSYLAWYQQKPGQAPRLLIYGASSRATGIP
DRFSGSGSGTDFTLTISRLEPEDFAVYYCQQYGSSP (SEQ ID NO: 114)

>A3
DIVMTQSPLSLPVTPGEPASISCRSSQSLLHSNGYNYLDWYLQKPGQSPQLLIYLGSNRA
SGVPDRFSGSGSGTDFTLKISRVEAEDVGVYYCMQALQTP (SEQ ID NO: 115)

>A30
DIQMTQSPSSLSASVGDRVTITCRASQGIRNDLGWYQQKPGKAPKRLIYAASSLQSGVPS
RFSGSGSGTEFTLTISSLQPEDFATYYCLQHNSYP (SEQ ID NO: 116)

FIG. 19B

>A5
EIVMTQTPLSLSITPGEQASISCRSSQSLLHSDGYTYLYWFLQKARPVSTLLIYEVSNRFSGVPDRFSGSGSGTDFTLKISRVEAEDFGVYYCMQDAQDPP (SEQ ID NO: 117)

>A7
DIVMTQTPLSSPVTLGQPASISFRSSQSLVHSDGNTYLSWLQQRPGQPPRLLIYKVSNRFSGVPDRFSGSGSGAGTDFTLKISRVEAEDVGVYYCTQATQFP (SEQ ID NO: 118)

>B2
ETTLTQSPAFMSATPGDKVNISCKASQDIDDDMNWYQQKPGEAAIFIIQEATTLVPGIPPRFSGSGYGTDFTLTINNIESEDAAYYFCLQHDNFP (SEQ ID NO: 119)

>B3
DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTP (SEQ ID NO: 120)

>L1
DIQMTQSPSSLSASVGDRVTITCRASQGISNYLAWFQQKPGKAPKSLIYAASSLQSGVPSRFSGSGSGTDFTLTISSLQPEDFATYYCQQYNSYP (SEQ ID NO: 121)

>L10
EIVMTQSPPTLSLSPGERVTLSCRASQSVSSSYLTWYQQKPGQAPRLLIYGASTRATSIPARFSGSGSGTDFTLTISSLQPEDFAVYYCQQDHNLPP (SEQ ID NO: 122)

>L11
AIQMTQSPSSLSASVGDRVTITCRASQGIRNDLGWYQQKPGKAPKLLIYAASSLQSGVPSRFSGSGSGTDFTLTISSLQPEDFATYYCLQDYNYP (SEQ ID NO: 123)

FIG. 19C

\>L12
DIQMTQSPSTLSASVGDRVTITCRASQSISSWLAWYQQKPGKAPKLLIYDASSLESGVPS
RFSGSGSGTEFTLTISSLQPDDFATYYCQQYNSYS (SEQ ID NO: 124)

\>L14
NIQMTQSPSPSAMSASVGDRVTITCRARQGISNYLAWFQQKPGKVPKHLIYAASSLQSGVPS
RFSGSGSGTEFTLTISSLQPEDFATYCLQHNSYP (SEQ ID NO: 125)

\>L15
DIQMTQSPSSLSASVGDRVTITCRASQGISSWLAWYQQKPEKAPKSLIYAASSLQSGVPS
RFSGSGSGTDFTLTISSLQPEDFATYYCQQYNSYP (SEQ ID NO: 126)

\>L16
EIVMTQSPATLSVSPGERATLSCRASQSVSSNLAWYQQKPGQAPRLLIYGASTRATGIPA
RFSGSGSGTEFTLTISSLQSEDFAVYYCQQYNNWP (SEQ ID NO: 127)

\>L18
AIQLTQSPSSLSASVGDRVTITCRASQGISSALAWYQQKPGKAPKLLIYDASSLESGVPS
RFSGSGSGTDFTLTISSLQPEDFATYYCQQFNNYP (SEQ ID NO: 128)

\>L19
DIQMTQSPSSVSASVGDRVTITCRASQGISSWLAWYQQKPGKAPKLLIYAASSLQSGVPS
RFSGSGSGTDFTLTISSLQPEDFATYYCQQANSFP (SEQ ID NO: 129)

\>L2
EIVMTQSPATLSVSPGERATLSCRASQSVSSNLAWYQQKPGQAPRLLIYGASTRATGIPA
RFSGSGSGTEFTLTISSLQSEDFAVYYCQQYNNWP (SEQ ID NO: 130)

FIG. 19D

>L20
EIVLTQSPATLSLSPGERATLSCRASQGVSSYLAWYQQKPGQAPRLLIYDASNRATGIPA
RFSGSGPGTDFTLTISSLEPEDFAVYYCQQRSNWH (SEQ ID NO: 131)

>L22
DIQMIQSPSFLSASVGDRVSIICWASEGISSNLAWYLQKPGKSPKLFLYDAKDLHPGVSS
RFSGRGSGTDFTLTIISLKPEDFAAYYCKQDFSYPP (SEQ ID NO: 132)

>L23
AIRMTQSPFSLSASVGDRVTITCWASQGISSYLAWYQQKPAKAPKLFIYYASSLQSGVPS
RFSGSGSGTDYTLTISSLQPEDFATYYCQQYYSTP (SEQ ID NO: 133)

>L24
VIWMTQSPSLLSASTGDRVTISCRMSQGISSYLAWYQQKPGKAPELLIYAASTLQSGVPS
RFSGSGSGTDFTLTISCLQSEDFATYYCQQYYSFP (SEQ ID NO: 134)

>L25
EIVMTQSPATLSLSPGERATLSCRASQSVSSSYLSWYQQKPGQAPRLLIYGASTRATGIP
ARFSGSGSGTDFTLTISSLQPEDFAVYYCQQDYNLP (SEQ ID NO: 135)

>L4/18a
AIQLTQSPSSLSASVGDRVTITCRASQGISSALAWYQQKPGKAPLLIYDASSLESGVPS
RFSGSGSGTDFTLTISSLQPEDFATYYCQQFNSYP (SEQ ID NO: 136)

>L5
DIQMTQSPSSVSASVGDRVTITCRASQGISSWLAWYQQKPGKAPKLLIYAASSLQSGVPS
RFSGSGSGTDFTLTISSLQPEDFATYYCQQANSFP (SEQ ID NO: 137)

FIG. 19E

>L6
EIVLTQSPATLSLSPGERATLSCRASQVSSYLAWYQQKPGQAPRLLIYDASNRATGIPA
RFSGSGSGTDFTLTISSLEPEDFAVYYCQQRSNWP (SEQ ID NO: 138)

>L8
DIQLTQSPSFLSASVGDRVTITCRASQGISSYLAWYQQKPGKAPKLLIYAASTLQSGVPS
RFSGSGSGTEFTLTISSLQPEDFATYYCQQLNSYP (SEQ ID NO: 139)

>L9
AIRMTQSPSSFSASTGDRVTITCRASQGISSYLAWYQQKPGKAPKLLIYAASTLQSGVPS
RFSGSGSGTDFTLTISCLQSEDFATYYCQQYYSYP (SEQ ID NO: 140)

>O1
DIVMTQTPLSLPVTPGEPASISCRSSQSLLDSDDGNTYLDWYLQKPGQSPQLLIYTLSYR
ASGVPDRFSGSGSGTDFTLKISRVEAEDVGVYYCMQRIEFP (SEQ ID NO: 141)

>O11
DIVMTQTPLSLPVTPGEPASISCRSSQSLLDSDDGNTYLDWYLQKPGQSPQLLIYTLSYR
ASGVPDRFSGSGSGTDFTLKISRVEAEDVGVYYCMQRIEFP (SEQ ID NO: 142)

>O12
DIQMTQSPSSLSASVGDRVTITCRASQSISSYLNWYQQKPGKAPKLLIYAASSLQSGVPS
RFSGSGSGTDFTLTISSLQPEDFATYYCQQSYSTP (SEQ ID NO: 143)

>O14
DIQLTQSPSSLSASVGDRVTITCRVSQGISSYLNWYRQKPGKVPKLLIYSASNLQSGVPS
RFSGSGSGTDFTLTISSLQPEDVATYYGQRTYNAPP (SEQ ID NO: 144)

FIG. 19F

>O18
DIQMTQSPSSLSASVGDRVTITCQASQDISNYLNWYQQKPGKAPKLLIYDASNLETGVPS
RFSGSGSGTDFTFTISSLQPEDIATYYCQQYDNLP (SEQ ID NO: 145)

>O2
DIQMTQSPSSLSASVGDRVTITCRASQSISSYLNWYQQKPGKAPKLLIYAASSLQSGVPS
RFSGSGSGTDFTLTISSLQPEDFATYYCQQSYSTP (SEQ ID NO: 146)

>O4
DIQLTQSPSSLSASVGDRVTITCRVSQGISSYLNWYRQKPGKVPKLLIYSASNLQSGVPS
RFSGSGSGTDFTLTISSLQPEDVATYYGQRTYNAPP (SEQ ID NO: 147)

>O8
DIQMTQSPSSLSASVGDRVTITCQASQDISNYLNWYQQKPGKAPKLLIYDASNLETGVPS
RFSGSGSGTDFTFTISSLQPEDIATYYCQQYDNLP (SEQ ID NO: 148)

FIG. 19G $V_{kappa}$ Gene Sequences

>A1
GATGTTGTGATGACTCAGTCTCCACTCTCCCTGCCCGTCACCCTTGGACAGCCGGCCTCC
ATCTCCTGCAGGTCTAGTCAAAGCCTCGTATACAGTGATGGAAACACCTACTTGAATTGG
TTTCAGCAGAGGCCAGGCCAATCTCCAAGGCGCCTAATTTATAAGGTTTCTAACTGGGAC
TCTGGGGTCCCAGACAGATTCAGCGGCAGTGGGTCAGGCACTGATTTCACACTGAAAATC
AGCAGGGTGGAGGCTGAGGATGTTGGGGTTTATTACTGCATGCAAGGTACACACTGGCCT
CC (SEQ ID NO: 149)

>A10
GAAATTGTGCTGACTCAGTCTCCAGACTTTCAGTCTGTGACTCCAAAGGAGAAAGTCACC
ATCACCTGCCGGGCCAGTCAGAGCATTGGTAGTAGCTTACACTGGTACCAGCAGAAACCA
GATCAGTCTCCAAAGCTCCTCATCAAGTATGCTTCCCAGTCCTTCTCAGGGGTCCCCTCG
AGGTTCAGTGGCAGTGGATCTGGGACAGATTTCACCCTCACCATCAATAGCCTGGAAGCT
GAAGATGCTGCAACGTATTACTGTCATCAGAGTAGTAGTTTACCTCA (SEQ ID NO: 150)

>A11
GAAATTGTGTTGACGCAGTCTCCAGCCACCCTGTCTTTGTCTCCAGGGGAAAGAGCCACC
CTCTCCTGCGGGGCCAGTCAGAGTGTTAGCAGCAGCTACTTAGCCTGGTACCAGCAGAAA
CCTGGCCCTGGCCGCCCAGGCTCCTCATCTATGATGCATCCAGCAGGGCCACTGGCATCCCA
GACAGGTTCAGTGGCAGTGGGTCTGGGACAGACTTCACTCTCACCATCAGCAGACTGGAG
CCTGAAGATTTTGCAGTGTATTACTGTCAGCAGTAGCTCACCTCC (SEQ ID NO: 151)

>A14
GATGTTGTGATGACACAGTCTCCAGCTTTCCTCTCTGTGACTCCAGGGGAGAAAGTCACC
ATCACCTGCCAGGCCAGTGAAGGCATTGAAGACTACTTATACTGGTACCAGCAGAAACCA
GATCAAGCCCCCAAAGCTCCTCATCAAGTATGCTTCCCAGTCCATCTCAGGGGTCCCCTCG
AGGTTCAGTGGCAGTGGATCTGGGACAGATTTCACCTTTACCATCAGTAGCCTGGAAGCT
GAAGATGCTGCAACATATTACTGTCAGCAGGGCAATAAGCACCCTCA (SEQ ID NO: 152)

FIG. 20A

>A17
GATGTTGTGATGACTCAGTCTCCACTCTCCCTGCCCGTCACCCTTGGACAGCCGGCCTCC
ATCTCCTGCAGTCTAGTCAAAGCCTCGTATACAGTGATGGAAACACCTACTTGAATTGG
TTTCAGCAGAGGCCAGGCCAATCTCCAAGGCGCCTAATTTATAAGGTTTCTAACCGGGAC
TCTGGGGTCCCAGACAGATTCAGCGGCAGTGGGTCAGGCACTGATTTCACACTGAAAATC
AGCAGGGTGGAGGCTGAGGATGTTGGGGTTTATTACTGCAAGGTACACACTGGCCT
CC (SEQ ID NO: 153)
>A18
GATATTGTGATGACCCAGACTCCACTCTCTCTGTCCGTCACCCCTGGACAGCCGGCCTCC
ATCTCCTGCAAGTCTAGTCAGAGCCTCCTGCATAGTGATGGAAAGACCTATTTGTATTGG
TACCTGCAGAAGCCAGGCCAGTCTCCACAGCTCCTGATCTATGAAGTTTCCAGCCGGTTC
TCTGGAGTGCCAGATAGGTTCAGTGGCAGCGGGTCAGGGACAGATTTCACACTGAAAATC
AGCCGGGTGGAGGCTGAGGCTGAAGATGTTGGGGTTTATTACTGAATGCAAGGTATACACCTTCCT
CC (SEQ ID NO: 154)
>A19
GATATTGTGATGACTCAGTCTCCACTCTCCCCTGCCCGTCACCCCTGGAGAGCCGGCCTCC
ATCTCCTGCAGGTCTAGTCAGAGCCTCCTGCATAGTAATGGATACAACTATTTGGATTGG
TACCTGCAGAAGCCAGGCCAGTCTCCACAGCTCCTGATCTATTTGGGTTCTAATCGGGCC
TCCGGGGTCCCTGACAGGTTCAGTGGCAGTGGATCAGGCACAGATTTTACACTGAAAATC
AGCAGAGTGGAGGCTGAGGATGTTGGGGTTTATTACTGCATGCAAGCTCTACAAACTCCT
CC (SEQ ID NO: 155)
>A2
GATATTGTGATGACCCAGACTCCACTCTCTCTGTCCGTCACCCCTGGACAGCCGGCCTCC
ATCTCCTGCAAGTCTAGTCAGAGCCTCCTGCATAGTGATGGAAAGACCTATTTGTATTGG
TACCTGCAGAAGCCAGGCCAGCCTCCACAGCTCCTGATCTATGAAGTTTCCAACCGGTTC
TCTGGAGTGCCAGATAGGTTCAGTGGCAGCGGGTCAGGGACAGATTTCACACTGAAAATC
AGCCGGGTGGAGGCTGAGGATGTTGGGGTTTATTACTGCATGCAAAGTATACAGCTTCCT
CC (SEQ ID NO: 156)

FIG. 20B

>A20
GACATCCAGATGACCCAGTCTCCATCCTCCCTGTCTGCATCTGTAGGAGACAGAGTCACC
ATCACTTGCCGGGCAGTCAGGGCATTAGCAATTATTTAGCCTGGTATCAGCAGAAACCA
GGGAAAGTTCCTAAGCTCCTGATCTATGCTGCATCCACTTTGCAATCAGGGGTCCCATCT
CGGTTCAGTGGCAGTGGATCTGGGACAGATTTCACTCTCACCATCAGCAGCCTGCAGCCT
GAAGATGTTGCAACTTATTACTGTCAAAAGTATAACAGTGCCCCTCC (SEQ ID NO: 157)
>A23
GATATTGTGATGACCCAGACTCCACTCTCCTCACCTGTCACCCTTGGACAGCCGGCCTCC
ATCTCCTGCAGGTCTAGTCAAAGCCTCGTACACAGTGATGAAACACCTACTTGAGTTGG
CTTCAGCAGAGGCCAGGCCAGCCTCCAAGCTCCTAATTTATAAGATTTCTAACCGGTTC
TCTGGGGTCCCAGACAGATTCAGTGGCAGTGGGGCAGGGACAGATTCACACTGAAAATC
AGCAGGGTGGAAGCTGAGGATGTCGGGGTTTATTACTGCATGCAAGCTACACAATTTCCT
CA (SEQ ID NO: 158)
>A26
GAAATTGTGCTGACTCAGTCTCCAGACTTTCAGTCTGTGACTCCAAAGGAGAAAGTCACC
ATCACCTGCCGGGCCAGTCAGAGCATTGGTAGTAGCTTACACTGGTACCAGCAGAAACCA
GATCAGTCTCCAAAGCTCCTCATCAAGTATGCTTCCCAGTCCTTCTCAGGGGTCCCCTCG
AGGTTCAGTGGCAGTGGATCTGGGACAGATTTCACCCTCACCATCAATAGCCTGGAAGCT
GAAGATGCTGCAACGTATTACTGTCATCAGAGTAGTTTACCTCA (SEQ ID NO: 159)
>A27
GAAATTGTGTTGACGCAGTCTCCAGGCACCCTGTCTTTGTCTCCAGGGGAAAGAGCCACC
CTCTCCTGCAGGGCCAGTCAGAGTGTTAGCAGCAGCTACTTAGCCTGGTACCAGCAGAAA
CCTGGCCAGGCTCCCAGGCTCCTCATCTATGGTGCATCCAGCAGGGCCACTGGCATCCCA
GACAGGTTCAGTGGCAGTGGGTCTGGGACAGACTTCACTCTCACCATCAGCAGACTGGAG
CCTGAAGATTTTGCAGATTTTACTGTCAGCAGTATGGTAGCTCACCTCC (SEQ ID NO: 160)

FIG. 20C

>A3
GATATTGTGATGACTCAGTCTCCACTCTCCCTGCCCGTCACCCCTGGAGAGCCGGCCTCC
ATCTCCTGCAGGTCTAGTCAGAGCCTCCTGCATAGTAATGGATACAACTATTTGGATTGG
TACCTGCAGAAGCCAGGCCAGTCTCCACAGCTCCTGATCTATTTGGGTTCTAATCGGGCC
TCCGGGGTCCCTGACAGGTTCAGTGGCAGTGGATCAGGCACAGATTTTACACTGAAAATC
AGCAGAGTGGAGGCTGAGGATGTTGGGGTTTATTACTGCATGCAAGCTCTACAAACTCCT
CC (SEQ ID NO: 161)
>A30
GACATCCAGATGACCCAGTCTCCATCCTCCCTGTCTGCATCTGTAGGAGACAGAGTCACC
ATCACTTGCCGGGCAAGTCAGGGCATTAGAAATGATTTAGGCTGGTATCAGCAGAAACCA
GGGAAAGCCCCTAAGCGCCTGATCTATGCTGACAGTTTGCACAATCAGCAGCCTGCAGCCT
AGGTTCAGCGGCAGTGGATCTGGGACAGAATTCACTCTCACAATAATAGTTACCCTCC (SEQ ID NO: 162)
>A5
GAGATTGTGATGACCCAGACTCCACTCTCCTGTCTATCACCCCTGGAGAGCAGGCCTCC
ATCTCCTGCAGGTCTAGTCAGAGCCTCCTGCATAGTGATGATACACCTATTTGTATTGG
TTTCTGCAGAAAGCCAGGCCAGTCTCCAGTTCAGTGGCAGTGGATCTATGAAGTTTCCAACCGGTTC
TCTGGAGTGCCAGATAGGTTCAGTGGCAGTGGGACAGATTTCACACTGAAAATC
AGCCGGGTGGAGGCTGAGGATGTTGGAGTTTATTACTGCATGCAAGATGCACAAGATCCT
CC (SEQ ID NO: 163)
>A7
GATATTGTGATGACCCAGACTCCACTCTCCTCCGCCTGTCACCCTTGGACAGCCGGCCTCC
ATCTCCTTCAGGTCTAGTCAAAGCCTCGTACACAGTGATGGAAACACCTACTTGAGTTGG
CTTCAGCAGAGGCCAGGCCAGTCTCCAAGACTCCTAATTTATAAGGTTTCTAACCGGTTC
TCTGGGGTCCCAGACAGATTCAGTGGCAGTGGGGCAGGACAGATTTCACACTGAAAATC
AGCAGGGTGGAGGCTGAAGCTGCGGATGTCGGGGTTTATTACTGCACGCAAGCTACACAATTTCCT
CA (SEQ ID NO: 164)

FIG. 20D

>B2
GAAACGACACTCACGCAGTCTCCAGCATTCATGTCAGCGACTCCAGGAGACAAAGTCAAC
ATCTCCTGCAAAGCCAGCCAAGACATTGATGATGATATGAACTGGTACCAACAGAAACCA
GGAGAAGCTGCTATTTCATTATTCAAGAAGCTACTACTCTCGTTCCTGGAATCCCACCT
CGATTCAGTGGCAGCGGGTATGGAACAGATTTTACCCTCACAATTAATAACATAGAATCT
GAGGATGCTGCATATTACTTCTGTCTACAACATGATAATTTCCCTCT (SEQ ID NO: 165)
>B3
GACATCGTGATGACCCAGTCTCCAGACTCCCTGGCTGTGTCTCTGGGCGAGAGGGCCACC
ATCAACTGCAAGTCCAGCCAGAGTGTTTTATACAGCTCCAACAATAAGAACTACTTAGCT
TGGTACCAGCAGAAACCAGGACAGCCTCCTAAGCTGCTCATTTACTGGGCATCTACCCGG
GAATCCGGGGTCCCTGACCGATTCAGTGGCAGCGGGTCTGGGACAGATTTCACTCTCACC
ATCAGCAGCCTGCAGGCTGAAGATGTGGCAGTTTATTACTGTCAGCAATATTATAGTACT
CCTCC (SEQ ID NO: 166)
>L1
GACATCCAGATGACCCAGTCTCCATCCTCACTGTCTGCATCTGTAGGAGACAGAGTCACC
ATCACTTGTCGGGCGAGTCAGGGCATTAGCAATTATTTAGCCTGGTTTCAGCAGAAACCA
GGGAAAGCCCCTAAGTCCCTGATCTATGCTGCATCCAGTTTGCAAAGTGGGGTCCCATCA
AGGTTCAGCGGCAGTGGATCTGGGACAGATTTCACTCTCACCATCAGCAGCCTGCAGCCT
GAAGATTTTGCAACTTATTACTGCCAACAGTATAATAGTTACCCTCC (SEQ ID NO: 167)
>L10
GAAATTGTAATGACACAGTCTCCAGCCACCCTGTCTCTTTGTCTCCAGGGGAAAGAGTCACC
CTCTCCTGCAGGGCCAGTCAGAGTGTTAGCAGCTACTTAACCTGGTATCAGCAGAAA
CCTGGCCAGGCGCCCAGGCTCCTCATCTATGGTGCATCCAGGGCCACTAGCATCCCA
GCCAGGTTCAGTGGCAGTGGGTCTGGGACAGACTTCACTCTCACCATCAGCAGCCTGCAG
CCTGAAGATTTTGCAGTTTATTACTGTCAGCAGGATCATAAACTTACCTCC (SEQ ID NO: 168)

FIG. 20E

>L11
GCCATCCAGATGACCCAGTCTCCATCCTCCCTGTCTGCATCTCTGTAGGAGACAGAGTCACC
ATCACTTGCCCGGGCAAGTCAGGGCATTAGAAATGATTTAGGCTGGTATCAGCAGAAACCA
GGGAAAGCCCCTAAGCTCCTGATCTATGCTGCATCCAGTTTACAAAGTGGGGTCCCATCA
AGGTTCAGCGGCAGTGGATCTGGGACAGATTTCACTCTCACCATCAGCAGCCTGCAGCCT
GAAGATTTTGCAACTTATTACTGTCTACAAGATTACAATTACCCTCC (SEQ ID NO: 169)

>L12
GACATCCAGATGACCCAGTCTCCTTCCACCCTGTCTGCATCTCTGTAGGAGACAGAGTCACC
ATCACTTGCCGGGCCAGTCAGAGTATTAGTAGCTGGTTGGCCTGGTATCAGCAGAAACCA
GGGAAAGCCCCTAAGCTCCTGATCTATGATGCCTCCAGTTTGGAAAGTGGGGTCCCATCA
AGGTTCAGCGGCAGTGGATCTGGGACAGAATTCACTCTCACCATCAGCAGCCTGCAGCCT
GATGATTTTGCAACTTATTACTGCCAACAGTATAATAGTTATTCTCC (SEQ ID NO: 170)

>L14
AACATCCAGATGACCCAGTCTCCATCTGCCATGTCTGTAGGAGACAGAGTCACC
ATCACTTGTCTGCCGAGGCAGGGCATTAGCAATTATTAGCCTGGTTTCAGCAGAAACCA
GGGAAAGTCCCTAAGCACCTGATCTATGCTGCATCCAGTTTGCAAAGTGGGGTCCCATCA
AGGTTCAGCGGCAGTGGATCTGGGACAGAATTCACTCTCACAATCAGCAGCCTGCAGCCT
GAAGATTTTGCAACTTATTACTGTCTACAGCATAATAGTTACCCTCC (SEQ ID NO: 171)

>L15
GACATCCAGATGACCCAGTCTCCATCCTCCACTGTCTGCATCTGTAGGAGACAGAGTCACC
ATCACTTGTCGGGCGAGTCAGGGTATTAGCAGCTGGTTAGCCTGGTATCAGCAGAAACCA
GAGAAAGCCCCTAAGCTCCCTGATCTATGCTGCATCCAGTTTGCAAAGTGGGGTCCCATCA
AGGTTCAGCGGCAGTGGATCTGGGACAGATTTCACTCTCACCATCAGCAGCCTGCAGCCT
GAAGATTTTGCAACTTATTACTGCCAACAGTATAATAGTTACCCTCC (SEQ ID NO: 172)

FIG. 20F

>L16
GAAATAGTGATGATGATGCAGTCTCCAGCCACCCTGTCTGTGTCTCCAGGGGAAAGAGCCACC
CTCTCCTGCAGGGCCAGTCAGAGTGTTAGCAGACAACTTAGCCTGGTACCAGCAGAAACCT
GGCCAGGCTCCCAGGCTCCTCATCTATGGTGCATCTACCAGGGCCACTGGCATCCCAGCC
AGGTTCAGTGGCAGTGGGTCTGGGACAGAGTTCACTCTCACCATCAGCAGCCTGCAGTCT
GAAGATTTTGCAGTTTATTACTGTCAGCAGTATAATAACTGACCTCC (SEQ ID NO: 173)

>L18
GCCATCCAGTTGACCCAGTCTCCATCCTCCCTGTCTGCATCTGTAGGAGACAGAGTCACC
ATCACTTGCCGGGCAAGTCAGGGCATTAGCAGTGCTTTAGCCTGGTATCAGCAGAAACCA
GGGAAAGCTCCTAAGCTCCTGATCTATGATGCATCTAGTTTGGAAAGTGGGGTCCCATCA
AGGTTCAGCGGCAGTGGATCTGGGACAGATTTCACTCTCACCATCAGCAGCCTGCAGCCT
GAAGATTTTGCAACTTATTACTGTCAACAGTTTAATAATTACCCTCA (SEQ ID NO: 174)

>L19
GACATCCAGATGACCCAGTCTCCATCTTCTGTGTCTGCATCTGTAGGAGACAGAGTCACC
ATCACTTGTCGGGCGAGTCAGAGCTATTAGCAGCTGGTTAGCCTGGTATCAGCAGAAACCA
GGGAAAGCCCCTAAGCTCCTGATCTATGCTGACAGATTTGCAAATGGGGTCCCATCA
AGGTTCAGCGGCAGTGGATCGGGACAGATTTCACTCTCACTATCAGCAGCCTGCAGCCT
GAAGATTTTGCAACTTATTGTCAACAGGCTAACAGTTTCCCTCC (SEQ ID NO: 175)

>L2
GAAATAGTGATGACGCAGTCTCCAGCCACCCTGTCTGTCTCCAGGGGAAAGAGCCACC
CTCTCCTGCAGGCTCCAGTCAGAGTGTTAGCAGCAACTTAGCCTGGTACCAGCAGAAACCT
GGCCAGGCTCCCAGGCTCCTCATCTATGGTGCATCTACCAGGGCCACTGGTATCCCAGCC
AGGTTCAGTGGCAGTGGGTCTGGGACAGAGTTCACTCTCACCATCAGCAGCCTGCAGTCT
GAAGATTTTGCAGTTTATTACTGTCAGCAGTATAATAACTGGCCTCC (SEQ ID NO: 176)

FIG. 20G

>L20
GAAATTGTGTTGACACAGTCTCCAGCCACCCTGTCTTTGTCTCCAGGGGAAAGAGCCACC
CTCTCCTGCAGGGCCAGTCAGGGTGTTAGCAGTACTTAGCCTGGTACCAGCAGAAACCT
GGCCAGGCTCCCAGGCTCCTCATCTATGATGCATCCAACAGGGCCACTGGCATCCCAGCC
AGGTTCAGTGGCAGTGGGCCTGGGACAGACTTCACTCTCACCATCAGCAGCCTAGAGCCT
GAAGATTTTGCAGTTTATTACTGTGTCAGCAGCGTAGCAACTGGCATCC (SEQ ID NO: 177)

>L22
GACATCCAGATGATCCAGTCTCCATCTTTCCTGTCTGCATCTGTAGGAGACAGAGTCAGT
ATCATTTGCTGGGCAAGTGAGGGCATTAGCAGTAATTAGCCTGGTATCTGCAGAAACCA
GGGAAATCCCCTAAGCTCTTCCTCTATGATGCAAAAGATTTGCACCTGGGGTCTCATCG
AGGTTCAGTGGCAGGGGATCTGGGACGGATTTCACTCTCACCATCATCAGCCTGAAGCCT
GAAGATTTTGCAGCTTATTACTGTAAACAGGACTTCAGTTACCCTCC (SEQ ID NO: 178)

>L23
GCCATCCGGATGACCCAGTCTCCCATTCTCCCTGTCTGCATCTGTAGGAGACAGAGTCACC
ATCACTTGCTGGGCCAGTCAGGGCATTAGCAGTTATTAGCCTGGTATCAGCAGAAAACCA
GCAAAAGCCCCTAAGCTCTTCATCTATTATGCATCCAGTTTGCAAAGTGGGGTCCCATCA
AGGTTCAGCGGCAGTGGATCTGGGACAGCGGATTACACTCTCACCATCAGCAGCCTGCAGCCT
GAAGATTTTGCAACTTATTACTGTCAACAGTATTATAGTACCCCTCC (SEQ ID NO: 179)

>L24
GTCATCTGGATGACCCAGTCTCCCATCTCCTTACTCTCTGCATCTACAGGAGACAGAGTCACC
ATCAGTTGTCGGATGAGTCAGGGCATTAGCAGTTATTAGCCTGGTATCAGCAGAAAACCA
GGGAAAGCCCCTGAGCTCCTGATCTATGCTGCATCCACTTTGCAAAGTGGGGTCCCATCA
AGGTTCAGTGGCAGTGGATCTGGGACAGATTTCACTCTCACCATCAGTTGCCTGCAGTCT
GAAGATTTTGCAACTTATTACTGTCAACAGTATTATAGTTTCCCTCC (SEQ ID NO: 180)

FIG. 20H

>L25
GAAATTGTAATGACACAGTCTCCAGCCACCCTGTCTTTGTCTCCAGGGGAAAGAGCCACC
CTCTCCTGCAGGGCCAGTCAGAGTGTTAGCAGCAGCTACTTATCCTGGTACCAGCAGAAA
CCTGGGCAGGCTCCCAGGCTCCTCATCTATGGTGCATCCACCAGGGCCACTGGCATCCCA
GCCAGGTTCAGTGGCAGTGGGTCTGGGACAGACTTCACTCTCACCATCAGCAGCCTGCAG
CCTGAAGATTTTGCAGTTTATTACTGTCAGCAGGATTATAACTTACCTCC
(SEQ ID NO: 181)

>L4/18a
GCCATCCAGTTGACCCAGTCTCCATCCTCCCTGTCTGCATCTGTAGGAGACAGAGTCACC
ATCACTTGCCGGGCAAGTCAGAGCATTAGCAGCTATTTAGCCTGGTATCAGCAGAAACCA
GGGAAAGCTCCTAAGCTCCTGATCTATGCTGCATCTAGTTTGCAAAGTGGGGTCCCATCA
AGGTTCAGCGGCAGTGGATCTGGGACAGATTTCACTCTCACCATCAGCAGCCTGCAGCCT
GAAGATTTTGCAACTTATTACTGTCAACAGTTTAATAGTTACCCTCA (SEQ ID NO: 182)

>L5
GACATCCAGATGACCCAGTCTCCATCTTCCGTGTCTGCATCTGTAGGAGACAGAGTCACC
ATCACTTGTCGGGCGAGTCAGGGTATTAGCAGCTGGTTAGCCTGGTATCAGCAGAAACCA
GGGAAAGCCCCTAAGCTCCTGATCTATGCTGCATCCAGTTTGCAAAGTGGGGTCCCATCA
AGGTTCAGCGGCAGTGGATCTGGGACAGATTTCACTCTCACCATCAGCAGCCTGCAGCCT
GAAGATTTTGCAACTTACTACTATTGTCAACAGGCTAACAGTTTCCCTCC (SEQ ID NO: 183)

>L6
GAAATTGTGTTGACACAGTCTCCAGCCACCCTGTCTTTGTCTCCAGGGGAAAGAGCCACC
CTCTCCTGCAGGGCCAGTCAGAGTGTTAGCAGCTACTTAGCCTGGTACCAACAGAAACCT
GGCCAGGCTCCCAGGCTCCTCATCTATGATGCATCCAACAGGGCCACTGGCATCCCAGCC
AGGTTCAGTGGCAGTGGGTCTGGGACAGACTTCACTCTCACCATCAGCAGCCTAGAGCCT
GAAGATTTTGCAGTTTATTACTGTCAGCAGCGTAGCAGCAACTGGCCTCC (SEQ ID NO: 184)

FIG. 20I

>L8
GACATCCAGTTGACCCAGTCTCCAGTCTCCATCCTTCCTGTCTGCATCTGTAGGAGACAGAGTCACC
ATCACTTGCCGGGCCAGTCAGGGCATTAGCAGTTATTTAGCCTGGTATCAGCAAAAACCA
GGGAAAGCCCCTAAGCTCCTGATCTATGCTGCATCCACTTTGCAAAGTGGGTCCCATCA
AGGTTCAGCGGCAGTGGATCTGGGACAGAATTCACTCTCACAATCAGCAGCCTGCAGCCT
GAAGATTTTGCAACTTATTACTGTCAACAGCTTAATAGTTACCCTCC (SEQ ID NO: 185)

>L9
GCCATCCGGATGACCCAGTCTCCATCCTCATTCTCTGCATCTACAGGAGACAGAGTCACC
ATCACTTGTCGGGCGAGTCAGGGTATTAGCAGTTATTTAGCCTGGTATCAGCAAAAACCA
GGGAAAGCCCCTAAGCTCCTGATCTATGCTGCATCCACTTTGCAAAGTGGGTCCCATCA
AGGTTCAGCGGCAGTGGATCTGGGACAGATTTCACTCTCACCATCAGCTGCCTGCAGTCT
GAAGATTTTGCAACTTATTACTGTCAACAGTATTATAGTTACCCTCC (SEQ ID NO: 186)

>O1
GATATTGTGATGACCCAGACTCCACTCTCCCCTGCCCGTCACCCTGGAGAGCCGGCCTCC
ATCTCCTGCAGGTCTAGTCAGAGCCTCTTGGATAGTGATGATGAAAACACCTATTTGAC
TGGTACCTGCAGAAGCCAGGGCAGTCTCCACAGCTCCTGATCTATACGCTTTCCTATCGG
GCCTCTGGAGTCCCAGACAGTTCAGTGGCAGTGGGTCAGGCACTGATTTCACACTGAAA
ATCAGCAGGGTGGAGGCTGAGGATGTTGGAGTTTATTACTGCATGCAACGTATAGAGTTT
CCTTC (SEQ ID NO: 187)

>O11
GATATTGTGATGACCCAGACTCCACTCTCCCCTGCCCGTCACCCTGGAGAGCCGGCCTCC
ATCTCCTGCAGGTCTAGTCAGAGCCTCTTGGATAGTGATGATGGAAAACACCTATTTGAC
TGGTACCTGCAGAAGCCAGGGCAGTCTCCACAGCTCCTGATCTATACGCTTTCCTATCGG
GCCTCTGGAGTCCCAGACAGTTCAGTGGCAGTGGGTCAGGCACTGATTTCACACTGAAA
ATCAGCAGGGTGGAGGCTGAGGATGTTGGAGTTTATTACTGCATGCAACGTATAGAGTTT
CCTTC (SEQ ID NO: 188)

FIG. 20J

>O12
GACATCCAGATGACCCAGTCTCCATCCTCCCTGTCTGCATCTGTAGGAGACAGAGTCACC
ATCACTTGCCGGCAAGTCAGAGCATTAGCAGCATTATCTAAATTGGTATCAGCAGAAACCA
GGGAAAGCCCCTAAGCTCCTGATCTATGCTGCATCCAGTTTGCAAAGTGGGGTCCCATCA
AGGTTCAGTGGCAGTGGATCTGGGACAGAGATTTCACTCTCACCATCAGCAGTCTGCAACCT
GAAGATTTTGCAACTTACTACTGTCAACAGAGTTACAGTACCCCCTCC (SEQ ID NO: 189)

>O14
GACATCCAGATGACCCAGTCTCCATCCTCCCTGTCTGCATCTGTAGGAGACAGAGTCACC
ATCACTTGCCGGGTGAGTCAGGGCATTAGCAGTTATTAAATTGGTATCGGCAGAAACCA
GGGAAAGTTCCTAAGCTCCTGATCTATAGTGCATCTATAGTGGACAGATTTGGAGTCCCATCT
CGGTTCAGTGGCAGTGGATCTGGGACAGATTTCACTCTCACTATCAGCAGCCTGCAGCCT
GAAGATGTTGCAACTTGCAACTTATTACGGTCAACGGACTTACAATGCCCCTCC (SEQ ID NO: 190)

>O18
GACATCCAGATGACCCAGTCTCCATCCTCCCTGTCTGCTGCATCTGTAGGAGACAGAGTCACC
ATCACTTGCCAGGCGAGTCAGGACATTAGCAACTATTAAATTGGTATCAGCAGAAACCA
GGGAAAGCCCCTAAGCTCCTGATCTACGATGCATCCAATTTGGAAACAGGGGTCCCATCA
AGTTCAGTGGAAGTGGATCTGGGACAGATTTCACTTTCACCATCAGCAGCCTGCAGCCT
GAAGATATTGCAACATATTACTGTCAACAGAGTATGATAATCTCCCCTCC (SEQ ID NO: 191)

>O2
GACATCCAGATGACCCAGTCTCCATCCTCCCTGTCTGCATCTGTAGGAGACAGAGTCACC
ATCACTTGCCGGGCAAGTCAGAGCATTAGCAGCATTATCAGCAGAAACCA
GGGAAAGCCCCTAAGCTCCTGATCTATGCTGCATCCAGTTTGCAAAGTGGGGTCCCATCA
AGGTTCAGTGGCAGTGGATCTGGGACAGATTTCACTCTCACCATCAGCAGTCTGCAACCT
GAAGATTTTGCAACTTACTACTGTCAACAGAGTTACAGTACCCCCTCC (SEQ ID NO: 192)

FIG. 20K

>O4
GACATCCAGTTGACCCAGTCTCCATCCTCCCTGTCTCTGCATCTGTAGGAGACAGAGTCACC
ATCACTTGCCGGGTGAGTCAGGGCATTAGCAGTTATTAAATTGGTATCGGCAGAAACCA
GGGAAAGTTCCTAAGCTCCTGATCTATAGTGCATCCAATTTGCAATCTGGAGTCCCATCT
CGGTTCAGTGGCAGTGGATCTGGGACAGATTTCACTCTCACTATCAGCAGCCTGCAGCCT
GAAGATGTTGCAACTTATTACGGTCAACGGACTTACAATGCCCCCTCC (SEQ ID NO: 193)

>O8
GACATCCAGATGACCCAGTCTCCATCCTCCCTGTCTGCATCTGTAGGAGACAGAGTCACC
ATCACTTGCCAGGCGAGTCAGGGCATTAGCAATTATTTAAATTGGTATCAGCAGAAACCA
GGGAAAGCCCCTAAGCTCCTGATCTACGATGCATCTACTTTGGAAACAGGGGTCCCATCA
AGGTTCAGTGGAAGTGGATCTGGGACAGATTTTACTTTCACCATCAGCAGCCTGCAGCCT
GAAGATATTGCAACATATTACTGTCAACAGTATGATAATCTCCCTCC (SEQ ID NO: 194)

FIG. 20L

V_lambda Gene Sequences

>V1-11
QSVLTQPPSVSEAPRQRVTISCSGSGSSSNIGNNAVNWYQQLPGKAPKLLIYDDLLPSGVS
DRFSGSKSGTSASLAISGLQSEDEADYYCAAWDDSLNGP (SEQ ID NO: 195)

>V1-13
QSVLTQPPSVSGAPGQRVTISCTGSSSNIGAGYDVHWYQQLPGTAPKLLIYGNSNRPSGV
PDRFSGSKSGTSASLAITGLQAEDEADYYCQSYDSSLSGS (SEQ ID NO: 196)

>V1-16
QSVLTQPPSASGTPGQRVTISCSGSSSNIGSNTVNWYQQLPGTAPKLLIYSNNQRPSGVP
DRFSGSKSGTSASLAISGLQSEDEADYYCAAWDDSLNGP (SEQ ID NO: 197)

>V1-17
QSVLTQPPSASGTPGQRVTISCTGSSSNIGSNYVYWYQQLPGTAPKLLIYSNNQRPSGVP
DRFSGSKSGTSASLAISGLRSEDEADYYCAAWDDSLSGP (SEQ ID NO: 198)

>V1-18
QSVLTQPPSVSGAPGQRVTISCTGSSSNIGAGYVVHWYQQLPGTAPKLLIYGNSNRPSGV
PDQFSGSKSGTSASLAITGLQSEDEADYYCKAWDNSLNA (SEQ ID NO: 199)

>V1-19
QSVLTQPPSVSAAPGQKVTISCSGSSSNIGNNYVSWYQQLPGTAPKLLIYDNNKRPSGIP
DRFSGSKSGTSATLGITGLQTGDEADYYCGTWDSSLSAG (SEQ ID NO: 200)

>V1-2
QSALTQPPSASGSPGQSVTISCTGTSSDVGGYNYVSWYQQHPGKAPKLMIYEVSKRPSGV
PDRFSGSKSGNTASLTVSGLQAEDEADYYCSSYAGSNNF (SEQ ID NO: 201)

FIG. 21A

>V1-20
QAGLTQPPSVSKGLRQTATLTCTGNSNIVGNQGAAWLQQHQGHPPKLLSYRNNNRPSGIS
ERFSASRSGNTASLTITGLQPEDEADYYCSALDSSLSA (SEQ ID NO: 202)

>V1-22
NFMLTQPHSVSESPGKTVTISCTRSSGSIASNYVQWYQQRPGSSPTTVIYEDNQRPSGVP
DRFSGSIDSSSNSASLTISGLKTEDEADYYCQSYDSSN (SEQ ID NO: 203)

>V1-3
QSALTQPRSVSGSPGQSVTISCTGTSSDVGGYNYVSWYQQHPGKAPKLMIYDVSKRPSGV
PDRFSGSKSGNTASLTISGLQAEDEADYYCCSYAGSYTF (SEQ ID NO: 204)

>V1-4
QSALTQPASVSGSPGQSITIISCTGTSSDVGGYNYVSWYQQHPGKAPKLMIYEVSNRPSGV
SNRFSGSKSGNTASLTISGLQAEDEADYYCSSYTSSSTL (SEQ ID NO: 205)

>V1-5
QSALTQPPSVSGSPGQSVTISCTGTSSDVGSYNRVSWYQQPPGTAPKLMIYEVSNRPSGV
PDRFSGSKSGNTASLTISGLQAEDEADYYCSLYTSSSTF (SEQ ID NO: 206)

>V1-7
QSALTQPASVSGSPGQSITIISCTGTSSDVGSYNLVSWYQQHPGKAPKLMIYEGSKRPSGV
SNRFSGSKSGNTASLTISGLQAEDEADYYCCSYAGSSTF (SEQ ID NO: 207)

>V1-9
QSALTQPPFVSGAPGQSVTISCTGTSSDVGDYDHVFWYQKRLSTTSRLLIYNVNTRPSGI
SDLFSGSKSGNMASLTISGLKSEVEANYHCSLYSSSYTF (SEQ ID NO: 208)

FIG. 21B

>V2-1
SYELTQPPSVSVSPGQTASITCSGDKLGDKYACWYQQKPGQSPVLVIYQDSKRPSGIPER
FSGSNSGNTATLTISGTQAMDEADYYCQAWDSSTA (SEQ ID NO: 209)

>V2-11
SYELTQPPSVSVSLGQMARITCSGEALPKKYAYWYQQKPGQFPVLVIYKDSERPSGIPER
FSGSSSGTIVTLTISGVQAEDEADYYCLSADSSGTYP (SEQ ID NO: 210)

>V2-13
SSELTQDPAVSVALGQTVRITCQGDSLRSYYASWYQQKPGQAPVLVIYGKNNRPSGIPDR
FSGSSSGNTASLTITGAQAEDEADYYCNSRDSSGNHL (SEQ ID NO: 211)

>V2-14
SYVLTQPPSVSVAPGQTARITCGGNNIGSKSVHWYQQKPGQAPVLVVYDDSDRPSGIPER
FSGSNSGNTATLTISRVEAGDEADYYCQVWDSSSDHP (SEQ ID NO: 212)

>V2-15
SYELTQLPSVSVSPGQTARITCSGDVLGENYADWYQQKPGQAPELVIYEDSERYPGIPER
FSGSTSGNTTLTISRVLTEDEADYYCLSGDEDNP (SEQ ID NO: 213)

>V2-17
SYELTQPPSVSVSPGQTARITCSGDALPKQYAYWYQQKPGQAPVLVIYKDSERPSGIPER
FSGSSSGTTVTLTISGVQAEDEADYYCQSADSSGTYP (SEQ ID NO: 214)

>V2-19
SYELTQPSSVSVSPGQTARITCSGDVLAKKYARWFQQKPGQAPVLVIYKDSERPSGIPER
FSGSSSGTTVTLTISGAQVEDEADYYCYSAADNNL (SEQ ID NO: 215)

FIG. 21C

>V2-6
SYELTQPLSVSVALGQTARITCGGNNIGSKNVHWYQQKPGQAPVLVIYRDSNRPSGIPER
FSGSNSGNTATLTISRAQAGDEADYYCQVWDSSTA (SEQ ID NO: 216)

>V2-7
SYELTQPPSVSVSPGQTARITCSGDALPKKYAYWYQQKSGQAPVLVIYEDSKRPSGIPER
FSGSSSGTMATLTISGAQVEDEADYYCYSTDSSGNH (SEQ ID NO: 217)

>V2-8
SYELTQPHSVSVATAQMARITCGGNNIGSKAVHWYQQKPGQDPVLVIYSDSNRPSGIPER
FSGSNPGNTATLTISRIEAGDEADYYCQVWDSSSDHP (SEQ ID NO: 218)

>V3-2
QTVVTQEPSLTVSPGGTVTLTCASSTGAVTSGYYPNWFQQKPGQAPRALIYSTNKHSWT
PARFSGSLLGGKAALTLSGVQPEDEAEYYCLLYYGGAQ (SEQ ID NO: 219)

>V3-3
QAVVTQEPSLTVSPGGTVTLTCGSSTGAVTSGHYPYWFQQKPGQAPRTLIYDTSNKHSWT
PARFSGSLLGGKAALTLLGAQPEDEAEYYCLLSYSGAR (SEQ ID NO: 220)

>V3-4
QTVVTQEPSFSVSPGGTVTLTCGLSSGSVSTSYYPSWYQQTPGQAPRTLIYSTNTRSSGV
PDRFSGSILGNKAALTITGAQADDESDYCVLYMGSGIS (SEQ ID NO: 221)

>V4-1
QPVLIQPPSSSASPGESARLTCTLPSDINVGSYNIYWYQQKPGSPPRYLLYYSDSDKGQ
GSGVPSRFSGSKDASANTGILLISGLQSEDEADYCMIWPSNAS (SEQ ID NO: 222)

FIG. 21D

>V4-2
QAVLTQPPSLSASPGASASLTCTLRSGINVGTYRIYWYQQKPGSPPQYLLRYKSDSDKQQ
GSGVPSRFSGSKDASANAGILLISGLQSEDEADYYCMIWHSSAS (SEQ ID NO: 223)

>V4-3
QPVLTQPTSLSASPGASARLTCTLRSGINLGSYRIFWYQQKPESPPRYLLSYYSDSSKHQ
GSGVPSRFSGSKDASSNAGILVISGLQSEDEADYYCMIWHSSAS (SEQ ID NO: 224)

>V4-4
QPVLTQPSSHSASSGASVRLTCMLSSGFSVGDFWIRWYQQKPGNPPRYLLYHSDSNKGQ
GSGVPSRFSGSNDASANAGILRISGLQPEDEADYYCGTWHSNSKT (SEQ ID NO: 225)

>V4-6
RPVLTQPPSLSASPGATARLPCTLSSDLSVGGKNMFWYQQKPGSSPRLFLYHYSDSDKQL
GPGVPSRVSGSKETSSNTAFLLISGLQPEDEADYYCQVYESSAN (SEQ ID NO: 226)

>V5-1
LPVLTQPPSASALLGASIKLTCTLSSEHSTYTIEWYQQRPGRSPQYIMKVKSDGSHSKGD
GIPDRFMGSSSGADRYLTFSNLQSDDEAEYHCGESHTIDGQVG (SEQ ID NO: 227)

>V5-2
QPVLTQPPSASASLGASVTLTCTLSSGYSNYKVDWYQQRPGKGPRFVMRVGTGGIVGSKG
DGIPDRFSVLGSGLNRYLTIKNIQEEDESDYHCGADHGSGSNFV (SEQ ID NO: 228)

>V5-4
QPVLTQSSSASASLGSSVKLTCTLSSGHSSYIIAWHQQQPGKAPRYLMKLEGSGSYNKGS
GVPDRFSGSSSGADRYLTISNLQFEDEADYYCETWDSNT (SEQ ID NO: 229)

FIG. 21E

>V5-6
QLVLTQSPSASASLGASVKLTCTLSSGHSSYAIAWHQQQPEKGPRYLMKLNSDGSHSKGD
GIPDRFSGSSSGAERYLTISSLQSEDEADYYCQTWGTG (SEQ ID NO: 230)

FIG. 21F

V_lambda Gene Sequences

>V1-11
CAGTCTGTGCTGACTCAGCCACCCTCGGTGTCTGAAGCCCCCAGGCAGAGGGTCACCATC
TCCTGTTCTGGAAGCAGCTCCAACATCGGAAATAATGCTGTAAACTGGTACCAGCAGCTC
CCAGGAAAGGCTCCCAAACTCCTCATCTATTATGATCTGCTGCCCTCAGGGGTCTCT
GACCGATTCTCTGGCTCCAAGTCTGGCACCTCAGCCTCCCTGGCCATCAGTGGGCTCCAG
TCTGAGGATGAGGCTGATTATTACTGTGCAGCATGGGATGACAGCCTGAATGGTCC
(SEQ ID NO: 231)

>V1-13
CAGTCTGTGCTGACGCAGCCGCCCTCAGTGTCTGGGGCCCCAGGGCAGAGGGTCACCATC
TCCTGCACTGGGAGCAGCTCCAACATCGGGGCAGGTTATGATGTATACACTGGTACCAGCAG
CTTCCAGGAACAGCCCCCAAACTCCTCATCTATGTAACAGAATCGGCCTCAGGGGTC
CCTGACCGATTCTCTGGCTCCAAGTCTGGCACCTCAGCCTCCCTGGCCATCACTGGGCTC
CAGGCTGAGGATGAGGCTGATTATTACTGCCAGTCCTATGACAGCAGCCTGAGTGGTTC
(SEQ ID NO: 232)

>V1-16
CAGTCTGTGCTGACTCAGCCACCCTCAGCGTCTGGGACCCCCGGGCAGAGGGTCACCATC
TCTTGTTCTGGAAGCAGCTCCAACATCGGAAGTAATACTGTAAACTGGTACCAGCAGCTC
CCAGGAACGGCCCCCAAACTCCTCATCTATAGTAATAATCAGCGGCCCTCAGGGGTCCCT
GACCGATTCTCTGGCTCCAAGTCTGGCACCTCAGCCTCCCTGGCCATCAGTGGGCTCCAG
TCTGAGGATGAGGCTGATTATTACTGTGCAGCATGGGATGACAGCCTGAATGGTCC
(SEQ ID NO: 233)

FIG. 22A

>V1-17
CAGTCTGTGCTGACTCAGCCACCCTCAGCGTCTGGGACCCCCGGGCAGAGGGTCACCATC
TCTTGTTCTGGAAGCAGCTCCAACATCGGAAGTAATTATGTATACTGGTACCAGCAGCTC
CCAGGAACGGCCCCCAAACTCCTCATCTATAGTAATAATCAGCGGCCCTCAGGGGTCCCT
GACCGATTCTCTGGCTCCAAGTCTGGCACCTCAGCCTCCCTGGCCATCAGTGGGCTCCGG
TCCGAGGATGAGGCTGATTATTACTGTGCAGCATGGGATGACAGCCTGAGTGGTCC
(SEQ ID NO: 234)
>V1-18
CAGTCTGTGCTGACGCAGCCGCCCTCAGTGTCTGGGGCCCCAGGGCAGAGGGTCACCATC
TCCTGCACTGGGAGCAGCTCCAACATTGGGGCGGTTATGTTGTACATTGGTACCAGCAG
CTTCCAGGAACAGCCCCCAAACTCCTCATCTATGGTAACAGCAATCGGCCCTCAGGGGTC
CCTGACCGATTCTCTGGCTCCAAGTCTGGCACCTCAGCCTCCCTGGCCATCACTGGACTC
CAGTCTGAGGATGAGGCTGATTATTACTGCAAAGCATGGGATAACAGCCTGAATGCTCA
(SEQ ID NO: 235)
>V1-19
CAGTCTGTGTTGACGCAGCCGCCCTCAGTGTCTGCGGCCCCAGGACAGAAGGTCACCATC
TCCTGCTCTGGAAGCAGCTCCAACATTGGGAATAATTATGTATCCTGGTACCAGCAGCTC
CCAGGAACAGCCCCCAAACTCCTCATTTATGACAATAATAAGCGACCCTCAGGGATTCCT
GACCGATTCTCTGGCTCCAAGTCTGGCACGTCAGCCACCCTGGGCATCACCGGACTCCAG
ACTGGGGACGAGGCCGATTATTACTGCGAACATGGGATAGCAGCCTGAGTGCTGG
(SEQ ID NO: 236)
>V1-2
CAGTCTGCCCCTGACTCAGCCTCGCTCCGGGTCTCCTGGACAGTCAGTCACCATC
TCCTGCACTGGAACCAGCAGTGACGTTGGTGGTTATAACTATGTCTCTGGTACCAACAG
CACCCAGGCAAAGCCCCCAAACTCATGATTTATGAGGTCAGTAAGCGGCCCTCAGGGGTC
CCTGATCGCTTCTCTGGCTCCAAGTCTGGCAACACGGCCTCCCTGACCGTCTCTGGGCTC
CAGGCTGAGGATGAGGCTGATTATTACTGCAGCTCATATGCAGGCAGCAACAATTTC
(SEQ ID NO: 237)

FIG. 22B

>V1-20
CAGGCAGGGCTGACTCAGCCACCCTCGGTGTCCAAGGGCTTGAGACAGACCGCCACACTC
ACCTGCACTGGGAACAGCAACATTGTTGGCAACCAAGGAGCAGCTTGGCTGCAGCAGCAC
CAGGGCCACCCCTCCAAACTCCTATCCTACAGGATAACAACCGGCCCTCAGGGATCTCA
GAGAGATTCTCTGCATCCAGGTCAGGAAAACACAGCCTCCCTGACCATTACTGGACTCCAG
CCTGAGGACGAGGCTGACTATTACTGCTCAGCATTGGACAGCAGCCTCAGTGCTCA
(SEQ ID NO: 238)
>V1-22
AATTTATGCTGACTCAGCCCCACTCTGTGTCGGAGTCTCCGGGGAAGACGGTAACCATC
TCCTGCACCCGCAGCAGTGGCAGCATTGCCAGCAACTATGTGCAGTGGTACCAGCAGCGC
CCGGGCAGTTCCCCACCACTGTGATCTATGAGGATAACAACAAAGACCCCTCTGGGGTCCCT
GATCGGTTCTCTGCTCCATCGACAGCTCCTCCAACTCTGCTCCTCCACCATCTCTGGA
CTGAAGACTGAGGACGAGGCTGACTACTACTGCTCAGTCTTATGATAGCAGCAATCA
(SEQ ID NO: 239)
>V1-3
CAGTCTGCCCTGACTCAGCCTCGCTCAGTGTCCGGGTCTCCTGGACAGTCAGTCACCATC
TCCTGCACTGGAACCAGCAGTGATGTTGGTTATAACTATGTCTCCTGGTACCAACAG
CACCCAGGCAAAGCCCCCAAACTCATGATTTATGATGTCAGTAAGCGGCCCTCAGGGGTC
CCTGATCGCTTCTCTGGCTCCAAGTCTGGCAACACGGCCTCCCTGACCATCTCTGGGCTC
CAGGCTGAGGATGAGGCTGATTATTACTGCTCATATGCAGGCAGCTACACTTTC
(SEQ ID NO: 240)
>V1-4
CAGTCTGCCCTGACTCAGCCTGCCTCCGTGTCTGGGTCTCCTGGACAGTCGATCACCATC
TCCTGCACTGGAACCAGCAGTGACGTTGGTGGTTATAACTATGTCTCCTGGTACCAACAG
CACCCAGGCAAAGCCCCCAAACTCATGATTTATGAGGTCAGTAATCGGCCCTCAGGGGTT
TCTAATCGCTTCTCTGGCTCTAAGTCTGGCAACACGGCCTCCCTGACCATCTCTGGGCTC
CAGGCTGAGGACGAGGCTGATTATTACTGCAGCTCATATACAAGCAGCAGCACTCTC
(SEQ ID NO: 241)

FIG. 22C

>V1-5
CAGTCTGCCCTGACTCAGCCTCCCTCCGTGTCCGGGTCTCCTGGACAGTCAGTCACCATC
TCCTGCACTGGAACCAGCAGTGACGTTGGTAGTTATAACCGTGTCTCCTGGTACCAGCAG
CCCCCAGGCACAGCCCCCAAACTCATGATTTATGAGGTCAGTAATCGGCCCTCAGGGGTC
CCTGATCGCTTCTCTGGGTCTCCAAGTCTGGCAACACGGCCTCCCTGACCATCTCTGGCTC
CAGGCTGAGGACGAGGCTGATTATTACTGCCAGCTTATATACAAGCAGCACTTTC
(SEQ ID NO: 242)
>V1-7
CAGTCTGCCCTGACTCAGCCTCGCCTCCGTGTCCTGGGTCTCCTGGACAGTCGATCACCATC
TCCTGCACTGGAACCAGCAGTGATGTTGGGAGTTATAACCTTGTCTCCTGGTACCAACAG
CACCCAGGCAAAGCCCCCAAACTCATGATTTATGAGGGCAGTAAGCGGCCCTCAGGGGTT
TCTAATCGCTTCTCTGGCTCCAAGTCTGGCAACACGGCCTCCCTGACAATCTCTGGGCTC
CAGGCTGAGGACGAGGCTGATTATTACTGCTGCTCATATGCAGGTAGTAGCACTTTC
(SEQ ID NO: 243)
>V1-9
CAATCTGCCCTGACTCAGCCTCGCCTCCTTTGTGTCCGGGGCTCCTGGACAGTCGGTCACCATC
TCCTGCACTGGAACCAGCAGTGACGTTGGGATTATGATCATGTCTTCTGGTACCAAAAG
CGTCTCAGCACTACCTCCAGACTCCGATTTACAATGTCAATACTCGGCCTTCAGGGATC
TCTGACCTCTTCTCAGGCTCCAAGTCTGGCAACATGGCCTTCCCTGACCATCTCTGGGCTC
AAGTCCGAGGTTGAGGTTGAGCTAATTATCACTGCAGCTTATATTCAAGTAGTTACACTTTC
(SEQ ID NO: 244)
>V2-1
TCCTATGAGCTGACTCAGCCACCCTCAGTGTCCGTGTCCCCAGGACAGACAGCCAGCATC
ACCTGCTCTGGAGATAAATTGGGGGATAAATATGCTTGCTGGTATCAGCAGAAGCCAGGC
CAGTCCCCCGTGTCTGCTGTCATCTATCAAGATAGCAAGCGCCCCTCAGGGATCCCTGAGCGA
TTCTCTGGCTCCAACTCTGGGAACACAGCCACTCTGACCATCAGCGGGACCCAGGCTATG
GATGAGGCTGACTATTACTGTCAGGCGTGGGACAGCAGCACTGCA
(SEQ ID NO: 245)

FIG. 22D

>V2-11
TCCTATGAGCTGACACAGCCACCCTCGGTGTCAGTGTCCCTAGGACAGATGGCCAGGATC
ACCTGCTCTGGAGAAGCAGCCATTGCCAAAAAATATGCTTATTGGTACCAGCAGAAGCCAGGC
CAGTTCCCTGTGCTGGTGATATATAAAGACAGCGAGAGGCCCTCAGGGATCCCTGAGCGA
TTCTCTGGCTCCAGCTCAGGGACAATAGTCACATTGACCATCAGTGGAGTCCAGGCAGAA
GACGAGGCTGACTATTACTGTCTATCAGCAGACAGCAGTGGTACTTATCC
(SEQ ID NO: 246)
>V2-13
TCTTCTGAGCTGACTCAGGACCCTGCTGTCTGTGCCTTGGGACAGACAGTCAGGATC
ACATGCCAAGGAGACAGCTCAGAAGCCTCAGAAGCTATTATGCAAGCTGGTACCAGCAGAAGCCAGGA
CAGGCCCCTGTACTTGTCATCTATGGTAAAAACAACCGGCCCTCAGGGATCCCAGACCGA
TTCTCTGGCTCCAGCTCAGGAGAAACACAGCTTCCTTGACCATCACTGGGGCTCAGGCGAA
GATGAGGCTGACTATTACTGTGTAACTCCCGGGACAGCAGTGGTAACCATCT
(SEQ ID NO: 247)
>V2-14
TCCTATGTGCTGACTCAGCCACCCTCGGTGTCAGTGGCCCCAGGACAGACGGCCAGGATT
ACCTGTGGGGGAAACAACATTGGAAGTAAAAGTGTGCACTGGTACCAGCAGAAGCCAGGC
CAGGCCCCTGTGCTGGTCTATGATAGCAGCGACCGGCCCTCAGGGATCCCTGAGCGA
TTCTCTGGCTCCAACTCTGGGAACACGGCCACCCTGACCATCAGCAGGGTCGAAGCCGGG
GATGAGGCCGACTATTACTGTCAGGTGTGGGATAGTAGTAGTGATCATCC
(SEQ ID NO: 248)
>V2-15
TCCTATGAGCTGACACAGCTACCCTCGGTGTCAGTGTCCCCAGGACAGACAGCCAGGATC
ACCTGCTCTGGAGATGTACTGGGGCAAAATTATGCTGACTGGTACCAGCAGAAGCCAGGC
CAGGCCCCTGAGTTGGTGATATACGAAGATATGAGCGTACCCTGAATCCCTGAACGA
TTCTCTGGGTCCACCTCAGGGAACAGACACCCTGACCATCAGCAGCAGGGTCCTGACCGAA
GACGAGGCTGACTATTACTGTTTGTCTGGGGATGAGGACAATCC
(SEQ ID NO: 249)

FIG. 22E

>V2-17
TCCTATGAGCTGACACAGCCACCCTCGGTGTCAGTGTCCCCAGGACAGACGGCCAGGATC
ACCTGCTCTGGAGATGCATTGCCAAAGCAATATGCTTATTGGTACCAGCAGAAGCCAGGC
CAGGCCCCTGTGCTGGTGATATATAAAGACAGTGAGAGGCCCTCAGGGATCCCTGAGCGA
TTCTCTGGCTCCAGCTCAGGGACAACAGTCACGTTGACCATCAGTGAGTCCAGGCAGAA
GATGAGGCTGACTATTACTGTCAATCAGCAGACAGCAGTGGTACTTATCC
(SEQ ID NO: 250)

>V2-19
TCCTATGAGCTGACACAGCCATCCTCAGTGTCAGTGTCTCCGGGACAGACAGCCAGGATC
ACCTGCTCAGGAGAGATGTACTGCCAAAAAAAATATGCTCGGTGGTTCCAGCAGAAGCCAGGC
CAGGCCCCTGTGCTGGTGATTTATAAAGACAGTGAGCGGCCCTCAGGGATCCCTGAGCGA
TTCTCCGGCTCCAGTCAGGGACCACAGTCACCTTGACCATCAGCGCGGGCCCAGTTGAG
GATGAGGCTGACTATTACTGTTACTCTGCGGCTGACAACAATCT (SEQ ID NO: 251)

>V2-6
TCCTATGAGCTGACTCAGCCACTCTCAGTGTCAGTGGCCTGGGACAGACGGCCAGGATT
ACCTGTGGGGGAAACAACATTGGAAGTAAAAATGTGCACTGGTACCAGCAGAAGCCAGGC
CAGGCCCCTGTGCTGGTCATCTATAGGGATAGCAACCGGCCCTCTGGGATCCCTGAGCGA
TTCTCTGGCTCCAACTCGGGGAACACGGCCACCCTGACCATCAGCAGACAGCCGGG
GATGAGGCTGACTATTACTGTCAGGTGTGGGACAGCAGCACTGCA (SEQ ID NO: 252)

>V2-7
TCCTATGAGCTGACACAGCCACCCTCGGTGTCAGTGTCCCCAGGACAAACGGCCAGGATC
ACCTGCTCTGGAGATGCATTGCCAAAAAATATGCTTATTGGTACCAGCAGAAGTCAGGC
CAGGCCCCTGTGCTGGTCATCTATGAGGACAGCAAACGACCCTCCGGGATCCCTGAGAGA
TTCTCTGGCTCCAGTCAGGGACACTGTTACTATCAGTGGGGCCCAGGTGGAG
GATGAAGCTGACTACTACTGTTACTCAACAGACAGCAGTGGTAATCATAG
(SEQ ID NO: 253)

FIG. 22F

>V2-8
TCCTATGAGCTGACTCAGCCACACTCAGTGTCAGTGGCCACACAGCACAGATGGCCAGGATC
ACCTGTGGGGGAAACAACATTGGAAGTAAAGCTGTGCACTGGTACCAGCAAAAGCCAGGC
CAGGACCCTGTGCTGGTCATCTATAGCGATAGCGATAGCAACCGGCCCTCAGGGATCCCTGAGCGA
TTCTCTGGCTCCAACCAGGGAACACCGCCACCCTAACCATCAGCAGGATCGAGGCTGGG
GATGAGGCTGACTATTACTGTCAGGTGTGGGACAGTAGTAGTGATCATCC
(SEQ ID NO: 254)
>V3-2
CAGACTGTGGTGACTCAGGAGCCCCTCACTGACTGTGTCCCCAGGAGGACAGTCACTCTC
ACCTGTGCTTCCAGCACTGGAGCAGTCACCAGTGGTTACTATCCAAACTGGTTCCAGCAG
AAACCTGGACAAGCACCCAGGGCACTGATTTATAGTACAAGCAACAAACACTCCTGGACC
CCTGCCCCGGTTCTCAGGCTCCCCTCCTTGGGGGCAAAGCTGCCCTGACACTGTCAGGTGTG
CAGCCCTGAGGACGAGGCTGAGTATTACTGCTGCTGCTCTACTACTATGGTGGTGCTCAG
(SEQ ID NO: 255)
>V3-3
CAGGCTGTGGTGACTCAGGAGCCCCTCACTGACTGTGTCCCCAGGAGGACAGTCACTCTC
ACCTGTGGCTCCAGCACTGGAGCTGTCACCAGTGGTCATTATCCCTACTGGTTCCAGCAG
AAGCCTGGCCAAGCCCCCAGGACACTGATTTATGATACAAGCAACAAACACTCCTGGACA
CCTGCCCGGTTCTCAGGCTCCCCTCCTTGGGGGCAAAGCTGCCCTGACCCTTTTGGGTGCG
CAGCCCTGAGGATGAGGCTGAGTATTACTGCTTGCTTCCTCCTATAGTAGTGGTGCTCGG
(SEQ ID NO: 256)
>V3-4
CAGACTGTGGTGACCCAGGAGCCATCGTTCTCAGTGTCCCCTGGAGGGACAGTCACACTC
ACTTGTGGCTTGAGCTCTGGCTCAGTCTCTACTAGTTACTACCCCAGCTGGTACCAGCAG
ACCCCAGGCCAGGCTCCACGCACGCTCATCTACAGCACAAACACTCGCTCTTCTGGGGTC
CCTGATCGCTTCTCTGGCTCCATCCTTGGGAACAAAGCTGCCCTCACCATCACGGGGCC
CAGGCAGATGATGAATCTGATTATTACTGTGTGCTGTATATGGGTAGTGCATTTC
(SEQ ID NO: 257)

FIG. 22G

>V4-1
CAGCCTGTGCTGACTCAGCCACCTTCCTCCTCCGCATCTCCTGGAGAATCCGCCAGACTC
ACCTGCACCTTGCCCAGTGACATCAATGTTGGTAGCTACTACTGTGACTCAGATAAGGCCAG
AAGCCAGGGAGCCCTCCCCAGCCGCTTCCCAGTGTATCTCCTGTACTACCAAAGATGCTTCAGCCAATACAGGATT
GGCTCTGGAGTCCCCAGCCGCTTCTCCAGTCTGAGGATGAGGCTGACTATTACTGTATGATTTGGCCA
TTACTCATCTCCGGGCTCCAGTCTGAGGATGAGGCTGACTATTACTGTATGATTTGGCCA
AGCAATGCTTCT (SEQ ID NO: 258)
>V4-2
CAGGCTGTGCTGACTCAGCCGTCTTCCCTCTCTGCATCTCCTGGAGCATCAGCCAGTCTC
ACCTGCACCTTGCGCAGTGGCATCAATGTTGGTACCTACAGGATATACTGGTACCAGCAG
AAGCCAGGAGTCCTCCCCAGCCGCTTCCTGAGGTACAAATCAGACTCAGATAAGCAGCAG
GGCTCTGGAGTCCCCAGCCGCTTCTCTGGATCCAAAGATGCTTCGGCCAATGCAGGGATT
TTACTCATCTCTGGGCTCCAGTCTGAGGATGAGGCTGACTATTACTGTATGATTTGGCAC
AGCAGCGCTTCT (SEQ ID NO: 259)
>V4-3
CAGCCTGTGCTGACTCAGCCAACTTCCCCTCTCAGCATCTCCTGGAGCATCAGCCAGACTC
ACCTGCACCTTGCGCAGTGGCATCAATCTTGGTAGCTACTACTGGTACCAGCAG
AAGCCAGAGAGCCCTCCCCAGCCGCTTCCTGAGCTACTACCAGACTCAAGTAAGCATCAG
GGCTCTGGAGTCCCCAGCCGCTTCTCTGGATCCAAAGATGCTTCGAGCAATGCAGGGATT
TTAGTCATCTCTGGGCTCCAGTCTGAGGATGAGGCTGACTATTACTGTATGATTGGCAC
AGCAGTGCTTCT (SEQ ID NO: 260)
>V4-4
CAGCCTGTGCTGACTCAGCCATTCAGCCATCTTCTGCATCTTCTGGAGCATCAGTCAGACTC
ACCTGCATGCTGAGCAGTGGCTTCAGTGTTGGGGACTTCTGGATAAGGTGGTACCAACAA
AAGCCAGGAACCCTCCCCGGTATCTCCTGTACTACCACTCAGACTCCAATAAGGGCCAA
GGCTCTGGAGTTCCCCAGCCGCTTCCTGGATCCAACGATGCATCAGCAATGCAGGGATT
CTGCGTATCTCTGGGCTCCAGCCTGAGGATGAGGCTGACTATTACTGTGTGGTACATGGCAC
AGCAACTCTAAGACTCA (SEQ ID NO: 261)

FIG. 22H

>V4-6
CGGCCCGTGCTGACTCAGCCGCCCCTCTCTGTCTGCATCCCCGGAGCAACAGCCAGACTC
CCCTGCACCCTGAGCAGTGACCTCAGTGTTGGTGGTAAAACATGTTCTGGTACCAGCAG
AAGCCAGGGAGCTCTCCCAGGTTATTCCTGGTTATCACTCAGGAGACAAGCAGCTG
GGACCTGGGGTCCCCCAGTCGAGTCTCGAGTCTCTGGCTCCAAGGAGACCTCAAGTAACACAGCGTTT
TTGCTCATCTCTGGGCTCGGCCTCCAGCTGAGGACGAGGCCGATTATTACTGCCAGGTGTACGAA
AGTAGTGCTAAT (SEQ ID NO: 262)
>V5-1
CTGCCTGTGCTGACTCAGCCCCCGTCTCTGCATCTGCCTTGCTGTGGGAGCCTCGATCAAGCTC
ACCTGCACCCTAAGCAGTGAGCACAGCACCTACACACCATCGAATGGTATCAACAGAGACCA
GGGAGTCCCCCAGTATATATAAGAAGGTTAAGAGTGATGGCAGCCACAGCAAGGGGAC
GGGATCCCCGATCGCTTCATGGGCTCCAGTTCTGGGGCTGACCGCTACCTCACCTTCTCC
AACCTCCAGTCCAGTCTGACGATGAGGCTGAGTATCACTGTGGAGAGAGCCACACGATTGATGGC
CAAGTCGGTTGA (SEQ ID NO: 263)
>V5-2
CAGCCTGTGCTGACTCAGCCACCTTCTGCATCAGCCTCCCTGGGAGCCTCGGTCACACTC
ACCTGCACCCTGAGCAGCGGCTACACAGTAATTATAAAGTGGACTGGTACCAGCAGAGACCA
GGGAAGGGCCCCCCAGGTTTGTGATCGCGAGTGGGCACTGTGGGATCGTGTGGGATCCAAGGGG
GATGGGCATCCCTGATCGCTTCTCAGTCTGCTTCTCAGTCTTGGGCTCAGGCTGAATCGGTACCTGACCATC
AAGAACATCCAGGAGAAGATGAGAGATGACTACCACTGTGGGGCAGACCATGGGCAGTGGG
AGCAACTTCGGTGTAA (SEQ ID NO: 264)
>V5-4
CAGCCTGTGCTGACTCAATCATCCCTCTGCCTCTGCCTTCCCTGGGATCCTCGGTCAAGCTC
ACCTGCACTCTGAGCAGTGGGCACAGTAGCTACATCATCGCATGGCATCAGCAGCCA
GGGAAGGCCCCTCGGTACTTGATGAAGCTTGAAGTAGTGGAAGCTACAACAAGGGAGC
GGAGTTCCTGATCGCTTCGGGCTCTGGGGCTGACCGCTACCTCACCATCTCC
AACCTCCAGTTTGAGGATGAGGCTGATTATTACTGTGAGACCTGGGACAGTAACACTCA
(SEQ ID NO: 265)

FIG. 22I

>V5-6
CAGCTTGTGCTGACTCAATCGCCCTCTGCCTCCCTGCCCTTGGGAGCCTCGGTCAAGCTC
ACCTGCACTCTGAGCAGTGGGCACAGCTACGCCATCGCTACGCTCAGCAGCCA
GAGAAGGGCCCTCGGTACTTGATGAAGCTTAACAGTGATGGCAGCCACAGCAAGGGGAC
GGGATCCCCTGATCGCTTCTCAGGCTCCAGCTCTGGGCTGAGCGCTACCTCACCATCTCC
AGCCTCCAGTCTGAGGATGAGGCTGACTATTACTGTCAGACCTGGGGCACTGGCATTCA
(SEQ ID NO: 266)

FIG. 22J

ADDITIONAL SEQ IDs

SEQ ID NO: 1  Light Chain VR

Asp Ile Gln Met Thr Gln Ser Pro Ser Ser Leu Ser Ala Ser Val Gly Asp Arg Val Thr Ile Thr Cys Arg Ala Ser Gln Gly Ile Arg Asn Tyr Leu Ala Trp Tyr Gln Gln Lys Pro Gly Lys Ala Pro Lys Leu Leu Ile Tyr Ala Ala Ser Thr Leu Gln Ser Gly Val Pro Ser Arg Phe Ser Gly Ser Gly Ser Gly Thr Asp Phe Thr Leu Thr Ile Ser Ser Leu Gln Pro Glu Asp Val Ala Thr Tyr Tyr Cys Gln Arg Tyr Asn Arg Ala Pro Tyr Thr Phe Gly Gln Gly Thr Lys Val Glu Ile Lys

SEQ ID NO: 2:  Heavy Chain VR

Glu Val Gln Leu Val Glu Ser Gly Gly Gly Leu Val Gln Pro Gly Arg Ser Leu Arg Leu Ser Cys Ala Ala Ser Gly Phe Thr Phe Asp Asp Tyr Ala Met His Trp Val Arg Gln Ala Pro Gly Lys Gly Leu Glu Trp Val Ser Ala Ile Thr Trp Asn Ser Gly His Ile Asp Tyr Ala Asp Ser Val Glu Gly Arg Phe Thr Ile Ser Arg Asp Asn Ala Lys Asn Ser Leu Tyr Leu Gln Met Asn Ser Leu Arg Ala Glu Asp Thr Ala Val Tyr Tyr Cys Ala Lys Val Ser Tyr Leu Ser Thr Ala Ser Ser Leu Asp Tyr Trp Gly Gln Gly Thr Leu Val Thr Val Ser Ser

SEQ ID NO: 3   Light Chain CDR3

Gln Arg Tyr Asn Arg Ala Pro Tyr Xaa

SEQ ID NO: 4   Heavy Chain CDR3

Val Ser Tyr Leu Ser Thr Ala Ser Ser Leu Asp Xaa

SEQ ID NO: 9

CQYIKANSKFIGITELKK

FIG. 23A

SEQ ID NO: 10

EVQLVESGGGLVQPGGSLRLSCAVSGYSITSGYSWNWIRQAPGKGLEWVA
SITYDGSTNYNPSVKGRITISRDDSKNTFYLQMNSLRAEDTAVYYCAR

SEQ ID NO: 11

DIQLTQSPSSLSASVGDRVTITCRASQSVDYDGDSYMNWYQQKPGKAPKLLIYAASYLESGVPSRFSGSGSGTDFTLTISSLQPEDFATYY
CQQSHEDPYTFGQGTKVEIKR
TVAAPSVFIFPPSDEQLKSGTASVVCLLNNFYPREAKVQWKVDNALQSGNSQESVTEQDSKDSTYSLSSTLTLSKADYEKHKVYACEVT
HQGLSSPVTKSFNRGEC

SEQ ID NO:12 LC--consensus for D2E7

DIQMTQSPSSLSASVGDRVTITCRASQGIRNYLAWYQQKPGKAPKLLIYAASTLQSGVPSRFSGSGSGTDFTLTISSHQPEDVATYYCQRY
NRAPYTFGQGTKVE

SEQ ID NO:13 HC

EVQLVESGGGLVQPGRSLRLSCAASGFTFDDYAMHWVRQAPGKGLEWVSAITWNSGHIDYADSVEGRFTISRDNAKNSLYLQMNSLRA
EDTAVYYCAKVSYLSTASSLDYWGQGTLVTVS

SEQ ID NO: 14

CCGGCAAGCTCCAGGGGAAGGGC

FIG. 23B

REDUCING THE RISK OF HUMAN ANTI-HUMAN ANTIBODIES THROUGH V GENE MANIPULATION

REFERENCE TO RELATED APPLICATION

The present application is a divisional of U.S. application Ser. No. 11/136,250, filed May 23, 2005, now U.S. Pat. No. 7,625,549, which is a continuation in part of U.S. nonprovisional application Ser. No. 11/084,554 filed Mar. 17, 2005, now abandoned, and PCT Application No.: PCT/US2005/009306, filed Mar. 17, 2005, both of which claim priority to U.S. provisional application No. 60/554,372, filed Mar. 19, 2004, and U.S. provisional application No. 60/574,661, filed May 24, 2004, all of which are hereby incorporated by reference in their entireties.

SEQUENCE LISTING

The present application is being filed along with a Sequence Listing in electronic format. The Sequence Listing is provided as a file entitled SeqList_ABGENIX-100CPD-V.txt, created Sep. 29, 2009, last modified Oct. 12, 2009, which is 177,809 bytes in size. The information in the electronic format of the Sequence Listing is incorporated herein by reference in its entirety.

FIELD OF THE INVENTION

Embodiments of the invention relate to the prediction, manipulation, and prevention of immunogenicity and to XenoMouse® animals and other similar organisms and methods of using them for predicting and altering the risk that a substance, such as an antibody, or a particular method will induce a human anti-human antibody response in a patient.

BACKGROUND OF THE INVENTION

The utility of antibodies in the therapy of clinically relevant diseases is well acknowledged. One of the primary dangers of these antibodies is the risk of an immune response by the patient, which receives the antibody, e.g., that the patient will make antibodies to the therapeutic antibodies.

Generally, previous research has focused on the risk associated with the addition of a mouse-based antibody to a human, resulting in the human patient launching an immune response against the mouse-based antibody. This immune response has also been termed a HAMA response, for "human anti-murine antibody."

One attempt to limit this HAMA response is described in U.S. Pub. No. 20040005630 to Gary Studnicka (Published Jan. 8, 2004) herein incorporated in its entirety by reference. This publication discloses possible methods for how one might compare sequences, on an amino acid level, in order to determine which amino acids one might be able to change without reducing the affinity of the antibody, while simultaneously reducing the immunogenicity of the antibody so that one could administer the altered antibody to heterologous species. This reference suggests that the way to overcome the problem of a HAMA response is to make a residue by residue comparison of a working antibody to a consensus sequence. Particular amino acid positions that are exposed to solvent are then changed, if the residue is not involved in binding and if that residue is highly or moderately conserved in a human consensus sequence.

Others have attempted to determine whether or not $V_H$ gene usage is correlated with autoimmune diseases in general. These attempts have had little success. One such attempt was made by Huang et al. (Clin. Exp. Immunol. 112:516-527, (1998)). Huang et al. attempted to determine if there was some correlation between $V_H$ usage in patients with rheumatoid arthritis. Previous studies had resulted in conflicting results. Huang et al. looked at eight different $V_H 3$ genes and three different $V_H 4$ genes. However, their conclusion was that usage of individual $V_H$ genes in peripheral blood B cells was not affected by the disease. Huang et al. concluded that while there may be some $V_H$ genes that are preferentially used in rheumatoid factors, the overall representation of $V_H$ genes in the peripheral B cells is not altered. Moreover, these experiments were limited to generalized autoimmune problems.

The complexities in attempting to reduce immunogenicity are numerous. For example, several factors to be considered include the following: murine constant regions, V-region sequences, human immunoglobulin allotypes, unusual glycosylation, method of administration, frequency of administration, dosage of antibody, patient's disease status, patient's immune status, patient's MHC haplotype, specificity of antibody, cell surface or soluble antigen, degree of aggregation of the biologic being administered, formation of immune complexes with antigen, complement activation by antibody, Fc receptor binding by antibody, inflammation and cytokine release. (Mike Clark, Immunology Today, August 2000). However, Clark noted that some of the immunogenicity issues associated with V-region sequences can be altered by humanization.

Several studies have addressed polymorphisms and repertoire expression of V genes, sometimes in relation to ethnicity, age or gender. These reports relied on a single or very few donors (Hufnagle et al., Ann N Y Acad Sci.; 764:293-295 (1995); Demaison et al., Immunogenetics., 42:342-352 (1995); Wang et al., Clin Immunol., 93:132-142 (1999); Rao et al., Exp Clin Immunogenet., 13:131-138 (1996); Brezinschek et al., J Immunol., 155:190-202 (1995); and Rassenti et al., Ann N Y Acad Sci., 764:463-473 (1995)), analyzed leukemia or autoimmune patients (Dijk-Hard et al., J Autoimmun. 12:57-63 (1999); Logtenberg et al., Int Immunol., 1:362-366 (1989); Dijk-Hard et al., Immunology, 107:136-144 (2002); Johnson et al., J Immunol., 158:235-246 (1997)), focused on a limited number of genes (Pramanik et al., Am J Hum Genet., 71:1342-1352 (2002); Rao et al., Exp Clin Immunogenet., 13:131-138 (1996); Huang et al., Mol Immunol., 33:553-560 (1996); and Sasso et al., Ann N Y Acad Sci., 764:72-73 (1995)), or categorized $V_H$ gene use by family (Hufnagle et al., Ann N Y Acad Sci., 764:293-295 (1995); Rassenti et al., Ann N Y Acad Sci., 764:463-473 (1995); and Logtenberg et al., Int Immunol., 1:362-366 (1989); Ebeling et al., Int Immunol., 4:313-320 (1992)).

Unfortunately, even when the HAMA response is eliminated, therapeutic antibodies can still elicit an immune response in patients. In other words, the antibody can elicit a human anti-human antibody (HAHA) response. This response can limit the antibodies' efficacy and can negatively affect their safety profile in the worst-case scenario. As an example, the fully human phage display-derived anti-TNF antibody HUMIRA® (Abbott Laboratories) unexpectedly provokes a HAHA response in approximately 12% of patients on monotherapy and about 5% in combination therapy with the methotrexate. Thus, while attempts have been made in overcoming the risks associated with a HAMA response, little has been done to address HAHA response issues.

SUMMARY OF THE INVENTION

Genes that are under-represented in the general population can contribute to the immunogenicity of a therapeutic antibody having a protein structure that can be encoded by such a gene. Identification of these genes will aid in the assessment of therapeutic candidate monoclonal antibodies and can be incorporated as a selection factor at the time of preclinical development. This represents the first study of a large number of normal donors with respect to the presence and usage of a large number of individual $V_H$ and $V_L$ genes and how these individual genes correlate with the risk of a HAHA response.

One aspect of the invention is a method of selecting an antibody for a host. The antibody has a decreased likelihood of causing a human anti-human antibody (HAHA) response in the host is provided. The method comprises providing an immunoglobulin gene encoding a candidate antibody, providing a host immunoglobulin gene from a host that is to receive the candidate antibody, comparing the immunoglobulin gene encoding the candidate antibody with the host immunoglobulin gene, and selecting the candidate antibody if the immunoglobulin gene encoding the antibody is the same as the host immunoglobulin gene, thereby selecting an antibody for the host that has a decreased likelihood of causing a HAHA response. In some embodiments, it further comprises repeating the steps of providing, comparing, and selecting for more than one immunoglobulin gene of the candidate antibody. In some embodiments, it further comprises repeating the steps of providing, comparing, and selecting for every immunoglobulin V gene of the candidate antibody. In some embodiments, the immunoglobulin gene is a V gene. In some embodiments, the V gene is a $V_H$ (heavy) gene. In some embodiments, the V gene is a $V_L$ (light) gene. In some embodiments, providing a gene comprises recognizing the identity of the immunoglobulin gene.

Another aspect of the invention is a method of selecting an antibody with a reduced risk of inducing a human anti-human antibody (HAHA) response for a host. It comprises comparing an antibody V gene set with a host V gene set and selecting the antibody that is encoded by a V gene set that is present in the set of host V genes. In some embodiments, the host V genes are transcribed in the host. In some embodiments, the host V genes are translated in the host. In some embodiments, the V genes are $V_H$ genes. In some embodiments, the V genes are $V_L$ genes.

Another aspect of the invention is a method of excluding an antibody from use in the treatment of a host. The method comprises providing a gene encoding at least a part of an antibody, determining if the gene is the same as a gene in a host to receive the antibody, and excluding the antibody if the gene encoding at least a part of the antibody is not also a gene in the host. In some embodiments, the method further comprises providing all genes encoding the antibody, determining if each of the genes is the same as any genes in the host, and excluding the antibody if any of the genes is not also a gene in the host. In some embodiments, the antibody is excluded if the gene encoding at least a part of an antibody is a $V_H3$-9, $V_H3$-13, or $V_H3$-64 gene.

Another aspect of the invention is a method of selecting an antibody for administration to a member of a population, the antibody having a reduced likelihood of causing a human anti-human antibody (HAHA) response in the population, comprising providing a V gene encoding at least a part of a candidate antibody to be administered to an individual in a population, providing a frequency of occurrence for the V gene in the population, and selecting the candidate antibody if the V gene has a high frequency of occurrence in the population. In some embodiments, the method further comprises providing all of the V genes for the candidate antibody, providing a frequency of occurrence for all of the V genes in the population, and selecting the candidate antibody if all of the V genes have a frequency of occurrence above a predetermined frequency of occurrence in the population. In some embodiments, the predetermined frequency of occurrence is at least 50% of the population. In some embodiments, the predetermined frequency of occurrence is at least 80% of the population. In some embodiments, the predetermined frequency of occurrence is at least 99% of the population. In some embodiments, the predetermined frequency of occurrence is at least 100% of the population. In some embodiments, the V gene is an immunoglobulin $V_H$ type gene or variant thereof. In some embodiments, the V gene is an immunoglobulin $V_L$ type gene or variant thereof. In some embodiments, the antibody is from a nonhuman animal that produces human antibodies.

Another aspect of the invention is a method of identifying an antibody with a high risk of inducing a human anti-human antibody (HAHA) response in a host. It comprises determining if a gene that encodes the antibody is one of a $V_H3$-9, a $V_H3$-13, and a $V_H3$-64 gene.

Another aspect of the invention is a method for selecting an antibody. The method comprises determining a frequency with which a gene encoding an antibody occurs in a particular human population and selecting the antibody as a function of the frequency, thereby reducing the risk that the antibody will induce a human anti-human antibody response in a human host.

Another aspect of the invention is a method of selecting an antibody for a patient in order to reduce the risk that the antibody will induce a human anti-human antibody response. The method comprises determining the ethnic background of a patient and selecting an antibody comprising a set of V genes that is optimized for the occurrence of a V gene that is common in the ethnic background so as to reduce the risk that the antibody will induce a human anti-human antibody response. In some embodiments, the method further comprises a step of initially determining which V genes are common in the ethnic background. In some embodiments, the antibody is selected by comparing substantially all of the V genes of the antibody to a normalized host V gene profile for the ethnic background.

Another aspect of the invention is a method for determining a risk of a human anti-human antibody (HAHA) response occurring for a particular antibody. The method comprises identifying a gene that encodes an antibody, comparing the identity of the gene to a gene profile, and scoring the gene if it occurs with less than a predetermined frequency of occurrence in the gene profile, wherein a score indicates a risk of a HAHA response occurring for the antibody. In some embodiments, the gene profile is a gene profile of an individual and the predetermined frequency of occurrence is 100%. In some embodiments, the gene profile is a normalized host V gene profile for a population. In some embodiments, the normalized host V gene profile is selected based on an individual's genetic makeup. In some embodiments, the normalized host V gene profile is selected based on an individual's ethnic background. In some embodiments, a V gene in the normalized host V gene profile has a frequency of occurrence that is below the predetermined frequency of occurrence and is selected from the group consisting of: $V_H3$-9, $V_H3$-13, and $V_H3$-64. In some embodiments, the predetermined frequency of occurrence is selected from the group consisting of: at least 50%, at least 60%, at least 70%, at least 80%, at least 90%, at least 95%, at least 99%, and at least 100%.

Another aspect of the invention is a transgenic animal for identifying antibodies that have a risk of inducing an immunological response for a particular human population. The transgenic mouse comprises a transgenic animal that has been modified to produce human antibodies in response to antigenic challenge, wherein a set of human immunoglobulin genes in the transgenic animal is the same as a gene set of a particular human population, and wherein the transgenic animal does not have any additional V genes apart from those in the gene set of the particular human population. In some embodiments, the transgenic animal has been modified to produce fully human antibodies in response to antigenic challenge. In some embodiments, the set of human immunoglobulin genes in the transgenic animal is present in at least 50% of the particular human population. In some embodiments, the set of human genes in the transgenic animal is present in at least 100% of the particular human population. In some embodiments, an endogenous loci of the transgenic animal has been inactivated. In some embodiments, the population consists of one person. In some embodiments, the population consists essentially of a genetically related family. In some embodiments, the population is defined across ethnic groups. In some embodiments, the population is defined within one ethnic group. In some embodiments, the transgenic animal further comprises an identifier that matches the transgenic animal with the population. In some embodiments, the transgenic animal further comprises a fully human or humanized antibody, and the fully human or humanized antibody is foreign to the transgenic animal.

Another aspect of the invention is a transgenic mouse for use in detecting an antibody with a relatively high-risk of inducing a human anti-human antibody (HAHA) response. It comprises a transgenic mouse that can express a fully human antibody, wherein the transgenic mouse comprises a human immunoglobulin gene set, and wherein the transgenic mouse lacks V genes in the human immunoglobulin gene set that a patient that is to receive an antibody tested by the transgenic mouse also lacks, and a human antibody in the transgenic mouse, wherein the human antibody is to be administered to the patient, and wherein the human antibody is an exogenous antibody to the transgenic mouse.

Another aspect of the invention is a transgenic mouse for use in identifying antibodies that will induce an immunological response in a particular patient population. The mouse comprises a transgenic mouse that is configured to produce humanized antibodies in response to antigenic challenge, wherein the mouse comprises a human immunoglobulin gene set, and wherein the human immunoglobulin gene set does not contain any high risk genes. In some embodiments, the gene set is a V gene set. In some embodiments, the high-risk genes are $V_H3-9$, $V_H3-13$, and $V_H3-64$. In some embodiments, the V gene set consists essentially of low-risk genes. In some embodiments, the high risk genes are any genes that do not occur in 100% of the population. In some embodiments, the mouse is used to determine if other substances or variations in methods increase the likelihood that a HAHA response will occur. Those that increase or decrease the likelihood of a HAHA response can then be identified. In some embodiments, the variable that is altered is the method of administration of the antibody, the amount of antibody administered, or the number of times that an antibody is administered. In some embodiments, substances to be added include adjuvants, antigenic substances, and/or candidate HAHA inhibitors.

Another aspect of the invention is a kit for detecting an antibody that can induce a human anti-human antibody (HAHA) response in a patient. The kit comprises a transgenic mouse that can express a fully human antibody, wherein the transgenic mouse comprises human immunoglobulin genes, and wherein the transgenic mouse lacks a V gene set that a patient that is to receive an antibody tested by the transgenic mouse also lacks and a means for administering an antibody to the transgenic mouse. In some embodiments, the kit further comprises a means for detecting a HAHA response in the transgenic mouse. In some embodiments, the kit further comprises an antigenic substance, wherein the antigenic substance is associated with an antibody to be tested to see if it will induce a HAHA response. In some embodiments, the antigenic substance is T cell epitope (TCE).

Another aspect of the invention is a method of selecting an antibody so as to reduce the risk of a human anti-human antibody (HAHA) response being induced in a human. The method comprises administering an antibody to a transgenic mouse, wherein the transgenic mouse comprises human genes allowing the mouse to be capable of producing a fully human or humanized antibody, observing if the antibody results in a HAHA response in the transgenic mouse, and selecting the antibody if it does not result in a HAHA response in the mouse. In some embodiments, the method further comprises the step of selecting a different antibody if the first administered antibody results in a HAHA response and repeating the steps until an antibody is observed that does not induce a HAHA response. In some embodiments, the antibody is a fully human antibody. In some embodiments, the observing if the antibody results in a HAHA response comprises examining a blood sample from the mouse for an antibody that can bind to the administered fully human antibody. In some embodiments, the transgenic mouse comprises the same V genes as the human that is to receive the antibody. In some embodiments, the method further comprises the step of first selecting the transgenic mouse based upon a similarity between a human immunoglobulin gene set in the transgenic mouse and a human immunoglobulin gene set in the human. In some embodiments, the transgenic mouse comprises the same $V_L$ genes as the human that receives the antibody. In some embodiments, the transgenic mouse comprises the same $V_H$ genes as the human that receives the antibody. In some embodiments, the V genes in the transgenic mouse consists essentially of the same V genes as the human that receives the antibody. In some embodiments, the $V_L$ genes in the transgenic mouse consists essentially of the same $V_L$ genes as the human that receives the antibody. In some embodiments, the $V_H$ genes in the transgenic mouse consists essentially of the same $V_H$ genes as the human that receives the antibody. In some embodiments, the transgenic mouse is essentially free of high risk genes. In some embodiments, the transgenic mouse essentially consists of low risk genes. In some embodiments, the transgenic mouse does not have a gene selected from the group consisting of: $V_H3-9$, $V_H3-13$, and $V_H3-64$ genes.

Another aspect of the invention is a method of determining a risk that an antibody will induce a human anti-human antibody (HAHA) response in a patient. The method comprises administering an antibody to a nonhuman animal that can produce human or humanized antibodies, waiting for a period of time sufficient to allow a HAHA response to occur, and observing if a HAHA response is induced by the antibody. In some embodiments, the nonhuman animal is a transgenic mouse, and wherein all of the somatic and germ cells of the mouse comprise a DNA fragment of human chromosome 14 from the five most proximal $V_H$ gene segments, continuing through the D segment genes, the J segment genes and the constant region genes through C-delta of the human immunoglobulin heavy chain locus, wherein the fragment does not contain a C-gamma gene, and wherein the fragment is operably linked to a human C-gamma-2 region gene. In some embodiments, the method further comprises the step of selecting a transgenic mouse based on a similarity between the patient immunoglobulin gene set and the transgenic mouse immunoglobulin gene set. In some embodiments, the similarity is that the gene sets lack a same immunoglobulin gene. In some embodiments, the same immunoglobulin gene is a high-risk gene.

Another aspect of the invention is a kit for assessing the risk of a human anti-human antibody (HAHA) response being induced by an antibody. The kit comprises a nonhuman animal that comprises a means for producing a fully human antibody, an exogenous antibody to be tested in the nonhuman animal, means for administering the antibody to the nonhuman animal, and means for testing if a HAHA response occurred in the nonhuman animal. In some embodiments, the non-human animal has no high-risk genes. In some embodiments, the high-risk genes are selected from the group consisting of: $V_H3$-9, $V_H3$-13, and $V_H3$-64.

Another aspect of the invention is a transgenic mouse for screening for agents that inhibit the induction of a human anti-human antibody (HAHA) response. The mouse comprises a human gene configured to allow the transgenic mouse to produce a fully human or humanized antibody, and a HAHA inducing antibody in the transgenic mouse. In some embodiments, the transgenic mouse further comprises a candidate HAHA inhibitor that is in the transgenic mouse. In some embodiments, the transgenic mouse lacks any high-risk genes. In some embodiments, the high-risk genes are selected from the group consisting of: $V_H3$-9, $V_H3$-13, and $V_H3$-64 and a combination thereof. In some embodiments, the HAHA inducing antibody is encoded by a high-risk gene. In some embodiments, the high risk gene is selected from the group consisting of: $V_H3$-9, $V_H3$-13, $V_H3$-64, and some combination thereof.

Another aspect of the invention is a method for screening for agents that inhibit the induction of a human anti-human antibody (HAHA) response. The method comprises administering a HAHA inducing antibody to a transgenic mouse, the transgenic mouse comprising a human gene configured to allow the transgenic mouse to produce a fully human or humanized antibody, administering a candidate HAHA inhibitor to the transgenic mouse, and observing if a resulting HAHA response is inhibited after an amount of time sufficient to allow for a HAHA response. In some embodiments, the HAHA inducing antibody is an antibody encoded by a high-risk gene. In some embodiments, the HAHA inducing antibody is an antibody with a high-risk V gene. In some embodiments, the HAHA inducing antibody is created by a transgenic mouse capable of making fully human antibodies. In some embodiments, the HAHA response is monitored through the production of an antibody that binds to the HAHA inducing antibody. In some embodiments, the candidate HAHA inhibitor is administered to the transgenic mouse before the HAHA inducing antibody is administered to the transgenic mouse. In some embodiments, more than one candidate HAHA inhibitor is administered to the transgenic mouse.

Another aspect of the invention is an antibody composition comprising a fully human or humanized antibody and a molecule of a T cell epitope (TCE), wherein the molecule of TCE is connected to the antibody. In some embodiments, the antibody composition further comprises more than one antigenic substance attached to the antibody. In some embodiments, the antigenic substance is attached to the antibody by a maleimide group.

Another aspect of the invention is a method of increasing the probability that a human anti-human antibody (HAHA) response will be detected in a transgenic mouse, the method comprising the steps of attaching an antigenic substance to a fully human or humanized antibody and administering the combined antigenic substance and antibody to a transgenic mouse that is capable of producing a fully human or humanized antibody to determine if the combination induces a HAHA response. In some embodiments, the transgenic mouse comprises human immunoglobulin V genes and lacks mouse immunoglobulin V genes. In some embodiments, the transgenic mouse comprises a set of V genes that essentially consists of a same set of V genes that a host that is to receive the fully human or humanized antibody has.

In some aspects, the invention is a transgenic mouse for screening for agents that inhibit the induction of a human anti-human antibody (HAHA) response. The transgenic mouse for screening for agents comprises a human gene configured to allow the transgenic mouse to produce a fully human or humanized antibody and a HAHA inducing antibody in the transgenic mouse. The HAHA inducing antibody is encoded by a gene that the transgenic mouse does not possess in its genome. In some embodiments, the transgenic mouse comprises a candidate HAHA inhibitor that is inside of said transgenic mouse. In some embodiments, the HAHA inducing antibody is encoded by a high-risk gene selected from the group consisting of $V_H3$-9 $V_H3$-13, and $V_H3$-64.

In some aspects, the invention is a method for screening for agents that inhibit the induction of a human anti-human antibody (HAHA) response. The method comprises administering a HAHA inducing antibody to a transgenic mouse where the transgenic mouse comprises a human gene configured to allow the transgenic mouse to produce a fully human or humanized antibody, administering a candidate HAHA inhibitor to the transgenic mouse, and observing if a resulting HAHA response is inhibited after an amount of time sufficient to allow for a HAHA response.

In some aspects, the invention is a method for monitoring a HAHA response. The method comprises providing a first transgenic mouse that comprises a human gene configured to allow the first transgenic mouse to produce a fully human or humanized antibody, administering to the first transgenic mouse a first foreign antibody under a first condition, and determining a presence of a HAHA response in the first transgenic mouse. In some embodiments, the method further comprises providing a second transgenic mouse that comprises a human gene configured to allow the second transgenic mouse to produce the fully human or humanized antibody, administering to the second transgenic mouse a second foreign antibody under a second condition, wherein the first condition and the second conditions are a same variable but are different from one another, determining a presence of a HAHA response in the second transgenic mouse, and comparing the presence of the HAHA response in the first transgenic mouse to the presence of the HAHA response in the second transgenic mouse, thereby determining which condition results in a greater HAHA response. In some embodiments, the first transgenic mouse and the second transgenic mouse are different mice but produce a same fully human or humanized antibody. In some embodiments, the first foreign antibody and the second foreign antibody have a same amino acid sequence or primary structure. In some embodiments, the first condition is a first expression system and the second condition is a second expression system. In some embodiments, the first condition is a first formulation and the second condition is a second formulation, wherein the first formulation is used to produce the first foreign antibody and the second formulation is used to produce the second foreign antibody. In some embodiments, the first condition is a first degree of aggregation of the first foreign antibody and the second condition is a second degree of aggregation of the second foreign antibody. In some embodiments, the first condition is a first amount of the first foreign antibody and the second condition is a second amount of the second antibody. In some embodiments, the first condition is a first dosing regimen and the second condition is a second dosing regimen. In some embodiments, the first condition is a first route of administration and the second condition is a second route of administration. In some embodiments, the first and second routes of administration are different and are selected from the group consisting of: subcutaneously, intravenously, intraperitoneally, intracranially, intradermally, intramuscularly, and orally. In some embodiments, the first condition is a first immune system and the second condition is a second immune system, wherein the first and second immune systems have differing amounts of activity. In some embodiments, the first condition is a first isotype of the first foreign antibody and the second condition is a second isotype of the second foreign antibody. In some embodiments, the first and second foreign antibodies comprise a protein section encoded by a gene that is not expressed in the transgenic animal. In some embodiments, determining a presence of a HAHA response is a qualitative determination. In some embodiments, determining a presence of a HAHA response is a quantitative determination.

In some aspects, the invention is a method for increasing the probability that a human anti-human antibody (HAHA) response will be detected in a transgenic mouse. The method comprises the steps of attaching an antigenic substance to a fully human or humanized antibody, and administering the combined antigenic substance and antibody to a transgenic mouse that is capable of producing a fully human or humanized antibody to determine if the combination induces a HAHA response.

BRIEF DESCRIPTION OF THE DRAWINGS

FIG. 1A is a representation of an example of the raw data for a normalized host V gene profile. Host 1 has V genes for genes a-d.

FIG. 1B is a representation of an example of the raw data for a normalized host V gene profile, in a polypeptide or mRNA expression format. Host 1 only transcribes or translates genes A, C, and D.

FIG. 1C is a table depicting the frequency of occurrence for various genes in the population of hosts 1-5, as a function of the frequency of the gene's appearance.

FIG. 1D is a table depicting the frequency of occurrence for various genes in the same population of hosts 1-5, as a function of the frequency of the protein or mRNA appearance.

FIG. 8 depicts a table with a listing of some of the relevant genes of the present embodiments. The table also identifies genes that are relatively rare, or possible high-risk genes.

FIG. 16A is a depiction of an alignment of various $V_H$ genes.

FIG. 16B is a depiction of an alignment of various $V_H$ genes.

FIG. 17A through FIG. 17I are lists of amino acid sequences of various $V_H$ genes.

FIG. 18A through FIG. 18P are lists of nucleic acid sequences of various $V_H$ genes.

FIG. 19A through FIG. 19G are lists of amino acid sequences of various $V_{kappa}$ genes.

FIG. 20A through FIG. 20L are lists of nucleic acid sequences of various $V_{kappa}$ genes.

FIG. 21A through FIG. 21F are lists of amino acid sequences of various $V_{lambda}$ genes.

FIG. 22A through FIG. 22J are lists of nucleic acid sequences of various $V_{lambda}$ genes.

FIG. 23A and FIG. 23B are lists of additional sequences used herein.

DETAILED DESCRIPTION OF THE EMBODIMENTS

Figure 2:
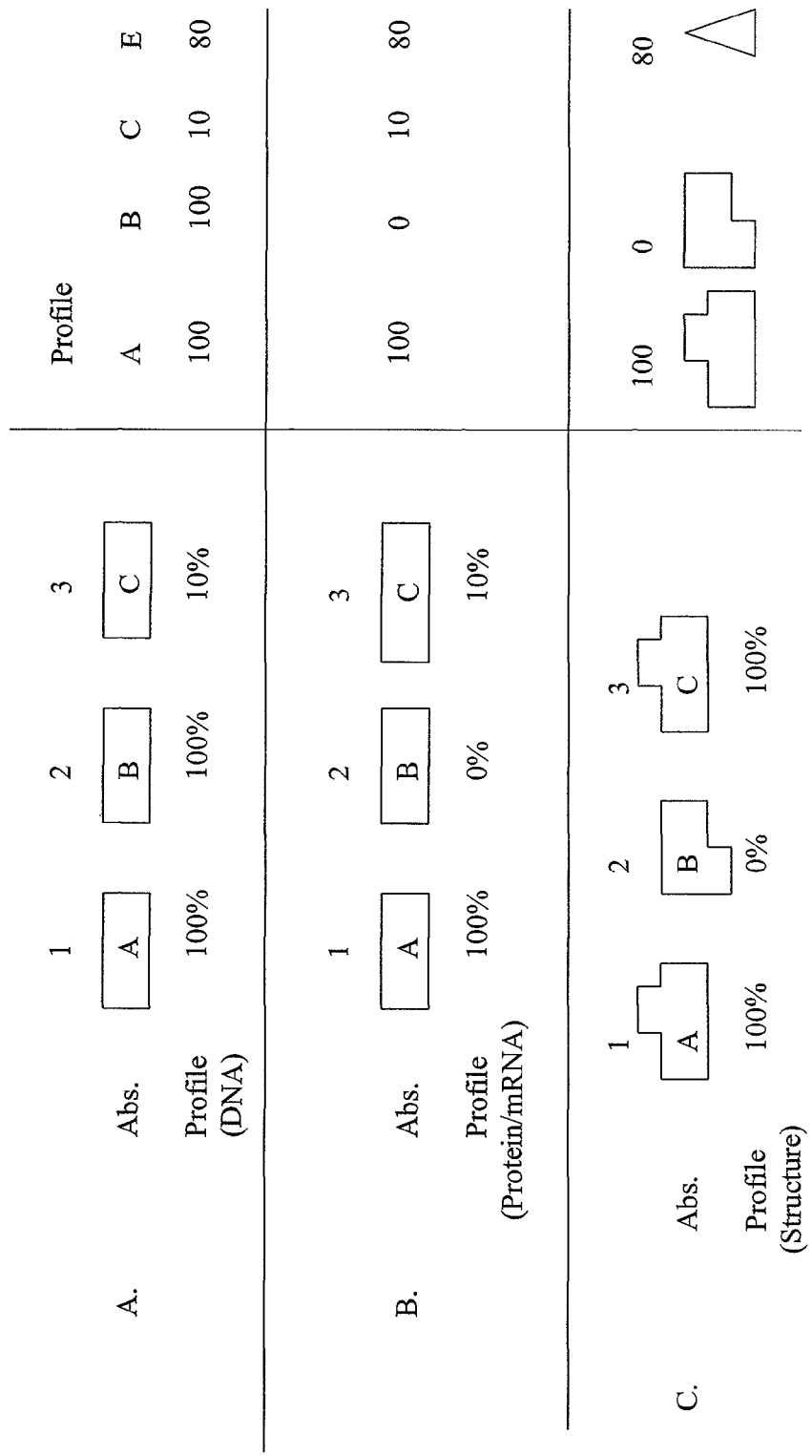
FIG. 2A is a representation of a series of antibody V genes compared to a profile.
FIG. 2B is a representation of a series of antibody V amino acid sequences compared to a profile.
FIG. 2C is a representation of antibody V region polypeptide structures compared to a profile.

It has been discovered that antibody genes that are underrepresented in the general population or in a host can contribute to the immunogenicity of a therapeutic antibody encoded by such a gene (e.g., a HAHA response). Identification and characterization of these genes will aid in the assessment of therapeutic candidate monoclonal antibodies and can be incorporated as a risk factor at the time of preclinical development. This information can be used, not only to estimate the risk that a HAHA response will occur, but in the creation of antibodies as well. Thus, antibodies with a reduced risk of inducing a human anti-human antibody (HAHA) response can readily be created and identified.

In general, there are two levels at which the risk that an antibody will induce a HAHA response can be measured: in an individual and across a population (although, in some embodiments, a population can be a population of one).

In one aspect, an antibody with a high-risk of inducing a HAHA response in a particular patient or host can be identified by comparing the gene(s) that can encode the particular antibody (e.g., an antibody gene set) with the genes in the patient or host (e.g., a host gene set). If the patient or host has the same genes as the genes encoding the antibody and if the genes are expressed in the host, then the antibody can be a low risk antibody. If the host lacks the genes or the protein encoded by the antibody genes, then there is a risk of a HAHA response occurring in the host with the particular antibody. Thus, it would be possible to pre-screen patients prior to administering an antibody so as to reduce the chance of a HAHA response that would negate the drug's efficacy or perhaps cause a serious or life-threatening allergic reaction.

In one aspect, the risk that an antibody will induce a HAHA response in an individual in a population can be determined. At the population level, the frequency of the gene in the population can be used to assess the risk that an individual in the population will experience a HAHA response if given the antibody. Thus, the methods and compositions can be used, on various levels, to gauge the risk of a HAHA response.

Some embodiments relate to methods and systems for reducing the risk that an antibody will induce a human antihuman antibody (HAHA) response in an individual.

In one aspect, the embodiments include a method for optimizing an antibody so that it has a reduced risk of inducing a HAHA response in a patient or population of patients. In this method, the antibody is optimized by identifying whether the antibody was encoded by one or more "risk genes" within the immunoglobulin gene family. If so, then the DNA or protein encoded by the risk gene is altered to reduce the likelihood that the antibody will induce a human anti-human antibody (HAHA) response when administered to a patient.

In one embodiment, the risk gene encodes at least a portion of the variable domain of the antibody. More preferably, the risk gene encodes an immunoglobulin variable ("V") region of either the heavy chain or the light chain of the antibody. The risk gene can encode a heavy V gene ($V_H$) gene. More preferably yet, the risk gene encodes a $V_H3$ gene. In another embodiment, the risk gene is a D or a J gene. In another embodiment, the risk gene is a light V gene ($V_L$) or a J gene. Preferably, the risk gene is selected from the following: $V_H3$-9, $V_H3$-13, and $V_H3$-64.

Some embodiments of the invention relate to the discovery that antibodies encoded from certain V family genes are more likely to induce a HAHA response than antibodies encoded from other V genes. Embodiments further relate to the discovery that it is possible to identify if a protein section from a V gene is likely to cause a HAHA response. This can be determined by examining how common the V gene is in the individuals of a population to which an antibody containing a portion of protein encoded by the V gene will be administered. V genes, and the proteins encoded by them, that appear throughout a population are not very likely to cause a HAHA response. On the other hand, V genes and their product proteins that are rare in the population have a greater risk of causing a HAHA response.

Because each antibody contains portions encoded by particular members of the V gene family, it is possible to screen for antibodies that were encoded by specific V genes. Accordingly, if an antibody is known to be encoded from an immunogenic (high-risk) V gene for a particular population or individual, it can be removed as a potential therapeutic antibody. Similarly, if the antibody is encoded by a V gene that is known to not be immunogenic (low-risk) for a particular population, it can be selected as a proper candidate for antibody therapy. This can allow one to assemble large pools of different antibodies, each antibody with a desired function and each antibody with a low risk of inducing a HAHA response. By being able to select or identify which antibodies have a relatively high-risk of inducing a HAHA response in a population, and eliminating those from the pool of antibodies, one can create and use large numbers of diverse antibodies, without as much concern over a HAHA response occurring.

In another aspect, the method involves the selection of particular low-risk genes (genes which appear with a frequency greater than a minimum frequency of occurrence or genes that are present in the individual). The antibody products from these genes are then assumed to have a low-risk of inducing a HAHA response in a patient. It should be realized that the selection of low risk genes or elimination of high risk genes applies not only to embodiments concerning the DNA, but also embodiments concerning proteins encoded by the genes. Thus, this aspect also includes a method for selecting low risk antibodies that are encoded by low risk genes.

In another aspect, the method is directed towards selecting an antibody for a particular patient to minimize the risk that the antibody will induce a HAHA response in that patient. In this aspect, for example, the set of genes encoding the antibody (antibody gene set) to be administered to the patient is compared to genomic, expressed, or combination of both, antibody gene information of the patient (host gene set). In this manner, one can select an antibody to administer that is encoded by genes known to be present in the patient's genome or expressed antibody repertoire. In one embodiment, the patient is first analyzed to determine the presence of V genes that are used to encode antibodies for that patient. If, for example, the $V_H3$-13 gene is used to encode antibodies in the patient, then an antibody utilizing that $V_H$ gene can be administered, as it does not have a high risk of causing a HAHA response in that patient. This can be achieved through sequence or gene comparisons, or through the use of correlative data between V gene usage and ethnic background, for example.

In another aspect, the method is directed to determining the likelihood of a HAHA response occurring in order to allow further customization and analysis of a patient's condition. Knowing this probability will allow the patient and the care provider to make a more educated guess about the cost benefit analysis of using the antibody. It will also provide additional information about future possible problems and allow the patient to start HAHA preventative treatments before any adverse side effects but when such side effects are likely.

In another aspect, a method for creating low risk antibodies through customized systems, such as an animal system or an antibody display system, is provided. For example, a XenoMouse® mouse can be created that has the same gene profile or gene set as a particular population that is identified. Similarly, antibody display libraries using a fixed number of V region frameworks can be pre-selected to use only V region frameworks from V genes assessed to have a low probability of eliciting HAHA. Thus, any antibodies generated from this customized animal or display library will be from those genes that are low risk genes for that population, thereby creating antibodies with desired characteristics that are encoded by genes that are not high-risk genes.

In another aspect, the XenoMouse® mouse, or customized version thereof, can be used to determine if an antibody will induce a HAHA response. As the XenoMouse® mouse can have the same gene set as a potential host (or host population), by administering the candidate antibody to the XenoMouse® mouse and observing if there is a HAHA response, one can determine if such a response will occur in the host.

In some embodiments, the XenoMouse® mouse has candidate antibodies administered to it and the mouse can then be observed to determine if the antibody induced a HAHA response. In some embodiments, additional substances (e.g., candidate HAHA inhibitors) are added to the mouse after, during, or before the administration of the antibody to determine if the additional substance can reduce or prevent the HAHA response. Thus, compositions and methods for identifying inhibitors of a HAHA response are also provided.

In some aspects, the XenoMouse® mouse, or similar transgenic organism, is used to determine if variations in the conditions of a treatment or experiment contribute to the immunogenicity of the antibody that is administered to the mouse. Variations of the conditions can include both variations on the substances used and variations on how the materials are used. For example, the amount, frequency of administration, type of constant domain for the antibody, or method of administration of the antibody can be varied and the resulting change in HAHA response, if any, observed.

In another aspect, various databases of information that are useful in determining or selecting various genes for the optimized antibodies are contemplated. There are several broad types of databases that are contemplated herein. There are normalized host V gene profiles that provide a general concept of the frequency of occurrence of a gene in the population. In a preferred embodiment, the V genes are heavy chain V genes or light chain V genes. Other databases include or are directed to D genes and J genes. In a preferred embodiment, the frequency of occurrence is used to predict and assign a risk value to each gene. The lower the frequency of occurrence, the higher the risk of a HAHA response in a population.

The risk can be correlated to a population in various ways. In one embodiment, the frequency of a gene is correlated to the ethnic background of an individual. In another embodiment, the frequency of a gene is correlated to the risk that the individual will have a HAHA response, based on the past history of the patient. Such a database can be produced by comparing antibodies with known sets of genes to the frequency of occurrence that the antibodies induced a HAHA response in a population of patients; thus, methods of creating these databases are also contemplated. Furthermore, additional information may be stored or examined in these databases, such as correlations by gene clustering, predicted protein sequences, predicted protein structures, necessary gene arrangement for binding, and predicted effects of altering the genes. These databases can be useful for determining both high frequency (low risk of inducing a HAHA response) genes and low frequency (high-risk of inducing a HAHA response) genes.

There are also compositions of various optimized antibodies that exhibit a reduced likelihood of inducing a human anti-human antibody response. These compositions comprise both amino acid and nucleic acid gene-optimized antibodies that can be substantially pure. Antibodies produced, optimized, or selected by the methods described herein are also contemplated. Gene-optimized antibodies containing only common or low-risk genes are also contemplated, as are gene-optimized antibodies, which have rare genes in the selection of V genes, wherein the rare genes are not functionally expressed as protein. Variants of these gene-optimized antibodies are also contemplated.

In one embodiment, a "gene-optimized" or "low-risk" antibody is created from an antibody gene set or gene pool by selecting a gene that is common in a host gene profile or a normalized host gene profile. In a preferred embodiment, the gene is a V gene and the host gene profile is a host V gene profile. In one embodiment, the gene-optimized antibody is created from the XenoMouse® mouse or customized version thereof.

In one aspect, any of the methods or compositions disclosed herein are contemplated for use not only for reducing the risk of a HAHA response, but also for reducing the risk of immunogenicity in general. In a more preferred embodiment, the methods and compositions disclosed herein are contemplated for reducing the risk of immunogenicity for humanized antibodies and chimeric and nonhuman antibodies.

In another aspect, the methods and compositions that are to be used in lowering the risk of a HAHA response can also be used to increase the risk of a HAHA response.

In another embodiment, D genes and J genes of the heavy chain and J and V genes of the light chain, as well as combinations of the genes can be analyzed and used as the $V_H$ genes can be used in the present disclosure.

I. DEFINITIONS

A HAHA response is an immunogenic response of a human host, or equivalent thereof, to a human part of an antibody. The antibody can be a fully human antibody from any source, for example, an antibody created by a human or a XenoMouse® mouse. The antibody can also be one that is humanized, as long as some part of the antibody is human. In some embodiments, the equivalent of a human host is a XenoMouse® mouse. Thus, a XenoMouse® mouse can have a HAHA response to, for example, administered human antibodies, humanized antibodies, antibodies that contain human protein sequence or are encoded by human nucleic acid sequence, or XenoMouse® mouse antibodies.

While the HAHA response is most likely induced by the proteins encoded by the risk genes; much of the analysis and data gathering may involve comparisons at the genetic level. Because of this, and for ease of disclosure, the terms "V gene," "high-risk gene," and "low-risk gene" can be used to describe not only the genetic material, but also the protein encoded by the genetic material. Thus, for the purposes of this specification, an antibody protein can "have or comprise a high-risk gene." This is not meant to suggest that an antibody protein is attached to a piece of DNA. Rather, it refers to the fact that the antibody contains protein sections that can be encoded by those genes. Since one feature of many of the present embodiments is the correlation between genes (or proteins encoded by the genes) and HAHA risk, it is convenient to discuss these structures generically in terms of units of genes, regardless of whether the actual gene is described or the protein is being discussed. Thus, an "antibody that has a $V_H3$-9 gene" actually means that there is a section of protein in the antibody that is encoded by a $V_H3$-9 gene. However, this use of the term "gene" only applies when it is describing a protein of some sort (e.g., an antibody). Thus, a mouse with a $V_H3$-9 gene or a vector with a $V_H3$-9 gene, unless otherwise specified, is referring to actual DNA material. Additionally, in some embodiments, the term "risk" can be replaced by the term "probability;" thus, for example, the probability that a HAHA response will occur can be determined or genes with a high probability of inducing a HAHA response identified or manipulated. As will be appreciated by one of skill in the art, the terms can, in some situations, be used interchangeably.

"Host V gene profile" refers to the set of V genes of a potential host or patient. The profile has information concerning the types of genes in the host and may have information concerning the frequency of those genes occurring, in protein form or mRNA, in the host. A profile can exist for individuals or for populations. An example of such a profile, the raw data that makes it up, and alternative variations of profiles, is shown in FIG. 1A-D. By comparing a gene in an antibody to the genes in the host V gene profile, one is able to determine if the potential gene is common in the host, and thus, if the gene is likely to induce a HAHA response. Similarly, if one compares the frequency of usage of the gene in the profile with a gene of an antibody, one is also able to determine if a HAHA response has a greater probability of occurring. "Host V gene set" can be used interchangeably with the "host V gene profile" for individuals and simply refers to the set of relevant genes in the host.

"Normalized host V gene profile" refers to a host V gene profile that has been normalized by some standard. A normalized host V gene profile may be normalized in many different ways. For example, at a simple level, it is normalized across several people to show the frequency that a gene occurs in any given population. A "family" normalized host V gene profile would involve using the host V gene profiles of the genetically related members of a family in order to determine which genes occur and with what frequency for those family members. An ethnic normalized host V gene profile would compare various members of particular ethnic groups in order to determine what the average frequency of occurrence for particular genes are in that particular ethnic group. A "human" normalized host V gene profile would weigh the relative frequencies of occurrence without any other defining feature, apart from the fact that the host must be human. A normalized host V gene profile allows one to determine which genes are risk genes and which genes occur with at least a common frequency of occurrence. As a normalized host V gene profile will contain genes from different people, the results are tabulated as a frequency of occurrence of each gene in the entire population. Other profiles may exist for non-human beings as well. For instance, a normalized host V gene profile could be made for cats, mice, pigs, dogs, horses, etc. Host V gene profiles can be made across species as well. These profiles can be used for any organism that contains a V gene or V gene functionally equivalent system. The larger the normalized host V gene profile, the less customized each gene-optimized antibody will be, and thus the more likely the gene-optimized antibody will induce a HAHA response. Gene-optimized antibodies selected from these larger normalized profiles can be used to produce "universal gene-optimized antibodies." These antibodies can have a reduced risk of inducing a HAHA response in the host animals, but can still be used on many different organisms or patients with different host V gene profiles. These universally optimized V gene antibodies genes can be useful when it is not convenient to determine the V gene profile of the patient to be treated.

In a population, a "risk gene" is a gene, which because of its low frequency of occurrence in the normalized host V gene profile, presents a noticeable risk that its presence in an antibody will induce a HAHA response in the patient. In one embodiment, a risk gene is one that occurs in a gene profile less than 1% of the time. In another embodiment, a gene is considered a risk gene if it occurs with a frequency of about less than 100% in the normalized host V gene profile, for example: 2%, 3%, 4%, 5%, 6%, 7%, 8%, 9%, 10%, 11%, 12%, 13%, 14%, 15%, 30%, 49%, 50%, 70%, or 99%. This is also referred to as a "high risk gene." In one embodiment, a risk gene is any gene that occurs with a frequency of occurrence that is less than a predetermined frequency of occurrence. In an individual, a "high risk gene" is a gene that the individual lacks or does not express protein for. As appreciated by one of skill in the art, the high-risk gene itself may not be responsible for inducing the HAHA response. As used herein, the term "high-risk gene" refers to the fact that a protein encoded by the gene has a high risk of inducing a HAHA response. However, because of the various techniques in which this information is obtained and can be applied, it is often easier and more accurate to simply refer to these genes as high-risk genes, rather than the proteins encoded by high-risk genes.

"Low-risk gene" is a gene that does not present a noticeable risk of inducing a HAHA response. Alternatively, the low-risk gene may actually reduce the risk of inducing a HAHA response. In a population, these genes can be identified by their common frequency of occurrence in the host V gene profile. A gene is a low-risk gene if it occurs with a frequency of at least about 1-100%, for example, 1%, 5%, 10%, 15%, 20-29%, 30-39%, 40-49%, 50-59%, 60-69%, 70-79%, 80-89%, 90-94%, 95%, 99%, and 100%. A low-risk gene can also be called a "common gene." In one embodiment, a low-risk gene is a gene that occurs with a greater frequency, in a population, than a minimum or predetermined frequency of occurrence. In an individual, a low risk gene is a gene that is expressed by the individual; and thus, there is a low risk of a HAHA response. As appreciated by one of skill in the art, the low-risk gene itself may not be responsible for not inducing the HAHA response. As used herein, the term "low-risk gene" refers to the fact that a protein encoded by the gene has a low risk of inducing a HAHA response. However, because of the various techniques in which this information is obtained and can be applied, it is often easier to refer to these as low-risk genes, rather than the proteins encoded by low risk genes. As will be appreciated by one of skill in the art, a minimum frequency of occurrence can vary depending upon the particular situation and desired treatment for a patient. One of skill in the art, in light of the present disclosure, will be able to readily determine or set the desired minimum frequency of occurrence (or predetermined frequency of occurrence). As above, a "low-risk" or similar term can be replaced with the term, "low probability", in some embodiments.

"Antibody gene set" is the set of genes that encode a particular antibody or antibodies. The entire gene set can be "optimized," which means that the composition of genes in the gene set share a degree of similarity with a possible host gene set (e.g., host V gene profile for an individual or a population). The gene set consists of V, D, J genes for the heavy chain and V and J genes for the light chain. A gene set can include all of the above genes as well.

"V gene" is an immunoglobulin variable gene.

The human immunoglobulin $V_H$ (variable, heavy chain) germline repertoire comprises at least 123 elements (Matsuda et al., J Exp Med., 188:2151-2162 (1998)), with 41 of these representing functional genes. Several studies have addressed polymorphisms and repertoire expression, sometimes in relation to ethnicity, age or gender. These reports relied on a single or very few donors (Hufnagle et al., Ann N Y Acad Sci.; 764:293-295 (1995); Demaison et al., Immunogenetics., 42:342-352 (1995); Wang et al., Clin Immunol., 93:132-142 (1999); Rao et al., Exp Clin Immunogenet., 13:131-138 (1996); Brezinschek et al., J Immunol., 155:190-202 (1995); and Rassenti et al., Ann N Y Acad Sci., 764:463-473 (1995)), analyzed leukemia or autoimmune patients (Dijk-Hard et al., J Autoimmun. 12:57-63 (1999); Logtenberg et al., Int Immunol., 1:362-366 (1989); Dijk-Hard et al., Immunology, 107: 136-144 (2002); Li et al., Blood, 103:4602-4609 (2004); Messmer et al., Blood, 103:3490-3495 (2004); Johnson et al., J Immunol., 158:235-246 (1997)), focused on a limited number of genes (Pramanik et al., Am J Hum Genet., 71:1342-1352 (2002); Rao et al., Exp Clin Immunogenet., 13:131-138 (1996); Huang et al., Mol Immunol., 33:553-560 (1996); and Sasso et al., Ann N Y Acad Sci., 764:72-73 (1995)), or categorized $V_H$ gene use by family (Hufnagle et al., Ann N Y Acad Sci., 764:293-295 (1995); Rassenti et al., Ann NY Acad Sci., 764:463-473 (1995); Logtenberg et al., Int Immunol., 1:362-366 (1989); Ebeling et al., Int Immunol., 4:313-320 (1992); and Feuchtenberger et al., J Immunol Methods, 276: 121-127 (2003)). In addition to $V_H$, various $V_L$ (variable, light chain) genes are also contemplated. The $V_L$ genes can be encoded by the $V_{kappa}$ or $V_{lambda}$ locus. One of skill in the art, given the present disclosure, will be able to apply the current teachings to determine the various HAHA associated issues regarding the various $V_{lambda}$ genes. The various sequences of these V genes are included in SEQ ID NOs: 15-266 and a listing of some of the various genes themselves, for $V_H$, $V_{lambda}$, and $V_{kappa}$, are shown in FIG. 8 and FIGS. 17A-17I, 18A-18P, 19A-19G, 20A-20L, 21A-21F, and 22A-22J.

"Optimized gene" is a gene that is present in both an antibody (in terms of encoding a part of the antibody), and in the genes of a potential host. When the gene is a V gene, it can be optimized if it is in the "normalized host V gene profile," or if an individual has the V gene as well. Such genes are generally considered "low-risk" genes, with some exceptions discussed herein. A gene can be optimized if it is identified as being a low-risk gene for a host. Alternatively, a gene can be optimized if, after a comparison of the gene in the antibody and the host gene profile, the gene is then changed so that the gene more closely resembles the genes in the host gene profile. For example, a gene of one antibody may not be present in a host gene profile; deletion of this gene will result in it being optimized.

"Gene-optimized antibody" is an antibody that has at least one low-risk gene. A gene-optimized antibody can be made or selected. If a V gene-optimized antibody is created, then the antibody contains at least one low-risk gene for a host V gene profile. If a gene-optimized antibody is selected, the antibody is relatively enriched for low-risk genes or relatively depleted of high-risk genes. In one embodiment, a gene-optimized antibody is an antibody that is selected based on similarities defined by the gene set of the antibodies and the genes of a potential host. In another embodiment, a gene-optimized antibody is an antibody that is engineered or created to contain as few genes that are different from a potential host's V gene profile. In another embodiment, a gene will be optimized if a D gene appears in a host D gene profile. In another embodiment, a gene will be optimized if a J gene appears in a host J gene profile.

As used herein, the twenty conventional amino acids and their abbreviations follow conventional usage. See *Immunology—A Synthesis* (2$^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, lactic acid, and other unconventional amino acids can also be suitable components for polypeptides of the present invention. Examples of unconventional amino acids include: 4-hydroxyproline, γ-carboxyglutamate, ε-N,N,N-trimethyllysine, 1-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. Binding fragments also include "single domain" antibodies such as produced from single $V_H$ domain display libraries or derived from camelids. An antibody other than a "bispecific" or "bifunctional" antibody is understood to have each of its binding sites identical. An antibody substantially inhibits adhesion of a receptor to a counterreceptor when an excess of antibody reduces the quantity of receptor bound to counterreceptor by at least about 20%, 40%, 60% or 80%, and more, usually greater than about 85% (as measured in an in vitro competitive binding assay). Antibodies cannot only block binding but can assist in binding and various enzymatic processes. Additionally, antibodies can be made that, alone, can activate receptors as a ligand normally would.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain defines a constant region primarily responsible for effector function. Human light chains are classified as either kappa or lambda light chains. Heavy chains are classified as either mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody-binding site.

Thus, an intact antibody has two to ten binding sites, depending on the antibody's isotype. Except in bifunctional or bispecific antibodies, the binding sites are identical.

The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab fragments. See, e.g., Songsivilai & Lachmann *Clin. Exp. Immunol.* 79: 315-321 (1990), Kostelny et al. *J. Immunol.* 148:1547-1553 (1992). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab and Fv).

The heavy chain variable region is comprised of V, D, and J gene segments that are rearranged resulting in the large diversity of variable regions. There are multiple genes that may encode each of the V regions, D regions and J regions in the mammalian genome, any one of which can be combined in a recombination process to encode a mature antibody chain, thus creating more diversity. Similarly, a light chain variable region is comprised of a combination of a Vκ (or $V_k$ or $V_{kappa}$) or Vλ (or $V_{lambda}$) gene selected from a large number of Vκ and Vλ genes present in the mammalian genome, with any of a number of Jκ or Jλ genes, respectively. The heavy chain and light chain variable regions also undergo other alterations, such as the introduction of N sequences, which further increases the variability and specificity of the variable regions. Thus, the $V_H$ region is a combination of any one of several different heavy chain V, D, and J genes, and the $V_L$ region is a combination of any one of several different light chain V and J genes which are created and modified by several different mechanisms.

The term "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another. An antibody is said to specifically bind an antigen when the dissociation constant is $\leq 1$ μM, preferably $\leq 100$ nM and most preferably $\leq 10$ nM. Once a desired epitope on an antigen is determined, it is possible to generate antibodies to that epitope. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another; e.g., the antibodies compete for binding to the antigen. A high throughput process for "binning" antibodies based upon their cross-competition is described in International Patent Application No. WO 03/48731. As will be appreciated by one of skill in the art, practically anything to which an antibody can specifically bind could be an epitope. An epitope can comprise those residues to which the antibody binds. As will be appreciated by one of skill in the art, the space that is occupied by a residue or side chain that creates the shape of a molecule helps to determine what an epitope is. Likewise, any functional groups associated with the epitope, van der Waals interactions, degree of mobility of side chains, etc. can all determine what an epitope actually is. Thus, an epitope may also include energetic interactions.

The term "paratope" is meant to describe the general structure of a binding region that determines binding to an epitope. This structure influences whether or not and in what manner the binding region might bind to an epitope. Paratope can refer to an antigenic site of an antibody that is responsible for an antibody or fragment thereof, to bind to an antigenic determinant. Paratope also refers to the idiotype of the antibody, and the complementary determining region (CDR) region that binds to the epitope.

The terms "specifically" or "preferentially" binds to, or similar phrase are not meant to denote that the antibody exclusively binds to that epitope. Rather, what is meant is that the antibody or variant thereof, can bind to that epitope, to a higher degree than the antibody binds to at least one other substance to which the antibody is exposed.

The term "agent" is used herein to denote a chemical compound, a mixture of chemical compounds, a biological macromolecule, or an extract made from biological materials.

"Mammal" when used herein refers to any animal that is considered a mammal. Preferably, the mammal is human.

Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in a $F(ab')_2$ fragment in which the two arms of the antibody molecule remain linked and comprise two-antigen binding sites. A $F(ab')_2$ fragment has the ability to crosslink antigen.

"Fv" when used herein refers to the minimum fragment of an antibody that retains both antigen-recognition and antigen-binding sites. These fragments can also be considered variants of the antibody.

"Fab" when used herein refers to a fragment of an antibody that comprises the constant domain of the light chain and the CH1 domain of the heavy chain.

The term "mAb" refers to monoclonal antibody.

"Label" or "labeled" as used herein refers to the addition of a detectable moiety to a polypeptide, for example, a radiolabel, fluorescent label, enzymatic label chemiluminescent labeled or a biotinyl group. Radioisotopes or radionuclides may include $^{3}H$, $^{14}C$, $^{15}N$, $^{35}S$, $^{90}Y$, $^{99}Tc$, $^{111}In$, $^{125}I$, $^{131}I$, fluorescent labels may include rhodamine, lanthanide phosphors or FITC and enzymatic labels may include horseradish peroxidase, β-galactosidase, luciferase, alkaline phosphatase.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), (incorporated herein by reference).

As used herein, "substantially pure" means an object species is the predominant species present (i.e., on a molar basis it is more abundant than any other individual species), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, or 99%. Most preferably, the object species is purified to essential homogeneity (contaminant species cannot be detected in the composition by conventional detection methods) wherein the composition consists essentially of a single macromolecular species.

The term "patient" includes human and veterinary subjects.

The term "SLAM® Technology" refers to the "Selected Lymphocyte Antibody Method" (Babcook et al., *Proc. Natl. Acad. Sci. USA*, i93:7843-7848 (1996), and Schrader, U.S. Pat. No. 5,627,052, both of which are incorporated by reference in their entirety).

The term "XENOMAX"™ refers to the use of SLAM Technology with XenoMouse® mice (as described below).

Methods of Identifying High Risk Genes

The identification of genes that have a high risk or a low risk of inducing a HAHA response in a patient, a population, or an individual in a population can be achieved by determining how frequently the gene appears in the patient or population. Regarding populations and individuals in populations, $V_H$ genes that are relatively common in a population have a low risk of inducing a HAHA response in a random member of the population. Genes that are relatively rare in a population have a high risk of inducing a HAHA response in a host patient. Similarly, V genes that are present in an individual are low risk genes for that individual, while V genes that are absent are high risk genes for the individual. Thus, the determination of whether or not an antibody expressing a particular gene will result in a HAHA response can be determined with a database containing information on the frequency with which particular genes are found in a population. In one embodiment, for a population, the database is a normalized host V gene profile. By comparing the gene set of an antibody to this normalized host V gene profile one is able to predict the presence of high-risk genes and low-risk genes. The more similar the population is in genetic makeup to the patient, the better the prediction should be.

As discussed in more detail below, high risk and low risk genes and antibodies encoded thereby can also be determined experimentally, for example, by administering a candidate antibody to a XenoMouse® mouse that has no more V genes than those of the host or host population. If the XenoMouse® mouse exhibits a HAHA response, then the gene and antibody encoded by the gene will be a high risk gene.

Normalized Host V Gene Profile

A normalized host V gene profile reflects the frequency of a gene in a population. There are several alternatives by which this relationship can be described. For example, in FIG. 1A, examples of various V genes of five different people are represented. FIG. 1A represents a selection of genes in a host and is not meant to suggest any relationship in spatial order or other arrangement. From this, or alternatively, instead of this, one can use protein expression or mRNA for compiling the profile, as shown in FIG. 1B. In this example, only genes A, C, D, and E are expressed as mRNA or protein. From the data in FIG. 1A, a frequency of occurrence can be determined, the results of which are presented in FIG. 1C. Alternatively, one can obtain a frequency of occurrence as a function of the gene frequency in the patient, in which cases the fact that a gene can appear as zero copies, one copy, or two copies will further influence the above analysis.

Additionally, it can be important to consider not only the frequency of the genes, but also the frequency of the proteins that are actually expressed. Thus, a "normalized host V protein profile" or "mRNA profile" can be an appropriate means of comparison as well. In a preferred embodiment, it can be a normalized host V mRNA profile that is determined. These last two profiles have the added benefit of removing from consideration those genes that, while common, simply never produce a protein product. This could be important, especially for those genes in a modified antibody that might normally not be expressed, but for the modification of the antibody. Thus, in situations where one is going to modify an antibody, it can be advantageous to remove any genes that are also not functionally expressed. The frequency of occurrence for the genes can be observed in FIG. 1D. Here, as shown in FIG. 1B, only A, C, D, and E are transcribed or translated.

In a preferred embodiment, the mRNA transcribed from each gene is actually the unit that is examined and compared between profiles. Thus, normalized host V mRNA profiles, and uses thereof are contemplated embodiments. As understood by one of skill in the art, an mRNA profile can be used anytime one desires a profile that represents if the gene was transcribed, and thus can be more useful than a DNA sequence. An amino acid sequence will also provide this type of information, and will have a greater likelihood of having structurally important regions conserved.

There are at least two levels at which the frequency of the antibody protein can be examined. At a normalized level, the frequency of the protein is that determined by whether or not a protein product for a particular gene is produced in a given person. At another level, the frequency of the use of a protein product of a particular gene is examined within each person. In this situation, if the gene creates a protein product that is common in the antibodies of that person, then it will have a very high frequency of occurrence, and thus be a low-risk gene.

The various frequencies generated in FIG. 1 demonstrate that how one counts the appearance of each gene, as either for an individual or in a population, can influence the frequencies generated, and thus the course to be taken in later steps. Additionally, a comparison of FIG. 1C to FIG. 1D reveals the large possible differences between a nucleic acid based gene approach and an amino acid (or mRNA) profile approach. All embodiments directed to normalized host V gene profiles can also be created as normalized host V protein profiles, and preferably are.

The two levels of analysis can be combined to produce a normalized host V gene protein profile where both factors are considered in determining what a low or high risk gene is. This combined approach may be especially useful when there otherwise is a small number of samples in the profile.

As discussed below, there may also be structural normalized host V gene profiles (or normalized host V protein structure profiles). Alternative embodiments will include D and J versions of these profiles.

Comparisons Using Normalized Host V Gene Profiles:

Once one has a host V gene profile, the information can be compared against the gene set of the antibody in question, or future antibody to be made. While there are many possible ways of comparing sequences, the comparisons described herein involve comparisons that involve a gene-wise comparison for many of the preferred embodiments, although higher levels of comparison are also contemplated for all of the embodiments.

FIG. 2 depicts several different methods of comparing the pieces of information, and how that information can differ depending on how one analyzes the information. Starting with FIG. 2A, the A gene is compared with the frequency of the genes in the gene profile to reveal that gene A is common in the profile as its frequency of occurrence is 100%. This could also be an mRNA level of analysis.

At a different level of analysis, in FIG. 2B, the protein sequence of gene A is compared to a protein or mRNA profile that again results in a frequency of occurrence of 100% (as gene A again occurs at a frequency of 100% in the profile).

Finally, at another level of analysis, in FIG. 2C, the structure of the protein encoded by gene A is compared to a structure profile to again reveal that the protein structure is very common as its frequency of occurrence is 100%.

The next gene, gene B, is also compared using the three different methods. At the first level of comparison, in FIG. 2A, gene B would be interpreted as a low risk gene as it occurs with a high frequency of occurrence, 100%, as can be seen in the profile. At an mRNA/amino acid sequence level of analysis, as shown in FIG. 2B, the B gene protein product is not present in the population. Thus, the B gene can be classified as a high-risk gene. Finally, at the protein structure level, in FIG. 2C, the B gene displays a structure, if it had been created, that is not present in the structure profile; therefore, gene B would be considered a high-risk gene. Thus, this can be considered a high-risk gene.

The next gene, gene C, is also compared using the different methods. In FIG. 2A, gene C could be interpreted as a possible high-risk gene as its frequency of occurrence is only 10% in the gene profile. In FIG. 2B, gene C could once again be interpreted as a possible high-risk gene as its frequency of occurrence is still only 10% in the mRNA/protein profile. However, in FIG. 2C, the structure of the protein product of gene C is a very common structure in the structure profile (e.g., 100%); thus, gene C is a low risk gene.

All of the profiles and comparisons described above can also be done using mRNA.

Not all of the comparisons need to be gene-wise comparisons. For instance, in situations in which one knows a particular gene that is a risk gene, one can further refine the usefulness of the antibodies by attempting a nucleic acid wise optimization within that particular gene. Thus, if one were interested in optimizing an antibody so that the $V_H3$ genes presented less of a risk of inducing a HAHA response, one could start off optimization by trying to alter the sequence of the particular $V_H3$ gene to resemble another gene. Thus, normalized host V sequence profiles are contemplated where sequences are to be compared rather than entire genes or protein segments.

It could be that following a gene wise comparison and optimization, an additional level of optimization is desired, at which point the particular sequences of the genes can be compared in order to further reduce aspects of the antibodies that may induce a HAHA response. It is important to understand that the sequences are still compared within each of the genes of the gene set, e.g., V genes, $V_H$ genes, $V_H3$ genes, or the $V_H3$-9 gene. The risk that is associated with the gene's frequency of occurrence can be correlated to the particular structure encoded by the gene.

A gene, for use as described herein, can mean the coding and noncoding aspects of the piece of DNA. Alternatively, rather than looking at the entire gene, only the coding sections can be compared to the potential host's V gene background.

Additionally, structural motifs or the entire structure of the antibody can be compared at the protein level. As many of these gene sections are very short, the amino acid sequences can be modeled in silico easily and accurately.

A structure can be generated through homology modeling, aided with a commercial package, such as Insight II modeling package from Accelrys (San Diego, Calif.). Briefly, one can use the sequence of the antibody to be examined to search against a database of proteins of known structures, such as the Protein Data Bank. After one identifies homologous proteins with known structures, these homologous proteins are used as modeling templates. Each of the possible templates can be aligned, thus producing structure based sequence alignments among the templates. The sequence of the antibody with the unknown structure can then be aligned with these templates to generate a molecular model for the antibody with the unknown structure. As will be appreciated by one of skill in the art, there are many alternative methods for generating such structures in silico, any of which can be used. For instance, a process similar to the one described in Hardman et al., issued U.S. Pat. No. 5,958,708 (incorporated by reference in its entirety) employing QUANTA (Polygen Corp., Waltham, Mass.) and CHARM (Brooks, B. R., Bruccoleri, R. E., Olafson, B. D., States, D. J., Swaminathan, S. and Karplus, M., 1983, J. Comp. Chem., 4:187) can be used.

Alternatively, traditional structural examination approaches can be used, such as NMR or x-ray crystallography. These approaches can examine the structure of a paratope alone, or while it is bound to an epitope. Alternatively, these approaches may be used to look at the individual protein segments that are each encoded by particular V genes.

These structural motifs are again divided or defined by the actual genes, even though, as they are incorporated into an antibody, they would be connected to other amino acids. While the comparisons used to match an Ab protein section and a protein section in a profile are protein structures, the important element of the protein section examined is the gene and the risk associated with that gene, as determined by its relative frequency of occurrence. The comparison can be performed on many different levels. For example, at a relatively simple level, the primary factor in the comparison can be the side-chains of each amino acid in the chain. Thus, the space-filling model of the side chains of a protein encoded by a V gene can be compared to a similar space-filling model of the protein encoded by the V gene types of the patient. A more complicated comparison would involve the use of electrostatic interactions of each amino acid in the protein encoded by the gene, for example. Another method of comparison involves the technique taught by U.S. Pub. No. 20040005630

(Published Jan. 8, 2004, to Studnicka). This describes a process whereby individual amino acid positions are compared and particular solvent-exposed side chains are altered. While the current embodiments are still directed to antibody optimization through gene manipulation, rather than a residue by residue approach, this process can still be useful in altering the residues in the high-risk gene, once the high-risk gene has been identified by the methods described herein. The level of modeling for the comparison can be increased as much as desired. For example, the proteins encoded by the genes could be modeled as an entire three dimensional protein structure of the antibody, again with the genes being used to identify the sections to be compared between the possible antibody and the gene make up or background of the patient. The structural interactions between each of the protein segments encoded by the V gene segments and other protein in the antibody can also be used to compare and contrast potential antibodies, or genes of the potential antibodies, to the set of genes of the patient. By using this comparison, a database of protein structures is used to determine the risk that a particular gene structure will induce a HAHA response.

Alternatively, if one wishes to emphasize the similarity of the genes themselves, then the comparison can be performed on the nucleic acid level.

In one embodiment, clusters of particular genes within a gene set are important in determining which genes are high-risk genes and which genes are low-risk genes for a particular antibody in a particular patient. In such an embodiment, a particular V gene may be a low-risk gene when the gene is compared to a simple normalized host V gene profile; however, when the particular V gene is paired with another gene (e.g. a D or J gene, or a pairing of a particular $V_H$ gene with a particular $V_L$ gene), which may also, independently, be a low-risk gene, the combination results in a cluster of genes which is a high risk cluster. It is the particular combination of two or more common genes that is an uncommon combination, and thus has a high risk, combination. Thus, an antibody that contains such a cluster could have a substantial likelihood of inducing a HAHA response in the patient, even though a simple, non-cluster, analysis would suggest that all of the genes were low-risk genes. Whether or not a gene cluster is a high-risk or low-risk cluster is determined and defined in the same way as these terms are used for high-risk and low-risk genes. A cluster can consist of two or more genes that constitute an antibody.

Another general issue to consider in comparing the frequency of occurrence of one gene compared to a gene in the profile is whether or not to consider the exact sequence of one gene as the only way that the gene can be described or if there is more than one sequence for a gene, that is, are there variants for the genes. There are times where it may be advantageous to include variants, as they allow a compression of data. However, in some instances, especially where, even though very similar in terms of sequence, there is a difference in terms of frequency of occurrence between the genes, it would then be detrimental to use the concept of variants in the analysis.

The term "variant" as used herein, is a polypeptide, polynucleotide, or molecule that differs from the recited polypeptide or polynucleotide, but only such that the activity of the protein is not detrimentally altered unless specified. There can be variants of antibodies, both at the protein level and at the nucleic acid level. In a preferred embodiment, the ability of a protein variant to function is not detrimentally altered. In another embodiment, the protein variant can function with 10-500% or more of the ability of the wild type mAb. For example, the protein variant can function with 10%, 50%, 110%, 500%, or greater than 500% of the ability of the wild type mAb. In one embodiment, the range of functional abilities between 10-500% is included. In one embodiment, binding ability is the functionality and it can be reflected in many ways, including, but not limited to the $k_a$, $k_d$, or $K_D$ of the variant to an epitope. In one embodiment, variants of V genes possess the same probability of risk for inducing a HAHA response. Such variants are called "risk constant variants." In an alternative embodiment, variants of V genes possess different probabilities for inducing a HAHA response. Such variants may be grouped in "function constant variants," or more specifically called "risk variable variants."

Variant antibodies can differ from the wild-type sequence by substitution, deletion, or addition of five amino acids or fewer. Such variants can generally be identified by modifying one of the disclosed polypeptide sequences, and evaluating the binding properties of the modified polypeptide using, for example, the representative procedures described herein. Polypeptide variants preferably exhibit at least about 70%, at least about 90% at least about 95%, or 99% identity to the identified polypeptides. Preferably, the variant differs only in conservative substitutions and/or modifications. Variant proteins include those that are structurally similar and those that are functionally equivalent to other antibody protein structures. In another embodiment, the antibody protein is a variant if it is functionally equivalent to another antibody protein, so long as the paratope of the variant is similar to the paratopes of the other antibody variant.

In one embodiment, the antibody is a variant if the nucleic acid sequence can selectively hybridize to the wild-type sequence under stringent conditions. Suitable moderately stringent conditions include prewashing in a solution of 5×SSC; 0.5% SDS, 1.0 mM EDTA (pH 8:0); hybridizing at 50° C.-65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing DNA sequences are also within the scope of this invention, as are nucleotide sequences that, due to code degeneracy, encode an antibody polypeptide that is encoded by a hybridizing DNA sequence. The term "selectively hybridize" referred to herein means to detectably and specifically bind. Polynucleotides, oligonucleotides, and fragments thereof selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically at least 85-89%, 90-94%, 95-98%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

One of skill in the art will realize that, because of the high degree of similarity between many of the V genes, that certain genes may be categorized as variants of the same V gene when they are in fact different genes. For the purposes of the present methods and compositions, even if a V gene is considered a variant of another V gene, the two genes will not, unless specifically denoted ("variant gene" or "variant gene set"), be considered to be the same gene with an additive degree of risk.

Variant genes, variant gene sets, and variant host V gene profiles are contemplated in the present embodiments as a higher level of possible analysis. The variant genes, variant gene sets, and variant host V gene profiles can be used for any of the disclosed embodiments. One particular advantage of such a higher level of analysis is that combining the particular genes in this manner allows one to add a little variability into each level of analysis. This allows the genes selected for to be more acceptable to a larger group of people. In other words, by breaking down the pure gene level of analysis and using a variant gene level of analysis, it is more likely that the genes selected will be low-risk genes for a larger group of people.

In one embodiment, these closely related variant genes could be considered to be the same. In such an embodiment, if one were developing a V gene profile, such variant genes can be considered as a single type of V gene. In such a situation, this could result in fewer individual genes being categorized in each profile. However, those genes that were present would generally have a higher apparent risk of inducing a HAHA response. To the extent that the risk associated with each of the genes rises the same amount, this is not truly indicative of core protein structures that are responsible for inducing a HAHA response. However, to the extent that only certain combinations of variant genes have a higher risk associated with them when the variants are combined across genes, then this is indicative of core structures that probably are related to inducing a HAHA response.

In light of this, while the use of variants in defining gene sets may not always be useful for developing profiles, the variants can be useful in determining or estimating relevant sections of genes to be altered in order to alter the risk that a particular gene will induce a HAHA response. As an example, one has three different genes of interest, A at 10% frequency, B at 100% frequency, and C at 1% frequency in the particular gene profile, and one wants to optimize gene A. If genes B and C are structural variants of gene A, and genes B and C have a different level of risk associated with them than the risk associated with gene A, then one can compare the three structures and modify gene A so that its protein structure will be similar to B, and different to C (see e.g., the discussion below regarding FIG. 6 and FIG. 7). Ideally, the differences between C and B should not alter the functionality of the antibody, as all three proteins have the same function, and should result in an antibody with a reduced risk of inducing a HAHA response.

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window can comprise additions, deletions, substitutions, and the like (e.g., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which can include deletions or additions which total 20 percent or less of the reference sequence over the comparison window. The reference sequence can be a subset of a larger sequence. Amino acids or nucleic acids with substantial identity to the wild-type protein or nucleic acid are examples of variants of the wild-type protein or nucleic acid.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are valine-leucine-isoleucine, phenylalanine-tyrosine, lysine-arginine, alanine-valine, glutamic-aspartic, and asparagine-glutamine. Polypeptides with substantial identity can be variants.

Variant proteins also include proteins with minor variations. As discussed herein, minor variations in the amino acid sequences of antibodies or immunoglobulin molecules are contemplated as being encompassed by the present invention, providing that the variations in the amino acid sequence maintain at least 75%, between 75-99% identity, for example, 80-89%, 90%, 91%, 92%, 93%, 94%, 95%, 96%, 97%, 98%, and 99% identity. In another embodiment the variants are all encoded by a gene located at a particular chromosomal address. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine, and isoleucine is an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative.

Such assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991). Thus, the foregoing examples demonstrate that those of skill in the art can recognize sequence motifs and structural conformations that may be used to define structural and functional domains in accordance with the antibodies described herein.

Preferred amino acid substitutions are those which: (1) reduce the risk of the induction of a HAHA response to the protein (2) increase the structural similarity of a peptide with a risk of inducing a HAHA response to a peptide with a lower risk of inducing a HAHA response (3) reduce susceptibility to proteolysis, (4) reduce susceptibility to oxidation, (5) alter binding affinity for forming protein complexes, (6) alter binding affinities, and (7) confer or modify other physicochemical or functional properties of such analogs. Analogs or variants can include various muteins of a sequence other than the naturally occurring peptide sequence. For example, single or multiple amino acid substitutions (preferably conservative amino acid substitutions) may be made in the naturally occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et al. *Nature* 354:105 (1991), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5-70 amino acids long, and include fragments that are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence. Analogs typically are at least 20 amino acids long, preferably at least 50 amino acids long or longer, and can often be as long as a full-length naturally-occurring polypeptide. Both fragments and analogs are forms of variants Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) can be used to generate more stable peptides. In addition, constrained peptides comprising a consensus sequence or a substantially identical consensus sequence variation can be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide. Peptide mimetics and peptidomimetics are both forms of variants.

As will be appreciated by one of skill in the art, while the above discussion focused on comparisons of V genes and with normalized V gene profiles, these techniques, where appropriate, can also be used to compare V genes in a candidate antibody to the V genes present in an individual. Of course, the major difference being that, in this later situation, risk is defined by the presence or absence of the gene, rather than frequencies in a population.

Methods of Selecting Genes for Creating Gene-Optimized Antibodies.

One embodiment is directed to the method of selecting genes to be expressed in a gene-optimized antibody. Such a gene-optimized antibody is a functional antibody that has a reduced likelihood of inducing a HAHA response. How the genes are selected, if they are selected for modification, and what type of modification they receive are possible issues. These can be addressed by examining the gene set of an antibody and the frequency of each gene's occurrence in a normalized host V gene profile or if the gene occurs in an individual's V gene profile. With this information, V genes for an antibody (or an antibody itself) can be selected in order to make or obtain a gene-optimized antibody. By "antibody gene set" what is meant is the genetic composition of the antibody. By "host gene set" what is meant is the body of relevant genes, in this case V genes, which are in the host. In one embodiment this will include the V gene, the J gene, and the D gene. In another embodiment, this includes the $V_H$ gene and the $V_L$ gene. In another embodiment, this includes the $V_H$ gene. Of course, the set may also refer to the mRNA, protein sequence, or structural versions of each of the genes. Additionally, a gene set can refer to the set of genes in the gene profile of the host, a population, or a XenoMouse® mouse. For example, these can be denoted as an "antibody V gene set" or a "host V gene set." When the host V gene profile is for a single person, it will be the same as the host V gene set. In other words, while a normalized profile can describe the percent of people that have various genes, the V gene set simply denotes which genes they have.

Figure 3:
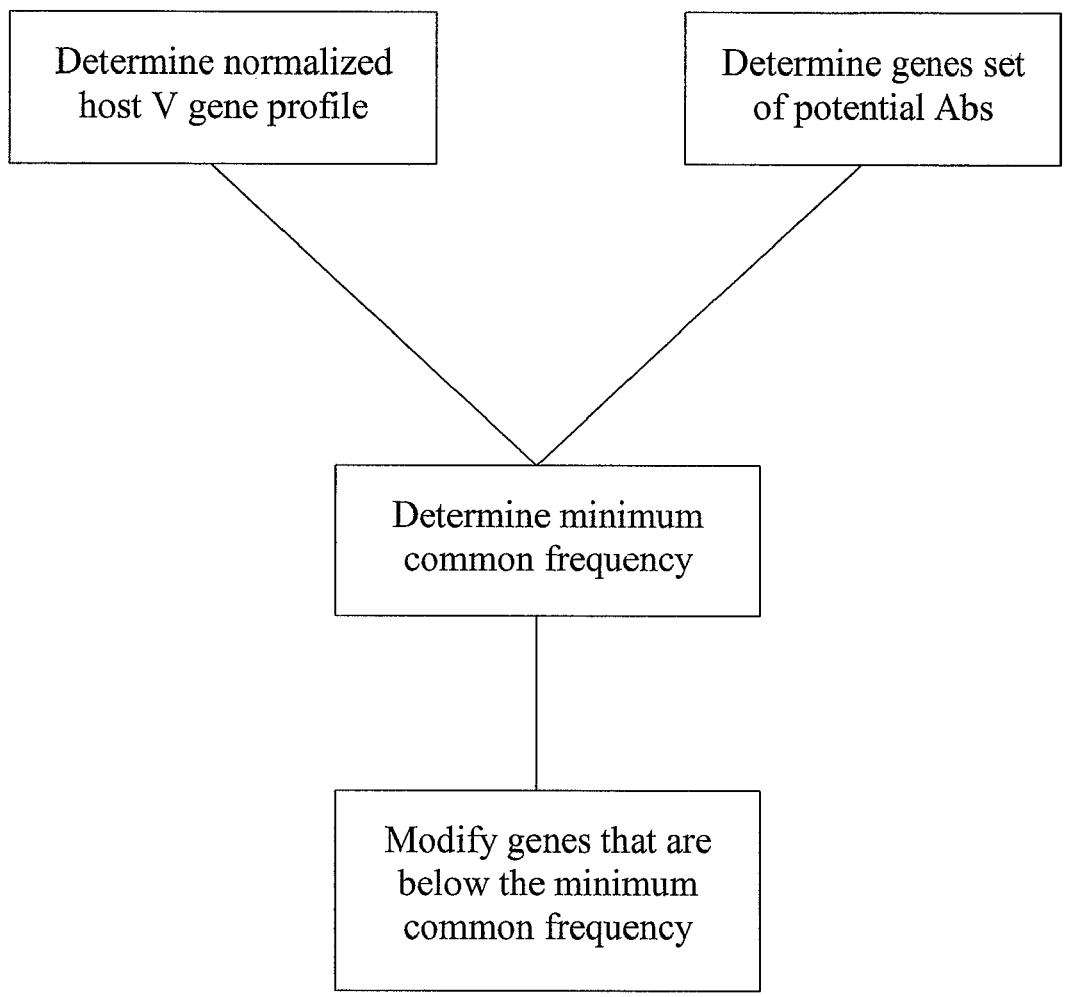
FIG. 3 depicts a flow chart for a method for determining if a gene is a high-risk gene for inducing a HAHA response, and then altering the gene to decrease the risk.

In one embodiment, the selection criterion involves minimizing the number of high-risk genes, or variants thereof, and/or a maximizing the number of low-risk genes or variants thereof. In another embodiment, genes that occur with a frequency beneath a certain minimum frequency of occurrence are removed, as shown in FIG. 3. Alternatively, any high risk genes or variants that are present can be acceptable, as long as they are not functional, meaning that they do not produce protein, or the protein produced is a low-risk variant of the normally high risk gene protein.

The minimum frequency of occurrence, the frequency of occurrence that is the boundary between a high-risk and a low-risk gene, can vary depending upon the effect on the antibody's functionality. In one embodiment, a frequency of occurrence of more than 50% will be considered high frequency, while a frequency of occurrence of less than 50% will be considered low frequency. In another embodiment, a frequency of occurrence between 50-100% is considered high frequency (e.g., low risk), while a frequency of occurrence of less than 50% will be considered low frequency. In another embodiment a frequency of occurrence of any of: 0-99, including 0-1, 1, 2, 3, 4-15, 15-30, 30-50, 50-70, 70-90, or 90-99 percent can each be considered a low frequency of occurrence. In another embodiment, a frequency of occurrence of any of 100 or less, including: 100, 100-99, 98, 97, 96-85, 85-50, 50-30, 30-10, or 10-minimal percent could each be considered a high frequency of occurrence.

While it may seem counterintuitive that a gene that occurs in 99 percent of the antibodies in a population could be deemed low frequency, these are relative terms, and the range of these terms varies by the population or subpopulation examined and the intended use. Thus, in a very small population, or in a population that has a very small selection of V genes, where there is very little variation in the genes used to create the antibodies, it can be that the frequency of occurrence is well above 50% for any of the genes. However, this does not mean that removal of such a gene would not reduce the likelihood that a HAHA response can be induced by an organism creating antibodies to the antigens.

An additional factor to consider in deciding to alter a particular gene is how rare the gene is. As described in detail below, there are several alternative ways in which one may characterize a gene as high risk. Additionally, as demonstrated in FIG. 1, the exact frequencies of occurrence can vary depending on how the data is analyzed. For example, in an embodiment with a minimum frequency of occurrence, any gene that is less frequent than the minimum frequency of occurrence will be deemed a high risk gene, such as that shown in FIG. 3. A more in depth analysis is provided by correlating the frequency of the gene to a value that represents the risk associated with the gene. For example, given two possible high risk genes, if one occurs in a normalized V gene profile with a frequency of 1% and the other appears with a frequency of 10%, the gene with a frequency of 10% could be ten fold less likely to cause a HAHA response in any person in the population. As appreciated by one of skill in the art, this relationship of risk need not be linear, can include certain minimum frequencies of occurrence, and can be determined in many ways, including experimentally, as described below. This percentage-weighted degree of risk allows one to also estimate the degree of change that may be required in order to avoid the risk gene inducing a HAHA response. For example, a gene that is very rare may require a much larger modification than one that is only slightly rare. While this may not be an absolute indicator of how gene modification should occur, when this is combined with sequence comparisons of the high-risk gene and low-risk genes, as well as sequence comparisons between genes with similar sequences, but different degrees of risk, one skilled in the art will be able to determine how large a modification would be prudent.

As will be appreciated by one of skill in the art, the relatively simple "high risk" or "low risk" characterization of a gene may not be as advantageous as more detailed description of the risk associated with the gene. For example, in some embodiments, the risk associated with the gene can be characterized as a "medium risk."

Alternatively, the risk can also be described in terms of amount of the V gene in the profile. This can be done across a population, or within an individual. For example, across a population, the risk can be calculated in various weighted manners, a simple method would be through percentages of the people having the gene. For example, a first V gene can be present in 90% of a population, a second V gene present in 99% and a third present in 100%. As such, the first V gene can be described as having a 10% risk, the second a 1% risk, and the third, no risk. Thus, the risk denotes the chance that a random person from the population will not have the gene and thus treat an antibody expressing the gene in an adverse manner. Within an individual, the percentage can describe, the similarity of the protein product of the V gene of interest with a protein in the host.

Methods for Creating Gene-Optimized Antibodies.

Figure 4:
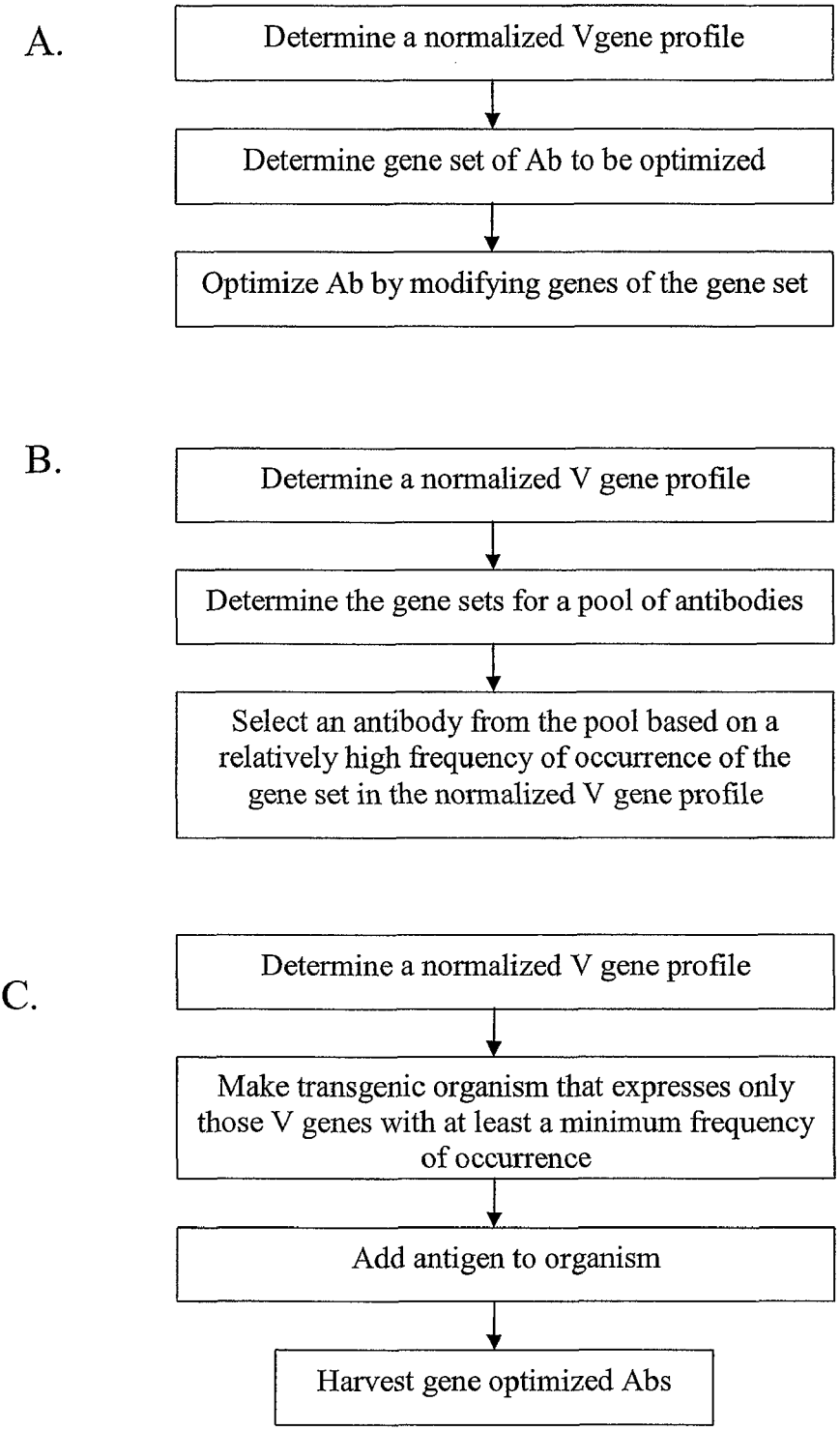
FIG. 4A depicts a flow chart for one method for optimizing an antibody.
FIG. 4B depicts a flow chart for another method for optimizing an antibody.
FIG. 4C depicts a flow chart for another method for optimizing an antibody.

As will be appreciated by one of skill in the art, there are many alternatives for creating the antibodies described herein, some of which, without limitation, are described in FIG. 4.

Antibody Modification

The antibodies can be modified as described herein in order to eliminate protein product of high-risk genes, as in FIG. 4A. For instance, in one embodiment, a point mutation is used to reduce the risk that the protein will induce a HAHA response.

In one embodiment, the high-risk gene is altered so it resembles a lower risk gene in certain important aspects, such as protein structure, as described in detail below. This can be advantageous in that relatively minor changes in the protein structure can easily result in a great reduction in the risk of a HAHA response being induced. These changes in protein structure can be achieved and directed by a comparison of the high-risk gene and a low-risk gene. One can find the closest low-risk gene that is similar to the high-risk gene and change the high-risk gene so that the protein structure of the high-risk gene resembles the protein structure of the low-risk gene. Of course, through routine experimentation and testing, this process can be optimized through multiple rounds of comparing sequences of V genes, altering the sequence of the high-risk gene in the antibody to more closely resemble the low-risk gene, and then testing the antibody for retention of binding and activity or its risk of inducing a HAHA response or both. Additionally, multiple gene comparisons of high-risk genes can be used to determine trends in the high-risk genes; these trends could then be selectively targeted for alteration in order to produce optimized antibodies.

In another embodiment, the high-risk gene can be replaced by a low-risk gene. The replacement can be similar to the high-risk gene (apart from the fact that the new gene should have a lower risk associated with the gene). Alternatively, the replacement gene can be a gene that, on a protein level, would be structurally similar to the gene it is replacing. Certain characteristics of the high probability gene that confer function such as the CDR3 or somatic mutations can be engineered onto the framework of the low probability gene in order to retain binding specificity and functional activity. Alternatively, the replacement gene can be a gene that possesses an especially good ability to replace other V genes. Such a gene can be determined through the course of the above-described experimental process.

In one embodiment, the gene-optimized antibodies are then tested to see that they still function as desired.

Antibody Selection

The low risk antibodies can be selected from a group of antibodies based on the antibodies's lower risk of inducing a HAHA response, as is shown in FIG. 4B. At a simple level, this is done by selecting an antibody that is minimized for high-risk genes in a normalized host gene profile. Another example by which this can be done, described more fully below, is to determine the ethnic background of a patient and then to select an antibody from a pool of antibodies, wherein the antibody comprises a set of genes that are optimized for the occurrence of genes that are common in the particular ethnic background of the patient. In a preferred embodiment, the genes examined in the gene set are V genes and the profile is a normalized host V gene, mRNA, amino acid, or protein structure profile.

In one method of selecting an antibody for a patient, the gene sets in the antibody is compared with the possible genes in the patient. When the genes are similar, this indicates that the type of gene is not likely to cause a HAHA response in the patient. When this is applied to a population, a weighted degree of risk is associated with each gene; thus, the presence of a very rare gene (e.g. 0.001%) will indicate a greater degree of risk than the presence of only a rare gene (e.g. 0.01%). Additionally, any risk associated with particular host V gene profiles can be considered. For example, if an antibody with a particular gene set would normally be considered low-risk, based on a normalized host V gene profile, but the gene set has a high risk for one particular subset of the population which makes up the normalized host V gene profile, then whether or not to administer this to an individual in the population can be questioned. This is especially relevant if the individual shows any indicators of being part of the high-risk subset of the normalized host V gene profile.

One of skill in the art will recognize that this type of comparison is not a simple base-by-base sequence comparison. Rather, gene sequences, mRNA, protein sequences, or protein structures are compared that are defined by the boundaries of the gene. Thus, the results from a full sequence comparison can be different from the results of a gene-by-gene comparison. Because of this, the determination of whether or not the particular antibody will induce a HAHA response need not be the same in most situations. This is especially relevant to situations in which one develops a profile based on recurring sequences compared to a profile based on recurring genes. Sequences that are common across all V genes, even those that are high-risk, will show up in a profile as low-risk elements. This could result in sequences that are actually high-risk being incorrectly lowered in their risk evaluation if high risk genes have these common structures. In contrast to this, by correlating frequency of occurrence or presence or absence with entire genes, only the genes that are high-risk will be classified as high-risk and only the genes that are low-risk will be classified as low risk.

While one could simply select genes that are low-risk genes for a particular patient and then make such an antibody with those genes, the ability to create an antibody for each patient may not be desirable or practical. Additionally, the precise V gene profile of the patient may not be known, or there may not be enough time to create a novel antibody. Thus, in these situations, selecting an antibody for a patient, based on the patient's assumed V gene profile is a useful alternative.

In the selection of V gene-optimized antibodies by comparing the genes in a pool of antibodies with an assumed host V gene profile, a larger selection of antibodies comprising various combinations of V genes can be beneficial in obtaining an antibody with a particular combination of V genes that is minimized for risk genes. In such a situation, it is not that having a large number of different V genes is necessarily required in obtaining a V gene-optimized antibody, but that having a larger pool of antibodies makes it more likely that one antibody in the pool will contain few risk genes or many low-risk genes for a given patient.

In one embodiment, the method of selecting an antibody for a patient involves a collection of all available antibodies comprising different types of genes in a "pool." The pool can comprise antibodies with nonhuman V genes, or other nonhuman genes. For example, V genes from rodents, XenoMouse® mice, or pigs. In one embodiment, these pools may be computational databases where one can computationally compare the likelihood of any particular V gene inducing a HAHA response in any particular person, group of people, or entire population. The likelihood is determined as described herein, where commonly occurring V genes have a low likelihood and rare V genes have a high likelihood of inducing a HAHA response. Alternatively the pools could be physically embodied as an actual collection of the various antibodies, or genes thereof. In some embodiments, these pools may comprise D and J genes, either in combination or as separate pools.

Alternatively, in order to reduce cost and storage space requirements, the pools can consist of "universally gene-optimized antibodies." This means that the antibodies are selected so that they will reduce the risk of inducing a HAHA response when administered across a large population (e.g., 1000-10,000, 10,000-one million, one million to 100 million, 100 million to 6 billion). Thus, while these antibodies may not be completely optimized to each individual, they will allow a single gene-optimized antibody (or a single set) to be administered to many different people, with a benefit occurring across the population as a whole.

As will be appreciated by one of skill in the art, it is possible to have pools that are customized to particular groups of people. This is especially useful where particular groups of people share common V gene usage. Thus, without knowing the precise host V gene profile, one is able to obtain a better fit of profile to risk, than if one simply selected possible antibodies based on an entire population host V gene profile.

In one embodiment, the V gene profile is created, and thus the pool of genes from which one can create or select an antibody for a patient, is based on ethnic background. For example, there are four different ethnic groups, Northern European, Southern European/African, Southern Asian, and Northeastern Asia. This particular division is especially significant since data on ethnicity appears to be warranted because of previously published work on the segregation of human IgG1 allotypes with these four different ethnic origins. (See, for example, Pandey, J. P., *Vaccine*. 19 (6), 613-617, (2000); Hougs, et al., *Tissue Antigens*, 61 (3), 231-239, (2003); Juul, et al., *Tissue Antigens*, 49 (6), 595-604, (1997); Atkinson, et al., *Immunogenetics*, 44 (2), 115-120, (1996)). Similarly, among the two human IgG2 allotypes, one is predominant in humans with African ethnic background and the other is predominantly used by the rest of world's population. While allotypes refer to allelic variations in the sequence of the constant region of antibody chains, it is reasonable that V gene usage also segregates with ethnicity.

The pool of antibodies can comprise any type of antibody. In one embodiment, the pool comprises human antibodies. In another embodiment, the pool comprises antibodies from any human Ig-transgenic animal. In another embodiment, the pool comprises antibodies from a XenoMouse® animal. In another embodiment, the pool of antibodies comprises gene-optimized antibodies. The gene-optimized antibodies can be any of the gene-optimized antibodies disclosed herein. In another embodiment, the pool comprises universally gene-optimized antibodies. In another embodiment, the pool comprises a mixture of all of these types of antibodies.

Additionally, the pools themselves can be optimized according to other characteristics of people. For example, there can be a pool that is optimized for patients with a particular characteristic, such as family medical history, or for a particular genotype of the patient.

As appreciated by one of skill in the art, the selection process for matching an antibody or gene-optimized antibody to a patient can vary from situation to situation. As described above, additional factors, such as the size of the pool and the nature of the pool will come into play.

Organisms that Produce Gene-Optimized Antibodies

Transgenic animals can be produced that only or primarily possess low-risk genes, or at least no genes that are high risk, in order to produce the optimized protein, as is described in FIG. 4C. Different animals can be produced for each host V gene profile. Thus, such an animal might have only the V genes that are common in a particular family or even an individual. Alternatively, an animal might have only those V genes that are common for an ethnic group. The advantage is that the antibodies can be directly made from such an organism, and thus there is no concern that one would lose the functionality of the antibody when one was making the gene-optimized antibodies. Of course genetically altered mice, methods of making them, as well as their use in creating gene-optimized antibodies are all included as current embodiments. In one embodiment, the gene-optimized antibody of the transgenic organism contains no $V_H3$-9, $V_H3$-13, $V_H3$-64 genes, or some combination thereof. In some embodiments, the transgenic organism contains no genes that are not present in the population.

In theory, any organism can be used as an antibody producing system. In one embodiment, all of the low frequency genes and variants thereof are removed from the organism; thus, when the organism launches an immune response to generate and select antibodies, only antibodies with high frequency genes will be used. While transgenic organisms can be used, other approaches, such as antisense RNA, siRNA, or antibodies directed towards protein sections of low frequency genes can also be employed to bias the selection and production of antibodies to those that do not contain low frequency genes. In one embodiment, a rabbit is the organism of interest, wherein all of the low frequency V genes are removed from the rabbit.

In one embodiment, a XenoMouse® mouse is genetically altered to only have high frequency (low-risk) genes; thus, any antibodies produced by the mouse in response to the antigen will comprise only high frequency genes. Alternatively, the mouse can be altered to remove all, or some of, of the low frequency genes; thus, any antibody produced will have no, or fewer, low frequency genes; and thus, have a reduced risk of inducing a HAHA response when administered to a patient.

As will be appreciated by one of skill in the art, this particular arrangement allows one to produce practically any type of antibody in general, such as catalytic or agonistic (activating), and do so in a background which is going to result in an antibody with a reduced likelihood of inducing a HAHA response when administered to a patient. Thus, one does not have to worry about altering the functionality of an antibody when one is trying to optimize it by removing low frequency genes, since there will be no low frequency genes to begin with.

In one embodiment, several different types of genetically altered organisms are created, each missing various low frequency genes or comprising additional high frequency genes, or both. Each of the different types of genetically altered organisms will have a particular frequency of occurrence profile. This recognizes the fact that even though there are genes that are common throughout the entire population and genes that are rare throughout the entire population, there may be subsets of the population in which particular genes are common and other genes are rare, in contrast to the entire population. Thus, it can be desirable to customize the V gene selection in each genetically altered organism for each of these subpopulations, in order to further reduce the likelihood of the antibody inducing a HAHA response. Thus, in one embodiment, there can be a genetically altered organism comprising only V genes that are common in subpopulation 1, while there would be a second genetically altered organism comprising only V genes that are common in subpopulation 2. The result would be a further customization of the genes used in the antibody creation and thus a further reduction in the risk of the final antibody producing a HAHA response for that particular subpopulation. This customization could be useful for any aspect of the herein-described embodiments.

The subpopulations can be created or individualized in any manner that the databases could be organized, which is discussed more fully later. Briefly, in one embodiment, these subpopulations are created based upon databases that are divided between various ethnic lines. In another embodiment, the populations are divided by family medical information. In a further embodiment, the genes selected are based on the patient's individual gene set, for instance, their own set of $V_H$ genes.

In one embodiment, the genes that are selected from the database are V genes. In another embodiment, the genes are $V_H$ genes. In another embodiment, the genes are $V_H 3$ genes. In yet another embodiment, the $V_H 3$-9 gene is removed from the selection of possible genes that an organism may use in the creation and selection of an antibody. This results in an organism that creates antibodies, wherein none of the antibodies have the $V_H 3$-9 gene, and thus one has an organism capable of producing antibodies with a reduced risk of inducing a HAHA response. In another embodiment, the gene that is removed is selected from: $V_H 3$-9, $V_H 3$-13, $V_H 3$-64, and some combination thereof.

In some embodiments, the organisms are part of a kit for determining the risk of a HAHA response being induced by a particular antibody. In one embodiment, the kit comprises a transgenic animal that produces human antibodies, such as a XenoMouse® mouse, where the animal lacks the same V genes that the human or population of humans to receive the antibody lack. That is, the V gene set for the animal is the same, or approximately the same, as the V gene set for the population. In other words, the V gene profile of the animal is the same as the V gene profile of the population. The kit can further comprise an antibody that will bind to human antibodies, to detect if a HAHA response has resulted. Additionally, the kit can comprise an antigenic substance (e.g., TCE), to associate with an antibody to be tested. The kit can comprise a device for administering an antibody to an animal. In some embodiments, the transgenic animal only has low risk genes. In some embodiments, the transgenic animal only has high risk genes.

Methods of Determining which Modification to Make to Optimize an Antibody to have a Reduced Risk of Inducing a Human Anti-Human Antibody (HAHA) Response.

Figure 5:
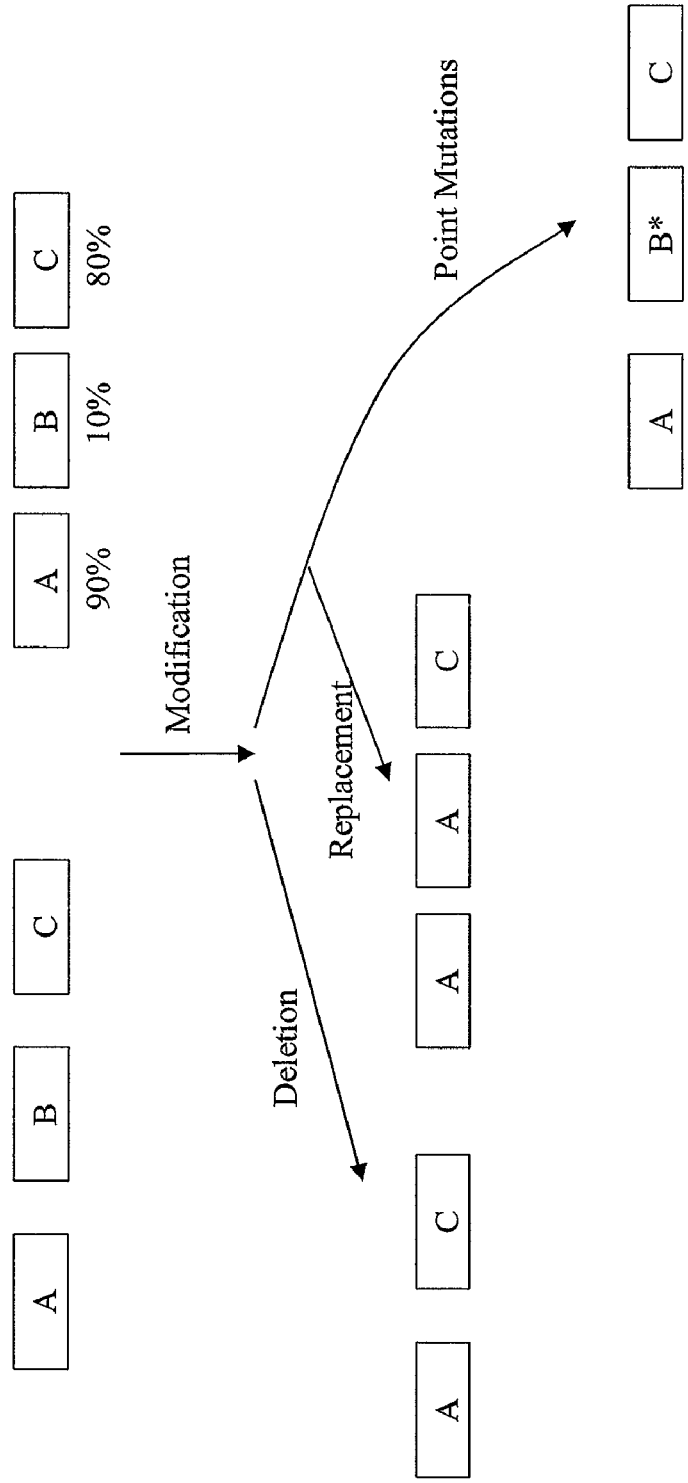
FIG. 5 depicts a flow chart for various methods of selecting and modifying genes to reduce an antibody's risk of inducing a HAHA response. These methods can be used to alter individual antibodies, for example by removing a $V_H$ gene or a $V_L$ gene, or to alter the genomes of HAHA customized XenoMouse® or other transgenic mice, for example by removing a high-risk gene from the genome. Similarly, antibody display libraries using a fixed number of V region frameworks can be pre-selected to use only V region frameworks from V genes assessed to have a low probability of eliciting HAHA.

The genes of an antibody can be modified by various means; FIG. 5 shows several simple examples by which the modification can occur. This figure provides guidance for both how to modify the genes of a potential organism, for instance, by removing a risk gene through deletion, and it provides guidance for how the changes can be made at the protein level, such as through point mutations. In one embodiment, the genes are simply removed from the genome, and there is no possibility that the antibody with the gene will be produced. Thus, gene deletion can achieve the desired effect. Alternatively, the genetic material may not need to be removed, rather the expression of the genetic material can be inhibited, such as through siRNA or anti-sense RNA. More preferably, transcription of the V gene can be inhibited by altering the noncoding regions of the genes or by adding specific transcription blockers. Alternatively, the particular gene can be altered to a sequence which is either more common (thus lower risk), or so that it no longer induces a HAHA response. For example, site directed mutagenesis of the gene sequence can be sufficient to transform a high-risk gene into a low-risk or neutral risk gene. The benefit of not completely removing the gene is that it allows greater V gene diversity.

As will be appreciated by one of skill in the art, the modification of a gene can have a substantial impact upon the function of the antibody. Thus, a testing of the functionality and HAHA response induction by the antibody, as described above, can be desirable following each modification. Additionally, these tests can allow one to select which modification should be made. Standard antibody binding assays will be sufficient to determine if any modification has a negative impact on the function of the antibody. These assays include surface plasmon resonance type tests, such as BIAcore affinity measurements and column elution type binding assays, appropriate functional assays, as well as many other techniques known in the art.

Furthermore, similar functional examinations can be achieved for other functionalities of antibodies, such as antigenic antibodies. In such cases, the appropriate test to determine that the modification of the antibody has not destroyed the usefulness of the antibody can be performed to determine that the antibody is still useful. Additionally, the in silico tests described above could be used to predict the impact of any gene modification on the paratope of the antibody. Alternatively, in silico tests can be performed to determine if the removal of particular genes would be predicted to have detrimental effects on the functionality of the protein, such as protein structure modeling, further described herein and in U.S. Pat, Pub. 20040005630 (Published Jan. 8, 2004, to Studnicka).

As will be appreciated by one of skill in the art, there are a variety of ways in which these functionalities can be studied, especially with regard to epitope binding by the paratope. One way is to use a structural model generated, perhaps as described herein, and then to use a program such as InsightII (Accelrys, San Diego, Calif.), which has a docking module, which, among other things, is capable of performing a Monte Carlo search on the conformational and orientational spaces between the paratope and its epitope. The result is that one is able to estimate where and how the epitope interacts with the paratope. In one embodiment, only a fragment, or variant, of the epitope is used to assist in determining the relevant interactions. In one embodiment, the entire epitope is used in the modeling of the interaction between the paratope and the epitope. As will be appreciated by one of skill in the art, these two different approaches have different advantages and disadvantages. For instance, using only a fragment of the epitope allows for a more detailed examination of the possible variations of each side chain, without taking huge amounts of time. On the other hand, by using only a fragment of the epitope, or simply the epitope instead of the entire protein, it is possible that the characteristics of the epitope fragment may not be the same as the characteristics for the whole epitope, thus possibly increasing the risk of being mislead during the computational modeling. In one embodiment, both approaches are used to a limited extent, in order to cross check the results. In a preferred embodiment, if a variant of an epitope is used, it will be selected so that the variant of the epitope comprises the most important residues of the epitope. The identity of the most important residues can be determined in any number of ways.

With these generated structures, one is able to determine which residues are the most important in the interaction between the epitope and the paratope. Thus, in one embodiment, one is able to readily select which residues to change in order to avoid altering the binding characteristics of the antibody. For instance, it can be apparent from the docking models that the side chains of certain residues in the paratope can sterically hinder the binding of the epitope, thus altering these residues to residues with smaller side chains can be beneficial for binding and less likely to induce a HAHA response. One can determine this in many ways. For example, one can simply look at the two models and estimate interactions based on functional groups and proximity. Alternatively, one can perform repeated pairings of epitope and paratope, as described above, in order to obtain more favorable energy interactions. One can also determine these interactions for a variety of variants of the antibody to determine alternative ways in which the antibody can bind to the epitope. One can also combine the various models to determine how one should alter the structure of the antibodies in order to obtain an antibody with the particular characteristics that are desired.

Figure 6:
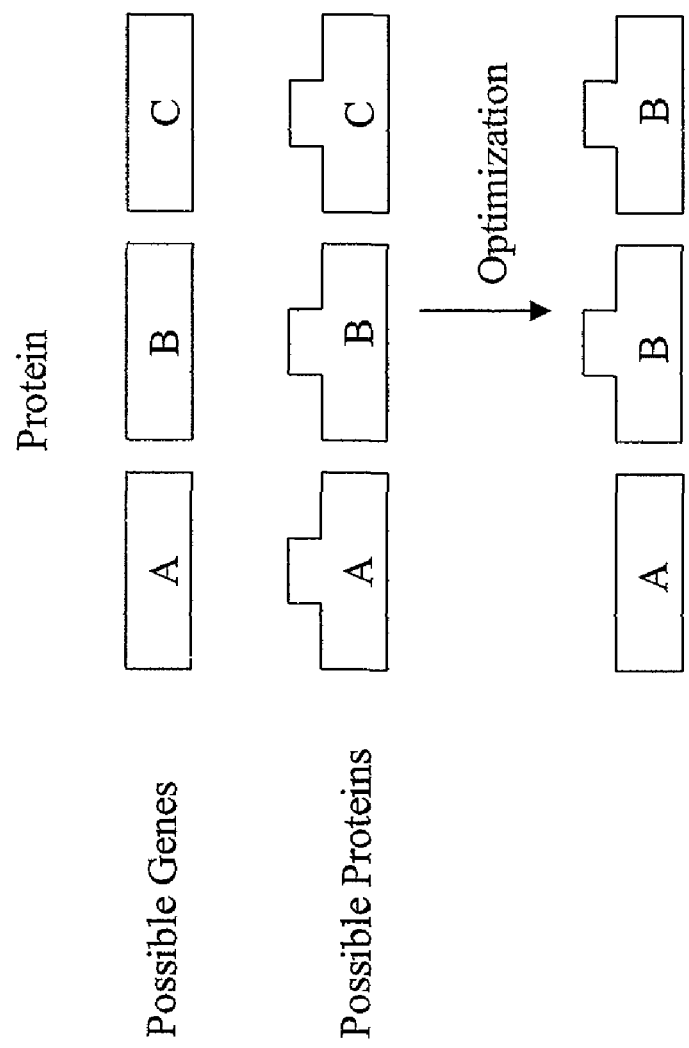
FIG. 6 depicts a representation of a method for determining which and how a gene can be changed to avoid the loss of functionality but reduce the risk of a HAHA response.

For example, consensus sequences for the protein products of the V genes can be created. The V genes can be combined into consensus sequences, either as a function of their structural similarities when translated into protein, or through the genes' determined probabilities of inducing a HAHA response. This latter option allows one to develop a model of what a low-risk and what a high-risk protein product from a gene looks like. Thus, the structure of a protein encoded in part by a V gene, which is responsible for inducing a HAHA response, can be predicted. Additionally, the structures of proteins from a V gene that does not produce HAHA responses can also be predicted. For instance, in FIG. 2C, it is apparent from the structures that an antibody with gene A will occur with a frequency of 100%, an antibody with the structure of gene B will not occur, and an antibody with the structure of Gene C will also occur with a frequency of occurrence of 100%. Additionally, this information can be used to selectively change the genes that are available for creating antibodies, as shown in FIG. 6. FIG. 6 displays the frequencies of occurrence for three genes, A, B, and C. While one can observe that gene C has a greater risk of inducing HAHA (in a population) than gene A or B, since the protein structures predicted by genes C and gene B are similar, instead of simply removing gene C from an animal used to produce these proteins, one can substitute a second copy of the B gene, or another gene with a structure similar to the B gene, instead. This replacement by similar structure can also prove useful in replacing V genes that are high-risk for one population of people, with a structurally similar, but HAHA inducing dissimilar gene.

Figure 7:
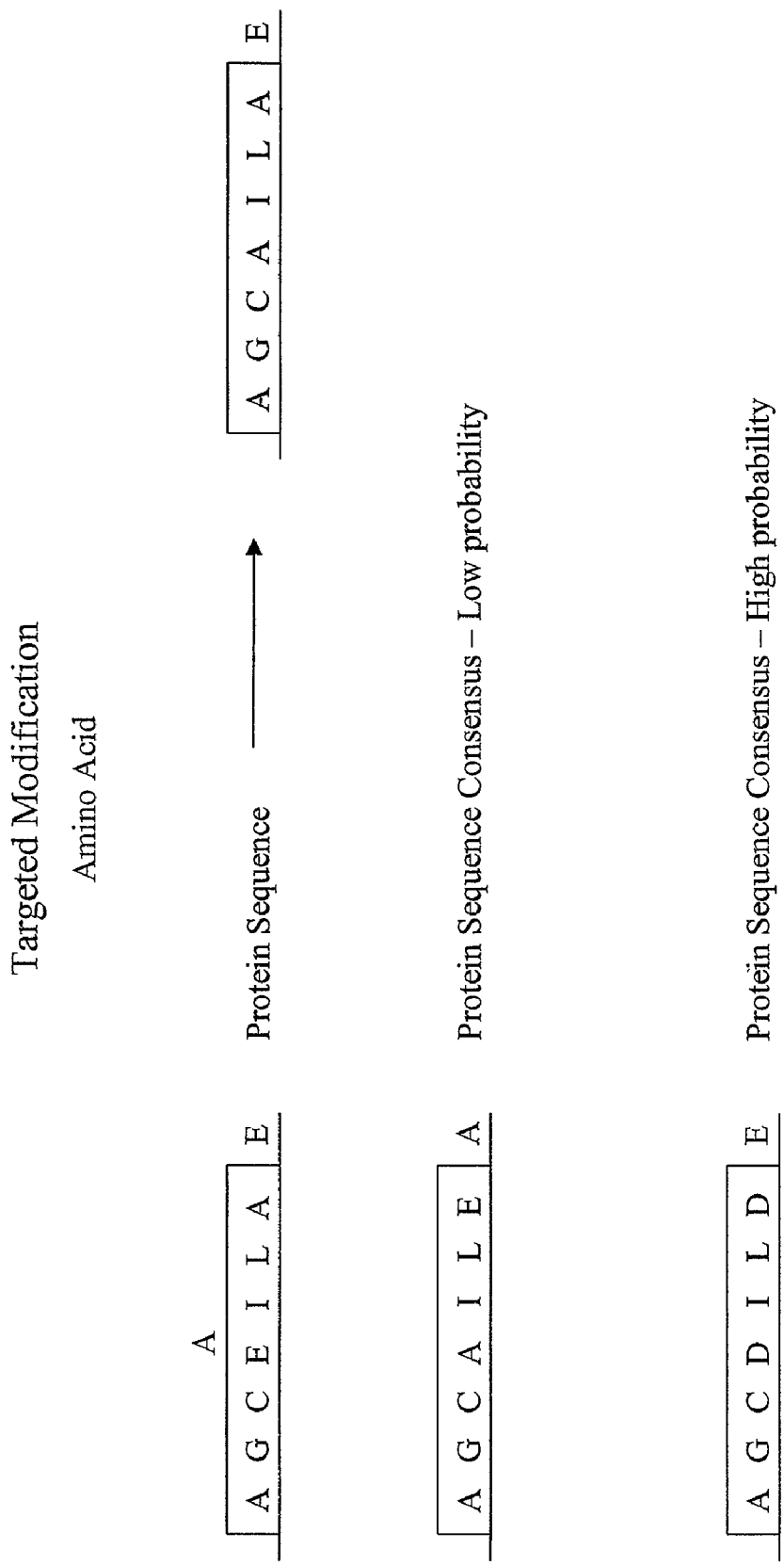
FIG. 7 depicts a representation of a method for determining which and how an amino acid can be changed to avoid the loss of functionality but reduce the risk of a HAHA response.
Figure 16A:
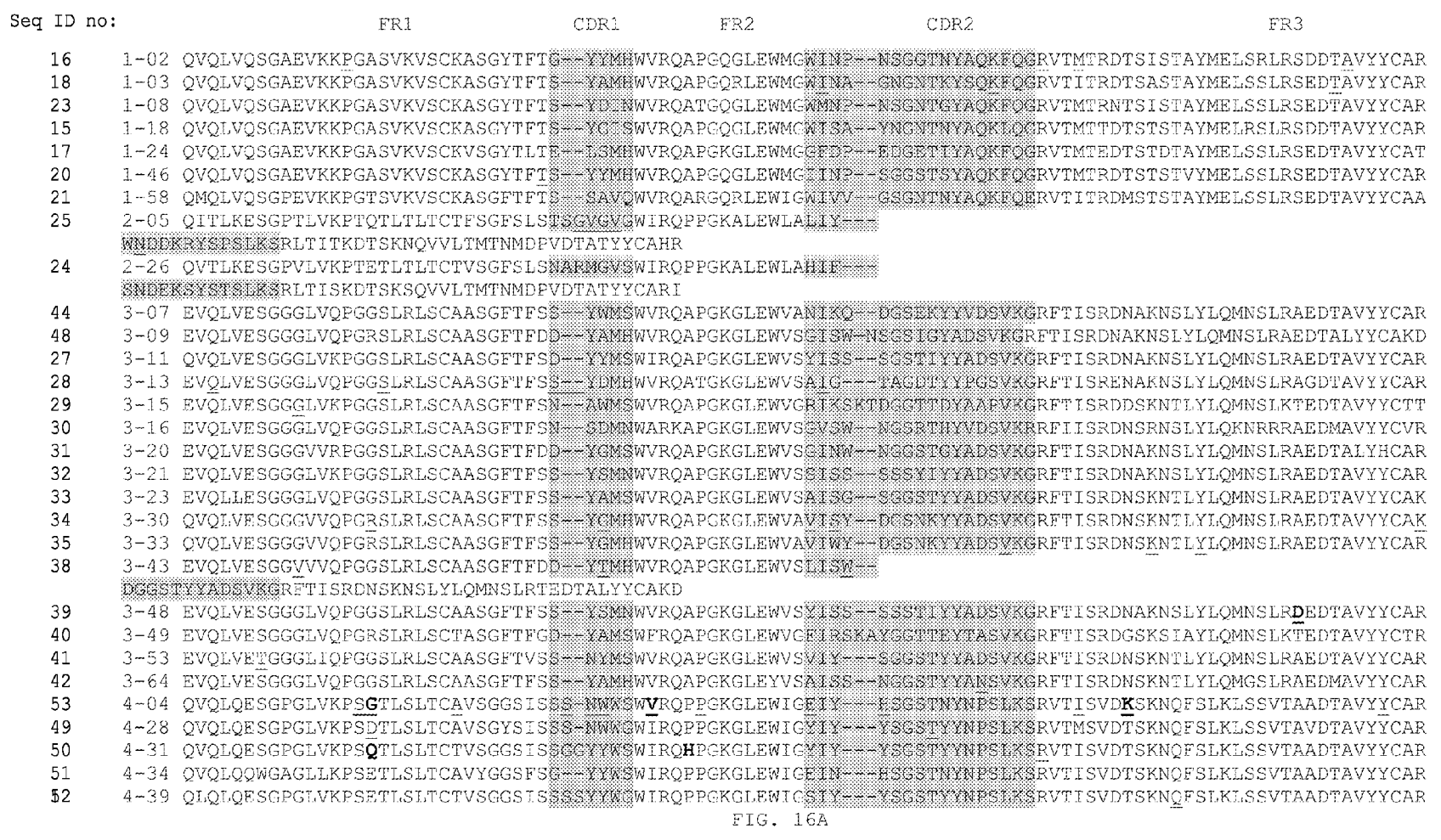

The structural information can also be used to select particular amino acids to change in order to reduce the risk of a HAHA response. One example of this is shown in FIG. 7. The amino acid sequences from the genes are obtained from high-risk and low-risk genes in order to make a high-risk consensus sequence and a low-risk consensus sequence. With both of these consensus sequences, and then the predicted structure of an antibody, or V gene thereof, the residues that need to be changed should be obvious from a comparison of the high risk consensus sequence to the individual predicted structure. For instance, in FIG. 7, the comparison between the protein sequence of the V gene and the consensus sequence of the high-risk gene, in protein form, suggests that both the fourth and last amino acids are possible targets for modification. What the residues should be changed to will be apparent from a comparison of the individual sequence to the low-risk consensus sequence. For instance, in FIG. 7, the comparison between the protein sequence of the V gene and the low-risk consensus sequence suggests that the fourth position should be changed to a noncharged sidechain. Additionally, this second comparison suggests that the last position in the A gene is not that important. It is also important to note that the single amino acid outside of the section defined as gene A, is not relevant to the analysis here. It is possible to use only a single consensus sequence; however, this could results in an increased risk of loss of functionality. One example of a possible alignment of the various genes is shown in FIG. 16A and FIG. 16B, for $V_H$ genes.

These consensus sequences and structures therefrom, can be weighted in any manner described herein. For example, if one is given three genes A, 1% (high-risk), B 50% (low-risk) and C, 100% (low to no risk) for a given population, while A and B can be compared to develop a consensus sequence, A can have more weight in developing a consensus sequence that is representative for high risk V genes.

The models determined above can be tested through various techniques. For example, the interaction energy can be determined with the programs discussed above in order to determine which of the variants to further examine. In addition, Coulombic and van der Waals interactions are used to determine the interaction energies of the epitope and the variant paratopes. Also site directed mutagenesis can be used to see if predicted changes in antibody structure actually result in the desired changes in binding characteristics. Alternatively, changes can be made to the epitope to verify that the models are correct or to determine general binding themes that can be occurring between the paratope and the epitope.

The above methods for modeling structures can be used to determine what changes in protein structure will result in particular desired characteristics of an antibody. These methods can be used to determine what changes in protein structure will not result in the desired characteristics.

As will be appreciated by one of skill in the art, while these models will provide the guidance necessary to make the antibodies and variants thereof of the present embodiments, it may still be necessary to perform routine testing of the in silico models, perhaps through in vitro studies. In addition, as will be apparent to one of skill in the art, any modification may also have additional side effects on the activity of the antibody. For instance, while any alteration predicted to result in greater binding may induce greater binding, it may also cause other structural changes that might reduce or alter the activity of the antibody. The determination of whether or not this is the case is routine in the art and can be achieved in many ways.

It is important to realize that a reduction in the functionality of the antibody is not necessarily detrimental to the usefulness of the present embodiment. Thus, a modification that reduces 99% of the functionality of the antibody, but also reduces the likelihood of a HAHA response being initiated by as much or more, can still be useful. Indeed, in some embodiments, a greater reduction in functionality than in reduced likelihood of HAHA response initiation may be sufficient or even desirable. In one embodiment, the reduction in functionality is one of the following: 0% to less than 1%, between 1% and 5%, between 5% and 30%, between 30% and 60%, between 60% and 90%, between 90% and 99%. Alternatively, an acceptable decrease in functionality is determined as a function of effective decrease in the risk of a HAHA response being induced, either for a population of people, or for a particular individual. Alternatively, the modification can result in an increase in functionality. In one embodiment, acceptable decreases in the risk of a HAHA response for any individual in a population is one of the following: less than 1%, between 1% and 5%, between 5% and 30%, between 30% and 60%, between 60% and 90%, between 90% and 100%, and 100%. Alternatively, the acceptable decrease can be determined as a function of the change in functionality, where smaller decreases in the risk of a HAHA response is desirable where little or positive changes occur in functionality, while larger decreases are desirable where larger negative changes in functionality occur.

By "functionality" it is meant the usefulness of the antibody. For example, an antibody may simply be a binding antibody, perhaps useful in detection assays, and requiring tight binding, but not necessarily rapid binding. Thus, the $K_D$ of such an antibody would be the factor that one would look at to determine if the modification had adversely impacted the antibody too much to be useful. Alternatively, if fast binding was desirable, then the $k_a$ would be the primary functionality examined following the modification. Alternatively, specificity, either towards a particular epitope of an antibody, for instance to allow the antibody to act as a blocker on a receptor, or as regards one target versus another target, for instance in an in vivo situation to reduce the likelihood of cross reactivity. Alternatively, the antibody may be an agonist type antibody and be useful as a ligand in activating receptors. Alternatively, the antibody could be an enzymatic or catalytic antibody and be functional in the sense that it promotes particular chemical reactions, such as in U.S. Pat. Nos. 6,043,069, issued to Koentgen et al., Mar. 28, 2000; 5,683,694 issued to Landry, Sep. 7, 1999; and 5,258,289 issued to Davis et al., Nov. 2, 1993). As will be appreciated by one of skill in the art, a single antibody may have a combination of any of these, as well as many other, functionalities. The relative importance of each can be easily determined on a case by case basis.

In one embodiment, the genes compared are V, D, or J genes. In another embodiment, the genes are V genes. In another embodiment, the genes compared are $V_H$ genes, $V_k$, or $V_{lambda}$ genes. In another embodiment, the genes are $V_H 3$ genes. In one embodiment, the presence of the $V_H 3$-9, $V_H 3$-13, and $V_H 3$-64 genes, or variants thereof, is an indicator of a high likelihood that the particular antibody will have an increased risk of inducing a HAHA response in some populations. In another embodiment, the genes are any of the genes published in Matsuda et al. (J. Exp. Med. 188:2151-2162, (1998)). In one embodiment, it is actually the protein segments that are examined; thus, only functionally coding $V_H$ genes are relevant. In another embodiment, it is only the mRNA from the genes that is analyzed or compared. In another embodiment, the segments are only transcribed. In another embodiment, the segments are only ORFs. In another embodiment, the segments are only pseudogenes with point mutations. In another embodiment, the segments are only pseudogenes with truncations. In one embodiment, the $V_H$ gene is selected from one of the following: 1-2, 1-3, 1-8, 1-18, 1-24, 1-45, 1-46, 1-58, 1-69, 2-5, 2-26, 2-70, 3-7, 3-9, 3-11, 3-13, 3-15, 3-20, 3-21, 3-23, 3-30, 3-33, 3-43, 3-48, 3-49, 3-53, 3-64, 3-66, 3-72, 3-73, 3-74, 4-4, 4-31, 4-34, 4-39, 4-59, 4-61, 5-51, 6-1. A more complete listing of $V_H$ and other genes can be found in FIG. 8 and FIG. 17A through FIG. 22J.

As will be appreciated by one of skill in the art, the minimization of high-risk genes will result in an antibody that has a reduced likelihood of inducing a HAHA response. However, the optimization of low-risk genes can also be a useful method of achieving the same end goal of an antibody with a lower risk of inducing a HAHA response. Thus, in one embodiment, the antibodies can be optimized by replacing high-risk genes with low-risk genes. In one embodiment, this refers to replacing a high-risk V gene of an antibody with a structurally similar low risk gene of a V gene.

Methods of Determining the Probability of a HAHA Response Occurring for a Particular Individual for a Given Antibody.

In some situations, the risk of a HAHA response may not be able to be minimized to a desired amount. However, knowing the risk associated with a particular antibody gene set for a particular host V gene profile of a patient can allow people to realize the degree of the risk involved in administering the particular antibody to the particular patient. With this information they can either take preventative measures against a HAHA response, or make the patient fully aware of the risks. Having this information can also aid in the diagnosis of future possible problems, if they occur. These comparison and data analysis techniques are also generally useful for any of the comparisons of high-risk and low-risk genes.

These calculations can be performed using any of the gene profiles disclosed herein. This can be done by determining which genes have a low risk and high risk of inducing a HAHA response. While knowing the precise host V gene profile of a patient may be desirable in some situations, it is also possible to predict the probability that a HAHA response will occur by using different types of host V gene profiles, such as those based on ethnic background or broader profiles. One of skill in the art will appreciate that the ability of these comparisons to predict such HAHA responses will decrease when less customized profiles are used.

In one embodiment, each gene in the particular antibody gene set that is a low-risk gene is given a negative single point value and each gene that is a high risk gene is given a positive value. One can then add each of the values corresponding to each of the genes in the gene set of each antibody to determine the risk of a HAHA response occurring. The more positive the number, the greater the chance that a HAHA response will occur. Thus, if the gene set only involves V genes, the presence of a high-risk V gene will represent risk. In this embodiment, all high-risk V genes will have the same total risk value, namely 1. In some embodiments, only high-risk genes are scored; thus, a gene is given a point value if it occurs with less than a minimum or predetermined frequency of occurrence and a score will indicate that there is a risk of a HAHA response. Higher scores can indicate a greater risk.

In another embodiment that involves a profile of a population, instead of each risk gene being assigned a single point value, the point value is determined based upon the frequency of the genes in the profile. For example, a gene that occurs with a frequency of 1% is assigned a greater point value than a gene that occurs with a frequency of 10%. Likewise, a gene which occurs with a frequency of 99% would be assigned a greater number than a gene which occurs with a frequency of 100%. Of course, if all four genes were being compared, the relative weights of the point value would be 1%>10%>99%>100%. Each of the values for each of the genes are added and the higher the number, the greater the risk of a HAHA response occurring. In one embodiment, the point values assigned are directly related to their frequency of occurrence in the profile. For example, the point value for a gene that has a frequency of occurrence of 10% in the profile would be approximately 10 fold smaller than that of a gene, which occurs at 1% in the profile. In the end, the lower the number, the lower the risk associated with that antibody. Thus, in the embodiment in which the gene set only contemplates V genes, the total risk score or value for the antibody would be the risk value assigned to that V gene.

Alternatively, one can examine the risk associated with certain gene frequencies in antibodies in inducing a HAHA response when the antibodies are administered to a subject. Thus, in one embodiment, actual previous experimental data is also included in these calculations.

Figure 9:
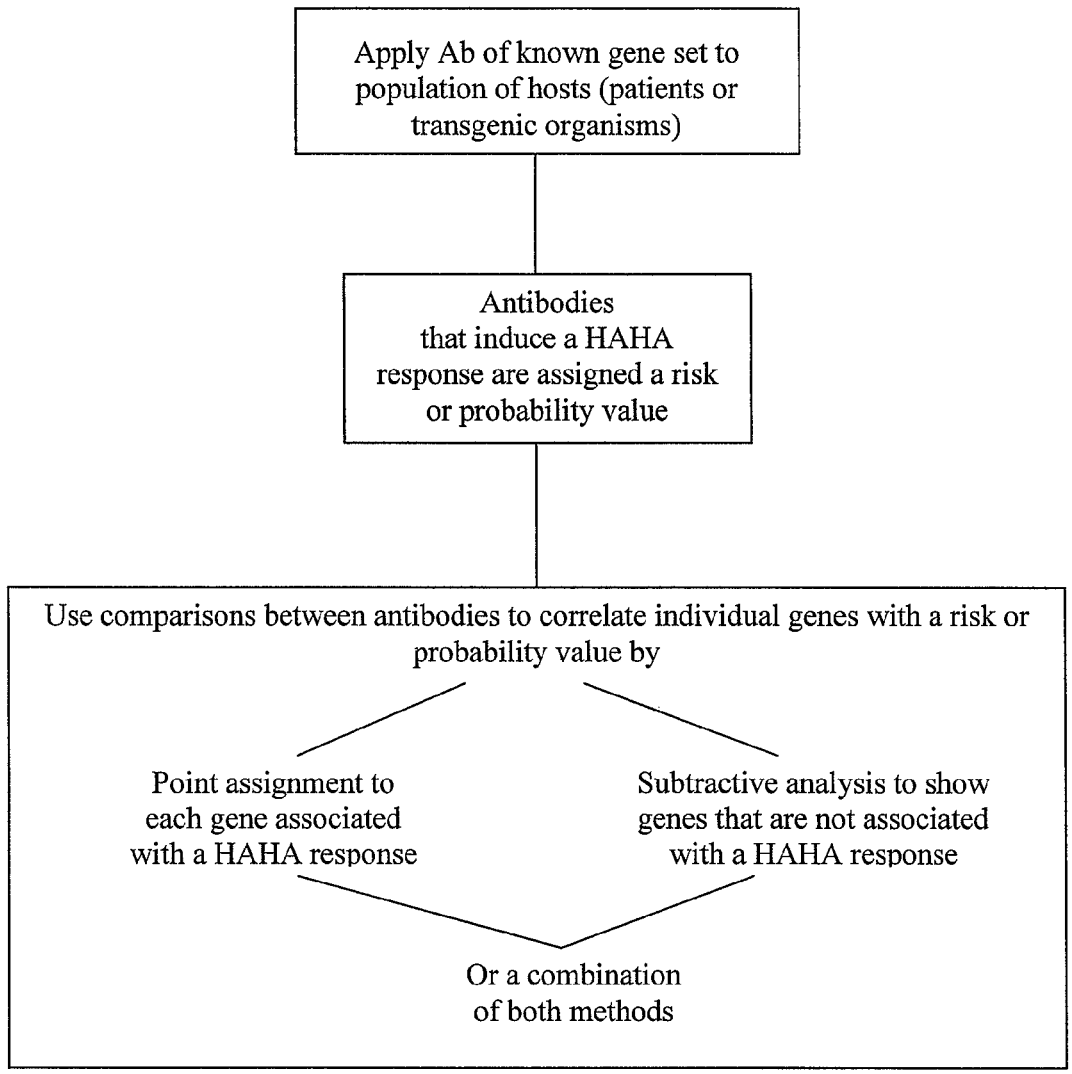
FIG. 9 depicts a flow chart of one method by which experimental data can be used to determine the risk values of genes.
Figure 10:
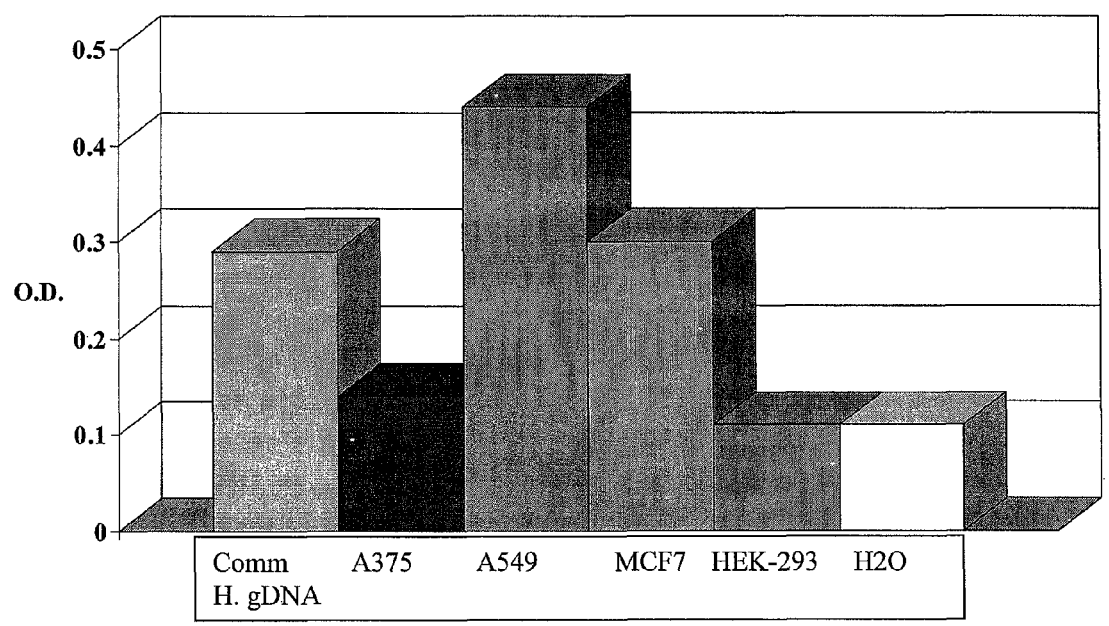
FIG. 10 is a bargraph depicting the presence of $V_H3$-9 in various cells.

In one embodiment, the data can be taken from previous administrations of antibodies to patients and an examination of whether or not any HAHA response was initiated from the use of the antibody. An example of how this can be done is shown in FIG. 9. This also allows one to correlate risks in different genetic backgrounds, such as the ethnic backgrounds discussed herein. The simple correlation of antibody to HAHA response will allow one to determine the probability of an antibody inducing a HAHA response. In one embodiment, illustrated on the left side of FIG. 9, one can obtain the degree of risk associated with each V gene by awarding points to the V gene that occurs in an antibody that has been shown to cause a HAHA response. Each time the antibody is administered and elicits a HAHA response; the genes of the antibody will be awarded a point. The genes with the highest point value, or "total risk score" are the genes most likely to be high-risk genes. In embodiments in which the only genes examined are the V genes, the point value awarded is only correlated to the risk associated with the V gene.

Alternatively, as shown on the right hand side of FIG. 9, one can apply a subtractive process to the analysis. Thus, while those genes that occur in antibodies that induce a HAHA response would be awarded a point value, if the same gene appeared in another antibody and did not induce a HAHA response, then one would subtract the points awarded for this gene. Again, the genes with the highest total risk score will have the greatest risk of inducing a HAHA response. While such a subtractive approach can remove many possible high-risk genes, those genes that are identified by the process will be high-risk genes. Alternatively, one can combine the two embodiments to help filter out more of the false positives and keep more of the false negatives. This can be done so as to correct for differences in the possible genetic backgrounds of the patients.

In another embodiment, a humanized organism is used to see if a particular antibody or gene has a high risk of inducing a HAHA response. This is discussed in greater detail below.

Of course, multiple testings will increase the certainty of whether or not it is a high-risk antibody. There are at least two methods by which one can determine if a gene is a high-risk gene for this embodiment. First, after determining a low-risk antibody, which is any antibody that rarely or, preferably, does not induce a HAHA response, one then alters the gene set composition of the antibody, substituting in a new V gene and testing the modified antibody. If the modified antibody results in a HAHA response, then the introduced gene could be a high-risk gene.

In another embodiment, a human or XenoMouse® mouse is used as the test subject to determine if a V gene or an antibody is a high risk compound.

As appreciated by one of skill in the art, the use of these experimental results eliminates or greatly reduces the role that a host V gene profile will play in the current embodiments. However, the correlation of a particular gene with a particular likelihood of a HAHA response being induced is still important.

Such experimental data can be similarly useful in defining high-risk genes or low-risk genes as well. The above mentioned methods for calculating the risk of a HAHA response occurring due to a particular gene, gene set, or antibody can be used for the other methods involving individual genes as well. Thus, while determining which genes and how the gene should be modified can involve an analysis of a single gene, the different methods of weighing each gene, discussed above, can be incorporated into their analysis.

In some embodiments, the risk of a HAHA response is calculated for a particular individual. In one embodiment, the gene set of the candidate antibody to be administered to the individual will be compared to the antibody gene set of the individual. Low risk genes will be those that the antibody and the individual have and express and high risk genes will be those that the antibody has (i.e., encode the protein structure of the antibody) but are not present in the individual's genes.

In another embodiment, the risk of a HAHA response is calculated on a broader basis. For instance, the risk can be calculated from different normalized host V gene profiles. Thus, if the host V gene profile is for an entire family, then the risk value produced from the comparison will be for the entire family. Likewise, if an ethnic host V gene profile is used, then any risk value produced will be for the entire ethnic group. One of skill in the art will recognize that while the accuracy of the risk value will decrease as the variation in the host V gene profile increases (for example a V gene profile of identical twins will be much more accurate than one for an entire ethnic group), there is still a value in being able to assign a general level of risk to the antibodies.

Any of the additional methods also discussed herein can also be used as described above, in order to correlate a patient's risk of developing a HAHA response following the administration of an antibody. Additionally, even if the antibody being administered is a gene-optimized antibody, it may still be useful to determine the risk associated with that antibody for that patient.

Databases and Methods of Making Host V Gene Profile Databases to Determine High-Risk and Low-Risk Genes.

At a simple level, one need only define a population for the host V gene profile and then determine the V genes in that population. The frequency with which those V genes appear in that population can then be determined. In one embodiment, the frequency with which the mRNA appears from the genes is determined. Alternatively, the frequency with which the genes are actually used in protein, in the population can be determined. Alternatively, either the structure or functionality of the protein is actually determined. Thus, the mere presence of a V gene would not automatically mean that a V gene was added to the profile to be counted as a common gene, instead, the protein product would have to be expressed in the population in order for the gene to be added to the profile.

As discussed above, these profiles can be directed to the DNA level, mRNA level, amino acid level or protein structure level. The profiles can be directed to the basic building blocks of protein structure or the larger structure of the antibody. The databases can also factor in aspects of clustering comparing the risk (or probability) associated with combinations of particular $V_H$ and $V_L$ genes within an antibody, or particular $V_H$, $D_H J_H$, and $J_L$ genes within an antibody chain. In one embodiment, the databases can include any method of analyzing genetic material, so long as the defining elements of each V gene coding region are the primary level at which the analysis occurs.

The profiles can be directed to populations of any size. In one embodiment, the profiles are split into ethnic groups, as explained above. In another embodiment, the profiles are split into family groups. The profile can also be a universal profile as well.

The profiles can be supplemented with additional information from experimental findings or test results. For instance, an examination of the frequency of V genes in antibodies administered to patients and correlating this to those individuals that experienced a HAHA response could be very useful in identifying those genes that are so rare that they are not included in the profile. An example of this is shown in FIG. 9. This can be a problem, as genes that are very rare not only have the greatest chance of inducing a HAHA response, but also the least chance of being in the profile. Fortunately, once a profile is developed that is sufficient in size; the simple absence of the V gene from the profile is an indication that the gene is a risk gene. As appreciated by one of skill in the art, there can be some situations where, even though a V gene is a low-risk gene, its actual use still induces a HAHA response. In such circumstances, it is possible for the profile to reflect this fact and adjust the scoring system to predict risk or suggest gene modification for making gene-optimized antibodies accordingly.

As understood by one of skill in the art, many of the adjustments made to the profile could also be incorporated into the actual comparison of the profile to other genes. Such an analysis is acceptable so long as factors are not inadvertently incorporated into the calculations in a duplicitous manner.

In some embodiments, high risk genes are $V_H3$-9, $V_H3$-13, and $V_H3$-64, for a particular population. As will be appreciated by one of skill in the art, whether a gene is a high-risk gene or not can depend upon the particular population or individual that is to be host to the antibody encoded by the gene. Thus, it is often helpful to note the particular population that has the associated risk. As will be appreciated by one of skill in the art, given the present disclosure, a categorization of various genes into high, medium, or low risk, or risk percentages can be easily achieved, by, for example, following the examples below.

Gene-Optimized Antibody Proteins, Nucleic Acids, and Variants Thereof, V Gene Profile Customized XenoMouse® Mice.

Also included in the present embodiments are the actual gene-optimized antibodies, the nucleic acids encoding the gene-optimized antibodies and variants thereof. While the antibodies need not be human, there are advantages to either human or humanized antibodies.

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of human antibody function into a rodent so that the rodent produces fully human antibodies.

The ability to clone and reconstruct megabase-sized human loci in YACs (yeast artificial chromosome) and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression. Thus, in one embodiment, the compositions of the embodiments are placed in the mouse germline. This allows one to create an organism with a particular host gene profile, V gene profile, or normalized V gene profile which can then be used to make optimized antibodies or V gene optimized antibodies.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (mAbs)—an important milestone towards fulfilling the promise of antibody therapy in human disease. Fully human antibodies are expected to minimize the immunogenic and allergic responses intrinsic to murine or murine-derivatized mAbs and thus to increase the efficacy and safety of the administered antibodies. The use of fully human antibodies can be expected to provide a substantial advantage in the treatment of chronic and recurring human diseases, such as inflammation, autoimmunity, and cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human mAbs with the desired specificity could be readily produced and selected. This general strategy was demonstrated in connection with our generation of the first XenoMouse® mouse strains as published in 1994. See Green et al. Nature Genetics 7:13-21 (1994). The XenoMouse® strains were engineered with yeast artificial chromosomes (YACs) containing 245 kb and 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human mAbs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively. See Mendez et al. Nature Genetics 15:146-156 (1997) and U.S. patent application Ser. No. 08/759,620, filed Dec. 3, 1996, the disclosures of which are hereby incorporated by reference.

One method for generating fully human antibodies is through the use of XENOMOUSE® strains of mice that have been engineered to contain 245 kb and 190 kb-sized germline configuration fragments of the human heavy chain locus and kappa light chain locus. Other XenoMouse strains of mice contain 980 kb and 800 kb-sized germline configuration fragments of the human heavy chain locus and kappa light chain locus. Still other XenoMouse strains of mice contain 980 kb and 800 kb-sized germline configuration fragments of the human heavy chain locus and kappa light chain locus plus a 740 kb-sized germline configured complete human lambda light chain locus. See Mendez et al. Nature Genetics 15:146-156 (1997) and Green and Jakobovits J. Exp. Med. 188:483-495 (1998). The XENOMOUSE® strains are available from Abgenix, Inc. (Fremont, Calif.).

The production of the XenoMouse® mice is further discussed and delineated in U.S. patent application Ser. Nos. 07/466,008, filed Jan. 12, 1990, 07/610,515, filed Nov. 8, 1990, 07/919,297, filed Jul. 24, 1992, 07/922,649, filed Jul. 30, 1992, filed 08/031,801, filed Mar. 15, 1993, 08/112,848, filed Aug. 27, 1993, 08/234,145, filed Apr. 28, 1994, 08/376, 279, filed Jan. 20, 1995, 08/430, 938, Apr. 27, 1995, 08/464, 584, filed Jun. 5, 1995, 08/464,582, filed Jun. 5, 1995, 08/463, 191, filed Jun. 5, 1995, 08/462,837, filed Jun. 5, 1995, 08/486, 853, filed Jun. 5, 1995, 08/486,857, filed Jun. 5, 1995, 08/486, 859, filed Jun. 5, 1995, 08/462,513, filed Jun. 5, 1995, 08/724, 752, filed Oct. 2, 1996, and 08/759,620, filed Dec. 3, 1996 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also Mendez et al. Nature Genetics 15:146-156 (1997) and Green and Jakobovits J. Exp. Med. 188:483-495 (1998). See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000, WO 03/47336. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661, 016, 5,770,429, 5,789,650, 5,814,318, 5,877,397, 5,874,299, and 6,255,458 each to Lonberg and Kay, U.S. Pat. Nos. 5,591, 669 and 6,023.010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. No. 07/574,748, filed Aug. 29, 1990, 07/575,962, filed Aug. 31, 1990, 07/810,279, filed Dec. 17, 1991, 07/853,408, filed Mar. 18, 1992, 07/904, 068, filed Jun. 23, 1992, 07/990,860, filed Dec. 16, 1992, 08/053,131, filed Apr. 26, 1993, 08/096,762, filed Jul. 22, 1993, 08/155,301, filed Nov. 18, 1993, 08/161,739, filed Dec. 3, 1993, 08/165,699, filed Dec. 10, 1993, 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference.

Xenerex Biosciences is developing a technology for the potential generation of human antibodies. In this technology, SCID mice are reconstituted with human lymphatic cells, e.g., B and/or T cells. Mice are then immunized with an antigen and can generate an immune response against the antigen. See U.S. Pat. Nos. 5,476,996, 5,698,767, and 5,958, 765.

Human antibodies can also be derived by in vitro methods. Suitable examples include, but are not limited to, phage display (CAT, Morphosys, Dyax, Biosite/Medarex, Xoma, Symphogen, Alexion (formerly Proliferon), Affimed) ribosome display (CAT), yeast display, and the like.

Antibodies

As discussed above, there are substantial benefits of making transgenics that contain only a subset of the possible V genes, in particular, a subset of $V_H$ or $V_{kappa}$ or V lambda genes. Thus, a transgenic XenoMouse® animal that lacks certain high-risk genes is particularly desirable for producing antibodies. However, as appreciated by one of skill in the art, there is no need that the transgenic has to be a mouse or a XenoMouse® mouse.

Antibodies, as described herein, can be prepared through the utilization of the XenoMouse® technology, as described below. Such mice, then, are capable of producing human immunoglobulin molecules and antibodies and are deficient in the production of murine immunoglobulin molecules and antibodies. Technologies utilized for achieving the same are disclosed in the patents, applications, and references cited herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. Nature Genetics 15:146-156 (1997), the disclosure of which is hereby incorporated by reference.

Through use of such technology, fully human monoclonal antibodies to a variety of antigens can be produced. Essentially, XenoMouse® lines of mice are immunized with an antigen of interest, lymphatic cells are recovered (such as B-cells) from the mice that expressed antibodies, and such cells are fused with a myeloid-type cell line to prepare immortal hybridoma cell lines, and such hybridoma cell lines are screened and selected to identify hybridoma cell lines that produce antibodies specific to the antigen of interest. Antibodies produced by such cell lines are further characterized, including nucleotide and amino acid sequences of the heavy and light chains of such antibodies.

Alternatively, instead of being fused to myeloma cells to generate hybridomas, the antibody produced by recovered cells, isolated from immunized XenoMouse® lines of mice, are screened further for reactivity against the initial antigen. Such screening includes ELISA, in vitro binding to cells stably expressing the antigen. The antibodies can also be screened to determine if it has a risk of inducing a HAHA response. Single B cells secreting antibodies of interest are then isolated using an antigen-specific hemolytic plaque assay (Babcook et al., *Proc. Natl. Acad. Sci. USA*, i93:7843-7848 (1996)). Cells targeted for lysis are preferably sheep red blood cells (SRBCs) coated with the antigen. In the presence of a B cell culture secreting the immunoglobulin of interest and complement, the formation of a plaque indicates specific antigen-mediated lysis of the target cells. The single antigen-specific plasma cell in the center of the plaque can be isolated and the genetic information that encodes the specificity of the antibody is isolated from the single plasma cell. Using reverse transcriptase PCR, the DNA encoding the variable region of the antibody secreted can be cloned. Such cloned DNA can then be further inserted into a suitable expression vector, preferably a vector cassette such as a pcDNA, more preferably such a pcDNA vector containing the constant domains of immunoglobulin heavy and light chain. The generated vector can then be transfected into host cells, preferably CHO cells, and cultured in conventional nutrient media modified as appropriate for inducing promoters, selecting transformants, or amplifying the genes encoding the desired sequences.

B cells from XenoMouse® mice can be also be used as a source of genetic material from which antibody display libraries can be generated. Such libraries can be made in bacteriophage, yeast or in vitro via ribosome display using ordinary skills in the art. Hyperimmunized XenoMouse® can may be a rich source from which high-affinity, antigen-reactive antibodies may be isolated. Accordingly, XenoMouse® mice hyperimmunized against an antigen can be used to generate antibody display libraries from which high-affinity antibodies against an antigen may be isolated. Such libraries could be screened against an appropriate target such as an oligopeptide or protein and the resultingly derived antibodies screening against cells expressing an antigen to confirm specificity for the natively display antigen. Full IgG antibody may then be expressed using recombinant DNA technology. See e.g., WO 99/53049.

In general, antibodies produced by the above-mentioned cell lines possess fully human IgG heavy chains with human light chains. The antibodies possess high affinities, typically possessing $K_d$'s of from about $10^{-9}$ through about $10^{-13}$ M, when measured by either solid phase and solution phase.

As will be appreciated, antibodies as described herein can be expressed in cell lines other than hybridoma cell lines. Sequences encoding particular antibodies can be used for transformation of a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introduction of heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines.

The XenoMouse® Animal as an Assay System for Determining the Risk of HAHA Response Induction Types of XenoMouse® Animals In one embodiment, a humanized organism is used to see if a particular antibody or gene encoding for part of an antibody has a risk of inducing a HAHA response. In one embodiment, the organism is a XenoMouse® animal. Thus, if an antibody administered to a XenoMouse® animal results in a HAHA response in the animal, then the antibody will be a high-risk antibody for any patient with a immunogenic gene set that is similar to the XenoMouse® animal's immunogenic gene set. In particular, the similar absence of high-risk genes between a patient and the XenoMouse® animal will determine if the XenoMouse® animal is an appropriate model for that patient.

In one embodiment, the XenoMouse® animal is customized for an individual or for a group of individuals, such as an ethnic group as discussed above. For example, a customized XenoMouse® animal will lack the same high-risk genes that the patient, for whom the XenoMouse® animal is customized, lacks. Thus, a patient of a particular ethnic background can use a customized XenoMouse® animal that lacks the same high-risk genes that the patient and the ethnic group lack as a test subject to determine if a particular antibody will result in a HAHA response in the patient. Thus, the risk of that patient experiencing a HAHA response is more accurately assessed. This also allows antibody administration to patients to be more customized.

In one embodiment, the XenoMouse® animal only has the same low risk genes that the patient or population, which is to accept the antibody, has. Other customized XenoMouse® animal test subjects can also be created once a trend of high risk or low risk genes is identified for any group of people. A risk profile can be turned into a XenoMouse® animal that is an indicator of risk that a HAHA response will occur if the Ab is administered. In one embodiment, the XenoMouse® animal has a minority of the high-risk genes for a population it is to represent. In another embodiment, the XenoMouse® animal has from about 50% or fewer of the high-risk genes for a population to be treated, for example 50-20, 20-10, 10-5, 5-1, or 1-0%. In another embodiment, the XenoMouse® animal has none of the high-risk genes for a population to be treated with an antibody. In another embodiment, the XenoMouse® animal only has low risk genes from a consensus of a population of people. In one embodiment, the consensus is across ethnic groups. In one embodiment, the consensus is within ethnic groups.

In one embodiment, the XenoMouse® animal lacks all high risk genes and medium risk genes. In one embodiment, the high risk genes include $V_H3$-9, $V_H3$-13, and $V_H3$-64. In one embodiment, low risk genes will be those that are not high-risk genes. In some embodiments, the XenoMouse® animal only contains low risk genes.

In one embodiment, the XenoMouse® animal comprises all, or substantially all, of the V, D, and/or J genes from *Homo sapiens*. Such a XenoMouse® animal should not display a HAHA response to human antibodies and can be useful as a negative control to demonstrate an absence of a HAHA response.

Methods of Using a XenoMouse® Animal for Detection or Determination of the Risk of Inducing a HAHA Response In one embodiment, a method of using a XenoMouse® animal to determine if an antibody will induce a HAHA response in a human is provided. The method involves administering a candidate antibody to a XenoMouse® animal, allowing a sufficient amount of time to pass so that a HAHA response can occur, withdrawing a sample from the XenoMouse® animal, testing the sample for the presence of antibodies directed against the test antibody, and examining the sample for the presence or absence of substances (e.g., antibodies) that bind to the test antibody. An Example of such a use is shown in Example 7 below.

In one embodiment, two antibodies are given to two similar XenoMouse® animals. One antibody will be a candidate antibody, whose HAHA inducing activity is uncertain, the second antibody will be a control antibody whose induced HAHA response will be used as a reference point against the test antibody's HAHA response. Any antibody with a known or predicted risk for inducing a HAHA response can be used as a control.

For example, one possible control antibody is HUMIRA®, antibody D2E7, which is known to induce a HAHA response in humans (SEQ ID NO.: 1-4, LCVR, HCVR, LC CDR3, HC CDR3, respectively, FIG. 23A). The resulting HAHA response from the administration of such an antibody to a XenoMouse® animal can be seen in FIG. 12A through FIG. 12C. It is evident that the administration of D2E7 to the XenoMouse® animals resulted in a significant amount of immunogenicity. On the other hand, a candidate human IgG1, kappa antibody, A, did not induce a significant HAHA response (See, FIGS. 11A-C). The candidate antibody, antibody A, is an antibody described in co-pending U.S. Pat. Application 60/430,729, filed Dec. 2, 2002, herein incorporated in its entirety by reference and has a sequence identified in SEQ ID NO.: 71-74 in that application, and SEQ ID NO.: 5-8 in the present specification (FIG. 23A).

Any XenoMouse® animal, or other transgenic organism, that has the ability to generate human or humanized antibodies can be used. In one embodiment, a XenoMouse® animal that has no high-risk genes of a human can be used. Such "universal" organisms are useful in that they have the greatest ability to detect if there is a risk of the induction of a HAHA response. Such a XenoMouse® animal may not be as useful as another XenoMouse® animal with a different gene set in predicting if a particular antibody will induce a HAHA response in a particular patient, as such a XenoMouse® animal may result in many false positives as concerns individual members of a population. However, in one embodiment, universal mice are useful in identifying universal antibodies that will not induce a HAHA response across a population of people. For example, while a transgenic organism that lacked all high-risk genes would exhibit a HAHA response to any antibody with a high risk gene for anyone in a population, any antibody that did not induce a HAHA response will have a low probability of inducing a HAHA response in anyone in the population. Thus, such organisms are useful in screens for universal HAHA antibodies.

In one embodiment, high-risk genes that are not in the patient's gene set are not in the customized XenoMouse® animal to which the test antibody will be administered. By using these customized XenoMouse® animals, one is able to reduce the number of false positives that may occur. In one embodiment, the customized XenoMouse® animal and the patient lack all of the same high-risk genes. In another embodiment, the customized XenoMouse® animal and the patient or the population that the patient belongs to lack 100% or fewer of the same high-risk genes, for example 100-99, 99-98, 98-95, 95-90, 90-80, 80-70, 70-50, 50-30, 30-1, 1-0 percent of the same high-risk genes. In another embodiment, the customized XenoMouse® animal has the same gene set for V, D, and J genes as the patient or population that the patient belongs to. In one embodiment, the customized XenoMouse® animal and the patient or population have at least 1 gene in common. For example, they may have 100, 100-90, 90-70, 70-50, 50-30, 30-10, 10-1, or 1-0 percent of the same V, D, or J genes in common.

In another embodiment, the XenoMouse® animal need not be customized exactly to the patient that is going to receive the antibody. Thus, the XenoMouse® animal can have a high-risk gene that the patient lacks; thus, raising the possibility that the administration of an antibody to the XenoMouse® animal will result in a false negative. However, the administration of the antibodies to the XenoMouse® animal can take this into account. Antibodies with that particular high-risk gene will not be included as possible antibodies for the patient, even if no HAHA response is created by the XenoMouse® animal.

Figure 12:
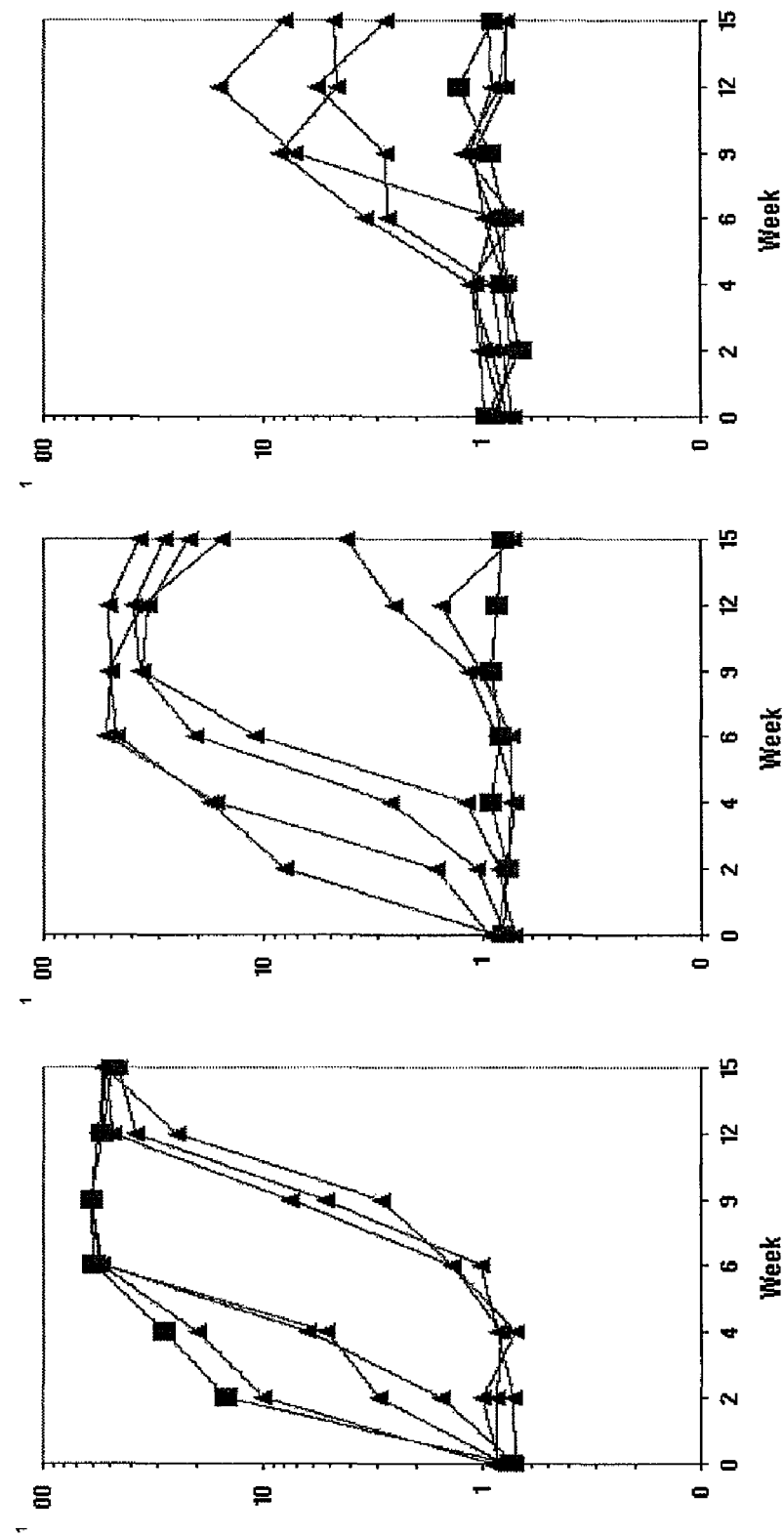
FIG. 12A is a graph displaying the level of immunogenicity induced by antibody B when administered to a XenoMouse® animal via a BIP/ADJ route.
FIG. 12B is a graph displaying the level of immunogenicity induced by antibody B when administered to a XenoMouse® animal subcutaneously.
FIG. 12C is a graph displaying the level of immunogenicity induced by antibody B when administered to a XenoMouse® animal intravenously.
FIG. 12D is a graph displaying the level of immunogenicity induced by a positive control, KLH via the BIP route (left panel) or subcutaneously (right panel)

Any method of administration that allows a HAHA response to occur or be monitored is adequate for the purposes of these embodiments. In one embodiment, the test or candidate antibody is administered into the mice using an approach similar to what would be used in patients. In another embodiment, methods that optimize the likelihood of inducing a HAHA response can be useful. For example, as shown in FIGS. 12A-C, while intravenous administration can lead to the detection of a HAHA response in the mouse of an antibody that can induce a HAHA response, higher responses are produced when the antibody is given subcutaneously or with an adjuvant. In one embodiment, the antibody is administered as a protein or as a nucleic acid.

Additionally, as HAHA responses are more likely to occur after multiple administrations of an antibody, it can be advantageous to repeatedly administer the test antibody to the XenoMouse® animal to see if a HAHA response will be induced.

The immunogenic response can be measured by any method, as long as it reveals the presence of antibodies directed to the original test antibody. For example, as discussed in Example 7, a bridging ELISA assay can be used. Alternatively, as the original test antibody is generally known, it is easy to apply the test antibody to beads or on a chip, such as a BIAcore assay system, to detect if there are proteins in the test subject's serum sample that bind to the candidate or test antibody. Binding of a substance to the test antibody indicates the presence of a possible immunogenic response. In one embodiment, the particular response examined for is a HAHA response. This can be done by administering a human antibody, or humanized antibody, to a XenoMouse® animal.

In general, the level of immunogenic response generated by an antibody can be compared to either a positive or negative control antibody. In one embodiment, whether or not an immunogenic or HAHA response is generated is a binary answer, with any deviation from the negative control or set standard indicating that a HAHA response has occurred. In another embodiment, the presence or absence of a HAHA response is correlated with time or concentration of the antibody administered. The presence or absence of a response can also factor in the method of administration. In one embodiment, a positive HAHA response is a response that displays an amount of a substance that binds to the antibody greater than the amount in a negative control, or a set negative response standard, in an amount of at least above 100 percent of a negative control, for example, 101, 101-200, 200-300, 300-500, 500-800, 800-1500, 1500 percent or more, of the negative control. In one embodiment, the substance that binds to the administered antibody is defined as a host antibody; thus, only an increase in host antibodies that bind to the administered, or test, antibody will be encompassed by the term "substance that binds to the administered antibody." In another embodiment, there need be no increase in a substance that binds to the administered antibody. For example, the host may already have an established immunogenic response to the administered antibody. Thus, any substantial amount of binding to the administered antibody, even if it does not later result in an increase in a substance that binds to the administered antibody, can indicate that the antibody will induce a HAHA response. Such comparisons of data are usually made through an expected or standard of responses.

The significance of the response will depend upon many factors, such as how long the response takes to occur in addition to factors such as the need and benefit of the antibody compared to the risk of a HAHA response occurring and possible medication that may be co-administered with the antibody.

One benefit of knowing the risk of a HAHA response being induced is whether or not other agents should be added with the antibody to reduce the risk of a HAHA response occurring.

One additional use of these XenoMouse® animals and the disclosed methods is that the XenoMouse® animals and the HAHA inducing antibodies, can be combined to screen for drugs or substances that are able to decrease the risk of a HAHA response occurring (anti-HAHA response, or HAHA inhibitor compounds). For example, given an antibody that induces a HAHA response in a XenoMouse® animal, a candidate anti-HAHA response compound can be added to the XenoMouse® animal, in addition to the HAHA inducing antibody, in order to determine if the candidate anti-HAHA response compound is adequate to reduce the risk of a HAHA response occurring. Similarly, XenoMouse® animal with antibodies that induce a HAHA response can be used to screen for substances that block a HAHA response (HAHA inducing antibodies). Similarly, the mice and antibodies can be used to help determine the effective dosage of the compounds.

In some embodiments, the above substances and methods of administering the antibodies are varied so that other factors associated with the induction of a HAHA response can be examined. As discussed in more detail below, the particular route of administration, or frequency of administration can be altered, while keeping the particular antibody the same, to determine whether the altered condition affects the HAHA response. Additionally, substances other than antibodies can be administered to determine if the alternative substances inhibit or exacerbate a HAHA response.

As appreciated by one of skill in the art, the above discussion occasionally details the XenoMouse® animal and methods of its use with regard to high-risk V genes; however, the genes may also be D or J genes as well. Additionally, both light and heavy chain genes are considered.

Eliminating or Minimizing Additional Variables in the Above Methods

As appreciated by one of skill in the art, there are additional possible differences between the mouse and human systems that could complicate the application of any transgenic organism as a detector of HAHA induction risk. One such factor, discussed below, is the role and possible differences in the T cell epitope repertoire. This factor and the theories behind it are for means of illustration only and are not intended as limitations upon the present invention.

B cell-mediated antibody responses to protein antigens are primarily dependent on T cell help in the form of cognate interactions and soluble factors released by activated T cells. This help is triggered by the activation of T-helper (Th) cells upon recognition of the antigen once it is has been taken up and proteolytically processed by antigen presenting cells (APC). Such recognition occurs when the T cell receptor (TCR) on a Th cell binds specifically to the combination of an antigen-derived peptide presented in the groove of major histocompatibility complex (MHC) class II heterodimer molecules on the surface of the APC. Peptide recognition by a Th cell is dependent on both the ability of the class II MHC to bind the peptide (which is genetically constrained as it is dependent on the haplotype of the class II MHC molecule), and the ability of the TCR to recognize that peptide sequence ("T cell epitope" or TCE) in the context of class II MHC.

When immunization with a protein antigen fails to elicit a B cell response (observed as antibodies produced by such B cells and present in the serum), several causes may exist. For example, it may reflect tolerance mechanisms at work in the organism, whether T cell or B cell tolerance, that lead to an inability to activate the immune response at some level. Alternatively, it is recognized that proteolytic antigen processing, as well as class II MHC presentation constraints, result in a finite repertoire of antigen-derived peptides being presented to Th cells. Consequently, it is possible that a particular antigen may yield peptides that either are not presented by class II MHC molecules of the organism's expressed haplotype, or do not represent T cell epitopes that can be recognized by TCR on Th cells. Collectively, such a peptide repertoire fails to elicit Th cell activation and consequently the events leading to B cell activation and antibody production do not occur. When using nonhuman organisms to predict immunogenicity in humans, the caveat exists that the T cell epitope repertoire in such organisms may differ from those present in humans, owing to the difference in class II MHC and the peptides that they can present. This could result in "false negative" results, in which the presence of B cell epitopes on an antigen (that is, epitopes recognized by antibodies produced by a B cell) may not accurately be reported.

There are several ways to address this possibility; one method is further discussed in Example 8 below. Broadly characterized, one can associate an antigenic substance with the antibody to be tested. For the purposes of this discussion, an antigenic substance is one that is capable of inducing an antigenic response. For example, it is capable of stimulating the production of an antibody. In one embodiment, the substance is antigenic in mice, humans, or mammals in general. In another embodiment, the substance is antigenic in the organism to which it is administered.

For example, a humanized IgG1,κ can be coupled to an antigenic protein sequence, for example, a synthetic peptide having the sequence CQYIKANSKFIGITELKK (SEQ ID NO: 9) (herein referred to as "T Cell Epitope" or "TCE" This sequence has been described as being universally antigenic (Panina-Bordignon, P., Tan, A., Termijtelen, A., Demotz, S., Corradin, G. P., and Lanzavecchia, A., Eur. J. Immunol. 19, 2237-2242 (1989)). When the combined antibody and antigenic substance are administered to the organism in which it is to elicit an immunogenic response, the presence of the antigenic substance will reduce the risk of the false negatives discussed above, as the antigenic substance will avoid the possible T cell receptor and/or major histocompatibility complex compatibility issues. Even in the absence of endogenous T cell epitopes the test antibody will elicit an antibody response if it possesses endogenous B cell epitopes (antibody binding sites). In one embodiment, a "TCE" is any exogenous peptide conjugated to a test article.

The antigenic segment can be attached to the antibody in any number of ways, as long as the antigenic segment can still function appropriately and as long as it does not unduly prevent the processing and recognition of the test antibody. In one embodiment, maleimide chemistry can be used to connect the antigenic segment to the test antibody. For example, a sulfo-SMCC can be used. It contains an NHS ester that reacts with amines on the antibody, and a maleimide group that reacts with the sulfhydryl group on the N-terminal cysteine of the TCE peptide to generate TCE-decorated antibody ("Ab-TCE"). As controls, additional antibodies can be treated identically, but without addition of TCE to the reaction ("Ab-sham"). These, along with the untreated antibody and TCE alone can then be administered to XenoMouse® animals. The results of such an experiment are described in detail below in connection with Example 9. As will described in detail below, the only samples that resulted in a significant induction of antibodies directed against the administered antibody was the antibody conjugated to TCE and the antibody administered via base of tail followed by intraperitoneally, in the presence of adjuvant. Thus, it appears that the use of TCE can effectively increase the probability of allowing the antibody to induce a HAHA response in a XenoMouse® animal. One can therefore use the XenoMouse® animal to effectively test for factors that increase the risk of a HAHA response occurring.

Transgenic XenoMouse® Animals for Testing for HAHA Response Inhibitors.

In one embodiment, a XenoMouse® animal that exhibits a HAHA response to an antibody is used to screen for possible anti-HAHA compounds (AHAHA compounds or HAHA inhibitor compounds). For example, given that the XenoMouse® animal will exhibit a HAHA response when it is administered a HAHA inducing antibody, any substance that is administered to the XenoMouse® animal that blocks the induction of the expected HAHA response when the HAHA inducing antibody is administered to the XenoMouse® animal will be useful in preventing the induction of a HAHA response in a human system as well. Thus, in one embodiment, a XenoMouse® animal that exhibits a HAHA response with respect to a particular antibody is contemplated as a means for testing various compounds for the compounds' ability to inhibit a HAHA response. The resulting compounds can be effective for preventing the induction of HAHA responses generally, or for preventing the induction of a HAHA response for the particular antibody responsible for inducing the HAHA response.

In another embodiment, the compound to be tested for inhibiting HAHA responses, a candidate HAHA inhibitor, is administered to the XenoMouse® animal before, during, or after the HAHA inducing antibody is administered to the XenoMouse® animal. The XenoMouse® animal may also produce the HAHA inducing antibody internally as well. For example, the XenoMouse® animal may also be a transgenic mouse for the HAHA inducing antibody protein in question. Alternatively, the XenoMouse® animals can have a limited number of cells that are producing the protein. Alternatively, the XenoMouse® animal can produce the antibodies through the use of viruses or viral constructs to infect the cells of the XenoMouse® animal. Unless otherwise required, the HAHA inducing antibody can be administered to the XenoMouse® animal test subject in any manner that allows a HAHA response.

In one embodiment, a method for testing for HAHA inhibitors involves administering both 1) one or more candidate HAHA inhibitors and 2) a HAHA inducing antibody to a XenoMouse® animal. If necessary a continuous supply of either or both of the candidate HAHA inhibitor and the HAHA inducing antibody will be administered to the XenoMouse® animal for as long as would have been required for the onset of a HAHA response if there had been no HAHA inhibitor is present. A sample may then be taken from the XenoMouse® animal to determine if a HAHA response occurred. If no, or a lesser amount of a HAHA response occurred, then the candidate HAHA inhibitor will be considered a HAHA inhibitor. A HAHA inhibitor need not block 100% of a HAHA response. For example, the HAHA inhibitor will block at least some of the HAHA response, for example, 1, 2, 3-5, 5-7, 7-10, 15-20, 20-30, 30-50, 50-70, 70-80, 90-95, 95-97, 98, 99, or 100 percent of the HAHA response. This response can be measured in different ways, for example, by looking for substances that bind to the HAHA inducing antibody in the XenoMouse® animal's serum. A functional HAHA inhibitor will reduce or eliminate the presence of antibodies directed to the HAHA inducing antibody under a given set of conditions. In one embodiment, the HAHA inhibitor will delay the onset of a HAHA response. Thus, a HAHA response and the size of the HAHA response will still occur, it will simply take longer for that response to occur. The HAHA inhibitor will delay the response by at least 1 percent, for example, 1-5, 5-10, 10-20, 20-30, 30-40, 40-50, 50-60, 60-70, 70-80, 80-90, 90-100, 100-150, 150-200, 200-300 percent or more.

Optionally, an additional screening step can be performed to make certain that the HAHA inducing Ab is still functional for its binding ability in the presence of the HAHA inhibitor. Of course, as the HAHA inhibitor is also being administered to a XenoMouse® animal, immunogenic responses to the inhibitor can also be examined.

A HAHA inducing antibody is an antibody that induces a HAHA response when administered to a patient. This can be determined experimentally, as shown in FIGS. 11A-D and 12A-D. This can also be determined by examining the frequency of the genes and which genes are high risk and low risk genes. Antibodies comprising low frequency genes will be HAHA inducing antibodies for those people for which the genes are low frequency genes (e.g., absent from an individual).

While XenoMouse® animals have been used as an example, other organisms, with similar human based immune systems will also work for the described compositions and methods.

In some embodiments, the various conditions involved in a particular treatment or experiment can be tested with the use of a XenoMouse® mouse and an antibody. "Condition" is meant to encompass any aspect of the treatment or experiment that can be altered and includes, for example, altering various steps in the method of treatment or altering the particular substances being administered. A "first condition" and a "second condition" describe a same aspect of the method or material that is varied between experiments in order to determine the impact of the condition on the experiment. In other words, a condition can be the expression system. Thus, a first condition can be using expression system "X", while a second condition can be using expression system "Y." Alternatively, a condition can be the amount of antibody administered and a first condition can be "X" micrograms while the second condition can be "Y" micrograms. Thus, a first condition and a second condition are alternatives for a particular step or composition.

The importance of the condition in general, as well as a comparison of a first condition vs. a second condition, can be tested with the above mice, or other similar transgenic organisms. Examples of conditions are discussed in the following paragraphs, and include, for example, nonvariable regions of the antibody, the amount of antibody administered, the route of administration, the frequency of administration and the compositions that are administered together with the antibody. Thus, methods or compositions with a minimal or reduced risk of inducing a HAHA response can be identified by altering each condition and determining the effect of the altered condition on the HAHA response.

As will be appreciated by one of skill in the art, there are numerous methods by which different conditions can be tested for their ability to induce or suppress a HAHA response. In one embodiment, the impact that a particular condition has on the induction of a HAHA response is determined by 1) determining an immunogenic response in a first method or process using a first condition, 2) determining a second immunogenic response in a second method or process using a second condition, and 3) comparing the two responses.

In a preferred embodiment, other steps or compositions in the experiment are maintained while only a single condition is changed. For example, the method can involve 1) providing a first transgenic mouse that has a human gene configured to allow the first transgenic mouse to produce a fully human or humanized antibody, 2) administering to the first transgenic mouse a first foreign antibody under a first condition, 3) determining a presence of a HAHA response in the first transgenic mouse, 4) providing a second transgenic mouse that comprises a human gene configured to allow the second transgenic mouse to produce the fully human or humanized antibody, 5) administering to the second transgenic mouse a second foreign antibody under a second condition, wherein said first condition and said second condition are variations of the same variable, 6) determining a presence of a HAHA response in the second transgenic mouse, and 7) comparing the presence of the HAHA response in the first transgenic mouse to the presence of the HAHA response in the second transgenic mouse, thereby determining which condition results in a greater HAHA response.

As will be appreciated by one of skill in the art, various subsets of the above methods can also be performed, for example, steps 1-3 only. As will be appreciated by one of skill in the art "foreign antibody" merely means that the antibody is encoded by a gene that is not expressed in the animal host. "Foreign antibody" can include vectors or constructs encoding for the protein as well.

In some embodiments, the first transgenic mouse and the second transgenic mouse are different mice but produce a same fully human or humanized antibody. For example, the mice are genetically identical in their ability to produce a fully human antibody. In some embodiments, the first foreign antibody and the second foreign antibody are the same antibody or have the same structure. This is not meant to denote that the same foreign antibody molecule is used in step 2 and 5, but that the foreign antibodies are the same on the protein or nucleic acid level. Thus, the foreign antibodies can be the same and the mice can be the same type of mice. In a preferred embodiment, the only substantive difference between steps 1-3 and 4-6 is the first and second condition. As will be appreciated by one of skill in the art, the first and second foreign antibody and the first and second transgenic mouse can also be referred to as "foreign antibody" or "transgenic mouse" when the same or same type of antibody or mouse is being used.

An example of the general method described above is shown in Example 7 below. The example demonstrates how the level of immunogenicity depends upon the condition of route of administration of the antibody and how this can be determined for mice via S.C. administration (a first condition) or via I.V. administration (a second condition). As shown in the results, S.C. administration resulted in 5:7 mice exhibiting immunogenicity, while I.V. administration resulted in only 3:7 mice exhibiting immunogenicity. Thus, I.V. administration, for this particular experiment, has a lower chance of inducing a HAHA response.

In some embodiments, the effect of antibody isotype on immunogenicity is tested. Different human antibody isotypes have different abilities to bind Fc receptors on cells, activate complement, and generally induce effector functions such as antibody-dependent cellular cytotoxicity and complement-dependent cytotoxicity. Antibodies with an isotype that is more proficient at engaging Fc receptors can be more likely to be captured by Fc receptors, internalized, proteolytically processed, and presented as peptides on major histocompatibility complex molecules, thus increasing the probability of a cell mediated immune response that can lead to immunogenicity. The effects of isotype on immunogenicity can be tested in a transgenic animal, such as the XenoMouse® strain of mice expressing fully human antibodies of several isotypes, by comparing antibodies in which the antibody heavy chain variable region and light chain are identical, and the antibody heavy chain constant region is varied to represent different human isotypes (IgG1, IgG2, IgG3, IgG4, IgA, IgE, and/or IgM). In some embodiments, the human immunoglobulin transgenic animals are further genetically modified to express one or more human Fc receptors. In some embodiments, the relative immunogenicity of antibodies differing only in their isotype is compared.

In some embodiments, the impact of post-translational modifications is examined. The expression system used to produce antibodies for human treatment can impact immunogenicity. For example, the selected system can result in the addition of non-human glycans to the antibody, or the absence of glycosylation. Mammalian antibodies possess a complex biantennary oligosaccharide on heavy chain residue Asn297 (reviewed by Chadd and Chamow in *Curr. Opin. Biotechnol.* 12, 188-194 (2001)). Expression of human antibodies in non-human systems—most commonly hamster CHO cells and mouse NS0 cells and hybridomas—results in distinct glycosylation patterns (id.). Certain expression systems, such as yeast or transgenic livestock, also exhibit differences in glycosylation. Upon administration to an animal or human subject, this can lead to complement activation or antibody binding to mannose-binding lectin. Enhanced binding to the mannose receptor on dendritic cells may enhance antibody uptake and processing by these professional antigen presenting cells (Dong et al., *J. Immunol.* 163, 5427-5434 (1999)), thereby increasing the potential for triggering immunogenicity. Antibodies made in plants and *E. coli* lack oligosaccharides altogether. In addition, the nature of antibody glycosylation (or lack thereof) may also alter antibody structure (Krapp et al., *J Mol. Biol.* 325, 979-989 (2003)), thus creating potentially immunogenic conformers. A transgenic animal, such as the XenoMouse® strain of mice expressing fully human antibodies, can be used to assess the effects on immunogenicity of different glycosylation patterns using different expression systems, keeping the antibody protein sequence constant. As will be appreciated by one of skill in the art, the antibodies can be made in the particular expression system, isolated, and then administered to the transgenic animal for testing.

In some embodiments, the formulation of an antibody preparation influences immunogenicity. For example, the formulation can cause an antibody to assume a different tertiary conformation, or to form aggregates. The effects on immunogenicity can be tested in transgenic human immunoglobulin-expressing mice, such as XenoMouse® mice, by administering the same dose via the same route of administration, of an antibody with an identical amino acid sequence, which has been formulated using any of several different approaches. In this manner, data can be obtained that will provide information on the least immunogenic formulation method for a given antibody to be administered to humans.

In some embodiments, the association of dose quantity, frequency, and/or route of administration of the antibody with the induction of a HAHA response is determined. As discussed herein, there is evidence that the amount of antibody given to a subject can affect the risk of immunogenicity. An inverse relationship between dose and immunogenicity risk has been reported. Also, antibody administered after a longer interval has been reported to cause more immunogenicity than antibody administered repeatedly with shorter intervals. The route of antibody administration to the subject can also affect immunogenicity, with subcutaneous administration generally understood to carry a higher risk of immunogenicity than intramuscular or intravenous administration. These aspects can be tested in transgenic human immunoglobulin-expressing mice, such as XenoMouse® mice, by comparing the immunogenicity of a particular chimeric, human, or humanized antibody in animals that receive the antibody by one of several routes, including but not limited to subcutaneous, intravenous, intraperitoneal, intracranial, intradermal, intramuscular, or oral.

In some embodiments, the immunocompetence of the subject being administered the antibody is examined with the transgenic animals. As appreciated by one of skill in the art, it is understood that an antibody that is either inherently immunogenic, or is administered in a way that can cause an immune response to the antibody, may not be seen as immunogenic when administered to a subject whose immune system is impaired. Consequently, an antibody that has a high incidence of immunogenicity in a patient population considered to be immune sufficient, such as humans suffering from chronic inflammatory diseases, can have a low incidence of immunogenicity in a patient population that is immunosuppressed, such as the elderly or those receiving radio- or chemotherapy regimens. The immunogenicity of an antibody can be related to the immune status of the recipient patient. This can be tested in transgenic human immunoglobulin-expressing mice, such as XenoMouse® mice, by comparing the effect of a particular chimeric, human, or humanized antibody in animals that have been subjected to sublethal irradiation or received chemotherapeutic agents to those that have not been manipulated.

In some embodiments, identical antibody proteins are administered to a first animal that has been pretreated with an antibody that differs from the test antibody only in its heavy and light chain variable regions. The first animal also has circulating antibodies that bind to the pre-treatment antibody. The immune response to the subsequent antibody in the first animal can be compared to the immune response in an animal that has not been pre-treated in this manner. Thus, pre-treatment of a subject with various antibodies can be one condition that can also be examined.

Therapeutic Administration and Formulations

A prolonged duration of action will allow for less frequent and more convenient dosing schedules by alternate parenteral routes such as intravenous, subcutaneous or intramuscular injection.

When used for in vivo administration, antibody formulations described herein should be sterile. This is readily accomplished, for example, by filtration through sterile filtration membranes, prior to or following lyophilization and reconstitution. Antibodies ordinarily will be stored in lyophilized form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, or by sustained release systems as noted below. Antibodies are preferably administered continuously by infusion or by bolus injection.

An effective amount of antibody to be employed therapeutically will depend, for example, upon the therapeutic objectives, the route of administration, and the condition of the patient. Accordingly, it is preferred for the therapist to titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

Antibodies as described herein can be prepared in a mixture with a pharmaceutically acceptable carrier. Therapeutic compositions can be administered intravenously or through the nose or lung, preferably as a liquid or powder aerosol (lyophilized). Composition can also be administered parenterally or subcutaneously as desired. When administered systemically, therapeutic compositions should be sterile, pyrogen-free and in a parenterally acceptable solution having due regard for pH, isotonicity, and stability. These conditions are known to those skilled in the art. Briefly, dosage formulations of the compounds of the present invention are prepared for storage or administration by mixing the compound having the desired degree of purity with physiologically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in *Remington's Pharmaceutical Sciences* (18$^{th}$ ed, Mack Publishing Company, Easton, Pa., 1990). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice. As will be appreciated by one of skill in the art, the risk that any of the above compositions or materials will reduce, prevent, induce, or exacerbate a HAHA response can also be examined. This can be achieved in the manner outlined above, where an antibody with a known risk or degree of inducing a HAHA response is administered to a XenoMouse® mouse, together with the substance to be tested. Any increase in the HAHA response, compared to a normalized level of HAHA response, can demonstrate that the substance is adding to the HAHA response. Alternatively, the substance can be tested alone (without the HAHA response inducing antibody), to determine if it can independently induce a HAHA response. Of course, the various methods of administration, and how they relate to the risk of a HAHA response can also be examined. For example, the amount, frequency, or time (compared to other relevant events in the day) of administration can all readily be examined.

Suitable examples of sustained-release preparations include semipermeable matrices of solid hydrophobic polymers containing the polypeptide, which matrices are in the form of shaped articles, films, or microcapsules. Examples of sustained-release matrices include polyesters, hydrogels (e.g., poly (2-hydroxyethyl-methacrylate) as described by Langer et al., *J. Biomed Mater. Res.*, (1981) 15:167-277 and Langer, *Chem. Tech.*, (1982) 12:98-105, or poly(vinylalcohol)), polylactides (U.S. Pat. No. 3,773,919, EP 58,481), copolymers of L-glutamic acid and gamma ethyl-L-glutamate (Sidman et al., *Biopolymers*, (1983) 22:547-556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

Sustained-released compositions also include preparations of crystals of the antibody suspended in suitable formulations capable of maintaining crystals in suspension. These preparations when injected subcutaneously or intraperitoneally can produce a sustain release effect. Other compositions also include liposomally entrapped antibodies of the invention. Liposomes containing such antibodies are prepared by methods known per se: U.S. Pat. No. DE 3,218,121; Epstein et al., Proc. Natl. Acad. Sci. USA, (1985) 82:3688-3692; Hwang et al., *Proc. Natl. Acad. Sci. USA*, (1980) 77:4030-4034; EP 52,322; EP 36,676; EP 88,046; EP 143,949; 142,641; Japanese patent application 83-118008; U.S. Pat. Nos. 4,485,045 and 4,544,545; and EP 102,324.

The dosage of the antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the antibody to be employed therapeutically will depend, for example, upon the therapeutic objectives, the route of administration, and the condition of the patient. Accordingly, it is preferred that the therapist titer the dosage and modify the route of administration as required to obtain the optimal therapeutic effect. A typical daily dosage might range from about 0.001 mg/kg to up to 100 mg/kg or more, depending on the factors mentioned above. Typically, the clinician will administer the therapeutic antibody until a dosage is reached that achieves the desired effect. The progress of this therapy is easily monitored by conventional assays or as described herein.

It will be appreciated that administration of therapeutic entities in accordance with the compositions and methods set forth herein will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences ($18^{th}$ ed, Mack Publishing Company, Easton, Pa. (1990)), particularly Chapter 87 by Block, Lawrence, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2):210-8 (2000), Wang W. "Lyophilization and development of solid protein pharmaceuticals." *Int. J. Pharm.* 203(1-2): 1-60 (2000), Charman W N "Lipids, lipophilic drugs, and oral drug delivery—some emerging concepts." *J Pharm Sci.* 89(8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists. The amount and route of administration can depend upon the results obtained from experiments described herein.

EXAMPLES

Example 1

This example demonstrates how a normalized host $V_H$ gene profile can be generated. First, one determines which $V_H$ genes are present in all of the members of the profile. As the sequence of all the V genes are currently known, as well as methods for their identification, this is routine for one of skill in the art. Next, the frequency of occurrence for each gene is determined by determining the number of people in which the gene occurred and dividing that number by the number of people in the profile. As shown in FIG. 1A, the genes of five hosts are determined, and then normalized in various ways, as shown FIG. 1C. This is repeated for each gene to develop a full profile of V genes for a given population.

Example 2

This example demonstrates how a normalized host V protein profile can be generated. The normalized host V gene profile of Example 1 is converted to various amino acid sequences for the genes that are actually expressed. An example of the proteins expressed from the V genes in FIG. 1A is shown in FIG. 1B and the resulting frequencies are shown in FIG. 1D.

As can be seen in comparing FIG. 1C and FIG. 1D, the frequency and thus the risk associated with the gene, can vary depending upon whether the analysis is performed at the DNA level or the protein level.

Example 3

This example demonstrates changes that can be made in order to reduce the risk associated with a selection of genes. Once a high-risk gene is identified in a selection of genes, as shown in FIG. 3, it can be optimized. In order to increase the likelihood of reducing a HAHA response, and decrease the risk of a loss in functionality, the modification can be directed by information in the normalized host V protein profile. An example of this is demonstrated in FIG. 6. In FIG. 6, the gene to be optimized is gene C as it has the lowest frequency of occurrence (20%). In this example, gene C will be removed. If a replacement gene is required, the replacement of gene C will be determined by examining the profile to determine other genes with similar protein structures. Here, this can be gene B, or another gene that is more similar to gene B than it is to gene C.

Example 4

This example demonstrates how one can determine the risk associated with a particular V gene, when the V gene is given to a patient in the form of an antibody. First, a normalized host V gene profile is selected for the population to which the patient belongs. This can be done by determining which V genes a patient has or likely has. Next, the V gene of the antibody to be administered to the patient will be determined. Next, the V gene of the antibody will be compared to the V genes in the profile.

For example, there can be five genes in the profile of the population, A, B, C, D, and E, with frequencies of, gene A at 30%, gene B at 2%, gene C at 5% gene D at 100%, and gene E at 99%. If part of the antibody is encoded by an A gene, the antibody will be considered a 70% risk gene. If part of the antibody is encoded by a B gene, it will be considered a 98% risk gene. If part of the antibody is encoded by a C gene, it can be considered a 95% risk gene. If part of the antibody is encoded by a D or an E gene, it can be considered a 0 or 1% risk gene.

Example 5

This example describes how one can verify the correlation between frequency of occurrence of a $V_H$ gene and the risk that the gene will induce a HAHA response in a patient.

First, antibodies with known gene sets are administered to patients. Next, the patients are tested for a HAHA response. Antibodies that induce a HAHA response will have their gene sets given a point value. All of the genes of all of the antibodies administered will have each of their point values totaled. These values will then be normalized to how frequently the gene occurred. Thus, a gene that will be in 10 antibodies, but only one of which caused a HAHA response, will be assigned 0.1 point value, while a gene that is in one antibody, but causes a HAHA response in all individuals in a given profile will be assigned 1.0 point value. Genes with the highest point value will be those genes with the greatest association with the induction of a HAHA response. These point values will then be compared to the gene frequency of occurrence a normalized host V gene profile to determine how close the correlation is. This will demonstrate that common genes have a lower frequency of being associated with a HAHA response, and rare genes, in a population, have a higher frequency of being associated with a HAHA response.

Example 6

The presence of the $V_H$3-9 gene was examined in various samples. A standard PCR-ELISA technique was used to search for the appearance of $V_H$3-9 in genomic DNA of a human donor and four human cell lines, A375, A549, MCF7, and HEK-293 cells. The biotin-labeled probe which was used in PCR-ELISA had the sequence (5'→3') [BioTEG]CCG-GCAAGCTCCAGGGAAGGGC (SEQ ID NO: 14, FIG. 23B). The results, shown in FIG. 10, demonstrate that $V_H$3-9, and variability in the presence of $V_H$3-9, can be detected through PCR-ELISA with this probe.

Example 7

This example demonstrates that the XenoMouse® animal is useful in determining if an antibody will induce a HAHA response. Groups of XenoMouse® mice capable of producing fully human antibodies were immunized with a selected fully human antibody. Each mouse received three doses of one of two different antibodies (A or B), spaced two weeks apart, 10 micrograms antibody per dose. Additionally, some mice received 10 micrograms keyhole limpet hemocyanin (KLH; Pierce, Rockford Ill.) as a positive control immunogen, while others were injected only with the carrier as a negative control. Antibody A was an antibody created from a XenoMouse® mouse and directed against TNFalpha. Antibody A was previously disclosed in U.S. Pat. Application No. 60/430,729 (SEQ ID NO.: 71-74; currently SEQ ID NOs.: 5-8, with SEQ ID NOs.: 12 and 13 showing the consensus sequences of the light chain and heavy chain respectively, FIG. 23B), and identified as 299v2. Antibody B was an antibody that was also directed to TNFalpha. Antibody B is also known as HUMIRA (D2E7, adalimumab), and the antibody was the subject of U.S. Pat. No. 6,258,562, issued to Salfeld et al., Jul. 10, 2001, both herein incorporated in their entireties by reference. The U.S. Pat. No. 6,258,562 characterizes this antibody as a human antibody that binds to human TNF alpha. (See generally, the U.S. Pat. No. 6,258,562). However, previous studies have demonstrated that antibody B can elicit a HAHA response when administered to humans. (information available on the FDA website, pdf ada1abb123102r1p2.pdf)

The antibody, KLH, or carrier was administered intravenously ("I.V."), subcutaneously ("S.C."), or emulsified in complete Freund's adjuvant (Sigma, St. Louis, Mo.) and then administered in the base of the tail (first dose) followed by article emulsified in incomplete Freund's adjuvant (Sigma) and administered intraperitoneally (second and third doses) ("BIP/ADJ"). Serum was obtained from the mice by retro-orbital bleeds taken at the times indicated in FIGS. 11A-C and FIGS. 12A-C, and stored at −80° C. until all samples could be tested, as described in the following paragraphs.

The serum samples were assayed for the presence of components reactive to the injected antibody using a bridging ELISA. In this ELISA assay, Maxisorp 96-well plates (Nunc, Rochester, N.Y.) were coated with the test antibody or KLH, as appropriate, and the plates were then washed and blocked with bovine albumin. XenoMouse® animals' serum samples were then added in duplicate in a 1:10 dilution. As negative and positive controls, 10% normal mouse serum (Equitech-Bio, Kerrville, Tex.) and rabbit anti-human IgG (Southern Biotechnology, Birmingham, Ala.) or XenoMouse® animal-derived anti-KLH (Abgenix) diluted in 10% mouse serum, respectively, were used. Following incubation, the serum was washed away and a biotinylated form of the test antibody or KLH (prepared using the EZ-Link™ Sulfo-NHS-LC-Biotinylation kit and accompanying protocol, Pierce) was added to the wells, followed by additional washing and incubation with streptavidin coupled to horseradish peroxidase. Visualization was with Enhanced K-blue TMB substrate (Neogen, Lexington, Ky.), and the reaction was stopped with 2 molar sulfuric acid. Plates were read in a plate reader at 450 nm wavelength. Data are presented as O.D. multiple, which was calculated using the following formula:

$$\frac{\text{Sample average } OD \text{ (duplicate wells)}}{\text{Negative control average } OD \text{ (6 – 8 wells per plate)}}$$

Figure 11:
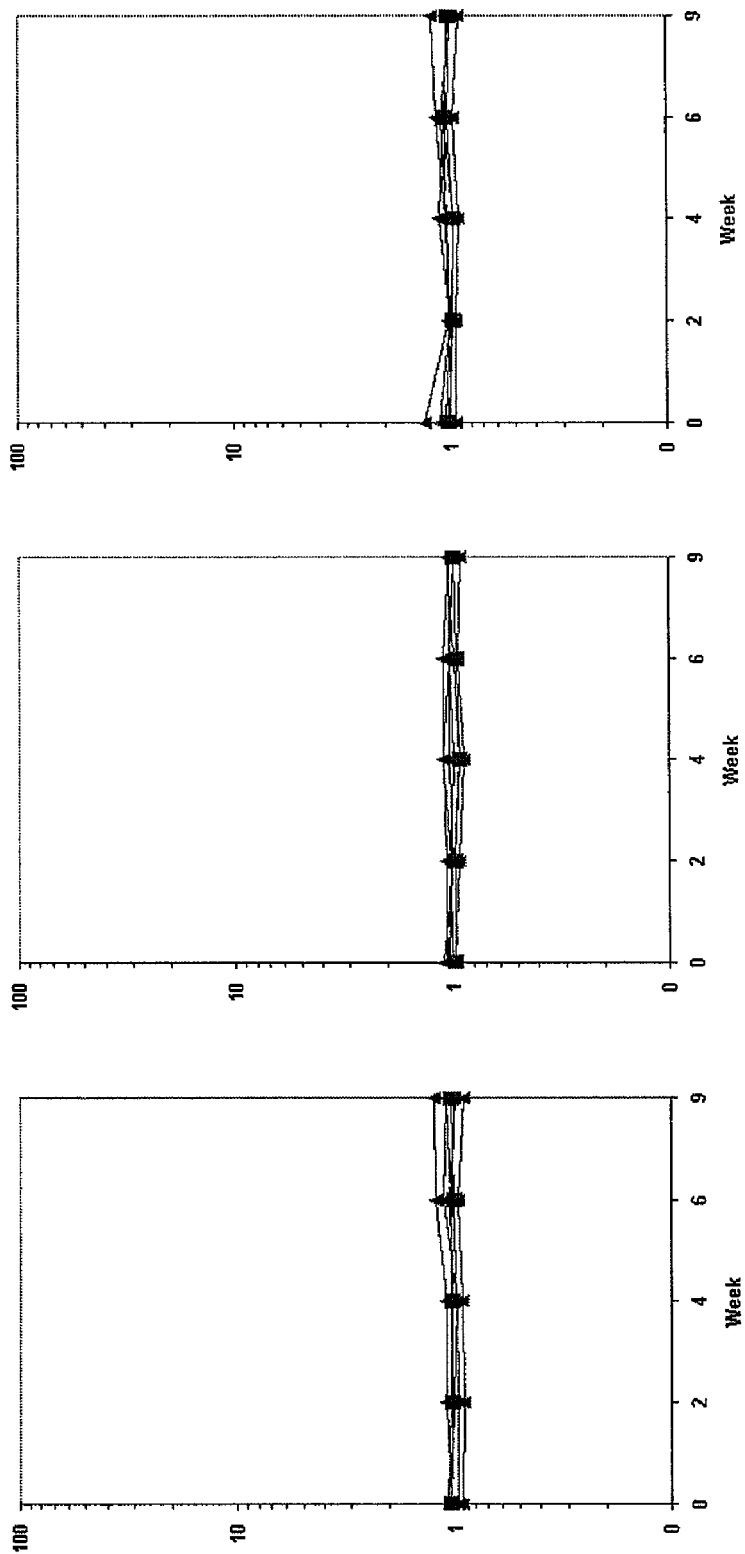
FIG. 11A is a graph displaying the level of immunogenicity induced by antibody A when administered to a XenoMouse® animal via base of tail followed by intraperitoneal route in the presence of adjuvant ("BIP/ADJ").
FIG. 11B is a graph displaying the level of immunogenicity induced by antibody A when administered to a XenoMouse® animal subcutaneously.
FIG. 11C is a graph displaying the level of immunogenicity induced by antibody A when administered to a XenoMouse® animal intravenously.

O.D. multiples >2 were considered positive for serum antibodies to the test antibody. Data from two fully human IgG1 test antibodies is shown in FIGS. 11A-11C and FIGS. 12A-12C. BIP/ADJ results are shown in FIGS. 11A and 12A, S.C. results are shown in FIGS. 11B and 12B, and I.V. results are shown in FIGS. 11C and 12C.

Figure 12D:
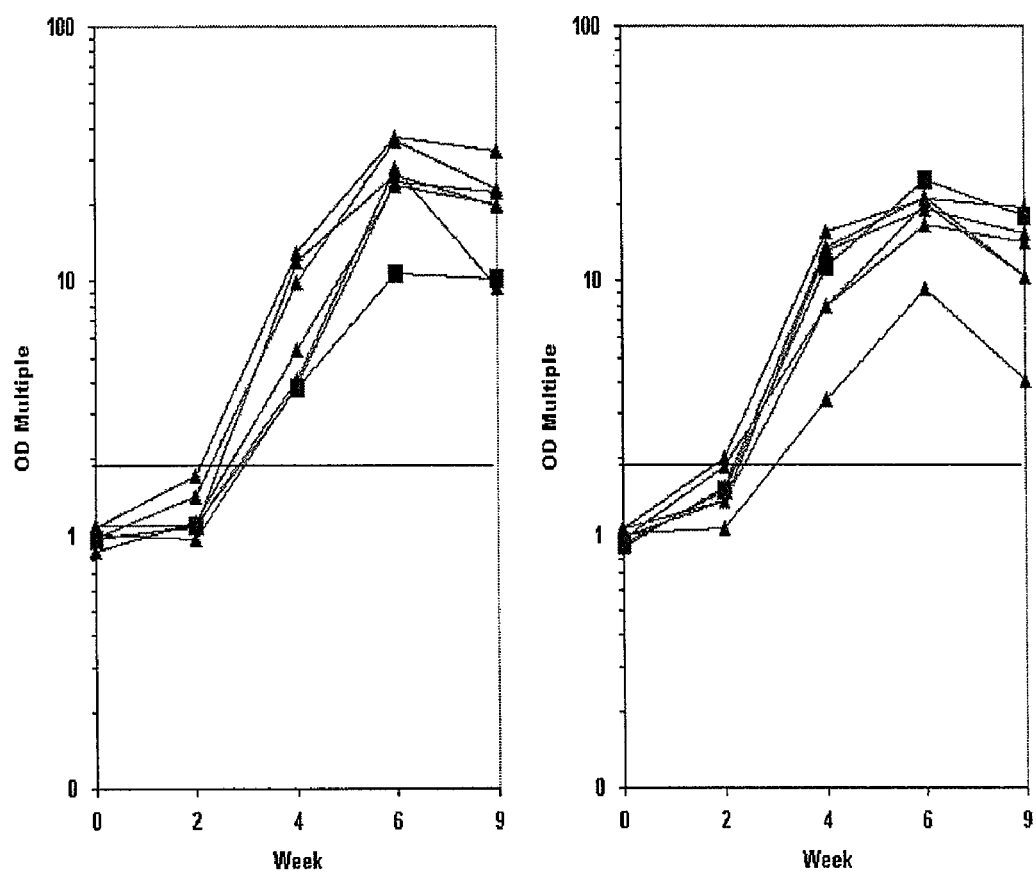
Figure 13:
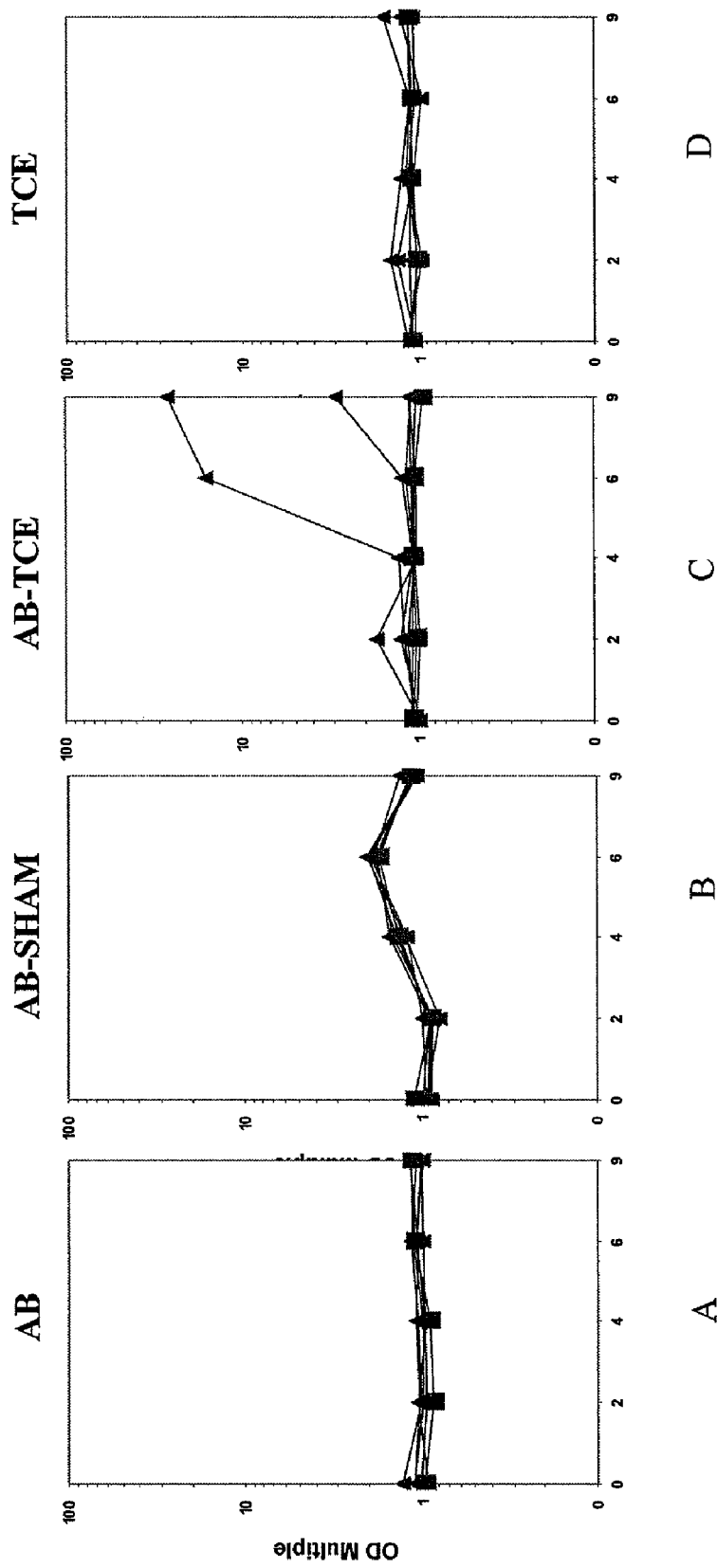
FIG. 13A is a graph displaying the level of immunogenicity induced by an antibody ("Ab") administered subcutaneously.
FIG. 13B is a graph displaying the level of immunogenicity induced by a sham-conjugated Ab ("Ab-sham"), administered subcutaneously.
FIG. 13C is a graph displaying the level of immunogenicity induced by an Ab conjugated to TCE peptide ("Ab-TCE"), administered subcutaneously.
FIG. 13D is a graph displaying the level of immunogenicity induced by TCE peptide administered subcutaneously.
Figure 14:
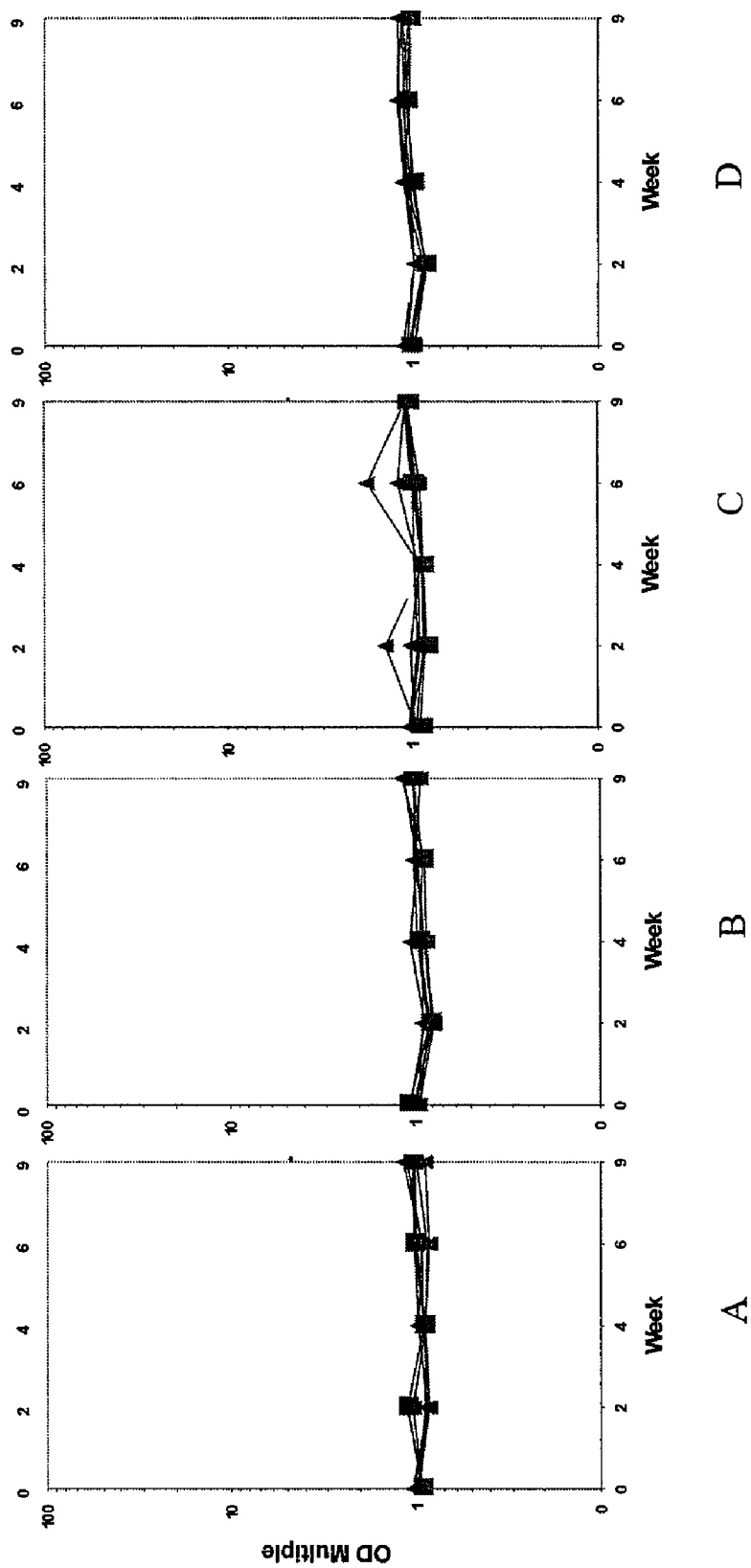
FIG. 14A is a graph displaying the level of immunogenicity induced by an Ab administered intravenously.
FIG. 14B is a graph displaying the level of immunogenicity induced by a sham-conjugated Ab ("Ab-sham"), administered intravenously.
FIG. 14C is a graph displaying the level of immunogenicity induced by an Ab conjugated to TCE peptide ("Ab-TCE"), administered intravenously.
FIG. 14D is a graph displaying the level of immunogenicity induced by TCE peptide, administered intravenously.
Figure 15:
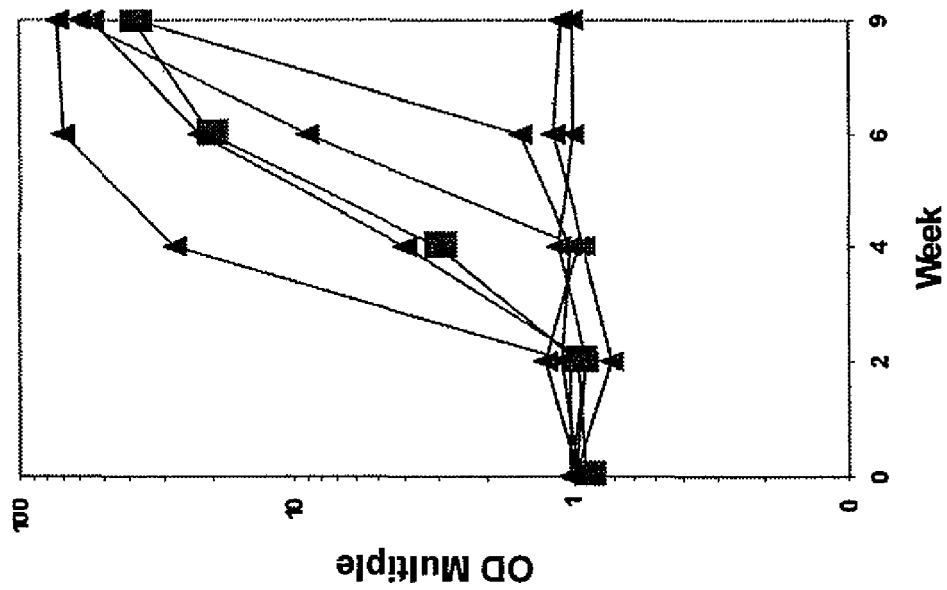
FIG. 15 is a graph displaying the level of immunogenicity induced by the Ab and an adjuvant, administered via the BIP route.

As can be seen from the data in FIGS. 11A-C, antibody A resulted in no immunogenicity being detected in the XenoMouse® animals, regardless of the method of administration of the antibody. On the other hand, as can be seen in FIGS. 12A-C, antibody B elicited a high level of immunogenicity. The negative control results from the 10% normal mouse serum and the positive control rabbit anti-human IgG were as follows: for Antibody A, negative control had an average OD of 0.05, standard deviation of 0.01 and OD multiple 1.00; the positive control had an average OD of 0.19, standard deviation of 0.02 and an OD multiple of 3.81; for Antibody B, negative control had an average OD of 0.07, standard deviation of 0.00, and an OD multiple of 1.00; and the positive control had an average OD of 0.11, standard deviation of 0.02 and an OD multiple of 1.55. FIG. 12D shows the results from the positive control immunogen, KLH, experiment.

As can be seen, while I.V. administration of antibody B elicited an immunogenic response in three of the seven mice, the number of mice exhibiting immunogenicity to antibody B increased to five of seven in the XenoMouse® animals that received antibody S.C., and finally to seven of seven for antibody administered with an adjuvant, as shown in FIG. 12A. Thus, this example demonstrates that the XenoMouse® animals can be used to distinguish the degree of immunogenicity of two human or humanized antibodies, both of which are directed to the same protein.

This also demonstrates that antibodies produced from the XenoMouse® mouse will not induce a HAHA response in a host with the same gene profile. This also demonstrates that various methods of administration of the antibody to a subject can impact the resulting likelihood that a compound will induce a HAHA response. Additionally, this demonstrates that the materials added to the subject with the antibody can also alter the risk or likelihood that an antibody (or the substance itself) will induce a HAHA response in the subject.

As appreciated by one of skill in the art, many of the above variables may be adjusted without altering the general concept taught. For example, an O.D. multiple of >2 need not be the precise cutoff. For example, the cutoff can be set at 3 standard deviations above the background, or more complex statistical methods can be used.

Example 8

This example demonstrates one method for avoiding possible false negatives in using a XenoMouse® mouse described herein. A humanized IgG1,κ antibody, Xolair (E25, Omalizumab) (heavy chain V region, SEQ ID NO.: 10 and light chain region, SEQ ID NO.: 11) was coupled to a synthetic peptide having the sequence CQYIKANSKFIG-ITELKK (SEQ ID NO.: 9) (herein referred to as "TCE"). Maleimide chemistry was performed using sulfo-SMCC to generate TCE-decorated antibody ("Ab-TCE"). Additional antibody was treated identically, but without addition of TCE to the reaction ("Ab-sham").

Groups of XenoMouse® mice capable of producing fully human antibodies were immunized with 10 micrograms of either the unmodified, untreated test antibody ("Ab"), Ab-TCE or Ab-sham. Additional groups of mice received 10 micrograms of TCE peptide only as a control. Each mouse was administered three doses, spaced two weeks apart, either intravenously ("I.V.") or subcutaneously ("S.C."). In addition, unmodified Ab was emulsified in complete Freund's adjuvant (Sigma, St. Louis, Mo.) and administered to one group of mice in the base of the tail (first dose) followed by Ab emulsified in incomplete Freund's adjuvant (Sigma) (second and third doses) ("BIP/ADJ") administered intraperitoneally. Serum was obtained from the mice by retro-orbital bleeds taken at the times indicated in the figure below and stored at −80° C. until all samples could be tested.

The serum samples were assayed for the presence of components, which includes antibodies, reactive to the injected antibody using a bridging ELISA. In this ELISA assay, Maxisorp 96-well plates (Nunc, Rochester, N.Y.) were coated with the unmodified test antibody, and the plates were then washed and blocked with bovine albumin. XenoMouse® animals' serum samples were then added in duplicate in a 1:10 dilution. As negative and positive controls, 10% normal mouse serum (Equitech-Bio, Kerrville, Tex.) and rabbit anti-human IgG (Southern Biotechnology, Birmingham, Ala.) diluted in 10% mouse serum were used. Following incubation, the serum was washed away and a biotinylated form of the test antibody (prepared using the EZ-Link™ Sulfo-NHS-LC-Biotinylation kit and accompanying protocol, Pierce) was added to the wells, followed by additional washing and incubation with streptavidin coupled to horseradish peroxidase. Visualization was with Enhanced K-blue TMB substrate (Neogen, Lexington, Ky.), and the reaction was stopped with 2 molar sulfuric acid. Plates were read in a plate reader at 450 nm wavelength. Data are presented as O.D. multiple, which was calculated using the following formula:

$$\frac{\text{Sample average } OD \text{ (duplicate wells)}}{\text{Negative control average } OD \text{ (6 – 8 wells per plate)}}$$

O.D. multiples >2 were considered positive for serum antibodies to the test antibody.

FIGS. 13A-D, FIGS. 14A-D, and FIG. 15 show the results from the experiment. The results indicate that TCE addition to an antibody resulted in immunogenicity in 2 of 7 mice, whereas unmodified and sham-conjugated antibody were not immunogenic in 14 mice tested. Thus, TCE conjugation to a protein will allow the reporting of B cell-mediated immunogenicity. XenoMouse® mice did produce antibody in response to unmodified antibody when it was administered with adjuvant, suggesting that the test antibody contains endogenous T cell epitopes.

Example 9

This example demonstrates a normalized host $V_H$ gene profile or analysis of the $V_H$ gene repertoire across a population, on both genomic DNA and RNA levels, from blood peripheral cells from 96 donors, using gene-specific probes. The presence of transcripts and genomic sequence in PBMC was determined $V_H$ gene segments Probes for the $V_H$ genes were designed and validated on plasmids and/or cDNA from hybridomas expressing the target gene and related family members.

Donors, PBMC Isolation and Nucleic Acid Preparation

Peripheral blood was obtained from 66 donors and from 32 individuals through a commercial source (Bioreclamation, Inc.). Data on age, gender and ethnicity of all donors was collected. Peripheral blood mononuclear cells (PBMC), from 45 ml of blood were isolated. Cells were counted and genomic DNA was isolated from 5×10e6 cells using Qiagen's DNeasy 96 Tissue Kit, according to the manufacturer's instructions. Quantitation was performed with PicoGreen (from Molecular Probes) and 50 ng of gDNA was used in real-time PCR reactions. RNA was isolated using RNeasy mini columns, according to manufacturer's instructions. Residual DNA was removed with TURBO DNA-free from Ambion. RiboGreen (Molecular Probes) was used for quantitation of RNA samples and cDNA was made with Invitrogen's SuperScript First-Strand Synthesis System for RT-PCR, using 80 ng of total RNA. One-twelfth of the final reaction mixture was used in real-time PCR analysis.

Primer and Probe Design

Primers and probes were designed based on sequence information available in Vbase (and shown in FIG. 17A-FIG. 22J), using Primer Express software version 2.0 (Applied Biosystems). Minor Groove Binding (MGB) probes had a Tm of 65-67° C. Where possible, probes were designed in FR1, otherwise they were in the FR2, FR3 or leader regions. CDR regions and reported polymorphisms were avoided. This can be done in a variety of ways, for example, by sequence comparisons, as shown in FIG. 16A and FIG. 16B between various $V_H$ genes. As will be appreciated by one of skill in the art, any wrap around in FIGS. 16A and 16B (e.g., genes 2-05, 2-26, 3-43, and 7.41) is a result of spatial constraints and not meant to indicate alignment properties. PCR amplicons were kept as short as possible, not to exceed 200 bp. Sequences of the probes and 20 bases upstream and downstream were searched against the human genome database according to the method referenced in Altschul, Stephen F., Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402 to minimize cross-reactivity with pseudogenes.

Real-Time PCR

Real-time PCR was carried out on an ABI Prism 7700 analyzer. Annealing/extension temperature (from 60 to 68° C.) for each primer/probe pair was optimized using plasmids or hybridoma cDNA samples containing the sequence of interest, and closely related family members. cDNA was analyzed first and if not all donors expressed the gene, gDNA was analyzed.

The results for $V_H3$-9, $V_H3$-13 and $V_H3$-64 genes are summarized in Table 1. High risk genes were those that were absent, not expressed in a subpopulation of subjects (e.g., less than 100%), or that had mRNA levels at lower than detectable levels.

TABLE 1

| V gene | cDNA | gDNA |
|---|---|---|
| 3-9 | 90% | 91% |
| 3-13 | 99% | 100% |
| 3-64 | 97% | 100% |

Based on this data, it can be seen that, for this population, $V_H3$-9 occurs with much less frequency that the other two genes. Additionally, that 3-13 and 3-64, while occurring at the genomic level in the entire population, did not appear at the mRNA level for the entire population.

Risk-assessment at an early stage of development can be a valuable tool in the evaluation of potential therapeutic antibodies. The results presented here can be used as additional criteria for selection of lead candidate molecules for (pre) clinical development.

Of course, as will be appreciated by one of skill in the art and as discussed in detail above, the groupings into which the various V genes fall can vary depending upon the selected cutoff lines for high-risk and low-risk genes in the population. For example, with a simple analysis, any time a V gene is less than 100% present as gDNA, it can be a high risk gene. More preferably, anytime a V gene is less than 100% present as mRNA, it can be a high risk gene. However, for example, in a more quantitative analysis, anytime a gene is present as cDNA in less than 80% of the population, it is a high risk gene. Alternatively, it can be referred to based on its frequency; thus, instead of high medium or low, a gene that appears in 80% of the population could be a 20% risk gene (or have a 20% probability of inducing a HAHA response in any individual in the population), as the odds that a person in the population will not have the same gene is 20%. In some embodiments, the values for high and low risk for populations can vary based on the particular uses of the antibody. However, one of skill in the art will readily be able to decide their desired values based on their particular circumstances and the teachings herein.

Example 10

The germline $V_k$ locus contains 132 genes, with 45 of these possessing an open reading frame, 25 of which are present in XenoMouse® animals. This includes 7 duplicated gene pairs with identical sequences, which can be treated as a single gene. Thus, a total of 18 different functional $V_k$ gene sequences are present in XenoMouse® animals. The same techniques and analysis as shown in Example 9 can be performed on $V_{kappa}$ or $V_{lambda}$ genes. The process will be the same, only the genes and primers, etc., should be switched. Some of the various V genes that can be tested are displayed in FIG. 8 and sequences of particular V genes, for $V_{lambda}$, and $V_{kappa}$ are shown in FIGS. 19A-19G, 20A-20L, 21A-21F, and 22A-22J. The methods are the same as that shown in Example 10 above. The results will reveal which genes are common in the population or individual and which genes are not.

Example 11

This example demonstrates how the XenoMouse® animal can be used to detect other variables that influence the likelihood that a HAHA response will occur. The effect of isotype on immunogenicity is tested in a transgenic animal, such as the XenoMouse® strain of mice expressing fully human antibodies of several isotypes. This can be done by comparing the HAHA response induced by foreign antibodies in which the antibody heavy chain variable region and light chain are identical, and the antibody heavy chain constant region is varied to represent different human isotypes (e.g., IgG1, IgG2, IgG3, IgG4, IgA, IgE). The various antibodies (e.g., first and second foreign antibodies) that represent the various isotypes are each administered to the transgenic animal and the presence and degree of a HAHA response is measured. The isotype that demonstrates the greater HAHA response will be the one with the larger risk of inducing a HAHA response in humans. Of course, alternatively, this could be used to determine the isotype with the lowest risk of inducing a HAHA response.

Example 12

This example demonstrates how the XenoMouse® animal can be used to detect other variables that influence the likelihood that a HAHA response will occur. The effect of the expression system on immunogenicity is tested in a transgenic animal, such as a XenoMouse® strain of mice expressing fully human antibodies. The XenoMouse® strain of mice can be used to assess the effects on immunogenicity of different glycosylation patterns using different expression systems, keeping the antibody protein sequence constant.

A first foreign antibody can be administered to a first transgenic animal. The first antibody will be created from an *E. coli* expression system. Next, a second foreign antibody can be administered to a second transgenic animal (that is the same in terms of species and strain). The second foreign antibody will be produced in yeast or transgenic livestock. A third foreign antibody, created in Chinese hamster ovary cells, can be administered to animals of the same transgenic strain. The antibody from the expression system that demonstrates the greatest HAHA response will be the one with the larger risk of inducing a HAHA response.

Example 13

This example demonstrates how the XenoMouse® animal can be used to detect other variables that influence the likelihood that a HAHA response will occur.

The effect of the formulation on immunogenicity is tested in transgenic human immunoglobulin-expressing mice, such as XenoMouse® mice, by administering the same dose via the same route of administration, of a foreign antibody with an identical amino acid sequence, which has been formulated using a variety of different approaches (e.g., a first formulation condition and a second formulation condition). In this manner, data is obtained that will provide information on the least immunogenic formulation method for a given antibody to be administered to humans.

Example 14

This example demonstrates how the XenoMouse® animal can be used to detect other variables that influence the likelihood that a HAHA response will occur.

The impact of the route of administration and the amount of antibody administered can also be examined. These can be tested in transgenic human immunoglobulin-expressing mice, such as XenoMouse® mice, by comparing the immunogenicity of a particular antibody in animals that receive the antibody by one of several routes, including but not limited to subcutaneous, intravenous, intraperitoneal, intracranial, intradermal, intramuscular, and/or oral. This comparison will demonstrate the risk associated with the route or amount of antibody administered with the risk of a HAHA response. This can also be repeated with various amounts of the antibody to determine if certain levels of administration are more likely to induce a HAHA response.

As will be appreciated by one of skill in the art, a similar protocol to that described above can be used where the time interval between multiple doses is altered to determine if certain dosing schedules are more likely to induce a HAHA response.

Example 15

This example demonstrates how the XenoMouse® animal can be used to detect other variables that influence the likelihood that a HAHA response will occur.

How the immunocompetence of the subject being administered the antibody influences the induction of a HAHA response can be examined. This can be tested in transgenic human immunoglobulin-expressing mice, such as XenoMouse® mice, by comparing the effect of a particular chimeric, human, or humanized antibody in animals that have been subjected to sublethal irradiation or received chemotherapeutic agents to those animals that have not been so manipulated. First, a first XenoMouse® mouse has its immunocompetence impaired by administering a sublethal amount of radiation to the mouse. Next, a test antibody is administered to the mouse and any HAHA response from the mouse observed. Next, a second, unmanipulated and therefore immunocompetent XenoMouse® mouse is administered the same antibody and any HAHA response from the second mouse is observed. This comparison will demonstrate the impact of immunocompetence on the risk of inducing a HAHA response.

As can be seen from the data herein, there are several genes that can be described as high-risk genes in this particular population. This suggests that this approach can be used for various types of immunoglobulin genes, for example $V_{lambda}$ genes, as well as D and J genes.

INCORPORATION BY REFERENCE

All references cited herein, including patents, patent applications, papers, text books, and the like, and the references cited therein, to the extent that they are not already, are hereby incorporated herein by reference in their entirety.

EQUIVALENTS

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A transgenic mouse comprising:
   a genome comprising human immunoglobulin gene loci that following their B cell immunoglobulin gene rearrangements produce at least one human antibody, wherein the human immunoglobulin gene loci comprises genes that encode for a human antibody; and
   a foreign human antibody, wherein the foreign human antibody was encoded by a human immunoglobulin gene that is not present in the genome of the transgenic mouse wherein the foreign human antibody is capable of inducing a human-anti-human antibody (HAHA) response, and wherein the human antibody produced by the transgenic mouse binds to the foreign human antibody.

2. The transgenic mouse of claim 1, where the transgenic mouse has its mouse immunoglobulin genes inactivated.

3. The transgenic mouse of claim 1, wherein the genome lacks at least one human immunoglobulin gene, selected from the group consisting of $V_H3$-9, $V_H3$-13 and $V_H3$-64.

4. The transgenic mouse of claim 3, wherein said foreign human antibody is encoded by a gene selected from the group consisting of: $V_H3$-9, $V_H3$-13, and $V_H3$-64.

5. The transgenic mouse of claim 3, wherein the mouse lacks a $V_H3$-9 gene.

6. The transgenic mouse of claim 5, wherein the foreign human antibody is encoded by the VH3-9 gene.

7. The transgenic mouse of claim 1, further comprising a candidate HAHA inhibitor that is inside of said transgenic mouse.

8. The transgenic mouse of claim 1, wherein the transgenic mouse has its mouse immunoglobulin genes inactivated.

9. The transgenic mouse of claim 1, further comprising an antigenic substance, wherein the antigenic substance is attached to the foreign human antibody.

10. A transgenic mouse comprising:

a genome comprising human immunoglobulin gene loci that following their B cell immunoglobulin gene rearrangements produce at least one human antibody, wherein the human immunoglobulin gene loci comprises genes that encode for a human antibody; and a foreign human antibody, wherein the foreign human antibody was encoded by a human immunoglobulin gene that is not present in the genome of the transgenic mouse, wherein the foreign human antibody is capable of inducing a human-anti-human antibody (HAHA) response, and wherein the human antibody produced by the transgenic mouse binds to the foreign human antibody, and wherein at least a portion of the foreign human antibody is encoded by the human immunoglobulin gene that is not expressed in the genome of the transgenic mouse.

11. The transgenic mouse of claim 10, where the transgenic mouse has its mouse immunoglobulin genes inactivated.

12. The transgenic mouse of claim 10, wherein the genome lacks at least one human immunoglobulin gene, selected from the group consisting of $V_H3$-9, $V_H3$-13 and $V_H3$-64.

13. The transgenic mouse of claim 12, wherein said foreign human antibody is encoded by a gene selected from the group consisting of: $V_H3$-9, $V_H3$-13, and $V_H3$-64.

14. The transgenic mouse of claim 12, wherein the mouse lacks a $V_H3$-9 gene.

15. The transgenic mouse of claim 14, wherein the foreign human antibody is encoded by the VH3-9 gene.

* * * * *

UNITED STATES PATENT AND TRADEMARK OFFICE
CERTIFICATE OF CORRECTION

| | | |
|---|---|---|
| PATENT NO. | : 8,198,508 B2 | Page 1 of 1 |
| APPLICATION NO. | : 12/577696 | |
| DATED | : June 12, 2012 | |
| INVENTOR(S) | : Kellerman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 159 days.

Signed and Sealed this
Second Day of October, 2012

David J. Kappos
*Director of the United States Patent and Trademark Office*

UNITED STATES PATENT AND TRADEMARK OFFICE
CERTIFICATE OF CORRECTION

Page 1 of 1

PATENT NO.         : 8,198,508 B2
APPLICATION NO.    : 12/577696
DATED              : June 12, 2012
INVENTOR(S)        : Kellermann et al.

It is certified that error appears in the above-identified patent and that said Letters Patent is hereby corrected as shown below:

In column 8 at line 22, Change "$V_H3$-9" to --$V_H3$-9,--.

In column 11 at line 3, Change "FIG.171" to --FIG.17I--.

In column 18 at line 25, Change "1-N-acetyllysine," to --ε-N-acetyllysine,--.

In column 48 at line 36, Change "V lambda" to --$V_{lambda}$--.

In column 59 at line 58, Change "pretreated" to --pre-treated--.

In column 225 at line 60 (approx.), In Claim 1, change "mouse" to --mouse,--.

In column 226 at line 52 (approx.), In Claim 3, change "gene," to --gene--.

In column 228 at line 4 (approx.), In Claim 12, change "gene," to --gene--.

Signed and Sealed this
Thirtieth Day of October, 2012

David J. Kappos
*Director of the United States Patent and Trademark Office*

UNITED STATES PATENT AND TRADEMARK OFFICE
CERTIFICATE OF CORRECTION

PATENT NO. : 8,198,508 B2  Page 1 of 1
APPLICATION NO. : 12/577696
DATED : June 12, 2012
INVENTOR(S) : Kellermann et al.

It is certified that error appears in the above-identified patent and that said Letters Patent is hereby corrected as shown below:

In column 45 at line 2, Change "$D_H$ $J_H$," to --$D_H$, $J_H$,--.

In column 58 at line 45, Change "NS0" to --NSO--.

In column 226 at line 59 (approx.), In Claim 6, change "VH3-9" to --$V_H$3-9--.

In column 228 at line 13, In Claim 15, change "VH3-9" to --$V_H$3-9--.

Signed and Sealed this
Eighteenth Day of December, 2012

David J. Kappos
*Director of the United States Patent and Trademark Office*

SEQUENCE LISTING

<160> NUMBER OF SEQ ID NOS: 268

<210> SEQ ID NO 1
<211> LENGTH: 107
<212> TYPE: PRT
<213> ORGANISM: Homo sapiens

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Homo sapiens

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 9
<212> TYPE: PRT
<213> ORGANISM: Homo sapiens
<220> FEATURE:
<221> NAME/KEY: VARIANT
<222> LOCATION: 9
<223> OTHER INFORMATION: Xaa = Any Amino Acid

<400> SEQUENCE: 3

Gln Arg Tyr Asn Arg Ala Pro Tyr Xaa
1               5

```
<210> SEQ ID NO 4
<211> LENGTH: 12
<212> TYPE: PRT
<213> ORGANISM: Homo sapiens
<220> FEATURE:
<221> NAME/KEY: VARIANT
<222> LOCATION: 12
<223> OTHER INFORMATION: Xaa = Any Amino Acid

<400> SEQUENCE: 4

Val Ser Tyr Leu Ser Thr Ala Ser Ser Leu Asp Xaa
 1               5                  10

<210> SEQ ID NO 5
<211> LENGTH: 321
<212> TYPE: DNA
<213> ORGANISM: Homo sapiens

<400> SEQUENCE: 5
gacatccaga tgacccagtc tccatcctcc ctgtctgcat ctgtagggga cagagtcacc      60
atcacttgcc gggcaagtca gggcattaga attgatttag ctggtatca gcagaaacca     120 gggaaagccc ctaagcgcct gatctatgct gcatccactt tgcaaagtgg ggtcccatca    180
aggttcagcg gcagtggatc ggggacagaa ttcattttca caatcagcag cctgcagcct    240
gaagattttg caagttatta ctgtctacag cataaaagtt accctctcac tttcggcgga    300
gggaccaagg tggagatcaa a                                              321

<210> SEQ ID NO 6
<211> LENGTH: 107
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Ile Asp
            20                  25                  30

Leu Gly Trp Tyr Gln Gln Lys Pro Gly Lys Ala Pro Lys Arg Leu Ile
        35                  40                  45

Tyr Ala Ala Ser Thr Leu Gln Ser Gly Val Pro Ser Arg Phe Ser Gly
 50                  55                  60

Ser Gly Ser Gly Thr Glu Phe Ile Phe Thr Ile Ser Ser Leu Gln Pro
65                  70                  75                  80

Glu Asp Phe Ala Ser Tyr Tyr Cys Leu Gln His Lys Ser Tyr Pro Leu
                85                  90                  95

Thr Phe Gly Gly Gly Thr Lys Val Glu Ile Lys
            100                 105

<210> SEQ ID NO 7
<211> LENGTH: 375
<212> TYPE: DNA
<213> ORGANISM: Homo sapiens

<400> SEQUENCE: 7
caggtgcagc tggtggagtc tgggggaggc gtggtccagc ctgggaggtc cctgagactc      60
tcctgtgcag cgtctggatt caccttcagt agctatgaca tgcactgggt ccgccaggct    120
ccaggcaagg ggctggagtg ggtggcagtt atatggtctg atggaagtat taaatactat    180
gcagactccg tgaagggccg attcaccatc tccagagaca attccaagaa cacgctgtat    240
```

```
ctgcaaatga acagcctgag agccgaggac acggctgtgt attactgtgc gagagaagtg    300
gaatcagcta tgggagggtt ctactacaac ggtatggacg tctggggcca agggaccacg    360
gtcaccgtct cctca                                                     375
```

<210> SEQ ID NO 8
<211> LENGTH: 125
<212> TYPE: PRT
<213> ORGANISM: Homo sapiens

<400> SEQUENCE: 8

```
Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Trp Ser Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Val Glu Ser Ala Met Gly Gly Phe Tyr Tyr Asn Gly Met
            100                 105                 110

Asp Val Trp Gly Gln Gly Thr Thr Val Thr Val Ser Ser
        115                 120                 125
```

<210> SEQ ID NO 9
<211> LENGTH: 18
<212> TYPE: PRT
<213> ORGANISM: Homo sapiens

<400> SEQUENCE: 9

```
Cys Gln Tyr Ile Lys Ala Asn Ser Lys Phe Ile Gly Ile Thr Glu Leu
 1               5                   10                  15

Lys Lys
```

<210> SEQ ID NO 10
<211> LENGTH: 98
<212> TYPE: PRT
<213> ORGANISM: Homo sapiens

<400> SEQUENCE: 10

```
Glu Val Gln Leu Val Glu Ser Gly Gly Gly Leu Val Gln Pro Gly Gly
 1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Asn Pro Ser Val
    50                  55                  60

Lys Gly Arg Ile Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg
```

```
<210> SEQ ID NO 11
<211> LENGTH: 218
<212> TYPE: PRT
<213> ORGANISM: Homo sapiens

<400> SEQUENCE: 11

Asp Ile Gln Leu Thr Gln Ser Pro Ser Ser Leu Ser Ala Ser Val Gly
  1               5                  10                  15

Asp Arg Val Thr Ile Thr Cys Arg Ala Ser Gln Ser Val Asp Tyr Asp
             20                  25                  30

Gly Asp Ser Tyr Met Asn Trp Tyr Gln Gln Lys Pro Gly Lys Ala Pro
         35                  40                  45

Lys Leu Leu Ile Tyr Ala Ala Ser Tyr Leu Glu Ser Gly Val Pro Ser
     50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser His
                 85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 12
<211> LENGTH: 105
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
     50                  55                  60

Ser Gly Ser Gly Thr Asp Phe Thr Leu Thr Ile Ser Ser His Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu
            100                 105

<210> SEQ ID NO 13
```

```
<211> LENGTH: 120
<212> TYPE: PRT
<213> ORGANISM: Homo sapiens

<400> SEQUENCE: 13

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser
        115                 120

<210> SEQ ID NO 14
<211> LENGTH: 22
<212> TYPE: DNA
<213> ORGANISM: Artificial Sequence
<220> FEATURE:
<223> OTHER INFORMATION: Synthetic oligonucleotide probe sequence

<400> SEQUENCE: 14
ccggcaagct ccagggaagg gc                                                    22

<210> SEQ ID NO 15
<211> LENGTH: 98
<212> TYPE: PRT
<213> ORGANISM: Homo sapiens

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 16
<211> LENGTH: 98
<212> TYPE: PRT
<213> ORGANISM: Homo sapiens

<400> SEQUENCE: 16

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 17
<211> LENGTH: 98
<212> TYPE: PRT
<213> ORGANISM: Homo sapiens

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 18
<211> LENGTH: 98
<212> TYPE: PRT
<213> ORGANISM: Homo sapiens

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ser Asn Ala Gly Asn Gly Asn Thr Lys Tyr Ser Gln Glu Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg

<210> SEQ ID NO 19
<211> LENGTH: 98
<212> TYPE: PRT
<213> ORGANISM: Homo sapiens
```

-continued

<400> SEQUENCE: 19

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Arg
            20                  25                  30

Tyr Leu His Trp Val Arg Gln Ala Pro Gly Gln Ala Leu Glu Trp Met
        35                  40                  45

Gly Trp Ile Thr Pro Phe Asn Gly Asn Thr Asn Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg

<210> SEQ ID NO 20
<211> LENGTH: 98
<212> TYPE: PRT
<213> ORGANISM: Homo sapiens

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 21
<211> LENGTH: 98
<212> TYPE: PRT
<213> ORGANISM: Homo sapiens

<400> SEQUENCE: 21

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
            20                  25                  30

Ala Met Gln Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala

<210> SEQ ID NO 22

```
<211> LENGTH: 98
<212> TYPE: PRT
<213> ORGANISM: Homo sapiens

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 23
<211> LENGTH: 99
<212> TYPE: PRT
<213> ORGANISM: Homo sapiens

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly

<210> SEQ ID NO 24
<211> LENGTH: 100
<212> TYPE: PRT
<213> ORGANISM: Homo sapiens

<400> SEQUENCE: 24

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
                20                  25                  30

Arg Met Gly Val Ser Trp Ile Arg Gln Pro Pro Gly Lys Ala Leu Glu
            35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95
```

```
Cys Ala Arg Ile
            100

<210> SEQ ID NO 25
<211> LENGTH: 100
<212> TYPE: PRT
<213> ORGANISM: Homo sapiens

<400> SEQUENCE: 25

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg
            100

<210> SEQ ID NO 26
<211> LENGTH: 100
<212> TYPE: PRT
<213> ORGANISM: Homo sapiens

<400> SEQUENCE: 26

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile
            100

<210> SEQ ID NO 27
<211> LENGTH: 98
<212> TYPE: PRT
<213> ORGANISM: Homo sapiens

<400> SEQUENCE: 27

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg
```

<210> SEQ ID NO 28
<211> LENGTH: 97
<212> TYPE: PRT
<213> ORGANISM: Homo sapiens

<400> SEQUENCE: 28

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Asp Met His Trp Val Arg Gln Ala Thr Gly Lys Gly Leu Glu Trp Val
         35                  40                  45

Ser Ala Ile Gly Thr Ala Gly Asp Thr Tyr Tyr Pro Gly Ser Val Lys
 50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg
```

<210> SEQ ID NO 29
<211> LENGTH: 100
<212> TYPE: PRT
<213> ORGANISM: Homo sapiens

<400> SEQUENCE: 29

```
Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Lys Ser Lys Thr Asp Gly Gly Thr Thr Asp Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr
            100
```

<210> SEQ ID NO 30
<211> LENGTH: 98
<212> TYPE: PRT
<213> ORGANISM: Homo sapiens

<400> SEQUENCE: 30

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Ser
             20                  25                  30
```

```
Asp Met Asn Trp Ala Arg Lys Ala Pro Gly Lys Gly Leu Glu Trp Val
            35                  40                  45

Ser Gly Val Ser Trp Asn Gly Ser Arg Thr His Tyr Val Asp Ser Val
 50                  55                  60

Lys Arg Arg Phe Ile Ile Ser Arg Asp Asn Ser Arg Asn Ser Leu Tyr
 65                  70                  75                  80

Leu Gln Lys Asn Arg Arg Ala Glu Asp Met Ala Val Tyr Tyr Cys
            85                  90                  95

Val Arg

<210> SEQ ID NO 31
<211> LENGTH: 98
<212> TYPE: PRT
<213> ORGANISM: Homo sapiens

<400> SEQUENCE: 31

Glu Val Gln Leu Val Glu Ser Gly Gly Gly Val Val Arg Pro Gly Gly
 1               5                  10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
            35                  40                  45

Ser Gly Ile Asn Trp Asn Gly Ser Thr Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr His Cys
            85                  90                  95

Ala Arg

<210> SEQ ID NO 32
<211> LENGTH: 98
<212> TYPE: PRT
<213> ORGANISM: Homo sapiens

<400> SEQUENCE: 32

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Ser Ile Ser Ser Ser Ser Ser Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
            85                  90                  95

Ala Arg

<210> SEQ ID NO 33
<211> LENGTH: 98
<212> TYPE: PRT
<213> ORGANISM: Homo sapiens

<400> SEQUENCE: 33

Glu Val Gln Leu Leu Glu Ser Gly Gly Gly Leu Val Gln Pro Gly Gly
 1               5                  10                  15
```

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 34
<211> LENGTH: 98
<212> TYPE: PRT
<213> ORGANISM: Homo sapiens

<400> SEQUENCE: 34

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 35
<211> LENGTH: 98
<212> TYPE: PRT
<213> ORGANISM: Homo sapiens

<400> SEQUENCE: 35

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 36
<211> LENGTH: 98
<212> TYPE: PRT
<213> ORGANISM: Homo sapiens

```
<400> SEQUENCE: 36

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Ser
            20                  25                  30

Asp Met Asn Trp Val His Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

Lys Gly Arg Phe Ile Ile Ser Arg Asp Asn Ser Arg Asn Thr Leu Tyr
65                  70                  75                  80

Leu Gln Thr Asn Ser Leu Arg Ala Glu Asp Thr Ala Val Tyr Tyr Cys
            85                  90                  95

Val Arg

<210> SEQ ID NO 37
<211> LENGTH: 96
<212> TYPE: PRT
<213> ORGANISM: Homo sapiens

<400> SEQUENCE: 37

Glu Val Gln Leu Val Glu Ser Gly Gly Gly Leu Val Gln Pro Arg Gly
 1               5                  10                  15

Ser Leu Arg Leu Ser Cys Ala Ala Ser Gly Phe Thr Val Ser Ser Asn
            20                  25                  30

Glu Met Ser Trp Ile Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu Tyr Leu Gln
65                  70                  75                  80

Met Asn Asn Leu Arg Ala Glu Gly Thr Ala Val Tyr Tyr Cys Ala Arg
            85                  90                  95

<210> SEQ ID NO 38
<211> LENGTH: 99
<212> TYPE: PRT
<213> ORGANISM: Homo sapiens

<400> SEQUENCE: 38

Glu Val Gln Leu Val Glu Ser Gly Gly Val Val Gln Pro Gly Gly
 1               5                  10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Leu Ile Ser Trp Asp Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
            85                  90                  95

Ala Lys Asp

<210> SEQ ID NO 39
<211> LENGTH: 98
<212> TYPE: PRT
```

<213> ORGANISM: Homo sapiens

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg

<210> SEQ ID NO 40
<211> LENGTH: 100
<212> TYPE: PRT
<213> ORGANISM: Homo sapiens

<400> SEQUENCE: 40

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 41
<211> LENGTH: 97
<212> TYPE: PRT
<213> ORGANISM: Homo sapiens

<400> SEQUENCE: 41

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 42
<211> LENGTH: 98
<212> TYPE: PRT
<213> ORGANISM: Homo sapiens

<400> SEQUENCE: 42

Glu Val Gln Leu Val Glu Ser Gly Glu Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg

<210> SEQ ID NO 43
<211> LENGTH: 97
<212> TYPE: PRT
<213> ORGANISM: Homo sapiens

<400> SEQUENCE: 43

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Cys Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 44
<211> LENGTH: 98
<212> TYPE: PRT
<213> ORGANISM: Homo sapiens

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg

<210> SEQ ID NO 45
<211> LENGTH: 100
<212> TYPE: PRT
<213> ORGANISM: Homo sapiens

<400> SEQUENCE: 45

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp His
                20                  25                  30

Tyr Met Asp Trp Val Arg Gln Ala Pro Gly Lys Gly Leu Glu Trp Val
            35                  40                  45

Gly Arg Thr Arg Asn Lys Ala Asn Ser Tyr Thr Thr Glu Tyr Ala Ala
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg
            100

<210> SEQ ID NO 46
<211> LENGTH: 100
<212> TYPE: PRT
<213> ORGANISM: Homo sapiens

<400> SEQUENCE: 46

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Gly Ser
                20                  25                  30

Ala Met His Trp Val Arg Gln Ala Ser Gly Lys Gly Leu Glu Trp Val
            35                  40                  45

Gly Arg Ile Arg Ser Lys Ala Asn Ser Tyr Ala Thr Ala Tyr Ala Ala
        50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 47
<211> LENGTH: 98
<212> TYPE: PRT
<213> ORGANISM: Homo sapiens

<400> SEQUENCE: 47

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Trp Met His Trp Val Arg Gln Ala Pro Gly Lys Gly Leu Val Trp Val
            35                  40                  45

```
Ser Arg Ile Asn Ser Asp Gly Ser Ser Thr Ser Tyr Ala Asp Ser Val
        50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 48
<211> LENGTH: 99
<212> TYPE: PRT
<213> ORGANISM: Homo sapiens

<400> SEQUENCE: 48

Glu Val Gln Leu Val Glu Ser Gly Gly Gly Leu Val Gln Pro Gly Arg
 1               5                   10                  15

Ser Leu Arg Leu Ser Cys Ala Ala Ser Gly Phe Thr Phe Asp Asp Tyr
                 20                  25                  30

Ala Met His Trp Val Arg Gln Ala Pro Gly Lys Gly Leu Glu Trp Val
             35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp

<210> SEQ ID NO 49
<211> LENGTH: 98
<212> TYPE: PRT
<213> ORGANISM: Homo sapiens

<400> SEQUENCE: 49

Gln Val Gln Leu Gln Glu Ser Gly Pro Gly Leu Val Lys Pro Ser Asp
 1               5                   10                  15

Thr Leu Ser Leu Thr Cys Ala Val Ser Gly Tyr Ser Ile Ser Ser Ser
                 20                  25                  30

Asn Trp Trp Gly Trp Ile Arg Gln Pro Pro Gly Lys Gly Leu Glu Trp
             35                  40                  45

Ile Gly Tyr Ile Tyr Tyr Ser Gly Ser Thr Tyr Tyr Asn Pro Ser Leu
        50                  55                  60

Lys Ser Arg Val Thr Met Ser Val Asp Thr Ser Lys Asn Gln Phe Ser
 65                  70                  75                  80

Leu Lys Leu Ser Ser Val Thr Ala Val Asp Thr Ala Val Tyr Tyr Cys
                 85                  90                  95

Ala Arg

<210> SEQ ID NO 50
<211> LENGTH: 99
<212> TYPE: PRT
<213> ORGANISM: Homo sapiens

<400> SEQUENCE: 50

Gln Val Gln Leu Gln Glu Ser Gly Pro Gly Leu Val Lys Pro Ser Gln
 1               5                   10                  15

Thr Leu Ser Leu Thr Cys Thr Val Ser Gly Gly Ser Ile Ser Ser Gly
                 20                  25                  30
```

Gly Tyr Tyr Trp Ser Trp Ile Arg Gln His Pro Gly Lys Gly Leu Glu
                35                  40                  45

Trp Ile Gly Tyr Ile Tyr Tyr Ser Gly Ser Thr Tyr Tyr Asn Pro Ser
     50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 51
<211> LENGTH: 98
<212> TYPE: PRT
<213> ORGANISM: Homo sapiens

<400> SEQUENCE: 51

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
                35                  40                  45

Gly Glu Ile Asn His Ser Gly Ser Thr Asn Tyr Asn Pro Ser Leu Lys
             50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly

<210> SEQ ID NO 52
<211> LENGTH: 99
<212> TYPE: PRT
<213> ORGANISM: Homo sapiens

<400> SEQUENCE: 52

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
                35                  40                  45

Trp Ile Gly Ser Ile Tyr Tyr Ser Gly Ser Thr Tyr Tyr Asn Pro Ser
     50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 53
<211> LENGTH: 97
<212> TYPE: PRT
<213> ORGANISM: Homo sapiens

<400> SEQUENCE: 53

Gln Val Gln Leu Gln Glu Ser Gly Pro Gly Leu Val Lys Pro Ser Glu

```
                1               5                   10                  15
Thr Leu Ser Leu Thr Cys Thr Val Ser Gly Gly Ser Ile Ser Ser Tyr
                20                  25                  30

Tyr Trp Ser Trp Ile Arg Gln Pro Ala Gly Lys Gly Leu Glu Trp Ile
            35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 54
<211> LENGTH: 97
<212> TYPE: PRT
<213> ORGANISM: Homo sapiens

<400> SEQUENCE: 54

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 55
<211> LENGTH: 99
<212> TYPE: PRT
<213> ORGANISM: Homo sapiens

<400> SEQUENCE: 55

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
                20                  25                  30

Gly Tyr Tyr Trp Ser Trp Ile Arg Gln Pro Pro Gly Lys Gly Leu Glu
            35                  40                  45

Trp Ile Gly Tyr Ile Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 56
<211> LENGTH: 98
<212> TYPE: PRT
<213> ORGANISM: Homo sapiens
```

```
<400> SEQUENCE: 56

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 57
<211> LENGTH: 101
<212> TYPE: PRT
<213> ORGANISM: Homo sapiens

<400> SEQUENCE: 57

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg
            100

<210> SEQ ID NO 58
<211> LENGTH: 98
<212> TYPE: PRT
<213> ORGANISM: Homo sapiens

<400> SEQUENCE: 58

Gln Val Gln Leu Val Gln Ser Gly His Glu Val Lys Gln Pro Gly Ala
1               5                   10                  15

Ser Val Lys Val Ser Cys Lys Ala Ser Gly Tyr Ser Phe Thr Thr Tyr
            20                  25                  30

Gly Met Asn Trp Val Pro Gln Ala Pro Gly Gln Gly Leu Glu Trp Met
        35                  40                  45

Gly Trp Phe Asn Thr Tyr Thr Gly Asn Pro Thr Tyr Ala Gln Gly Phe
    50                  55                  60

Thr Gly Arg Phe Val Phe Ser Met Asp Thr Ser Ala Ser Thr Ala Tyr
65                  70                  75                  80

Leu Gln Ile Ser Ser Leu Lys Ala Glu Asp Met Ala Met Tyr Tyr Cys
                85                  90                  95

Ala Arg
```

<210> SEQ ID NO 59
<211> LENGTH: 296
<212> TYPE: DNA
<213> ORGANISM: Homo sapiens

<400> SEQUENCE: 59
caggttcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag ggcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgacgac acggccgtgt attactgtgc gagaga         296

<210> SEQ ID NO 60
<211> LENGTH: 296
<212> TYPE: DNA
<213> ORGANISM: Homo sapiens

<400> SEQUENCE: 60
caggtgcagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag ggcttgagtg gatgggatgg atcaacccta acagtggtgg cacaaactat     180
gcacagaagt ttcagggcag ggtcaccatg accagggaca cgtccatcag cacagcctac     240
atggagctga gcaggctgag atctgacgac acggccgtgt attactgtgc gagaga         296

<210> SEQ ID NO 61
<211> LENGTH: 296
<212> TYPE: DNA
<213> ORGANISM: Homo sapiens

<400> SEQUENCE: 61
caggtccagc tggtacagtc tggggctgag gtgaagaagc ctggggcctc agtgaaggtc      60
tcctgcaagg tttccggata caccctcact gaattatcca tgcactgggt gcgacaggct     120
cctggaaaag ggcttgagtg gatgggaggt tttgatcctg aagatggtga acaatctac      180 gcacagaagt tccagggcag agtcaccatg accgaggaca catctacaga cacagcctac     240
atggagctga gcagcctgag atctgaggac acggccgtgt attactgtgc aacaga         296

<210> SEQ ID NO 62
<211> LENGTH: 296
<212> TYPE: DNA
<213> ORGANISM: Homo sapiens

<400> SEQUENCE: 62
caggttcagc tggtgcagtc tggggctgag gtgaagaagc ctggggcctc agtgaaggtt      60
tcctgcaagg cttctggata caccttcact agctatgcta tgcattgggt gcgccaggcc     120
cccggacaaa ggcttgagtg gatgggatgg agcaacgctg gcaatggtaa cacaaaatat     180
tcacaggagt tccagggcag agtcaccatt accagggaca catccgcgag cacagcctac     240
atggagctga gcagcctgag atctgaggac atggctgtgt attactgtgc gagaga         296

<210> SEQ ID NO 63
<211> LENGTH: 296
<212> TYPE: DNA
<213> ORGANISM: Homo sapiens

<400> SEQUENCE: 63

```
cagatgcagc tggtgcagtc tggggctgag gtgaagaaga ctgggtcctc agtgaaggtt      60
tcctgcaagg cttccggata caccttcacc taccgctacc tgcactgggt gcgacaggcc     120
cccggacaag cgcttgagtg gatgggatgg atcacacctt caatggtaa caccaactac     180 gcacagaaat tccaggacag agtcaccatt accaggaca ggtctatgag cacagcctac     240
atggagctga gcagcctgag atctgaggac acagccatgt attactgtgc aagata         296

<210> SEQ ID NO 64
<211> LENGTH: 296
<212> TYPE: DNA
<213> ORGANISM: Homo sapiens

<400> SEQUENCE: 64
caggtgcagc tggtgcagtc tggggctgag gtgaagaagc ctggggcctc agtgaaggtt      60
tcctgcaagg catctggata caccttcacc agctactata tgcactgggt gcgacaggcc     120
cctggacaag ggcttgagtg gatgggaata atcaacccta gtggtggtag cacaagctac     180
gcacagaagt tccagggcag agtcaccatg accagggaca cgtccacgag cacagtctac     240
atggagctga gcagcctgag atctgaggac acggccgtgt attactgtgc gagaga        296

<210> SEQ ID NO 65
<211> LENGTH: 296
<212> TYPE: DNA
<213> ORGANISM: Homo sapiens

<400> SEQUENCE: 65
caaatgcagc tggtgcagtc tgggcctgag gtgaagaagc ctgggaccctc agtgaaggtc     60 tcctgcaagg cttctggatt cacctttact agctctgcta tgcagtgggt gcgacaggct    120
cgtggacaac gccttgagtg gataggatgg atcgtcgttg gcagtggtaa cacaaactac    180
gcacagaagt tccaggaaag agtcaccatt accaggaca tgtccacaag cacagcctac     240
atggagctga gcagcctgag atccgaggac acggccgtgt attactgtgc ggcaga        296

<210> SEQ ID NO 66
<211> LENGTH: 296
<212> TYPE: DNA
<213> ORGANISM: Homo sapiens

<400> SEQUENCE: 66
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggaca aatccacgag cacagcctac    240
atggagctga gcagcctgag atctgaggac acggccgtgt attactgtgc gagaga        296

<210> SEQ ID NO 67
<211> LENGTH: 296
<212> TYPE: DNA
<213> ORGANISM: Homo sapiens

<400> SEQUENCE: 67
caggtgcagc tggtgcagtc tggggctgag gtgaagaagc ctggggcctc agtgaaggtc      60
tcctgcaagg cttctggata caccttcacc agttatgata tcaactgggt gcgacaggcc    120
actggacaag ggcttgagtg gatgggatgg atgaacccta acagtggtaa cacaggctat    180
gcacagaagt tccagggcag agtcaccatg accaggaaca cctccataag cacagcctac    240
```

```
atggagctga gcagcctgag atctgaggac acggccgtgt attactgtgc gagagg       296
```

<210> SEQ ID NO 68
<211> LENGTH: 301
<212> TYPE: DNA
<213> ORGANISM: Homo sapiens

<400> SEQUENCE: 68

```
caggtcacct tgaaggagtc tggtcctgtg ctggtgaaac ccacagagac cctcacgctg    60
acctgcaccg tctctgggtt ctcactcagc aatgctagaa tgggtgtgag ctggatccgt   120
cagcccccag ggaaggccct ggagtggctt gcacacattt tttcgaatga cgaaaaatcc   180
tacagcacat ctctgaagag caggctcacc atctccaagg acacctccaa aagccaggtg   240
gtccttacca tgaccaacat ggaccctgtg gacacagcca catattactg tgcacggata   300
c                                                                   301
```

<210> SEQ ID NO 69
<211> LENGTH: 301
<212> TYPE: DNA
<213> ORGANISM: Homo sapiens

<400> SEQUENCE: 69

```
cagatcacct tgaaggagtc tggtcctacg ctggtgaaac ccacacagac cctcacgctg    60
acctgcacct tctctgggtt ctcactcagc actagtggag tgggtgtggg ctggatccgt   120
cagcccccag gaaaggccct ggagtggctt gcactcattt attggaatga tgataagcgc   180
tacagcccat ctctgaagag caggctcacc atcaccaagg acacctccaa aaaccaggtg   240
gtccttacaa tgaccaacat ggaccctgtg gacacagcca catattactg tgcacacaga   300
c                                                                   301
```

<210> SEQ ID NO 70
<211> LENGTH: 301
<212> TYPE: DNA
<213> ORGANISM: Homo sapiens

<400> SEQUENCE: 70

```
caggtcacct tgagggagtc tggtcctgcg ctggtgaaac ccacacagac cctcacactg    60
acctgcacct tctctgggtt ctcactcagc actagtggaa tgtgtgtgag ctggatccgt   120
cagcccccag ggaaggccct ggagtggctt gcactcattg attgggatga tgataaatac   180
tacagcacat ctctgaagac caggctcacc atctccaagg acacctccaa aaaccaggtg   240
gtccttacaa tgaccaacat ggaccctgtg gacacagcca cgtattattg tgcacggata   300
c                                                                   301
```

<210> SEQ ID NO 71
<211> LENGTH: 296
<212> TYPE: DNA
<213> ORGANISM: Homo sapiens

<400> SEQUENCE: 71

```
caggtgcagc tggtggagtc tgggggaggc ttggtcaagc ctggagggtc cctgagactc    60
tcctgtgcag cctctggatt caccttcagt gactactaca tgagctggat ccgccaggct   120
ccagggaagg ggctggagtg ggtttcatac attagtagta gtggtagtac catatactac   180
gcagactctg tgaagggccg attcaccatc tccagggaca cgccaagaa ctcactgtat   240
ctgcaaatga acagcctgag agccgaggac acggccgtgt attactgtgc gagaga       296
```

<210> SEQ ID NO 72
<211> LENGTH: 293
<212> TYPE: DNA
<213> ORGANISM: Homo sapiens

<400> SEQUENCE: 72

```
gaggtgcagc tggtggagtc tgggggaggc ttggtacagc ctggggggtc cctgagactc    60
tcctgtgcag cctctggatt caccttcagt agctacgaca tgcactgggt ccgccaagct   120
acaggaaaag gtctggagtg gtctcagct attggtactg ctggtgacac atactatcca   180
ggctccgtga agggccgatt caccatctcc agagaaaatg ccaagaactc cttgtatctt   240
caaatgaaca gcctgagagc cggggacacg gctgtgtatt actgtgcaag aga          293
```

<210> SEQ ID NO 73
<211> LENGTH: 302
<212> TYPE: DNA
<213> ORGANISM: Homo sapiens

<400> SEQUENCE: 73

```
gaggtgcagc tggtggagtc tgggggaggc ttggtaaagc ctggggggtc ccttagactc    60
tcctgtgcag cctctggatt cactttcagt aacgcctgga tgagctgggt ccgccaggct   120
ccagggaagg ggctggagtg ggttggccgt attaaaagca aaactgatgg tgggacaaca   180
gactacgctg cacccgtgaa aggcagattc accatctcaa gagatgattc aaaaaacacg   240
ctgtatctgc aaatgaacag cctgaaaacc gaggacacag ccgtgtatta ctgtaccaca   300
ga                                                                  302
```

<210> SEQ ID NO 74
<211> LENGTH: 296
<212> TYPE: DNA
<213> ORGANISM: Homo sapiens

<400> SEQUENCE: 74

```
gaggtgcagc tggtggagtc tgggggaggc ttggtacagc ctggggggtc cctgagactc    60
tcctgtgcag cctctggatt caccttcagt aacagtgaca tgaactgggc ccgcaaggct   120
ccaggaaagg ggctggagtg gtatcgggt gttagttgga atggcagtag gacgcactat   180
gtggactccg tgaagcgccg attcatcatc tccagagaca attccaggaa ctccctgtat   240
ctgcaaaaga acagacggag agccgaggac atggctgtgt attactgtgt gagaaa      296
```

<210> SEQ ID NO 75
<211> LENGTH: 296
<212> TYPE: DNA
<213> ORGANISM: Homo sapiens

<400> SEQUENCE: 75

```
gaggtgcagc tggtggagtc tgggggaggt gtggtacggc ctggggggtc cctgagactc    60
tcctgtgcag cctctggatt cacctttgat gattatggca tgagctgggt ccgccaagct   120
ccaggaaagg ggctggagtg gtctctggt attaattgga atggtggtag cacaggttat   180
gcagactctg tgaagggccg attcaccatc tccagagaca cgccaagaa ctccctgtat   240
ctgcaaatga acagtctgag agccgaggac acggccttgt atcactgtgc gagaga       296
```

<210> SEQ ID NO 76
<211> LENGTH: 296
<212> TYPE: DNA
<213> ORGANISM: Homo sapiens

```
<400> SEQUENCE: 76
gaggtgcagc tggtggagtc tgggggaggc ctggtcaagc ctggggggtc cctgagactc    60
tcctgtgcag cctctggatt caccttcagt agctatagca tgaactgggt ccgccaggct   120
ccagggaagg ggctggagtg ggtctcatcc attagtagta gtagtagtta catatactac   180
gcagactcag tgaagggccg attcaccatc tccagagaca acgccaagaa ctcactgtat   240
ctgcaaatga acagcctgag agccgaggac acggctgtgt attactgtgc gagaga       296

<210> SEQ ID NO 77
<211> LENGTH: 296
<212> TYPE: DNA
<213> ORGANISM: Homo sapiens

<400> SEQUENCE: 77
gaggtgcagc tgttggagtc tgggggaggc ttggtacagc ctggggggtc cctgagactc    60
tcctgtgcag cctctggatt caccttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtat attactgtgc gaaaga       296

<210> SEQ ID NO 78
<211> LENGTH: 296
<212> TYPE: DNA
<213> ORGANISM: Homo sapiens

<400> SEQUENCE: 78
caggtgcagc tggtggagtc tgggggaggc gtggtccagc ctggggaggtc cctgagactc    60 tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agctgaggac acggctgtgt attactgtgc gagaga       296

<210> SEQ ID NO 79
<211> LENGTH: 296
<212> TYPE: DNA
<213> ORGANISM: Homo sapiens

<400> SEQUENCE: 79
caggtgcagc tggtggagtc tgggggaggc gtggtccagc ctggggaggtc cctgagactc    60 tcctgtgcag cgtctggatt caccttcagt agctatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagaga       296

<210> SEQ ID NO 80
<211> LENGTH: 296
<212> TYPE: DNA
<213> ORGANISM: Homo sapiens

<400> SEQUENCE: 80
gaggtgcagc tgttggagtc tgggggaggc ttggtacagc ctgggggatc cctgagactc    60
tcctgtgcag cctctggatt caccttcagt aacagtgaca tgaactgggt ccatcaggct   120
ccaggaaagg ggctggagtg ggtatcgggt gttagttgga atggcagtag gacgcactat   180
```

```
gcagactctg tgaagggccg attcatcatc tccagagaca attccaggaa caccctgtat    240
ctgcaaacga atagcctgag ggccgaggac acggctgtgt attactgtgt gagaaa        296
```

<210> SEQ ID NO 81
<211> LENGTH: 290
<212> TYPE: DNA
<213> ORGANISM: Homo sapiens

<400> SEQUENCE: 81

```
gaggtgcagc tggtggagtc tgggggaggc ttggtacagc ctaggggtc cctgagactc     60 tcctgtgcag cctctggatt caccgtcagt agcaatgaga tgagctggat ccgccaggct   120
ccagggaagg ggctggagtg ggtctcatcc attagtggtg gtagcacata ctacgcagac   180
tccaggaagg gcagattcac catctccaga gacaattcca agaacacgct gtatcttcaa   240
atgaacaacc tgagagctga gggcacggcc gtgtattact gtgccagata              290
```

<210> SEQ ID NO 82
<211> LENGTH: 298
<212> TYPE: DNA
<213> ORGANISM: Homo sapiens

<400> SEQUENCE: 82

```
gaagtgcagc tggtggagtc tgggggagtc gtggtacagc ctgggggtc cctgagactc     60 tcctgtgcag cctctggatt cacctttgat gattatacca tgcactgggt ccgtcaagct   120
ccggggaagg gtctggagtg ggtctctctt attagttggg atggtggtag cacatactat   180
gcagactctg tgaagggccg attcaccatc tccagagaca acagcaaaaa ctccctgtat   240
ctgcaaatga acagtctgag aactgaggac accgccttgt attactgtgc aaaagata    298
```

<210> SEQ ID NO 83
<211> LENGTH: 296
<212> TYPE: DNA
<213> ORGANISM: Homo sapiens

<400> SEQUENCE: 83

```
gaggtgcagc tggtggagtc tgggggaggc ttggtacagc ctgggggtc cctgagactc     60 tcctgtgcag cctctggatt caccttcagt agctatagca tgaactgggt ccgccaggct   120
ccagggaagg ggctggagtg ggtttcatac attagtagta gtagtagtac catatactac   180
gcagactctg tgaagggccg attcaccatc tccagagaca atgccaagaa ctcactgtat   240
ctgcaaatga acagcctgag agacgaggac acggctgtgt attactgtgc gagaga       296
```

<210> SEQ ID NO 84
<211> LENGTH: 302
<212> TYPE: DNA
<213> ORGANISM: Homo sapiens

<400> SEQUENCE: 84

```
gaggtgcagc tggtggagtc tgggggaggc ttggtacagc caggcggtc cctgagactc      60 tcctgtacag cttctggatt cacctttggt gattatgcta tgagctggtt ccgccaggct   120
ccagggaagg ggctggagtg ggtaggtttc attagaagca aagcttatgg tgggacaaca   180
gaatacgccg cgtctgtgaa aggcagattc accatctcaa gagatgattc aaaagcatc    240 gcctatctgc aaatgaacag cctgaaaacc gaggacacag ccgtgtatta ctgtactaga   300
ga                                                                   302
```

<210> SEQ ID NO 85

<211> LENGTH: 293
<212> TYPE: DNA
<213> ORGANISM: Homo sapiens

<400> SEQUENCE: 85

```
gaggtgcagc tggtggagtc tggaggaggc ttgatccagc ctgggggtc cctgagactc      60
tcctgtgcag cctctgggtt caccgtcagt agcaactaca tgagctgggt ccgccaggct    120
ccagggaagg ggctggagtg ggtctcagtt atttatagcg gtggtagcac atactacgca    180
gactccgtga agggccgatt caccatctcc agagacaatt ccaagaacac gctgtatctt    240
caaatgaaca gcctgagagc cgaggacacg gccgtgtatt actgtgcgag aga           293
```

<210> SEQ ID NO 86
<211> LENGTH: 296
<212> TYPE: DNA
<213> ORGANISM: Homo sapiens

<400> SEQUENCE: 86

```
gaggtgcagc tggtggagtc tgggggaggc ttggtccagc ctgggggtc cctgagactc      60
tcctgtgcag cctctggatt caccttcagt agctatgcta tgcactgggt ccgccaggct    120
ccagggaagg gactggaata tgtttcagct attagtagta tgggggtag cacatattat     180
gcagactctg tgaagggcag attcaccatc tccagagaca attccaagaa cacgctgtat    240
cttcaaatgg gcagcctgag agctgaggac atggctgtgt attactgtgc gagaga         296
```

<210> SEQ ID NO 87
<211> LENGTH: 293
<212> TYPE: DNA
<213> ORGANISM: Homo sapiens

<400> SEQUENCE: 87

```
gaggtgcagc tggtggagtc tggaggaggc ttgatccagc ctgggggtc cctgagactc      60
tcctgtgcag cctctgggtt caccgtcagt agcaactaca tgagctgggt ccgccaggct    120
ccagggaagg ggctggagtg ggtctcagtt atttatagct gtggtagcac atactacgca    180
gactccgtga agggccgatt caccatctcc agagacaatt ccaagaacac gctgtatctt    240
caaatgaaca gcctgagagc tgaggacacg gctgtgtatt actgtgcgag aga           293
```

<210> SEQ ID NO 88
<211> LENGTH: 296
<212> TYPE: DNA
<213> ORGANISM: Homo sapiens

<400> SEQUENCE: 88

```
gaggtgcagc tggtggagtc tgggggaggc ttggtccagc ctgggggtc cctgagactc      60
tcctgtgcag cctctggatt caccttagt agctattgga tgagctgggt ccgccaggct    120
ccagggaagg ggctggagtg ggtggccaac ataaagcaag atggaagtga aaatactat    180
gtggactctg tgaagggccg attcaccatc tccagagaca cgccaagaa ctcactgtat   240
ctgcaaatga cagcctgag agccgaggac acggctgtgt attactgtgc gagaga        296
```

<210> SEQ ID NO 89
<211> LENGTH: 302
<212> TYPE: DNA
<213> ORGANISM: Homo sapiens

<400> SEQUENCE: 89

```
gaggtgcagc tggtggagtc tgggggaggc ttggtccagc ctggagggtc cctgagactc      60
```

```
tcctgtgcag cctctggatt caccttcagt gaccactaca tggactgggt ccgccaggct    120
ccagggaagg ggctggagtg ggttggccgt actagaaaca aagctaacag ttacaccaca    180
gaatacgccg cgtctgtgaa aggcagattc accatctcaa gagatgattc aaagaactca    240
ctgtatctgc aaatgaacag cctgaaaacc gaggacacgg ccgtgtatta ctgtgctaga    300
ga                                                                   302

<210> SEQ ID NO 90
<211> LENGTH: 302
<212> TYPE: DNA
<213> ORGANISM: Homo sapiens

<400> SEQUENCE: 90
gaggtgcagc tggtggagtc cggggggaggc ttggtccagc ctgggggtc cctgaaactc     60 tcctgtgcag cctctgggtt caccttcagt ggctctgcta tgcactgggt ccgccaggct    120
tccgggaaag ggctggagtg ggttggccgt attagaagca aagctaacag ttacgcgaca    180
gcatatgctg cgtcggtgaa aggcaggttc accatctcca gagatgattc aaagaacacg    240
gcgtatctgc aaatgaacag cctgaaaacc gaggacacgg ccgtgtatta ctgtactaga    300
ca                                                                   302

<210> SEQ ID NO 91
<211> LENGTH: 296
<212> TYPE: DNA
<213> ORGANISM: Homo sapiens

<400> SEQUENCE: 91
gaggtgcagc tggtggagtc cggggggaggc ttagttcagc ctgggggtc cctgagactc     60 tcctgtgcag cctctggatt caccttcagt agctactgga tgcactgggt ccgccaagct    120
ccagggaagg ggctggtgtg ggtctcacgt attaatagtg atgggagtag cacaagctac    180
gcggactccg tgaagggccg attcaccatc tccagagaca cgccaagaa cacgctgtat    240 ctgcaaatga acagtctgag agccgaggac acggctgtgt attactgtgc aagaga       296

<210> SEQ ID NO 92
<211> LENGTH: 298
<212> TYPE: DNA
<213> ORGANISM: Homo sapiens

<400> SEQUENCE: 92
gaagtgcagc tggtggagtc tgggggaggc ttggtacagc ctggcaggtc cctgagactc     60
tcctgtgcag cctctggatt caccttttgat gattatgcca tgcactgggt ccggcaagct    120
ccagggaagg gcctggagtg ggtctcaggt attagttgga atagtggtag cataggctat    180
gcggactctg tgaagggccg attcaccatc tccagagaca acgccaagaa ctccctgtat    240
ctgcaaatga acagtctgag agctgaggac acggccttgt attactgtgc aaaagata     298

<210> SEQ ID NO 93
<211> LENGTH: 296
<212> TYPE: DNA
<213> ORGANISM: Homo sapiens

<400> SEQUENCE: 93
caggtgcagc tgcaggagtc gggcccagga ctggtgaagc cttcggacac cctgtccctc     60
acctgcgctg tctctggtta ctccatcagc agtagtaact ggtggggctg gatccggcag    120
cccccaggga agggactgga gtggattggg tacatctatt atagtgggag cacctactac    180
```

```
aacccgtccc tcaagagtcg agtcaccatg tcagtagaca cgtccaagaa ccagttctcc    240
ctgaagctga gctctgtgac cgccgtggac acggccgtgt attactgtgc gagaaa        296

<210> SEQ ID NO 94
<211> LENGTH: 299
<212> TYPE: DNA
<213> ORGANISM: Homo sapiens

<400> SEQUENCE: 94
caggtgcagc tgcaggagtc gggcccagga ctggtgaagc cttcacagac cctgtccctc     60
acctgtactg tctctggtgg ctccatcagc agtggtggtt actactggag ctggatccgc    120
cagcacccag ggaagggcct ggagtggatt gggtacatct attacagtgg gagcacctac    180
tacaacccgt ccctcaagag tcgagttacc atatcagtag acacgtctaa gaaccagttc    240
tccctgaagc tgagctctgt gactgccgcg gacacggccg tgtattactg tgcgagaga    299

<210> SEQ ID NO 95
<211> LENGTH: 293
<212> TYPE: DNA
<213> ORGANISM: Homo sapiens

<400> SEQUENCE: 95
caggtgcagc tacagcagtg gggcgcagga ctgttgaagc cttcggagac cctgtccctc     60
acctgcgctg tctatggtgg gtccttcagt ggttactact ggagctggat ccgccagccc    120
ccagggaagg ggctggagtg gattggggaa atcaatcata gtggaagcac caactacaac    180
ccgtccctca agagtcgagt caccatatca gtagacacgt ccaagaacca gttctccctg    240
aagctgagct ctgtgaccgc cgcggacacg gctgtgtatt actgtgcgag agg           293

<210> SEQ ID NO 96
<211> LENGTH: 299
<212> TYPE: DNA
<213> ORGANISM: Homo sapiens

<400> SEQUENCE: 96
cagctgcagc tgcaggagtc gggcccagga ctggtgaagc cttcggagac cctgtccctc     60
acctgcactg tctctggtgg ctccatcagc agtagtagtt actactgggg ctggatccgc    120
cagcccccag ggaaggggct ggagtggatt gggagtatct attatagtgg gagcacctac    180
tacaacccgt ccctcaagag tcgagtcacc atatccgtag acacgtccaa gaaccagttc    240
tccctgaagc tgagctctgt gaccgccgca gacacggctg tgtattactg tgcgagaca    299

<210> SEQ ID NO 97
<211> LENGTH: 293
<212> TYPE: DNA
<213> ORGANISM: Homo sapiens

<400> SEQUENCE: 97
caggtgcagc tgcaggagtc gggcccagga ctggtgaagc cttcggagac cctgtccctc     60
acctgcactg tctctggtgg ctccatcagt agttactact ggagctggat ccggcagccc    120
gccgggaagg gactggagtg gattgggcgt atctatacca gtgggagcac caactacaac    180
ccctccctca agagtcgagt caccatgtca gtagacacgt ccaagaacca gttctccctg    240
aagctgagct ctgtgaccgc cgcggacacg gccgtgtatt actgtgcgag aga           293

<210> SEQ ID NO 98
<211> LENGTH: 293
<212> TYPE: DNA
```

<213> ORGANISM: Homo sapiens

<400> SEQUENCE: 98

| caggtgcagc tgcaggagtc gggcccagga ctggtgaagc cttcggagac cctgtccctc | 60 |
| acctgcactg tctctggtgg ctccatcagt agttactact ggagctggat ccggcagccc | 120 |
| ccagggaagg gactggagtg gattgggtat atctattaca gtgggagcac caactacaac | 180 |
| ccctccctca gagtcgagt caccatatca gtagacacgt ccaagaacca gttctccctg | 240 |
| aagctgagct ctgtgaccgc tgcggacacg gccgtgtatt actgtgcgag aga | 293 |

<210> SEQ ID NO 99
<211> LENGTH: 299
<212> TYPE: DNA
<213> ORGANISM: Homo sapiens

<400> SEQUENCE: 99

| caggtgcagc tgcaggagtc gggcccagga ctggtgaagc cttcggagac cctgtccctc | 60 |
| acctgcactg tctctggtgg ctccgtcagc agtggtggtt actactggag ctggatccgg | 120 |
| cagcccccag ggaagggact ggagtggatt gggtatatct attacagtgg gagcaccaac | 180 |
| tacaacccct ccctcaagag tcgagtcacc atatcagtag acacgtccaa gaaccagttc | 240 |
| tccctgaagc tgagctctgt gaccgctgcg gacacggccg tgtattactg tgcgagaga | 299 |

<210> SEQ ID NO 100
<211> LENGTH: 296
<212> TYPE: DNA
<213> ORGANISM: Homo sapiens

<400> SEQUENCE: 100

| gaggtgcagc tggtgcagtc tggagcagag gtgaaaaagc ccggggagtc tctgaagatc | 60 |
| tcctgtaagg gttctggata cagctttacc agctactgga tcggctgggt gcgccagatg | 120 |
| cccgggaaag gcctggagtg gatggggatc atctatcctg gtgactctga taccagatac | 180 |
| agcccgtcct tccaaggcca ggtcaccatc tcagccgaca gtccatcag caccgcctac | 240 |
| ctgcagtgga gcagcctgaa ggcctcggac accgccatgt attactgtgc gagaca | 296 |

<210> SEQ ID NO 101
<211> LENGTH: 305
<212> TYPE: DNA
<213> ORGANISM: Homo sapiens

<400> SEQUENCE: 101

| caggtacagc tgcagcagtc aggtccagga ctggtgaagc cctcgcagac cctctcactc | 60 |
| acctgtgcca tctccgggga cagtgtctct agcaacagtg ctgcttggaa ctggatcagg | 120 |
| cagtccccat cgagaggcct tgagtggctg ggaaggacat actacaggtc caagtggtat | 180 |
| aatgattatg cagtatctgt gaaaagtcga ataaccatca cccagacac atccaagaac | 240 |
| cagttctccc tgcagctgaa ctctgtgact cccgaggaca cggctgtgta ttactgtgca | 300 |
| agaga | 305 |

<210> SEQ ID NO 102
<211> LENGTH: 296
<212> TYPE: DNA
<213> ORGANISM: Homo sapiens

<400> SEQUENCE: 102

| caggtgcagc tggtgcagtc tggccatgag gtgaagcagc ctggggcctc agtgaaggtc | 60 |

```
tcctgcaagg cttctggtta cagtttcacc acctatggta tgaattgggt gccacaggcc    120
cctggacaag ggcttgagtg gatgggatgg ttcaacacct acactgggaa cccaacatat    180
gcccagggct tcacaggacg gtttgtcttc tccatggaca cctctgccag cacagcatac    240
ctgcagatca gcagcctaaa ggctgaggac atggccatgt attactgtgc agagata      296
```

<210> SEQ ID NO 103
<211> LENGTH: 100
<212> TYPE: PRT
<213> ORGANISM: Homo sapiens

<400> SEQUENCE: 103

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 104
<211> LENGTH: 95
<212> TYPE: PRT
<213> ORGANISM: Homo sapiens

<400> SEQUENCE: 104

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

<210> SEQ ID NO 105
<211> LENGTH: 96
<212> TYPE: PRT
<213> ORGANISM: Homo sapiens

<400> SEQUENCE: 105

Glu Ile Val Leu Thr Gln Ser Pro Ala Thr Leu Ser Leu Ser Pro Gly
1               5                   10                  15

Glu Arg Ala Thr Leu Ser Cys Gly Ala Ser Gln Ser Val Ser Ser Ser
            20                  25                  30

Tyr Leu Ala Trp Tyr Gln Gln Lys Pro Gly Leu Ala Pro Arg Leu Leu
        35                  40                  45

```
Ile Tyr Asp Ala Ser Ser Arg Ala Thr Gly Ile Pro Asp Arg Phe Ser
 50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                 85                  90                  95

<210> SEQ ID NO 106
<211> LENGTH: 95
<212> TYPE: PRT
<213> ORGANISM: Homo sapiens

<400> SEQUENCE: 106

Asp Val Val Met Thr Gln Ser Pro Ala Phe Leu Ser Val Thr Pro Gly
 1               5                   10                  15
Glu Lys Val Thr Ile Thr Cys Gln Ala Ser Glu Gly Ile Gly Asn Tyr
                 20                  25                  30
Leu Tyr Trp Tyr Gln Gln Lys Pro Asp Gln Ala Pro Lys Leu Leu Ile
             35                  40                  45
Lys Tyr Ala Ser Gln Ser Ile Ser Gly Val Pro Ser Arg Phe Ser Gly
 50                  55                  60
Ser Gly Ser Gly Thr Asp Phe Thr Phe Thr Ile Ser Ser Leu Glu Ala
 65                  70                  75                  80
Glu Asp Ala Ala Thr Tyr Tyr Cys Gln Gln Gly Asn Lys His Pro
                 85                  90                  95

<210> SEQ ID NO 107
<211> LENGTH: 100
<212> TYPE: PRT
<213> ORGANISM: Homo sapiens

<400> SEQUENCE: 107

Asp Val Val Met Thr Gln Ser Pro Leu Ser Leu Pro Val Thr Leu Gly
 1               5                   10                  15
Gln Pro Ala Ser Ile Ser Cys Arg Ser Ser Gln Ser Leu Val Tyr Ser
                 20                  25                  30
Asp Gly Asn Thr Tyr Leu Asn Trp Phe Gln Gln Arg Pro Gly Gln Ser
             35                  40                  45
Pro Arg Arg Leu Ile Tyr Lys Val Ser Asn Arg Asp Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Met Gln Gly
                 85                  90                  95
Thr His Trp Pro
         100

<210> SEQ ID NO 108
<211> LENGTH: 100
<212> TYPE: PRT
<213> ORGANISM: Homo sapiens

<400> SEQUENCE: 108

Asp Ile Val Met Thr Gln Thr Pro Leu Ser Leu Ser Val Thr Pro Gly
 1               5                   10                  15
Gln Pro Ala Ser Ile Ser Cys Lys Ser Ser Gln Ser Leu Leu His Ser
                 20                  25                  30
Asp Gly Lys Thr Tyr Leu Tyr Trp Tyr Leu Gln Lys Pro Gly Gln Ser
             35                  40                  45
```

```
Pro Gln Leu Leu Ile Tyr Glu Val Ser Ser Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                85                  90                  95

Ile His Leu Pro
            100

<210> SEQ ID NO 109
<211> LENGTH: 100
<212> TYPE: PRT
<213> ORGANISM: Homo sapiens

<400> SEQUENCE: 109

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 110
<211> LENGTH: 100
<212> TYPE: PRT
<213> ORGANISM: Homo sapiens

<400> SEQUENCE: 110

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu His Ser
                20                  25                  30

Asp Gly Lys Thr Tyr Leu Tyr Trp Tyr Leu Gln Lys Pro Gly Gln Pro
            35                  40                  45

Pro Gln Leu Leu Ile Tyr Glu Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ser
                85                  90                  95

Ile Gln Leu Pro
            100

<210> SEQ ID NO 111
<211> LENGTH: 95
<212> TYPE: PRT
<213> ORGANISM: Homo sapiens

<400> SEQUENCE: 111

Asp Ile Gln Met Thr Gln Ser Pro Ser Ser Leu Ser Ala Ser Val Gly
```

```
                1               5                  10                  15
Asp Arg Val Thr Ile Thr Cys Arg Ala Ser Gln Gly Ile Ser Asn Tyr
                    20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
                85                  90                  95

<210> SEQ ID NO 112
<211> LENGTH: 100
<212> TYPE: PRT
<213> ORGANISM: Homo sapiens

<400> SEQUENCE: 112

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
                20                  25                  30

Asp Gly Asn Thr Tyr Leu Ser Trp Leu Gln Gln Arg Pro Gly Gln Pro
            35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro
            100

<210> SEQ ID NO 113
<211> LENGTH: 95
<212> TYPE: PRT
<213> ORGANISM: Homo sapiens

<400> SEQUENCE: 113

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
                20                  25                  30

Leu His Trp Tyr Gln Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

<210> SEQ ID NO 114
<211> LENGTH: 96
<212> TYPE: PRT
<213> ORGANISM: Homo sapiens

<400> SEQUENCE: 114
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 115
<211> LENGTH: 100
<212> TYPE: PRT
<213> ORGANISM: Homo sapiens

<400> SEQUENCE: 115

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 116
<211> LENGTH: 95
<212> TYPE: PRT
<213> ORGANISM: Homo sapiens

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 117
<211> LENGTH: 101
<212> TYPE: PRT
<213> ORGANISM: Homo sapiens

<400> SEQUENCE: 117

Glu Ile Val Met Thr Gln Thr Pro Leu Ser Leu Ser Ile Thr Pro Gly
1               5                   10                  15

Glu Gln Ala Ser Ile Ser Cys Arg Ser Ser Gln Ser Leu Leu His Ser
            20                  25                  30

Asp Gly Tyr Thr Tyr Leu Tyr Trp Phe Leu Gln Lys Ala Arg Pro Val
        35                  40                  45

Ser Thr Leu Leu Ile Tyr Glu Val Ser Asn Arg Phe Ser Gly Val Pro
50                      55                  60

Asp Arg Phe Ser Gly Ser Gly Ser Gly Thr Asp Phe Thr Leu Lys Ile
65                  70                  75                  80

Ser Arg Val Glu Ala Glu Asp Phe Gly Val Tyr Tyr Cys Met Gln Asp
                85                  90                  95

Ala Gln Asp Pro Pro
            100

<210> SEQ ID NO 118
<211> LENGTH: 100
<212> TYPE: PRT
<213> ORGANISM: Homo sapiens

<400> SEQUENCE: 118

Asp Ile Val Met Thr Gln Thr Pro Leu Ser Ser Pro Val Thr Leu Gly
1               5                   10                  15

Gln Pro Ala Ser Ile Ser Phe Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Val Ser Asn Arg Phe Ser Gly Val Pro
50                      55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Thr Gln Ala
                85                  90                  95

Thr Gln Phe Pro
            100

<210> SEQ ID NO 119
<211> LENGTH: 95
<212> TYPE: PRT
<213> ORGANISM: Homo sapiens

<400> SEQUENCE: 119

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Pro Pro Arg Phe Ser Gly
50                      55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro
                85                  90                  95

<210> SEQ ID NO 120
<211> LENGTH: 101

```
<212> TYPE: PRT
<213> ORGANISM: Homo sapiens

<400> SEQUENCE: 120

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Ser Thr Pro
            100

<210> SEQ ID NO 121
<211> LENGTH: 95
<212> TYPE: PRT
<213> ORGANISM: Homo sapiens

<400> SEQUENCE: 121

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                85                  90                  95

<210> SEQ ID NO 122
<211> LENGTH: 97
<212> TYPE: PRT
<213> ORGANISM: Homo sapiens

<400> SEQUENCE: 122

Glu Ile Val Met Thr Gln Ser Pro Pro Thr Leu Ser Leu Ser Pro Gly
 1               5                  10                  15

Glu Arg Val Thr Leu Ser Cys Arg Ala Ser Gln Ser Val Ser Ser Ser
            20                  25                  30

Tyr Leu Thr Trp Tyr Gln Gln Lys Pro Gly Gln Ala Pro Arg Leu Leu
        35                  40                  45

Ile Tyr Gly Ala Ser Thr Arg Ala Thr Ser Ile Pro Ala Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Val Tyr Tyr Cys Gln Gln Asp His Asn Leu Pro
                85                  90                  95

Pro
```

-continued

<210> SEQ ID NO 123
<211> LENGTH: 95
<212> TYPE: PRT
<213> ORGANISM: Homo sapiens

<400> SEQUENCE: 123

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro
                85                  90                  95

<210> SEQ ID NO 124
<211> LENGTH: 95
<212> TYPE: PRT
<213> ORGANISM: Homo sapiens

<400> SEQUENCE: 124

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 125
<211> LENGTH: 95
<212> TYPE: PRT
<213> ORGANISM: Homo sapiens

<400> SEQUENCE: 125

Asn Ile Gln Met Thr Gln Ser Pro Ser Ala Met Ser Ala Ser Val Gly
 1               5                  10                  15

Asp Arg Val Thr Ile Thr Cys Arg Ala Arg Gln Gly Ile Ser Asn Tyr
            20                  25                  30

Leu Ala Trp Phe Gln Gln Lys Pro Gly Lys Val Pro Lys His Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 126

```
<211> LENGTH: 95
<212> TYPE: PRT
<213> ORGANISM: Homo sapiens

<400> SEQUENCE: 126

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 127
<211> LENGTH: 95
<212> TYPE: PRT
<213> ORGANISM: Homo sapiens

<400> SEQUENCE: 127

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95

<210> SEQ ID NO 128
<211> LENGTH: 95
<212> TYPE: PRT
<213> ORGANISM: Homo sapiens

<400> SEQUENCE: 128

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro
                85                  90                  95

<210> SEQ ID NO 129
<211> LENGTH: 95
<212> TYPE: PRT
```

<213> ORGANISM: Homo sapiens

<400> SEQUENCE: 129

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro
                85                  90                  95

<210> SEQ ID NO 130
<211> LENGTH: 95
<212> TYPE: PRT
<213> ORGANISM: Homo sapiens

<400> SEQUENCE: 130

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95

<210> SEQ ID NO 131
<211> LENGTH: 95
<212> TYPE: PRT
<213> ORGANISM: Homo sapiens

<400> SEQUENCE: 131

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His
                85                  90                  95

<210> SEQ ID NO 132
<211> LENGTH: 96
<212> TYPE: PRT
<213> ORGANISM: Homo sapiens

<400> SEQUENCE: 132

Asp Ile Gln Met Ile Gln Ser Pro Ser Phe Leu Ser Ala Ser Val Gly
1               5                   10                  15

Asp Arg Val Ser Ile Ile Cys Trp Ala Ser Glu Gly Ile Ser Ser Asn
            20                  25                  30

Leu Ala Trp Tyr Leu Gln Lys Pro Gly Lys Ser Pro Lys Leu Phe Leu
        35                  40                  45

Tyr Asp Ala Lys Asp Leu His Pro Gly Val Ser Arg Phe Ser Gly
50                  55                  60

Arg Gly Ser Gly Thr Asp Phe Thr Leu Thr Ile Ile Ser Leu Lys Pro
65                  70                  75                  80

Glu Asp Phe Ala Ala Tyr Tyr Cys Lys Gln Asp Phe Ser Tyr Pro Pro
                85                  90                  95

<210> SEQ ID NO 133
<211> LENGTH: 95
<212> TYPE: PRT
<213> ORGANISM: Homo sapiens

<400> SEQUENCE: 133

Ala Ile Arg Met Thr Gln Ser Pro Phe Ser Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Ala Lys Ala Pro Lys Leu Phe Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro
                85                  90                  95

<210> SEQ ID NO 134
<211> LENGTH: 95
<212> TYPE: PRT
<213> ORGANISM: Homo sapiens

<400> SEQUENCE: 134

Val Ile Trp Met Thr Gln Ser Pro Ser Leu Leu Ser Ala Ser Thr Gly
1               5                   10                  15

Asp Arg Val Thr Ile Ser Cys Arg Met Ser Gln Gly Ile Ser Ser Tyr
            20                  25                  30

Leu Ala Trp Tyr Gln Gln Lys Pro Gly Lys Ala Pro Glu Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Phe Pro
                85                  90                  95

<210> SEQ ID NO 135
<211> LENGTH: 96
<212> TYPE: PRT
<213> ORGANISM: Homo sapiens

<400> SEQUENCE: 135

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

<210> SEQ ID NO 136
<211> LENGTH: 95
<212> TYPE: PRT
<213> ORGANISM: Homo sapiens

<400> SEQUENCE: 136

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro
                85                  90                  95

<210> SEQ ID NO 137
<211> LENGTH: 95
<212> TYPE: PRT
<213> ORGANISM: Homo sapiens

<400> SEQUENCE: 137

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro
                85                  90                  95

<210> SEQ ID NO 138
<211> LENGTH: 95
<212> TYPE: PRT
<213> ORGANISM: Homo sapiens

<400> SEQUENCE: 138

Glu Ile Val Leu Thr Gln Ser Pro Ala Thr Leu Ser Leu Ser Pro Gly
1               5                   10                  15

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95
```

<210> SEQ ID NO 139
<211> LENGTH: 95
<212> TYPE: PRT
<213> ORGANISM: Homo sapiens

<400> SEQUENCE: 139

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro
                85                  90                  95
```

<210> SEQ ID NO 140
<211> LENGTH: 95
<212> TYPE: PRT
<213> ORGANISM: Homo sapiens

<400> SEQUENCE: 140

```
Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Tyr Pro
                85                  90                  95
```

<210> SEQ ID NO 141
<211> LENGTH: 101
<212> TYPE: PRT
<213> ORGANISM: Homo sapiens

<400> SEQUENCE: 141

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
```

```
                20                  25                  30

Asp Asp Gly Asn Thr Tyr Leu Asp Trp Tyr Leu Gln Lys Pro Gly Gln
            35                  40                  45

Ser Pro Gln Leu Leu Ile Tyr Thr Leu Ser Tyr Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                85                  90                  95

Arg Ile Glu Phe Pro
            100

<210> SEQ ID NO 142
<211> LENGTH: 101
<212> TYPE: PRT
<213> ORGANISM: Homo sapiens

<400> SEQUENCE: 142

Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Leu Asp Ser
                20                  25                  30

Asp Asp Gly Asn Thr Tyr Leu Asp Trp Tyr Leu Gln Lys Pro Gly Gln
            35                  40                  45

Ser Pro Gln Leu Leu Ile Tyr Thr Leu Ser Tyr Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                85                  90                  95

Arg Ile Glu Phe Pro
            100

<210> SEQ ID NO 143
<211> LENGTH: 95
<212> TYPE: PRT
<213> ORGANISM: Homo sapiens

<400> SEQUENCE: 143

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro
                85                  90                  95

<210> SEQ ID NO 144
<211> LENGTH: 96
<212> TYPE: PRT
<213> ORGANISM: Homo sapiens

<400> SEQUENCE: 144
```

```
Asp Ile Gln Leu Thr Gln Ser Pro Ser Ser Leu Ser Ala Ser Val Gly
1               5                   10                  15

Asp Arg Val Thr Ile Thr Cys Arg Val Ser Gln Gly Ile Ser Ser Tyr
                20                  25                  30

Leu Asn Trp Tyr Arg Gln Lys Pro Gly Lys Val Pro Lys Leu Leu Ile
            35                  40                  45

Tyr Ser Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Gly Gln Arg Thr Tyr Asn Ala Pro Pro
                85                  90                  95
```

<210> SEQ ID NO 145
<211> LENGTH: 95
<212> TYPE: PRT
<213> ORGANISM: Homo sapiens

<400> SEQUENCE: 145

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95
```

<210> SEQ ID NO 146
<211> LENGTH: 95
<212> TYPE: PRT
<213> ORGANISM: Homo sapiens

<400> SEQUENCE: 146

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95
```

<210> SEQ ID NO 147
<211> LENGTH: 96
<212> TYPE: PRT
<213> ORGANISM: Homo sapiens

<400> SEQUENCE: 147

```
Asp Ile Gln Leu Thr Gln Ser Pro Ser Ser Leu Ser Ala Ser Val Gly
1               5                   10                  15
```

Asp Arg Val Thr Ile Thr Cys Arg Val Ser Gln Gly Ile Ser Ser Tyr
            20                  25                  30

Leu Asn Trp Tyr Arg Gln Lys Pro Gly Lys Val Pro Lys Leu Leu Ile
        35                  40                  45

Tyr Ser Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Gly Gln Arg Thr Tyr Asn Ala Pro Pro
                85                  90                  95

<210> SEQ ID NO 148
<211> LENGTH: 95
<212> TYPE: PRT
<213> ORGANISM: Homo sapiens

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95

<210> SEQ ID NO 149
<211> LENGTH: 302
<212> TYPE: DNA
<213> ORGANISM: Homo sapiens

<400> SEQUENCE: 149
gatgttgtga tgactcagtc tccactctcc ctgcccgtca cccttggaca gccggcctcc      60
atctcctgca ggtctagtca aagcctcgta tacagtgatg aaacaccta cttgaattgg     120 tttcagcaga ggccaggcca atctccaagg cgcctaattt ataaggtttc taactgggac    180
tctggggtcc cagacagatt cagcggcagt gggtcaggca ctgatttcac actgaaaatc    240
agcagggtgg aggctgagga tgttggggtt tattactgca tgcaaggtac acactggcct    300
cc                                                                   302

<210> SEQ ID NO 150
<211> LENGTH: 287
<212> TYPE: DNA
<213> ORGANISM: Homo sapiens

<400> SEQUENCE: 150
gaaattgtgc tgactcagtc tccagacttt cagtctgtga ctccaaagga aaagtcacc      60 atcacctgcc gggccagtca gagcattggt agtagcttac actggtacca gcagaaacca    120
gatcagtctc caaagctcct catcaagtat gcttccagt ccttctcagg ggtcccctcg    180
aggttcagtg gcagtggatc tgggacagat ttcaccctca ccatcaatag cctggaagct    240
gaagatgctg caacgtatta ctgtcatcag agtagtagtt tacctca                  287

<210> SEQ ID NO 151
<211> LENGTH: 290
<212> TYPE: DNA
<213> ORGANISM: Homo sapiens

<400> SEQUENCE: 151
gaaattgtgt tgacgcagtc tccagccacc ctgtctttgt ctccagggga aagagccacc       60
ctctcctgcg gggccagtca gagtgttagc agcagctact tagcctggta ccagcagaaa      120
cctggcctgg cgcccaggct cctcatctat gatgcatcca gcagggccac tggcatccca      180
gacaggttca gtggcagtgg gtctgggaca gacttcactc tcaccatcag cagactggag      240
cctgaagatt ttgcagtgta ttactgtcag cagtatggta gctcacctcc                 290

<210> SEQ ID NO 152
<211> LENGTH: 287
<212> TYPE: DNA
<213> ORGANISM: Homo sapiens

<400> SEQUENCE: 152
gatgttgtga tgacacagtc tccagctttc ctctctgtga ctccagggga gaaagtcacc       60
atcacctgcc aggccagtga aggcattggc aactacttat actggtacca gcagaaacca      120
gatcaagccc caaagctcct catcaagtat gcttcccagt ccatctcagg ggtcccctcg      180
aggttcagtg gcagtggatc tgggacagat ttcaccttta ccatcagtag cctggaagct      240
gaagatgctg caacatatta ctgtcagcag ggcaataagc accctca                    287

<210> SEQ ID NO 153
<211> LENGTH: 302
<212> TYPE: DNA
<213> ORGANISM: Homo sapiens

<400> SEQUENCE: 153
gatgttgtga tgactcagtc tccactctcc ctgcccgtca cccttggaca gccggcctcc       60
atctcctgca ggtctagtca aagcctcgta tacagtgatg gaaacaccta cttgaattgg      120
tttcagcaga ggccaggcca atctccaagg cgcctaattt ataaggtttc taaccgggac      180
tctggggtcc cagacagatt cagcggcagt gggtcaggca ctgatttcac actgaaaatc      240
agcagggtgg aggctgagga tgttggggtt tattactgca tgcaaggtac acactggcct      300
cc                                                                     302

<210> SEQ ID NO 154
<211> LENGTH: 302
<212> TYPE: DNA
<213> ORGANISM: Homo sapiens

<400> SEQUENCE: 154
gatattgtga tgacccagac tccactctct ctgtccgtca cccctggaca gccggcctcc       60
atctcctgca agtctagtca gagcctcctg catagtgatg gaaagaccta tttgtattgg      120
tacctgcaga agccaggcca gtctccacag ctcctgatct atgaagtttc agccggttc        180 tctggagtgc cagataggtt cagtggcagc gggtcaggga cagatttcac actgaaaatc      240
agccgggtgg aggctgagga tgttggggtt tattactgaa tgcaaggtat acaccttcct      300
cc                                                                     302

<210> SEQ ID NO 155
<211> LENGTH: 302
<212> TYPE: DNA

```
<213> ORGANISM: Homo sapiens

<400> SEQUENCE: 155
gatattgtga tgactcagtc tccactctcc ctgcccgtca cccctggaga gccggcctcc      60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactcct    300
cc                                                                    302

<210> SEQ ID NO 156
<211> LENGTH: 302
<212> TYPE: DNA
<213> ORGANISM: Homo sapiens

<400> SEQUENCE: 156
gatattgtga tgacccagac tccactctct ctgtccgtca cccctggaca gccggcctcc      60
atctcctgca agtctagtca gagcctcctg catagtgatg gaaagaccta tttgtattgg    120
tacctgcaga agccaggcca gcctccacag ctcctgatct atgaagtttc caaccggttc    180
tctggagtgc cagataggtt cagtggcagc gggtcaggga cagatttcac actgaaaatc    240
agccgggtgg aggctgagga tgttggggtt tattactgca tgcaaagtat acagcttcct    300
cc                                                                    302

<210> SEQ ID NO 157
<211> LENGTH: 287
<212> TYPE: DNA
<213> ORGANISM: Homo sapiens

<400> SEQUENCE: 157
gacatccaga tgacccagtc tccatcctcc ctgtctgcat ctgtaggaga cagagtcacc      60
atcacttgcc gggcgagtca gggcattagc aattatttag cctggtatca gcagaaacca    120
gggaaagttc ctaagctcct gatctatgct gcatccactt tgcaatcagg ggtcccatct    180
cggttcagtg gcagtggatc tgggacagat ttcactctca ccatcagcag cctgcagcct    240
gaagatgttg caacttatta ctgtcaaaag tataacagtg cccctcc                   287

<210> SEQ ID NO 158
<211> LENGTH: 302
<212> TYPE: DNA
<213> ORGANISM: Homo sapiens

<400> SEQUENCE: 158
gatattgtga tgacccagac tccactctcc tcacctgtca cccttggaca gccggcctcc      60
atctcctgca ggtctagtca aagcctcgta cacagtgatg gaaacaccta cttgagttgg    120
cttcagcaga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgagga tgtcggggtt tattactgca tgcaagctac acaatttcct    300
ca                                                                    302

<210> SEQ ID NO 159
<211> LENGTH: 287
<212> TYPE: DNA
<213> ORGANISM: Homo sapiens
```

```
<400> SEQUENCE: 159
gaaattgtgc tgactcagtc tccagacttt cagtctgtga ctccaaagga gaaagtcacc    60
atcacctgcc gggccagtca gagcattggt agtagcttac actggtacca gcagaaacca   120
gatcagtctc caaagctcct catcaagtat gcttcccagt ccttctcagg ggtcccctcg   180
aggttcagtg gcagtggatc tgggacagat ttcaccctca ccatcaatag cctggaagct   240
gaagatgctg caacgtatta ctgtcatcag agtagtagtt tacctca                 287

<210> SEQ ID NO 160
<211> LENGTH: 290
<212> TYPE: DNA
<213> ORGANISM: Homo sapiens

<400> SEQUENCE: 160
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacctcc                290

<210> SEQ ID NO 161
<211> LENGTH: 302
<212> TYPE: DNA
<213> ORGANISM: Homo sapiens

<400> SEQUENCE: 161
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactcct   300
cc                                                                   302

<210> SEQ ID NO 162
<211> LENGTH: 287
<212> TYPE: DNA
<213> ORGANISM: Homo sapiens

<400> SEQUENCE: 162
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt accctcc                 287

<210> SEQ ID NO 163
<211> LENGTH: 302
<212> TYPE: DNA
<213> ORGANISM: Homo sapiens

<400> SEQUENCE: 163
gagattgtga tgacccagac tccactctcc ttgtctatca cccctggaga gcaggcctcc    60
atctcctgca ggtctagtca gagcctcctg catagtgatg gatacaccta tttgtattgg   120
```

```
tttctgcaga aagccaggcc agtctccaca ctcctgatct atgaagtttc caaccggttc     180
tctggagtgc cagataggtt cagtggcagc gggtcaggga cagatttcac actgaaaatc     240
agccgggtgg aggctgagga ttttggagtt tattactgca tgcaagatgc acaagatcct     300
cc                                                                     302

<210> SEQ ID NO 164
<211> LENGTH: 302
<212> TYPE: DNA
<213> ORGANISM: Homo sapiens

<400> SEQUENCE: 164
gatattgtga tgacccagac tccactctcc tcgcctgtca cccttggaca gccggcctcc     60
atctccttca ggtctagtca aagcctcgta cacagtgatg aaacaccta cttgagttgg     120 cttcagcaga ggccaggcca gcctccaaga ctcctaattt ataaggtttc taaccggttc     180
tctggggtcc cagacagatt cagtggcagt ggggcaggga cagatttcac actgaaaatc     240
agcagggtgg aagctgagga tgtcggggtt tattactgca cgcaagctac acaatttcct     300
ca                                                                     302

<210> SEQ ID NO 165
<211> LENGTH: 287
<212> TYPE: DNA
<213> ORGANISM: Homo sapiens

<400> SEQUENCE: 165
gaaacgacac tcacgcagtc tccagcattc atgtcagcga ctccaggaga caaagtcaac     60
atctcctgca aagccagcca agacattgat gatgatatga actggtacca acagaaacca     120
ggagaagctg ctatttttcat tattcaagaa gctactactc tcgttcctgg aatcccacct     180
cgattcagtg gcagcgggta tggaacagat tttacccctca caattaataa catagaatct     240
gaggatgctg catattactt ctgtctacaa catgataatt tccctct                    287

<210> SEQ ID NO 166
<211> LENGTH: 305
<212> TYPE: DNA
<213> ORGANISM: Homo sapiens

<400> SEQUENCE: 166
gacatcgtga tgacccagtc tccagactcc ctggctgtgt ctctgggcga gagggccacc     60
atcaactgca gtccagcca gagtgtttta tacagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtact     300
cctcc                                                                   305

<210> SEQ ID NO 167
<211> LENGTH: 287
<212> TYPE: DNA
<213> ORGANISM: Homo sapiens

<400> SEQUENCE: 167
gacatccaga tgacccagtc tccatcctca ctgtctgcat ctgtaggaga cagagtcacc     60
atcacttgtc gggcgagtca ggcattagc aattatttag cctggtttca gcagaaacca     120
gggaaagccc ctaagtccct gatctatgct gcatccagtt tgcaaagtgg ggtcccatca     180
```
aggttcagcg gcagtggatc tgggacagat ttcactctca ccatcagcag cctgcagcct        240
gaagattttg caacttatta ctgccaacag tataatagtt accctcc                     287

<210> SEQ ID NO 168
<211> LENGTH: 290
<212> TYPE: DNA
<213> ORGANISM: Homo sapiens

<400> SEQUENCE: 168
gaaattgtaa tgacacagtc tccacccacc ctgtctttgt ctccagggga aagagtcacc        60
ctctcctgca gggccagtca gagtgttagc agcagctact taacctggta tcagcagaaa       120
cctggccagg cgcccaggct cctcatctat ggtgcatcca ccagggccac tagcatccca       180
gccaggttca gtggcagtgg gtctgggaca gacttcactc tcaccatcag cagcctgcag       240
cctgaagatt ttgcagtttta ttactgtcag caggatcata acttacctcc                290

<210> SEQ ID NO 169
<211> LENGTH: 287
<212> TYPE: DNA
<213> ORGANISM: Homo sapiens

<400> SEQUENCE: 169
gccatccaga tgacccagtc tccatcctcc ctgtctgcat ctgtaggaga cagagtcacc        60
atcacttgcc gggcaagtca gggcattaga aatgatttag ctggtatca gcagaaacca       120 gggaaagccc ctaagctcct gatctatgct gcatccagtt tacaaagtgg ggtcccatca       180
aggttcagcg gcagtggatc tggcacagat ttcactctca ccatcagcag cctgcagcct       240
gaagattttg caacttatta ctgtctacaa gattacaatt accctcc                    287

<210> SEQ ID NO 170
<211> LENGTH: 287
<212> TYPE: DNA
<213> ORGANISM: Homo sapiens

<400> SEQUENCE: 170
gacatccaga tgacccagtc tccttccacc ctgtctgcat ctgtaggaga cagagtcacc        60
atcacttgcc gggccagtca gagtattagt agctggttgg cctggtatca gcagaaacca       120
gggaaagccc ctaagctcct gatctatgat gcctccagtt tggaaagtgg ggtcccatca       180
aggttcagcg gcagtggatc tgggacagaa ttcactctca ccatcagcag cctgcagcct       240
gatgattttg caacttatta ctgccaacag tataatagtt attctcc                    287

<210> SEQ ID NO 171
<211> LENGTH: 287
<212> TYPE: DNA
<213> ORGANISM: Homo sapiens

<400> SEQUENCE: 171
aacatccaga tgacccagtc tccatctgcc atgtctgcat ctgtaggaga cagagtcacc        60
atcacttgtc gggcgaggca gggcattagc aattatttag cctggtttca gcagaaacca       120
gggaaagtcc ctaagcacct gatctatgct gcatccagtt tgcaaagtgg ggtcccatca       180
aggttcagcg gcagtggatc tgggacagaa ttcactctca caatcagcag cctgcagcct       240
gaagattttg caacttatta ctgtctacag cataatagtt accctcc                    287

<210> SEQ ID NO 172
<211> LENGTH: 287
<212> TYPE: DNA

<213> ORGANISM: Homo sapiens

<400> SEQUENCE: 172

```
gacatccaga tgacccagtc tccatcctca ctgtctgcat ctgtaggaga cagagtcacc    60
atcacttgtc gggcgagtca gggtattagc agctggttag cctggtatca gcagaaacca   120
gagaaagccc ctaagtccct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgccaacag tataatagtt accctcc                 287
```

<210> SEQ ID NO 173
<211> LENGTH: 287
<212> TYPE: DNA
<213> ORGANISM: Homo sapiens

<400> SEQUENCE: 173

```
gaaatagtga tgatgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg catcccagcc   180
aggttcagtg gcagtgggtc tgggacagag ttcactctca ccatcagcag cctgcagtct   240
gaagattttg cagtttatta ctgtcagcag tataataact gacctcc                 287
```

<210> SEQ ID NO 174
<211> LENGTH: 287
<212> TYPE: DNA
<213> ORGANISM: Homo sapiens

<400> SEQUENCE: 174

```
gccatccagt tgacccagtc tccatcctcc ctgtctgcat ctgtaggaga cagagtcacc    60
atcacttgcc gggcaagtca gggcattagc agtgctttag cctggtatca gcagaaacca   120
gggaaagctc ctaagctcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaataatt accctca                 287
```

<210> SEQ ID NO 175
<211> LENGTH: 287
<212> TYPE: DNA
<213> ORGANISM: Homo sapiens

<400> SEQUENCE: 175

```
gacatccaga tgacccagtc tccatcttct gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ctatcagcag cctgcagcct   240
gaagattttg caacttacta ttgtcaacag gctaacagtt ccctcc                  287
```

<210> SEQ ID NO 176
<211> LENGTH: 287
<212> TYPE: DNA
<213> ORGANISM: Homo sapiens

<400> SEQUENCE: 176

```
gaaatagtga tgacgcagtc tccagccacc ctgtctgtgt ctccagggga aagagccacc    60
ctctcctgca gggccagtca gagtgttagc agcaacttag cctggtacca gcagaaacct   120
```

| | |
|---|---|
| ggccaggctc ccaggctcct catctatggt gcatccacca gggccactgg tatcccagcc | 180 |
| aggttcagtg gcagtgggtc tgggacagag ttcactctca ccatcagcag cctgcagtct | 240 |
| gaagattttg cagttattac tgtcagcag tataataact ggcctcc | 287 |

<210> SEQ ID NO 177
<211> LENGTH: 287
<212> TYPE: DNA
<213> ORGANISM: Homo sapiens

<400> SEQUENCE: 177

| | |
|---|---|
| gaaattgtgt tgacacagtc tccagccacc ctgtctttgt ctccagggga aagagccacc | 60 |
| ctctcctgca gggccagtca ggtgttagc agctacttag cctggtacca gcagaaacct | 120 |
| ggccaggctc ccaggctcct catctatgat gcatccaaca gggccactgg catcccagcc | 180 |
| aggttcagtg gcagtgggcc tgggacagac ttcactctca ccatcagcag cctagagcct | 240 |
| gaagattttg cagttattac tgtcagcag cgtagcaact ggcatcc | 287 |

<210> SEQ ID NO 178
<211> LENGTH: 287
<212> TYPE: DNA
<213> ORGANISM: Homo sapiens

<400> SEQUENCE: 178

| | |
|---|---|
| gacatccaga tgatccagtc tccatctttc ctgtctgcat ctgtaggaga cagagtcagt | 60 |
| atcatttgct gggcaagtga gggcattagc agtaatttag cctggtatct gcagaaacca | 120 |
| gggaaatccc ctaagctctt cctctatgat gcaaagatt tgcaccctgg ggtctcatcg | 180 |
| aggttcagtg gcaggggatc tgggacggat ttcactctca ccatcatcag cctgaagcct | 240 |
| gaagattttg cagcttatta ctgtaaacag gacttcagtt accctcc | 287 |

<210> SEQ ID NO 179
<211> LENGTH: 287
<212> TYPE: DNA
<213> ORGANISM: Homo sapiens

<400> SEQUENCE: 179

| | |
|---|---|
| gccatccgga tgacccagtc tccattctcc ctgtctgcat ctgtaggaga cagagtcacc | 60 |
| atcacttgct gggccagtca gggcattagc agtatttag cctggtatca gcaaaaacca | 120 |
| gcaaaagccc ctaagctctt catctattat gcatccagtt tgcaaagtgg ggtcccatca | 180 |
| aggttcagcg gcagtggatc tgggacggat tacactctca ccatcagcag cctgcagcct | 240 |
| gaagattttg caacttatta ctgtcaacag tattatagta cccctcc | 287 |

<210> SEQ ID NO 180
<211> LENGTH: 287
<212> TYPE: DNA
<213> ORGANISM: Homo sapiens

<400> SEQUENCE: 180

| | |
|---|---|
| gtcatctgga tgacccagtc tccatcctta ctctctgcat ctacaggaga cagagtcacc | 60 |
| atcagttgtc ggatgagtca gggcattagc agttatttag cctggtatca gcaaaaacca | 120 |
| gggaaagccc ctgagctcct gatctatgct gcatccactt tgcaaagtgg ggtcccatca | 180 |
| aggttcagtg gcagtggatc tgggacagat ttcactctca ccatcagttg cctgcagtct | 240 |
| gaagattttg caacttatta ctgtcaacag tattatagtt tccctcc | 287 |

<210> SEQ ID NO 181

```
<211> LENGTH: 290
<212> TYPE: DNA
<213> ORGANISM: Homo sapiens

<400> SEQUENCE: 181
gaaattgtaa tgacacagtc tccagccacc ctgtctttgt ctccagggga aagagccacc      60
ctctcctgca gggccagtca gagtgttagc agcagctact tatcctggta ccagcagaaa     120
cctgggcagg ctcccaggct cctcatctat ggtgcatcca ccagggccac tggcatccca     180
gccaggttca gtggcagtgg gtctgggaca gacttcactc tcaccatcag cagcctgcag     240
cctgaagatt ttgcagttta ttactgtcag caggattata acttacctcc                290

<210> SEQ ID NO 182
<211> LENGTH: 287
<212> TYPE: DNA
<213> ORGANISM: Homo sapiens

<400> SEQUENCE: 182
gccatccagt tgacccagtc tccatcctcc ctgtctgcat ctgtaggaga cagagtcacc      60
atcacttgcc gggcaagtca gggcattagc agtgctttag cctggtatca gcagaaacca     120
gggaaagctc ctaagctcct gatctatgat gcctccagtt tggaaagtgg ggtcccatca     180
aggttcagcg gcagtggatc tgggacagat ttcactctca ccatcagcag cctgcagcct     240
gaagattttg caacttatta ctgtcaacag tttaatagtt accctca                   287

<210> SEQ ID NO 183
<211> LENGTH: 287
<212> TYPE: DNA
<213> ORGANISM: Homo sapiens

<400> SEQUENCE: 183
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttacta ttgtcaacag gctaacagtt ccctcc                    287

<210> SEQ ID NO 184
<211> LENGTH: 287
<212> TYPE: DNA
<213> ORGANISM: Homo sapiens

<400> SEQUENCE: 184
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctcc                   287

<210> SEQ ID NO 185
<211> LENGTH: 287
<212> TYPE: DNA
<213> ORGANISM: Homo sapiens

<400> SEQUENCE: 185
gacatccagt tgacccagtc tccatccttc ctgtctgcat ctgtaggaga cagagtcacc      60
```

```
atcacttgcc gggccagtca gggcattagc agttatttag cctggtatca gcaaaaacca    120
gggaaagccc ctaagctcct gatctatgct gcatccactt tgcaaagtgg ggtcccatca    180
aggttcagcg gcagtggatc tgggacagaa ttcactctca caatcagcag cctgcagcct    240
gaagattttg caacttatta ctgtcaacag cttaatagtt accctcc                  287

<210> SEQ ID NO 186
<211> LENGTH: 287
<212> TYPE: DNA
<213> ORGANISM: Homo sapiens

<400> SEQUENCE: 186
gccatccgga tgacccagtc tccatcctca ttctctgcat ctacaggaga cagagtcacc     60
atcacttgtc gggcgagtca gggtattagc agttatttag cctggtatca gcaaaaacca    120
gggaaagccc ctaagctcct gatctatgct gcatccactt tgcaaagtgg ggtcccatca    180
aggttcagcg gcagtggatc tgggacagat ttcactctca ccatcagctg cctgcagtct    240
gaagattttg caacttatta ctgtcaacag tattatagtt accctcc                  287

<210> SEQ ID NO 187
<211> LENGTH: 305
<212> TYPE: DNA
<213> ORGANISM: Homo sapiens

<400> SEQUENCE: 187
gatattgtga tgacccagac tccactctcc ctgcccgtca cccctggaga gccggcctcc     60
atctcctgca ggtctagtca gagcctcttg gatagtgatg atggaaacac ctatttggac    120
tggtacctgc agaagccagg gcagtctcca cagctcctga tctatacgct ttcctatcgg    180
gcctctggag tcccagacag gttcagtggc agtgggtcag gcactgattt cacactgaaa    240
atcagcaggg tggaggctga ggatgttgga gtttattact gcatgcaacg tatagagttt    300
ccttc                                                                305

<210> SEQ ID NO 188
<211> LENGTH: 305
<212> TYPE: DNA
<213> ORGANISM: Homo sapiens

<400> SEQUENCE: 188
gatattgtga tgacccagac tccactctcc ctgcccgtca cccctggaga gccggcctcc     60
atctcctgca ggtctagtca gagcctcttg gatagtgatg atggaaacac ctatttggac    120
tggtacctgc agaagccagg gcagtctcca cagctcctga tctatacgct ttcctatcgg    180
gcctctggag tcccagacag gttcagtggc agtgggtcag gcactgattt cacactgaaa    240
atcagcaggg tggaggctga ggatgttgga gtttattact gcatgcaacg tatagagttt    300
ccttc                                                                305

<210> SEQ ID NO 189
<211> LENGTH: 287
<212> TYPE: DNA
<213> ORGANISM: Homo sapiens

<400> SEQUENCE: 189
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
```

-continued aggttcagtg gcagtggatc tgggacagat ttcactctca ccatcagcag tctgcaacct       240
gaagattttg caacttacta ctgtcaacag agttacagta cccctcc                    287

<210> SEQ ID NO 190
<211> LENGTH: 287
<212> TYPE: DNA
<213> ORGANISM: Homo sapiens

<400> SEQUENCE: 190
gacatccagt tgacccagtc tccatcctcc ctgtctgcat ctgtaggaga cagagtcacc       60
atcacttgcc gggtgagtca gggcattagc agttatttaa attggtatcg gcagaaacca      120
gggaaagttc ctaagctcct gatctatagt gcatccaatt tgcaatctgg agtcccatct      180
cggttcagtg gcagtggatc tgggacagat ttcactctca ctatcagcag cctgcagcct      240
gaagatgttg caacttatta cggtcaacgg acttacaatg cccctcc                    287

<210> SEQ ID NO 191
<211> LENGTH: 287
<212> TYPE: DNA
<213> ORGANISM: Homo sapiens

<400> SEQUENCE: 191
gacatccaga tgacccagtc tccatcctcc ctgtctgcat ctgtaggaga cagagtcacc       60
atcacttgcc aggcgagtca ggacattagc aactatttaa attggtatca gcagaaacca      120
gggaaagccc ctaagctcct gatctacgat gcatccaatt tggaaacagg ggtcccatca      180
aggttcagtg gaagtggatc tgggacagat tttactttca ccatcagcag cctgcagcct      240
gaagatattg caacatatta ctgtcaacag tatgataatc tccctcc                    287

<210> SEQ ID NO 192
<211> LENGTH: 287
<212> TYPE: DNA
<213> ORGANISM: Homo sapiens

<400> SEQUENCE: 192
gacatccaga tgacccagtc tccatcctcc ctgtctgcat ctgtaggaga cagagtcacc       60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta cccctcc                    287

<210> SEQ ID NO 193
<211> LENGTH: 287
<212> TYPE: DNA
<213> ORGANISM: Homo sapiens

<400> SEQUENCE: 193
gacatccagt tgacccagtc tccatcctcc ctgtctgcat ctgtaggaga cagagtcacc       60
atcacttgcc gggtgagtca gggcattagc agttatttaa attggtatcg gcagaaacca      120
gggaaagttc ctaagctcct gatctatagt gcatccaatt tgcaatctgg agtcccatct      180
cggttcagtg gcagtggatc tgggacagat ttcactctca ctatcagcag cctgcagcct      240
gaagatgttg caacttatta cggtcaacgg acttacaatg cccctcc                    287

<210> SEQ ID NO 194
<211> LENGTH: 287
<212> TYPE: DNA

<213> ORGANISM: Homo sapiens

<400> SEQUENCE: 194

```
gacatccaga tgacccagtc tccatcctcc ctgtctgcat ctgtaggaga cagagtcacc    60
atcacttgcc aggcgagtca ggacattagc aactatttaa attggtatca gcagaaacca   120
gggaaagccc ctaagctcct gatctacgat gcatccaatt tggaaacagg ggtcccatca   180
aggttcagtg aagtggatc tgggacagat tttactttca ccatcagcag cctgcagcct   240
gaagatattg caacatatta ctgtcaacag tatgataatc tccctcc                 287
```

<210> SEQ ID NO 195
<211> LENGTH: 99
<212> TYPE: PRT
<213> ORGANISM: Homo sapiens

<400> SEQUENCE: 195

```
Gln Ser Val Leu Thr Gln Pro Pro Ser Val Ser Glu Ala Pro Arg Gln
  1               5                  10                  15
Arg Val Thr Ile Ser Cys Ser Gly Ser Ser Asn Ile Gly Asn Asn
             20                  25                  30
Ala Val Asn Trp Tyr Gln Gln Leu Pro Gly Lys Ala Pro Lys Leu Leu
         35                  40                  45
Ile Tyr Tyr Asp Asp Leu Leu Pro Ser Gly Val Ser Asp Arg Phe Ser
     50                  55                  60
Gly Ser Lys Ser Gly Thr Ser Ala Ser Leu Ala Ile Ser Gly Leu Gln
 65                  70                  75                  80
Ser Glu Asp Glu Ala Asp Tyr Tyr Cys Ala Ala Trp Asp Asp Ser Leu
                 85                  90                  95
Asn Gly Pro
```

<210> SEQ ID NO 196
<211> LENGTH: 100
<212> TYPE: PRT
<213> ORGANISM: Homo sapiens

<400> SEQUENCE: 196

```
Gln Ser Val Leu Thr Gln Pro Pro Ser Val Ser Gly Ala Pro Gly Gln
  1               5                  10                  15
Arg Val Thr Ile Ser Cys Thr Gly Ser Ser Ser Asn Ile Gly Ala Gly
             20                  25                  30
Tyr Asp Val His Trp Tyr Gln Gln Leu Pro Gly Thr Ala Pro Lys Leu
         35                  40                  45
Leu Ile Tyr Gly Asn Ser Asn Arg Pro Ser Gly Val Pro Asp Arg Phe
     50                  55                  60
Ser Gly Ser Lys Ser Gly Thr Ser Ala Ser Leu Ala Ile Thr Gly Leu
 65                  70                  75                  80
Gln Ala Glu Asp Glu Ala Asp Tyr Tyr Cys Gln Ser Tyr Asp Ser Ser
                 85                  90                  95
Leu Ser Gly Ser
            100
```

<210> SEQ ID NO 197
<211> LENGTH: 99
<212> TYPE: PRT
<213> ORGANISM: Homo sapiens

<400> SEQUENCE: 197

```
Gln Ser Val Leu Thr Gln Pro Pro Ser Ala Ser Gly Thr Pro Gly Gln
```

```
            1               5                  10                 15
Arg Val Thr Ile Ser Cys Ser Gly Ser Ser Asn Ile Gly Ser Asn
                    20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                85                  90                  95

Asn Gly Pro

<210> SEQ ID NO 198
<211> LENGTH: 99
<212> TYPE: PRT
<213> ORGANISM: Homo sapiens

<400> SEQUENCE: 198

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
                    20                  25                  30

Tyr Val Tyr Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                85                  90                  95

Ser Gly Pro

<210> SEQ ID NO 199
<211> LENGTH: 99
<212> TYPE: PRT
<213> ORGANISM: Homo sapiens

<400> SEQUENCE: 199

Gln Ser Val Leu Thr Gln Pro Pro Ser Val Ser Gly Ala Pro Gly Gln
 1               5                  10                  15

Arg Val Thr Ile Ser Cys Thr Gly Ser Ser Asn Ile Gly Ala Gly
                    20                  25                  30

Tyr Val Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Gln Phe
        50                  55                  60

Ser Gly Ser Lys Ser Gly Thr Ser Ala Ser Leu Ala Ile Thr Gly Leu
 65                  70                  75                  80

Gln Ser Glu Asp Glu Ala Asp Tyr Tyr Cys Lys Ala Trp Asp Asn Ser
                85                  90                  95

Leu Asn Ala

<210> SEQ ID NO 200
<211> LENGTH: 99
<212> TYPE: PRT
<213> ORGANISM: Homo sapiens
```

<400> SEQUENCE: 200

Gln Ser Val Leu Thr Gln Pro Pro Ser Val Ser Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly

<210> SEQ ID NO 201
<211> LENGTH: 99
<212> TYPE: PRT
<213> ORGANISM: Homo sapiens

<400> SEQUENCE: 201

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Phe

<210> SEQ ID NO 202
<211> LENGTH: 98
<212> TYPE: PRT
<213> ORGANISM: Homo sapiens

<400> SEQUENCE: 202

Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Ile Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Phe Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Leu Asp Ser Ser Leu
                85                  90                  95

Ser Ala

<210> SEQ ID NO 203
<211> LENGTH: 98
<212> TYPE: PRT
<213> ORGANISM: Homo sapiens

<400> SEQUENCE: 203

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn

<210> SEQ ID NO 204
<211> LENGTH: 99
<212> TYPE: PRT
<213> ORGANISM: Homo sapiens

<400> SEQUENCE: 204

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Phe

<210> SEQ ID NO 205
<211> LENGTH: 99
<212> TYPE: PRT
<213> ORGANISM: Homo sapiens

<400> SEQUENCE: 205

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu

<210> SEQ ID NO 206
<211> LENGTH: 99
<212> TYPE: PRT
<213> ORGANISM: Homo sapiens

<400> SEQUENCE: 206

Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asp Val Gly Ser Tyr
            20                  25                  30

Asn Arg Val Ser Trp Tyr Gln Gln Pro Pro Gly Thr Ala Pro Lys Leu
        35                  40                  45

Met Ile Tyr Glu Val Ser Asn Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Leu Tyr Thr Ser Ser
                85                  90                  95

Ser Thr Phe

<210> SEQ ID NO 207
<211> LENGTH: 99
<212> TYPE: PRT
<213> ORGANISM: Homo sapiens

<400> SEQUENCE: 207

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Phe

<210> SEQ ID NO 208
<211> LENGTH: 99
<212> TYPE: PRT
<213> ORGANISM: Homo sapiens

<400> SEQUENCE: 208

Gln Ser Ala Leu Thr Gln Pro Pro Phe Val Ser Gly Ala Pro Gly Gln
1               5                   10                  15

Ser Val Thr Ile Ser Cys Thr Gly Thr Ser Ser Asp Val Gly Asp Tyr
            20                  25                  30

Asp His Val Phe Trp Tyr Gln Lys Arg Leu Ser Thr Thr Ser Arg Leu
        35                  40                  45

Leu Ile Tyr Asn Val Asn Thr Arg Pro Ser Gly Ile Ser Asp Leu Phe
    50                  55                  60

Ser Gly Ser Lys Ser Gly Asn Met Ala Ser Leu Thr Ile Ser Gly Leu

```
                65                  70                  75                  80
Lys Ser Glu Val Glu Ala Asn Tyr His Cys Ser Leu Tyr Ser Ser
                    85                  90                  95
Tyr Thr Phe
```

<210> SEQ ID NO 209
<211> LENGTH: 95
<212> TYPE: PRT
<213> ORGANISM: Homo sapiens

<400> SEQUENCE: 209

```
Ser Tyr Glu Leu Thr Gln Pro Pro Ser Val Ser Val Ser Pro Gly Gln
  1               5                  10                  15
Thr Ala Ser Ile Thr Cys Ser Gly Asp Lys Leu Gly Asp Lys Tyr Ala
                20                  25                  30
Cys Trp Tyr Gln Gln Lys Pro Gly Gln Ser Pro Val Leu Val Ile Tyr
            35                  40                  45
Gln Asp Ser Lys Arg Pro Ser Gly Ile Pro Glu Arg Phe Ser Gly Ser
        50                  55                  60
Asn Ser Gly Asn Thr Ala Thr Leu Thr Ile Ser Gly Thr Gln Ala Met
 65                  70                  75                  80
Asp Glu Ala Asp Tyr Tyr Cys Gln Ala Trp Asp Ser Ser Thr Ala
                    85                  90                  95
```

<210> SEQ ID NO 210
<211> LENGTH: 97
<212> TYPE: PRT
<213> ORGANISM: Homo sapiens

<400> SEQUENCE: 210

```
Ser Tyr Glu Leu Thr Gln Pro Pro Ser Val Ser Val Ser Leu Gly Gln
  1               5                  10                  15
Met Ala Arg Ile Thr Cys Ser Gly Glu Ala Leu Pro Lys Lys Tyr Ala
                20                  25                  30
Tyr Trp Tyr Gln Gln Lys Pro Gly Gln Phe Pro Val Leu Val Ile Tyr
            35                  40                  45
Lys Asp Ser Glu Arg Pro Ser Gly Ile Pro Glu Arg Phe Ser Gly Ser
        50                  55                  60
Ser Ser Gly Thr Ile Val Thr Leu Thr Ile Ser Gly Val Gln Ala Glu
 65                  70                  75                  80
Asp Glu Ala Asp Tyr Tyr Cys Leu Ser Ala Asp Ser Ser Gly Thr Tyr
                    85                  90                  95
Pro
```

<210> SEQ ID NO 211
<211> LENGTH: 97
<212> TYPE: PRT
<213> ORGANISM: Homo sapiens

<400> SEQUENCE: 211

```
Ser Ser Glu Leu Thr Gln Asp Pro Ala Val Ser Val Ala Leu Gly Gln
  1               5                  10                  15
Thr Val Arg Ile Thr Cys Gln Gly Asp Ser Leu Arg Ser Tyr Tyr Ala
                20                  25                  30
Ser Trp Tyr Gln Gln Lys Pro Gly Gln Ala Pro Val Leu Val Ile Tyr
            35                  40                  45
Gly Lys Asn Asn Arg Pro Ser Gly Ile Pro Asp Arg Phe Ser Gly Ser
        50                  55                  60
```

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu

<210> SEQ ID NO 212
<211> LENGTH: 97
<212> TYPE: PRT
<213> ORGANISM: Homo sapiens

<400> SEQUENCE: 212

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro

<210> SEQ ID NO 213
<211> LENGTH: 95
<212> TYPE: PRT
<213> ORGANISM: Homo sapiens

<400> SEQUENCE: 213

Ser Tyr Glu Leu Thr Gln Leu Pro Ser Val Ser Val Ser Pro Gly Gln
1               5                   10                  15

Thr Ala Arg Ile Thr Cys Ser Gly Asp Val Leu Gly Glu Asn Tyr Ala
                20                  25                  30

Asp Trp Tyr Gln Gln Lys Pro Gly Gln Ala Pro Glu Leu Val Ile Tyr
            35                  40                  45

Glu Asp Ser Glu Arg Tyr Pro Gly Ile Pro Glu Arg Phe Ser Gly Ser
        50                  55                  60

Thr Ser Gly Asn Thr Thr Thr Leu Thr Ile Ser Arg Val Leu Thr Glu
65                  70                  75                  80

Asp Glu Ala Asp Tyr Tyr Cys Leu Ser Gly Asp Glu Asp Asn Pro
                85                  90                  95

<210> SEQ ID NO 214
<211> LENGTH: 97
<212> TYPE: PRT
<213> ORGANISM: Homo sapiens

<400> SEQUENCE: 214

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
                20                  25                  30

Tyr Trp Tyr Gln Gln Lys Pro Gly Gln Ala Pro Val Leu Val Ile Tyr
            35                  40                  45

```
Lys Asp Ser Glu Arg Pro Ser Gly Ile Pro Glu Arg Phe Ser Gly Ser
        50                   55                   60

Ser Ser Gly Thr Thr Val Thr Leu Thr Ile Ser Gly Val Gln Ala Glu
65                   70                   75                   80

Asp Glu Ala Asp Tyr Tyr Cys Gln Ser Ala Asp Ser Ser Gly Thr Tyr
                85                   90                   95

Pro
```

```
<210> SEQ ID NO 215
<211> LENGTH: 95
<212> TYPE: PRT
<213> ORGANISM: Homo sapiens

<400> SEQUENCE: 215

Ser Tyr Glu Leu Thr Gln Pro Ser Ser Val Ser Val Ser Pro Gly Gln
1               5                   10                  15

Thr Ala Arg Ile Thr Cys Ser Gly Asp Val Leu Ala Lys Lys Tyr Ala
            20                  25                  30

Arg Trp Phe Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Ala Gln Val Glu
65                  70                  75                  80

Asp Glu Ala Asp Tyr Tyr Cys Tyr Ser Ala Ala Asp Asn Asn Leu
                85                  90                  95
```

```
<210> SEQ ID NO 216
<211> LENGTH: 95
<212> TYPE: PRT
<213> ORGANISM: Homo sapiens

<400> SEQUENCE: 216

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr Ala
                85                  90                  95
```

```
<210> SEQ ID NO 217
<211> LENGTH: 96
<212> TYPE: PRT
<213> ORGANISM: Homo sapiens

<400> SEQUENCE: 217

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45
```

```
Glu Asp Ser Lys Arg Pro Ser Gly Ile Pro Glu Arg Phe Ser Gly Ser
 50                  55                  60

Ser Ser Gly Thr Met Ala Thr Leu Thr Ile Ser Gly Ala Gln Val Glu
 65                  70                  75                  80

Asp Glu Ala Asp Tyr Tyr Cys Tyr Ser Thr Asp Ser Ser Gly Asn His
                 85                  90                  95

<210> SEQ ID NO 218
<211> LENGTH: 97
<212> TYPE: PRT
<213> ORGANISM: Homo sapiens

<400> SEQUENCE: 218

Ser Tyr Glu Leu Thr Gln Pro His Ser Val Ser Val Ala Thr Ala Gln
 1               5                  10                  15

Met Ala Arg Ile Thr Cys Gly Gly Asn Asn Ile Gly Ser Lys Ala Val
                 20                  25                  30

His Trp Tyr Gln Gln Lys Pro Gly Gln Asp Pro Val Leu Val Ile Tyr
             35                  40                  45

Ser Asp Ser Asn Arg Pro Ser Gly Ile Pro Glu Arg Phe Ser Gly Ser
 50                  55                  60

Asn Pro Gly Asn Thr Ala Thr Leu Thr Ile Ser Arg Ile Glu Ala Gly
 65                  70                  75                  80

Asp Glu Ala Asp Tyr Tyr Cys Gln Val Trp Asp Ser Ser Ser Asp His
                 85                  90                  95

Pro

<210> SEQ ID NO 219
<211> LENGTH: 98
<212> TYPE: PRT
<213> ORGANISM: Homo sapiens

<400> SEQUENCE: 219

Gln Thr Val Val Thr Gln Glu Pro Ser Leu Thr Val Ser Pro Gly Gly
 1               5                  10                  15

Thr Val Thr Leu Thr Cys Ala Ser Ser Thr Gly Ala Val Thr Ser Gly
                 20                  25                  30

Tyr Tyr Pro Asn Trp Phe Gln Gln Lys Pro Gly Gln Ala Pro Arg Ala
             35                  40                  45

Leu Ile Tyr Ser Thr Ser Asn Lys His Ser Trp Thr Pro Ala Arg Phe
 50                  55                  60

Ser Gly Ser Leu Leu Gly Lys Ala Ala Leu Thr Leu Ser Gly Val
 65                  70                  75                  80

Gln Pro Glu Asp Glu Ala Glu Tyr Tyr Cys Leu Leu Tyr Tyr Gly Gly
                 85                  90                  95

Ala Gln

<210> SEQ ID NO 220
<211> LENGTH: 98
<212> TYPE: PRT
<213> ORGANISM: Homo sapiens

<400> SEQUENCE: 220

Gln Ala Val Val Thr Gln Glu Pro Ser Leu Thr Val Ser Pro Gly Gly
 1               5                  10                  15

Thr Val Thr Leu Thr Cys Gly Ser Ser Thr Gly Ala Val Thr Ser Gly
                 20                  25                  30

His Tyr Pro Tyr Trp Phe Gln Gln Lys Pro Gly Gln Ala Pro Arg Thr
```

```
                    35                  40                  45
Leu Ile Tyr Asp Thr Ser Asn Lys His Ser Trp Thr Pro Ala Arg Phe
 50                  55                  60

Ser Gly Ser Leu Leu Gly Gly Lys Ala Ala Thr Leu Leu Gly Ala
 65                  70                  75                  80

Gln Pro Glu Asp Glu Ala Glu Tyr Tyr Cys Leu Leu Ser Tyr Ser Gly
                     85                  90                  95

Ala Arg

<210> SEQ ID NO 221
<211> LENGTH: 99
<212> TYPE: PRT
<213> ORGANISM: Homo sapiens

<400> SEQUENCE: 221

Gln Thr Val Val Thr Gln Glu Pro Ser Phe Ser Val Ser Pro Gly Gly
 1               5                  10                  15

Thr Val Thr Leu Thr Cys Gly Leu Ser Ser Gly Ser Val Ser Thr Ser
                 20                  25                  30

Tyr Tyr Pro Ser Trp Tyr Gln Gln Thr Pro Gly Gln Ala Pro Arg Thr
             35                  40                  45

Leu Ile Tyr Ser Thr Asn Thr Arg Ser Ser Gly Val Pro Asp Arg Phe
 50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Val Leu Tyr Met Gly Ser
                     85                  90                  95

Gly Ile Ser

<210> SEQ ID NO 222
<211> LENGTH: 104
<212> TYPE: PRT
<213> ORGANISM: Homo sapiens

<400> SEQUENCE: 222

Gln Pro Val Leu Thr Gln Pro Pro Ser Ser Ala Ser Pro Gly Glu
 1               5                  10                  15

Ser Ala Arg Leu Thr Cys Thr Leu Pro Ser Asp Ile Asn Val Gly Ser
                 20                  25                  30

Tyr Asn Ile Tyr Trp Tyr Gln Gln Lys Pro Gly Ser Pro Pro Arg Tyr
             35                  40                  45

Leu Leu Tyr Tyr Tyr Ser Asp Ser Asp Lys Gly Gln Gly Ser Gly Val
 50                  55                  60

Pro Ser Arg Phe Ser Gly Ser Lys Asp Ala Ser Ala Asn Thr Gly Ile
 65                  70                  75                  80

Leu Leu Ile Ser Gly Leu Gln Ser Glu Asp Glu Ala Asp Tyr Tyr Cys
                     85                  90                  95

Met Ile Trp Pro Ser Asn Ala Ser
             100

<210> SEQ ID NO 223
<211> LENGTH: 104
<212> TYPE: PRT
<213> ORGANISM: Homo sapiens

<400> SEQUENCE: 223

Gln Ala Val Leu Thr Gln Pro Ser Ser Leu Ser Ala Ser Pro Gly Ala
 1               5                  10                  15
```

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
            35                  40                  45

Leu Leu Arg Tyr Lys Ser Asp Ser Asp Lys Gln Gln Gly Ser Gly Val
        50                  55                  60

Pro Ser Arg Phe Ser Gly Ser Lys Asp Ala Ser Ala Asn Ala Gly Ile
 65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Ser
            100

<210> SEQ ID NO 224
<211> LENGTH: 104
<212> TYPE: PRT
<213> ORGANISM: Homo sapiens

<400> SEQUENCE: 224

Gln Pro Val Leu Thr Gln Pro Thr Ser Leu Ser Ala Ser Pro Gly Ala
 1               5                  10                  15

Ser Ala Arg Leu Thr Cys Thr Leu Arg Ser Gly Ile Asn Leu Gly Ser
            20                  25                  30

Tyr Arg Ile Phe Trp Tyr Gln Gln Lys Pro Glu Ser Pro Pro Arg Tyr
            35                  40                  45

Leu Leu Ser Tyr Tyr Ser Asp Ser Ser Lys His Gln Gly Ser Gly Val
        50                  55                  60

Pro Ser Arg Phe Ser Gly Ser Lys Asp Ala Ser Ser Asn Ala Gly Ile
 65                  70                  75                  80

Leu Val Ile Ser Gly Leu Gln Ser Glu Asp Glu Ala Asp Tyr Tyr Cys
                85                  90                  95

Met Ile Trp His Ser Ser Ala Ser
            100

<210> SEQ ID NO 225
<211> LENGTH: 105
<212> TYPE: PRT
<213> ORGANISM: Homo sapiens

<400> SEQUENCE: 225

Gln Pro Val Leu Thr Gln Pro Ser Ser His Ser Ala Ser Ser Gly Ala
 1               5                  10                  15

Ser Val Arg Leu Thr Cys Met Leu Ser Ser Gly Phe Ser Val Gly Asp
            20                  25                  30

Phe Trp Ile Arg Trp Tyr Gln Gln Lys Pro Gly Asn Pro Pro Arg Tyr
            35                  40                  45

Leu Leu Tyr Tyr His Ser Asp Ser Asn Lys Gly Gln Gly Ser Gly Val
        50                  55                  60

Pro Ser Arg Phe Ser Gly Ser Asn Asp Ala Ser Ala Asn Ala Gly Ile
 65                  70                  75                  80

Leu Arg Ile Ser Gly Leu Gln Pro Glu Asp Glu Ala Asp Tyr Tyr Cys
                85                  90                  95

Gly Thr Trp His Ser Asn Ser Lys Thr
            100                 105

<210> SEQ ID NO 226
<211> LENGTH: 104

```
<212> TYPE: PRT
<213> ORGANISM: Homo sapiens

<400> SEQUENCE: 226

Arg Pro Val Leu Thr Gln Pro Ser Leu Ser Ala Ser Pro Gly Ala
1               5                   10                  15

Thr Ala Arg Leu Pro Cys Thr Leu Ser Ser Asp Leu Ser Val Gly
                20                  25                  30

Lys Asn Met Phe Trp Tyr Gln Gln Lys Pro Gly Ser Ser Pro Arg Leu
            35                  40                  45

Phe Leu Tyr His Tyr Ser Asp Ser Asp Lys Gln Leu Gly Pro Gly Val
        50                  55                  60

Pro Ser Arg Val Ser Gly Ser Lys Glu Thr Ser Ser Asn Thr Ala Phe
65                  70                  75                  80

Leu Leu Ile Ser Gly Leu Gln Pro Glu Asp Glu Ala Asp Tyr Tyr Cys
                85                  90                  95

Gln Val Tyr Glu Ser Ser Ala Asn
            100

<210> SEQ ID NO 227
<211> LENGTH: 103
<212> TYPE: PRT
<213> ORGANISM: Homo sapiens

<400> SEQUENCE: 227

Leu Pro Val Leu Thr Gln Pro Ser Ala Ser Ala Leu Leu Gly Ala
1               5                   10                  15

Ser Ile Lys Leu Thr Cys Thr Leu Ser Ser Glu His Ser Thr Tyr Thr
                20                  25                  30

Ile Glu Trp Tyr Gln Gln Arg Pro Gly Arg Ser Pro Gly Tyr Ile Met
            35                  40                  45

Lys Val Lys Ser Asp Gly Ser His Ser Lys Gly Asp Gly Ile Pro Asp
        50                  55                  60

Arg Phe Met Gly Ser Ser Ser Gly Ala Asp Arg Tyr Leu Thr Phe Ser
65                  70                  75                  80

Asn Leu Gln Ser Asp Asp Glu Ala Glu Tyr His Cys Gly Glu Ser His
                85                  90                  95

Thr Ile Asp Gly Gln Val Gly
            100

<210> SEQ ID NO 228
<211> LENGTH: 104
<212> TYPE: PRT
<213> ORGANISM: Homo sapiens

<400> SEQUENCE: 228

Gln Pro Val Leu Thr Gln Pro Ser Ala Ser Ala Ser Leu Gly Ala
1               5                   10                  15

Ser Val Thr Leu Thr Cys Thr Leu Ser Ser Gly Tyr Ser Asn Tyr Lys
                20                  25                  30

Val Asp Trp Tyr Gln Gln Arg Pro Gly Lys Gly Pro Arg Phe Val Met
            35                  40                  45

Arg Val Gly Thr Gly Gly Ile Val Gly Ser Lys Gly Asp Gly Ile Pro
        50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95
```

His Gly Ser Gly Ser Asn Phe Val
              100

<210> SEQ ID NO 229
<211> LENGTH: 99
<212> TYPE: PRT
<213> ORGANISM: Homo sapiens

<400> SEQUENCE: 229

Gln Pro Val Leu Thr Gln Ser Ser Ala Ser Ala Ser Leu Gly Ser
 1               5                  10                  15

Ser Val Lys Leu Thr Cys Thr Leu Ser Ser Gly His Ser Ser Tyr Ile
            20                  25                  30

Ile Ala Trp His Gln Gln Pro Gly Lys Ala Pro Arg Tyr Leu Met
            35                  40                  45

Lys Leu Glu Gly Ser Gly Ser Tyr Asn Lys Gly Ser Gly Val Pro Asp
        50                  55                  60

Arg Phe Ser Gly Ser Ser Ser Gly Ala Asp Arg Tyr Leu Thr Ile Ser
65                  70                  75                  80

Asn Leu Gln Phe Glu Asp Glu Ala Asp Tyr Tyr Cys Glu Thr Trp Asp
                85                  90                  95

Ser Asn Thr

<210> SEQ ID NO 230
<211> LENGTH: 98
<212> TYPE: PRT
<213> ORGANISM: Homo sapiens

<400> SEQUENCE: 230

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gly His Ser Ser Tyr Ala
            20                  25                  30

Ile Ala Trp His Gln Gln Gln Pro Glu Lys Gly Pro Arg Tyr Leu Met
            35                  40                  45

Lys Leu Asn Ser Asp Gly Ser His Ser Lys Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gln Thr Trp Gly
                85                  90                  95

Thr Gly

<210> SEQ ID NO 231
<211> LENGTH: 296
<212> TYPE: DNA
<213> ORGANISM: Homo sapiens

<400> SEQUENCE: 231
cagtctgtgc tgactcagcc accctcggtg tctgaagccc ccaggcagag ggtcaccatc      60
tcctgttctg gaagcagctc caacatcgga aataatgctg taaactggta ccagcagctc     120
ccaggaaagg ctcccaaact cctcatctat tatgatgatc tgctgccctc agggtctct      180
gaccgattct ctggctccaa gtctggcacc tcagcctccc tggccatcag tgggctccag     240
tctgaggatg aggctgatta ttactgtgca gcatgggatg acagcctgaa tggtcc         296

<210> SEQ ID NO 232

```
<211> LENGTH: 299
<212> TYPE: DNA
<213> ORGANISM: Homo sapiens

<400> SEQUENCE: 232
cagtctgtgc tgacgcagcc gccctcagtg tctggggccc cagggcagag ggtcaccatc      60
tcctgcactg ggagcagctc caacatcggg gcaggttatg atgtacactg gtaccagcag     120
cttccaggaa cagcccccaa actcctcatc tatggtaaca gcaatcggcc ctcagggggtc    180 cctgaccgat tctctggctc caagtctggc acctcagcct ccctggccat cactgggctc     240
caggctgagg atgaggctga ttattactgc cagtcctatg acagcagcct gagtggttc      299

<210> SEQ ID NO 233
<211> LENGTH: 296
<212> TYPE: DNA
<213> ORGANISM: Homo sapiens

<400> SEQUENCE: 233
cagtctgtgc tgactcagcc accctcagcg tctgggaccc ccgggcagag ggtcaccatc      60
tcttgttctg gaagcagctc caacatcgga agtaatactg taaactggta ccagcagctc     120
ccaggaacgg cccccaaact cctcatctat agtaataatc agcggccctc agggtccct      180 gaccgattct ctggctccaa gtctggcacc tcagcctccc tggccatcag tgggctccag     240
tctgaggatg aggctgatta ttactgtgca gcatgggatg acagcctgaa tggtcc         296

<210> SEQ ID NO 234
<211> LENGTH: 296
<212> TYPE: DNA
<213> ORGANISM: Homo sapiens

<400> SEQUENCE: 234
cagtctgtgc tgactcagcc accctcagcg tctgggaccc ccgggcagag ggtcaccatc      60
tcttgttctg gaagcagctc caacatcgga agtaattatg tatactggta ccagcagctc     120
ccaggaacgg cccccaaact cctcatctat agtaataatc agcggccctc agggtccct      180 gaccgattct ctggctccaa gtctggcacc tcagcctccc tggccatcag tgggctccgg     240
tccgaggatg aggctgatta ttactgtgca gcatgggatg acagcctgag tggtcc         296

<210> SEQ ID NO 235
<211> LENGTH: 299
<212> TYPE: DNA
<213> ORGANISM: Homo sapiens

<400> SEQUENCE: 235
cagtctgtgc tgacgcagcc gccctcagtg tctggggccc cagggcagag ggtcaccatc      60
tcctgcactg ggagcagctc caacattggg gcggttatg ttgtacattg gtaccagcag     120
cttccaggaa cagcccccaa actcctcatc tatggtaaca gcaatcggcc ctcagggggtc    180 cctgaccaat tctctggctc caagtctggc acctcagcct ccctggccat cactggactc     240
cagtctgagg atgaggctga ttattactgc aaagcatggg ataacagcct gaatgctca     299

<210> SEQ ID NO 236
<211> LENGTH: 296
<212> TYPE: DNA
<213> ORGANISM: Homo sapiens

<400> SEQUENCE: 236
cagtctgtgt tgacgcagcc gccctcagtg tctgcggccc caggacagaa ggtcaccatc      60
```

```
tcctgctctg gaagcagctc aacattggg aataattatg tatcctggta ccagcagctc      120
ccaggaacag cccccaaact cctcatttat gacaataata gcgaccctc agggattcct      180 gaccgattct ctggctccaa gtctggcacg tcagccaccc tgggcatcac cggactccag     240 actgggacg aggccgatta ttactgcgga acatgggata gcagcctgag tgctgg         296

<210> SEQ ID NO 237
<211> LENGTH: 297
<212> TYPE: DNA
<213> ORGANISM: Homo sapiens

<400> SEQUENCE: 237
cagtctgccc tgactcagcc tccctccgcg tccgggtctc ctggacagtc agtcaccatc      60
tcctgcactg aaccagcag tgacgttggt ggttataact atgtctcctg gtaccaacag     120
cacccaggca agcccccaa actcatgatt tatgaggtca gtaagcggcc ctcaggggtc     180
cctgatcgct ctctggctc caagtctggc aacacggcct ccctgaccgt ctctgggctc     240
caggctgagg atgaggctga ttattactgc agctcatatg caggcagcaa caatttc      297

<210> SEQ ID NO 238
<211> LENGTH: 296
<212> TYPE: DNA
<213> ORGANISM: Homo sapiens

<400> SEQUENCE: 238
caggcagggc tgactcagcc accctcggtg tccaagggct tgagacagac cgccacactc      60
acctgcactg ggaacagcaa cattgttggc aaccaaggag cagcttggct gcagcagcac     120
cagggccacc ctcccaaact cctatcctac aggaataaca accggccctc agggatctca     180
gagagattct ctgcatccag gtcaggaaac acagcctccc tgaccattac tggactccag     240
cctgaggacg aggctgacta ttactgctca gcattggaca gcagcctcag tgctca         296

<210> SEQ ID NO 239
<211> LENGTH: 296
<212> TYPE: DNA
<213> ORGANISM: Homo sapiens

<400> SEQUENCE: 239
aattttatgc tgactcagcc ccactctgtg tcggagtctc cggggaagac ggtaaccatc      60
tcctgcaccc gcagcagtgg cagcattgcc agcaactatg tgcagtggta ccagcagcgc     120
ccgggcagtt cccccaccac tgtgatctat gaggataacc aaagaccctc tggggtccct     180
gatcggttct ctggctccat cgacagctcc tccaactctg cctccctcac catctctgga     240
ctgaagactg aggacgaggc tgactactac tgtcagtctt atgatagcag caatca         296

<210> SEQ ID NO 240
<211> LENGTH: 297
<212> TYPE: DNA
<213> ORGANISM: Homo sapiens

<400> SEQUENCE: 240
cagtctgccc tgactcagcc tcgctcagtg tccgggtctc ctggacagtc agtcaccatc      60
tcctgcactg gaaccagcag tgatgttggt ggttataact atgtctcctg gtaccaacag     120
cacccaggca agcccccaa actcatgatt tatgatgtca gtaagcggcc ctcaggggtc     180
cctgatcgct ctctggctc caagtctggc aacacggcct ccctgaccat ctctgggctc     240
caggctgagg atgaggctga ttattactgc tgctcatatg caggcagcta cactttc        297
```

<210> SEQ ID NO 241
<211> LENGTH: 297
<212> TYPE: DNA
<213> ORGANISM: Homo sapiens

<400> SEQUENCE: 241
cagtctgccc tgactcagcc tgcctccgtg tctgggtctc ctggacagtc gatcaccatc    60
tcctgcactg gaaccagcag tgacgttggt ggttataact atgtctcctg gtaccaacag   120
cacccaggca agccccccaa actcatgatt tatgaggtca gtaatcggcc ctcaggggtt   180
tctaatcgct tctctggctc caagtctggc aacacggcct ccctgaccat ctctgggctc   240
caggctgagg acgaggctga ttattactgc agctcatata aagcagcag cactctc      297

<210> SEQ ID NO 242
<211> LENGTH: 297
<212> TYPE: DNA
<213> ORGANISM: Homo sapiens

<400> SEQUENCE: 242
cagtctgccc tgactcagcc tccctccgtg tccgggtctc ctggacagtc agtcaccatc    60
tcctgcactg gaaccagcag tgacgttggt agttataacc gtgtctcctg gtaccagcag   120
cccccaggca cagccccaa actcatgatt tatgaggtca gtaatcggcc ctcaggggtc    180
cctgatcgct tctctgggtc caagtctggc aacacggcct ccctgaccat ctctgggctc   240
caggctgagg acgaggctga ttattactgc agcttatata aagcagcag cactttc      297

<210> SEQ ID NO 243
<211> LENGTH: 297
<212> TYPE: DNA
<213> ORGANISM: Homo sapiens

<400> SEQUENCE: 243
cagtctgccc tgactcagcc tgcctccgtg tctgggtctc ctggacagtc gatcaccatc    60
tcctgcactg gaaccagcag tgatgttggg agttataacc ttgtctcctg gtaccaacag   120
cacccaggca agccccccaa actcatgatt tatgagggca gtaagcggcc ctcaggggtt   180
tctaatcgct tctctggctc caagtctggc aacacggcct ccctgacaat ctctgggctc   240
caggctgagg acgaggctga ttattactgc tgctcatatg caggtagtag cactttc      297

<210> SEQ ID NO 244
<211> LENGTH: 297
<212> TYPE: DNA
<213> ORGANISM: Homo sapiens

<400> SEQUENCE: 244
caatctgccc tgactcagcc tccttttgtg tccggggctc ctggacagtc ggtcaccatc    60
tcctgcactg gaaccagcag tgacgttggg gattatgat atgtcttctg gtaccaaaag   120
cgtctcagca ctacctccag actcctgatt tacaatgtca atactcggcc ttcagggatc   180
tctgacctct tctcaggctc caagtctggc aacatggctt ccctgaccat ctctgggctc   240
aagtccgagg ttgaggctaa ttatcactgc agcttatatt caagtagtta cactttc      297

<210> SEQ ID NO 245
<211> LENGTH: 285
<212> TYPE: DNA
<213> ORGANISM: Homo sapiens

<400> SEQUENCE: 245

```
tcctatgagc tgactcagcc accctcagtg tccgtgtccc caggacagac agccagcatc    60
acctgctctg gagataaatt gggggataaa tatgcttgct ggtatcagca gaagccaggc   120
cagtcccctg tgctggtcat ctatcaagat agcaagcggc cctcagggat ccctgagcga   180
ttctctggct ccaactctgg gaacacagcc actctgacca tcagcgggac ccaggctatg   240
gatgaggctg actattactg tcaggcgtgg acagcagca ctgca                    285
```

<210> SEQ ID NO 246
<211> LENGTH: 290
<212> TYPE: DNA
<213> ORGANISM: Homo sapiens

<400> SEQUENCE: 246

```
tcctatgagc tgacacagcc accctcggtg tcagtgtccc taggacagat ggccaggatc    60
acctgctctg gagaagcatt gccaaaaaaa tatgcttatt ggtaccagca gaagccaggc   120
cagttccctg tgctggtgat atataaagac agcgagaggc cctcaggat ccctgagcga    180 ttctctggct ccagctcagg gacaatagtc acattgacca tcagtggagt ccaggcagaa   240
gacgaggctg actattactg tctatcagca gacagcagtg gtacttatcc               290
```

<210> SEQ ID NO 247
<211> LENGTH: 290
<212> TYPE: DNA
<213> ORGANISM: Homo sapiens

<400> SEQUENCE: 247

```
tcttctgagc tgactcagga ccctgctgtg tctgtggcct tgggacagac agtcaggatc    60
acatgccaag agacagcct cagaagctat tatgcaagct ggtaccagca gaagccagga    120
caggcccctg tacttgtcat ctatggtaaa acaaccggc cctcagggat cccagaccga    180
ttctctggct ccagctcagg aaacacagct tccttgacca tcactgggc tcaggcggaa    240 gatgaggctg actattactg taactcccgg gacagcagtg gtaaccatct              290
```

<210> SEQ ID NO 248
<211> LENGTH: 290
<212> TYPE: DNA
<213> ORGANISM: Homo sapiens

<400> SEQUENCE: 248

```
tcctatgtgc tgactcagcc accctcggtg tcagtggccc caggacagac ggccaggatt    60
acctgtgggg gaaacaacat tggaagtaaa agtgtgcact ggtaccagca gaagccaggc   120
caggcccctg tgctggtcgt ctatgatgat agcgaccggc cctcaggat ccctgagcga    180 ttctctggct ccaactctgg gaacacggcc accctgacca tcagcagggt cgaagccggg   240
gatgaggccg actattactg tcaggtgtgg gatagtagta gtgatcatcc              290
```

<210> SEQ ID NO 249
<211> LENGTH: 284
<212> TYPE: DNA
<213> ORGANISM: Homo sapiens

<400> SEQUENCE: 249

```
tcctatgagc tgacacagct accctcggtg tcagtgtccc caggacagac agccaggatc    60
acctgctctg gagatgtact gggggaaaat tatgctgact ggtaccagca gaagccaggc   120
caggcccctg agttggtgat atacgaagat agtgagcggt accctggaat ccctgaacga   180
ttctctgggt ccacctcagg gaacacgacc accctgacca tcagcagggt cctgaccgaa   240
```

```
gacgaggctg actattactg tttgtctggg gatgaggaca atcc            284
```

<210> SEQ ID NO 250
<211> LENGTH: 290
<212> TYPE: DNA
<213> ORGANISM: Homo sapiens

<400> SEQUENCE: 250

```
tcctatgagc tgacacagcc accctcggtg tcagtgtccc caggacagac ggccaggatc   60
acctgctctg gagatgcatt gccaaagcaa tatgcttatt ggtaccagca gaagccaggc  120
caggcccctg tgctggtgat atataaagac agtgagaggc cctcaggat ccctgagcga  180
ttctctggct ccagctcagg gacaacagtc acgttgacca tcagtggagt ccaggcagaa  240
gatgaggctg actattactg tcaatcagca gacagcagtg gtacttatcc             290
```

<210> SEQ ID NO 251
<211> LENGTH: 284
<212> TYPE: DNA
<213> ORGANISM: Homo sapiens

<400> SEQUENCE: 251

```
tcctatgagc tgacacagcc atcctcagtg tcagtgtctc cgggacagac agccaggatc   60
acctgctcag gagatgtact ggcaaaaaaa tatgctcggt ggttccagca gaagccaggc  120
caggcccctg tgctggtgat ttataaagac agtgagcggc cctcagggat ccctgagcga  180
ttctccggct ccagctcagg gaccacagtc accttgacca tcagcggggc ccaggttgag  240
gatgaggctg actattactg ttactctgcg gctgacaaca atct                   284
```

<210> SEQ ID NO 252
<211> LENGTH: 285
<212> TYPE: DNA
<213> ORGANISM: Homo sapiens

<400> SEQUENCE: 252

```
tcctatgagc tgactcagcc actctcagtg tcagtggccc tgggacagac ggccaggatt   60
acctgtgggg gaaacaacat tggaagtaaa aatgtgcact ggtaccagca gaagccaggc  120
caggcccctg tgctggtcat ctataggga agcaaccggc cctctgggat ccctgagcga  180
ttctctggct ccaactcggg gaacacggcc accctgacca tcagcagagc ccaagccggg  240
gatgaggctg actattactg tcaggtgtgg gacagcagca ctgca                  285
```

<210> SEQ ID NO 253
<211> LENGTH: 290
<212> TYPE: DNA
<213> ORGANISM: Homo sapiens

<400> SEQUENCE: 253

```
tcctatgagc tgacacagcc accctcggtg tcagtgtccc caggacaaac ggccaggatc   60
acctgctctg gagatgcatt gccaaaaaaa tatgcttatt ggtaccagca gaagtcaggc  120
caggcccctg tgctggtcat ctatgaggac agcaaacgac cctccgggat ccctgagaga  180
ttctctggct ccagctcagg gacaatggcc accttgacta tcagtggggc ccaggtggag  240
gatgaagctg actactactg ttactcaaca gacagcagtg gtaatcatag             290
```

<210> SEQ ID NO 254
<211> LENGTH: 290
<212> TYPE: DNA
<213> ORGANISM: Homo sapiens

<400> SEQUENCE: 254

```
tcctatgagc tgactcagcc acactcagtg tcagtggcca cagcacagat ggccaggatc      60
acctgtgggg gaaacaacat tggaagtaaa gctgtgcact ggtaccagca aaagccaggc     120
caggaccctg tgctggtcat ctatagcgat agcaaccggc cctcagggat ccctgagcga     180
ttctctggct ccaacccagg gaacaccgcc accctaacca tcagcaggat cgaggctggg     240
gatgaggctg actattactg tcaggtgtgg gacagtagta gtgatcatcc                290
```

<210> SEQ ID NO 255
<211> LENGTH: 294
<212> TYPE: DNA
<213> ORGANISM: Homo sapiens

<400> SEQUENCE: 255

```
cagactgtgg tgactcagga gccctcactg actgtgtccc caggagggac agtcactctc      60
acctgtgctt ccagcactgg agcagtcacc agtggttact atccaaactg gttccagcag     120
aaacctggac aagcacccag ggcactgatt tatagtacaa gcaacaaaca ctcctggacc     180
cctgcccggt tctcaggctc cctccttggg ggcaaagctg ccctgacact gtcaggtgtg     240
cagcctgagg acgaggctga gtattactgc ctgctctact atggtggtgc tcag           294
```

<210> SEQ ID NO 256
<211> LENGTH: 294
<212> TYPE: DNA
<213> ORGANISM: Homo sapiens

<400> SEQUENCE: 256

```
caggctgtgg tgactcagga gccctcactg actgtgtccc caggagggac agtcactctc      60
acctgtggct ccagcactgg agctgtcacc agtggtcatt atccctactg gttccagcag     120
aagcctggcc aagcccccag gacactgatt tatgatacaa gcaacaaaca ctcctggaca     180
cctgcccggt tctcaggctc cctccttggg ggcaaagctg ccctgaccct tttgggtgcg     240
cagcctgagg atgaggctga gtattactgc ttgctctcct atagtggtgc tcgg           294
```

<210> SEQ ID NO 257
<211> LENGTH: 296
<212> TYPE: DNA
<213> ORGANISM: Homo sapiens

<400> SEQUENCE: 257

```
cagactgtgg tgacccagga gccatcgttc tcagtgtccc ctggagggac agtcacactc      60
acttgtggct tgagctctgg ctcagtctct actagttact accccagctg gtaccagcag     120
accccaggcc aggctccacg cacgctcatc tacagcacaa acactcgctc ttctggggtc     180
cctgatcgct tctctggctc catccttggg aacaaagctg ccctcaccat cacggggscc     240
caggcagatg atgaatctga ttattactgt gtgctgtata tgggtagtgg catttc          296
```

<210> SEQ ID NO 258
<211> LENGTH: 312
<212> TYPE: DNA
<213> ORGANISM: Homo sapiens

<400> SEQUENCE: 258

```
cagcctgtgc tgactcagcc accttcctcc tccgcatctc ctggagaatc cgccagactc      60
acctgcacct tgcccagtga catcaatgtt ggtagctaca acatatactg gtaccagcag     120
aagccaggga gccctcccag gtatctcctg tactactact cagactcaga taagggccag     180
```

```
ggctctggag tccccagccg cttctctgga tccaaagatg cttcagccaa tacagggatt    240
ttactcatct ccgggctcca gtctgaggat gaggctgact attactgtat gatttggcca    300
agcaatgctt ct                                                       312

<210> SEQ ID NO 259
<211> LENGTH: 312
<212> TYPE: DNA
<213> ORGANISM: Homo sapiens

<400> SEQUENCE: 259
caggctgtgc tgactcagcc gtcttccctc tctgcatctc ctggagcatc agccagtctc     60
acctgcacct tgcgcagtgg catcaatgtt ggtacctaca ggatatactg gtaccagcag    120
aagccaggga gtcctcccca gtatctcctg aggtacaaat cagactcaga taagcagcag    180
ggctctggag tccccagccg cttctctgga tccaaagatg cttcggccaa tgcagggatt    240
ttactcatct ctgggctcca gtctgaggat gaggctgact attactgtat gatttggcac    300
agcagcgctt ct                                                       312

<210> SEQ ID NO 260
<211> LENGTH: 312
<212> TYPE: DNA
<213> ORGANISM: Homo sapiens

<400> SEQUENCE: 260
cagcctgtgc tgactcagcc aacttccctc tcagcatctc ctggagcatc agccagactc     60
acctgcacct tgcgcagtgg catcaatctt ggtagctaca ggatattctg gtaccagcag    120
aagccagaga gccctccccg gtatctcctg agctactact cagactcaag taagcatcag    180
ggctctggag tccccagccg cttctctgga tccaaagatg cttcgagcaa tgcagggatt    240
ttagtcatct ctgggctcca gtctgaggat gaggctgact attactgtat gatttggcac    300
agcagtgctt ct                                                       312

<210> SEQ ID NO 261
<211> LENGTH: 317
<212> TYPE: DNA
<213> ORGANISM: Homo sapiens

<400> SEQUENCE: 261
cagcctgtgc tgactcagcc atcttcccat tctgcatctt ctggagcatc agtcagactc     60
acctgcatgc tgagcagtgg cttcagtgtt ggggacttct ggataaggtg gtaccaacaa    120
aagccaggga accctccccg gtatctcctg tactaccact cagactccaa taagggccaa    180
ggctctggag ttcccagccg cttctctgga tccaacgatg catcagccaa tgcagggatt    240
ctgcgtatct ctgggctcca gcctgaggat gaggctgact attactgtgg tacatggcac    300
agcaactcta agactca                                                  317

<210> SEQ ID NO 262
<211> LENGTH: 312
<212> TYPE: DNA
<213> ORGANISM: Homo sapiens

<400> SEQUENCE: 262
cggcccgtgc tgactcagcc gccctctctg tctgcatccc gggagcaac agccagactc      60 ccctgcaccc tgagcagtga cctcagtgtt ggtggtaaaa acatgttctg gtaccagcag    120
aagccaggga gctctcccag gttattcctg tatcactact cagactcaga caagcagctg    180
```

| | | |
|---|---|---|
| ggacctgggg tccccagtcg agtctctggc tccaaggaga cctcaagtaa cacagcgttt | 240 | |
| ttgctcatct ctgggctcca gcctgaggac gaggccgatt attactgcca ggtgtacgaa | 300 | |
| agtagtgcta at | 312 | |

<210> SEQ ID NO 263
<211> LENGTH: 312
<212> TYPE: DNA
<213> ORGANISM: Homo sapiens

<400> SEQUENCE: 263

| | |
|---|---|
| ctgcctgtgc tgactcagcc cccgtctgca tctgccttgc tgggagcctc gatcaagctc | 60 |
| acctgcaccc taagcagtga gcacagcacc tacaccatcg aatggtatca acagagacca | 120 |
| gggaggtccc cccagtatat aatgaaggtt aagagtgatg gcagccacag caaggggggac | 180 |
| gggatccccg atcgcttcat gggctccagt tctggggctg accgctacct caccttctcc | 240 |
| aacctccagt ctgacgatga ggctgagtat cactgtggag agagccacac gattgatggc | 300 |
| caagtcggtt ga | 312 |

<210> SEQ ID NO 264
<211> LENGTH: 315
<212> TYPE: DNA
<213> ORGANISM: Homo sapiens

<400> SEQUENCE: 264

| | |
|---|---|
| cagcctgtgc tgactcagcc accttctgca tcagcctccc tgggagcctc ggtcacactc | 60 |
| acctgcaccc tgagcagcgg ctacagtaat tataaagtgg actggtacca gcagagacca | 120 |
| gggaagggcc cccggtttgt gatgcgagtg ggcactggtg ggattgtggg atccaagggg | 180 |
| gatggcatcc ctgatcgctt ctcagtcttg ggctcaggcc tgaatcggta cctgaccatc | 240 |
| aagaacatcc aggaagaaga tgagagtgac taccactgtg gggcagacca tggcagtggg | 300 |
| agcaacttcg tgtaa | 315 |

<210> SEQ ID NO 265
<211> LENGTH: 299
<212> TYPE: DNA
<213> ORGANISM: Homo sapiens

<400> SEQUENCE: 265

| | |
|---|---|
| cagcctgtgc tgactcaatc atcctctgcc tctgcttccc tgggatcctc ggtcaagctc | 60 |
| acctgcactc tgagcagtgg gcacagtagc tacatcatcg catggcatca gcagcagcca | 120 |
| gggaaggccc ctcggtactt gatgaagctt gaaggtagtg aagctacaa caaggggagc | 180 |
| ggagttcctg atcgcttctc aggctccagc tctggggctg accgctacct caccatctcc | 240 |
| aacctccagt ttgaggatga ggctgattat tactgtgaga cctgggacag taacactca | 299 |

<210> SEQ ID NO 266
<211> LENGTH: 299
<212> TYPE: DNA
<213> ORGANISM: Homo sapiens

<400> SEQUENCE: 266

| | |
|---|---|
| cagcttgtgc tgactcaatc gccctctgcc tctgcctccc tgggagcctc ggtcaagctc | 60 |
| acctgcactc tgagcagtgg gcacagcagc tacgccatcg catggcatca gcagcagcca | 120 |
| gagaagggcc ctcggtactt gatgaagctt aacagtgatg gcagccacag caaggggggac | 180 |
| gggatccctg atcgcttctc aggctccagc tctggggctg agcgctacct caccatctcc | 240 |

```
agcctccagt ctgaggatga ggctgactat tactgtcaga cctggggcac tggcattca      299

<210> SEQ ID NO 267
<211> LENGTH: 98
<212> TYPE: PRT
<213> ORGANISM: Homo sapiens

<400> SEQUENCE: 267

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Ser Phe Thr Ser Tyr
             20                  25                  30

Trp Ile Ser Trp Val Arg Gln Met Pro Gly Lys Gly Leu Glu Trp Met
         35                  40                  45

Gly Arg Ile Asp Pro Ser Asp Ser Tyr Thr Asn Tyr Ser Pro Ser Phe
     50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 268
<211> LENGTH: 98
<212> TYPE: PRT
<213> ORGANISM: Homo sapiens

<400> SEQUENCE: 268

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Ser Tyr
             20                  25                  30

Ala Met Asn Trp Val Arg Gln Ala Pro Gly Gln Gly Leu Glu Trp Met
         35                  40                  45

Gly Trp Ile Asn Thr Asn Thr Gly Asn Pro Thr Tyr Ala Gln Gly Phe
     50                  55                  60

Thr Gly Arg Phe Val Phe Ser Leu Asp Thr Ser Val Ser Thr Ala Tyr
 65                  70                  75                  80

Leu Gln Ile Cys Ser Leu Lys Ala Glu Asp Thr Ala Val Tyr Tyr Cys
                 85                  90                  95

Ala Arg
```